US012642870B2

(12) United States Patent
Rychak et al.

(10) Patent No.: US 12,642,870 B2
(45) Date of Patent: Jun. 2, 2026

(54) COMPOSITIONS AND METHODS FOR DELIVERY OF NUCLEIC ACIDS

(71) Applicants: Poseida Therapeutics, Inc., San Diego, CA (US); University of San Diego, San Diego, CA (US)

(72) Inventors: Joshua Rychak, San Diego, CA (US); Jivan Yewle, San Diego, CA (US); Sean Essex, San Diego, CA (US); Nicholas Cam, San Diego, CA (US); Peter M. Iovine, San Diego, CA (US); Jake R. Hughes, San Diego, CA (US); Gopi Nath Vemuri, San Diego, CA (US)

(73) Assignees: Poseida Therapeutics, Inc., San Diego, CA (US); University of San Diego, San Diego, CA (US)

( * ) Notice: Subject to any disclaimer, the term of this patent is extended or adjusted under 35 U.S.C. 154(b) by 630 days.

(21) Appl. No.: 18/249,871

(22) PCT Filed: Oct. 20, 2021

(86) PCT No.: PCT/US2021/055876
§ 371 (c)(1),
(2) Date: Apr. 20, 2023

(87) PCT Pub. No.: WO2022/087148
PCT Pub. Date: Apr. 28, 2022

(65) Prior Publication Data

US 2024/0000969 A1 Jan. 4, 2024

Related U.S. Application Data

(60) Provisional application No. 63/241,770, filed on Sep. 8, 2021, provisional application No. 63/094,813, filed on Oct. 21, 2020.

(51) Int. Cl.

| | |
|---|---|
| ***A61K 40/31*** | (2025.01) |
| ***A61K 9/51*** | (2006.01) |
| ***A61K 35/28*** | (2015.01) |
| ***A61K 35/407*** | (2015.01) |
| ***A61K 38/37*** | (2006.01) |
| ***A61K 38/45*** | (2006.01) |
| ***A61K 38/52*** | (2006.01) |
| ***A61K 40/11*** | (2025.01) |
| ***A61K 48/00*** | (2006.01) |

(52) U.S. Cl.
CPC ........ *A61K 48/0033* (2013.01); *A61K 9/5123* (2013.01); *A61K 35/28* (2013.01); *A61K 35/407* (2013.01); *A61K 38/37* (2013.01); *A61K 38/45* (2013.01); *A61K 38/52* (2013.01); *A61K 40/11* (2025.01); *A61K 40/31* (2025.01); *C12Y 201/03003* (2013.01); *C12Y 504/99002* (2013.01)

(58) Field of Classification Search
CPC ............................ A61K 48/0033; A61K 40/31
See application file for complete search history.

*Primary Examiner* — Andrew S Rosenthal
*Assistant Examiner* — Danielle Kim
(74) *Attorney, Agent, or Firm* — Leason Ellis LLP; Brian M. Gummow

(57) ABSTRACT

The present disclosure provides compositions and methods for the genetic modification of cells, including, but not limited to, resting T-cells and hepatocytes. The compositions and methods can comprise lipid nanoparticles, wherein the lipid nanoparticles comprise at least one multivalent cationic bolaform amphiphilic lipid, at least one structural lipid, at least one phospholipid and at least one PEGylated lipid.

20 Claims, 1 Drawing Sheet

Specification includes a Sequence Listing.

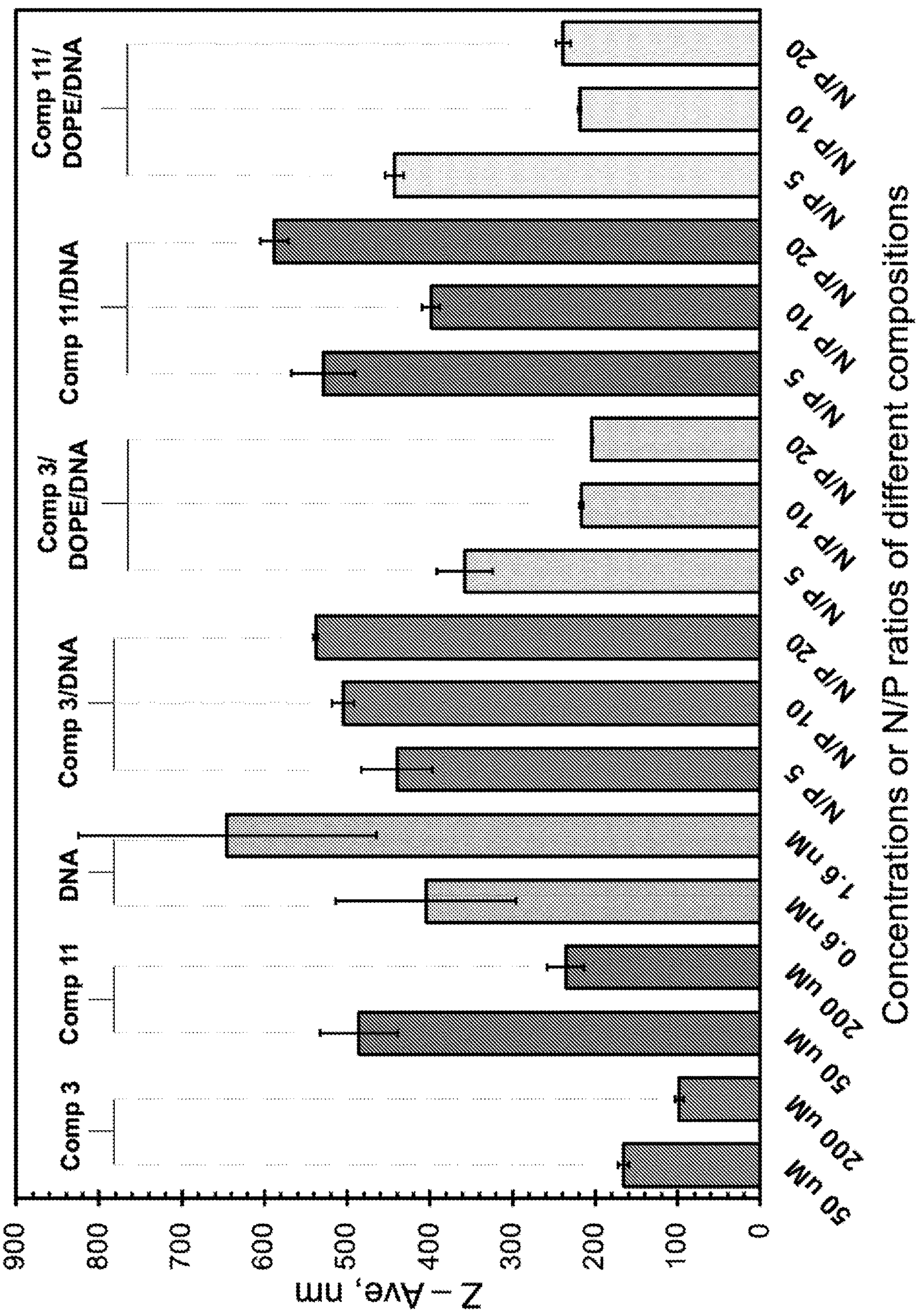
Comp 3
Comp 11
DNA
Comp 3/DNA
Comp 3/ DOPE/DNA
Comp 11/DNA
Comp 11/ DOPE/DNA
50 uM
200 uM
50 uM
200 uM
0.6 nM
1.6 nM
N/P 5
N/P 10
N/P 20
N/P 5
N/P 10
N/P 20
N/P 5
N/P 10
N/P 20
N/P 5
N/P 10
N/P 20
Concentrations or N/P ratios of different compositions
Z – Ave, nm
0
100
200
300
400
500
600
700
800
900

SEQUENCE LISTING

```
<160> NUMBER OF SEQ ID NOS: 1

<210> SEQ ID NO 1
<211> LENGTH: 594
<212> TYPE: PRT
<213> ORGANISM: Artificial Sequence
<220> FEATURE:
<223> OTHER INFORMATION: Synthetic Sequence

<400> SEQUENCE: 1

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
```

-continued

```
        275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe
```

COMPOSITIONS AND METHODS FOR DELIVERY OF NUCLEIC ACIDS

CROSS REFERENCE TO RELATED APPLICATIONS

This application is a U.S. National Phase application, filed under 35 U.S.C. § 371, of International Application No. PCT/US2021/055876, filed Oct. 20, 2021, which claims priority to, and the benefit of, U.S. Provisional Application No. 63/094,813, filed on Oct. 21, 2020, and U.S. Provisional Application No. 63/241,770, filed on Sep. 8, 2021. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Oct. 20, 2021, is named "POTH-064_001WO_SeqList.txt" and is about 5,433 bytes in size.

FIELD OF THE INVENTION

The present invention relates generally to novel lipid nanoparticles ("LNPs") comprising cationic bolaform amphiphilic lipids, methods of preparing these LNPs, and the use of these LNPs for gene therapy and cell-based therapy applications. The compositions and methods of the present disclosure have wide applicability to a diverse number of fields, including gene therapy and the production of cell-based therapeutics.

BACKGROUND OF THE INVENTION

There has been a long-felt but unmet need in the art for compositions and methods for delivering nucleic acids to cells and for genetically modifying cells in vivo, ex vivo and in vitro. Widely accepted gene delivery and genetic modification techniques, such as the use of viral vectors, including AAVs, can cause acute toxicity and harmful side-effects in patients. The present disclosure provides improved compositions, methods and kits for the delivery of nucleic acids to various types of cells, including T-cells and hepatocytes, in vivo, ex vivo and in vitro. More specifically, the present disclosure provides improved lipid nanoparticle compositions and methods of using the same. These lipid nanoparticle compositions and methods allow for the delivery of nucleic acids to cells with high efficiency and low toxicity. Thus, the compositions and methods of the present disclosure have wide applicability to a diverse number of fields, including gene therapy and the production of cell-based therapeutics.

SUMMARY OF THE INVENTION

In some aspects, provided are novel lipid nanoparticles ("LNPs") comprising a bolaform amphiphilic lipids. In one aspect, the bolaform amphiphilic lipid is a compound of Formula (I).

In some aspects, provided are novel lipoplex nanoparticles comprising a cationic bolaform amphiphilic lipids. In one aspect, the bolaform amphiphilic lipid is a compound of Formula (I).

In some aspects, provided are pharmaceutical compositions, comprising a composition of the present disclosure and at least one pharmaceutically-acceptable excipient or diluent.

In some aspects, provided are methods of delivering at least one nucleic acid to at least one cell comprising contacting the at least one cell with at least one composition of the present disclosure.

In some aspects, provided are methods of genetically modifying at least one cell comprising contacting the at least one cell with at least one composition of the present disclosure.

In some aspects, provided are methods of treating at least one disease or disorder in a subject in need thereof comprising administering to the subject at least one therapeutically effective amount of at least one composition of the present disclosure.

In some aspects, provided are methods of delivering at least one nucleic acid to at least one cell comprising contacting the at least one cell with at least one composition of the present disclosure.

In some aspects, provided are cells modified according to methods of the present disclosure.

Any of the aspects and/or embodiments described herein can be combined with any other aspect and/or embodiment described herein.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.100, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 1 is a bar graph showing the size of lipoplex nanoparticles formed with various concentrations of multivalent cationic bolaform amphiphilic lipids of the present disclosure.

DETAILED DESCRIPTION OF THE INVENTION

The present disclosure provides novel lipid nanoparticle compositions (LNPs) comprising novel multivalent bola amphiphilic lipids, methods for preparing the LNPs, and methods for using same. In a non-limiting example, the compositions and methods of the present limiting disclosure can be used gene delivery and cell-based therapeutics. In a non-limiting example, the compositions and methods of the present disclosure can be broadly used to deliver a nucleic acid to liver cells, in vivo, ex vivo or in vitro, for the treatment of certain diseases and disorders, including, but not limited to liver disorders. In a non-limiting example, the compositions and methods of the present disclosure can be broadly used to deliver a nucleic acid to T-cells, in vivo, ex vivo or in vitro, for the treatment of certain disorders, including, but not limited to cancer. In a non-limiting example, the compositions and methods of the present disclosure can be broadly used to deliver a nucleic acid to primary, unactivated T-cells, in vivo, ex vivo or in vitro, for the treatment of certain diseases and disorders, including, but not limited to cancer. In a non-limiting example, the compositions and methods of the present disclosure can be broadly used to deliver a nucleic acid for the purpose of vaccination. In a non-limiting example, the compositions and methods of the present disclosure can be broadly used to deliver a nucleic acid to induce the expression of a secreted therapeutic protein.

Without wishing to be bound by theory, the multivalent bolaform amphiphilic lipids of the present disclosure comprise multivalent cationic lipids that can form lipoplexes with greater surface charge density than their monovalent counterparts, thereby resulting in enhanced binding to nucleic acids, (e.g., DNA) and enhanced delivery. Without wishing to be bound by theory, the presence of protonation sites with different pKa values in the multivalanet bolaform amphiphilic lipids of the present disclosure can result in buffering of the endosomal acidification, thereby protecting nucleic acids from degradation and facilitating its escape from the endosome. With more protonation sites per molecule, the lipoplexes resulting from multivalent cationic lipids can achieve the same charge density (P/N ratio) as monofunctional cationic lipids with lesser amounts of cationic lipids in the formulation thereby potentially lessening cationic lipid-associated cytotoxicity.

Compositions of the Present Disclosure-Lipid Nanoparticles

The present disclosure provides a composition comprising at least one lipid nanoparticle comprising a multivalent cationic bolaform amphiphilic lipid of the present disclosure and at least one nucleic acid molecule. In some aspects, a lipid nanoparticle can further comprise at least one structural lipid. In some aspects, a lipid nanoparticle can further comprise at least one phospholipid. In some aspects, a lipid nanoparticle can further comprise at least one PEGylated lipid.

Multivalent Bolaform Amphiphilic Lipids

In some aspects, multivalent bolaform amphiphilic lipids are derived from certain terpenes or polyterpenes and amine, hydroxyalkyl and polyalkylenoxide functional thiols. In some aspects, the multivalent cationic bolaform amphiphilic compositions are comprised of a hydrophobic chain ("C") covalently linked at both ends to a multivalent hydrophilic cationic head groups ("A") built on a terpene frame using a thiol-ene click addition.

In some aspects, multivalent bolaform amphiphilic lipids are represented by Formula (I):

Formula (I)

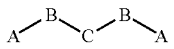

or a salt thereof, wherein:

each A is independently:

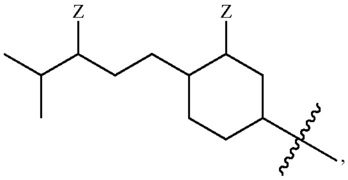,

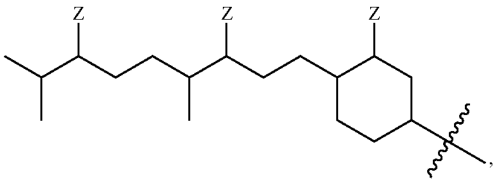,

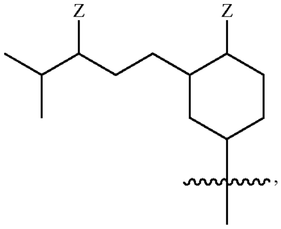,

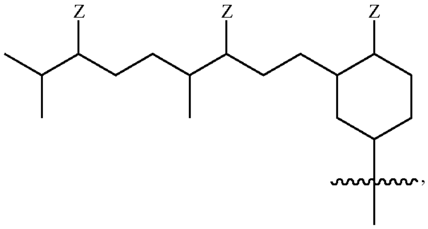,

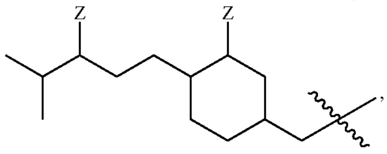,

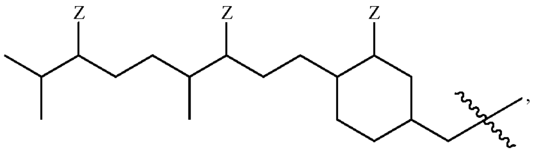,

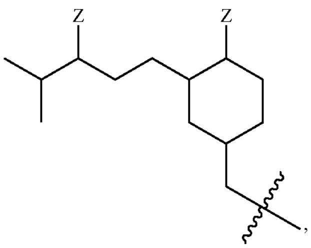,

-continued

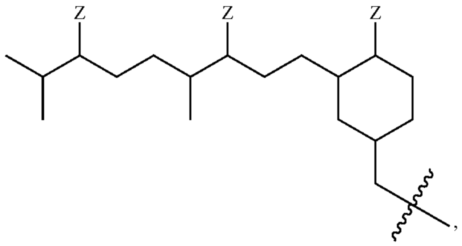,

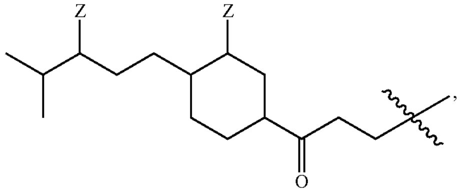,

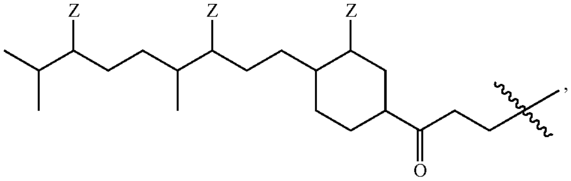,

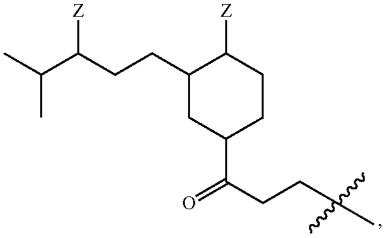,

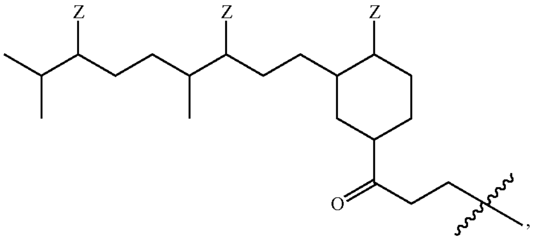,

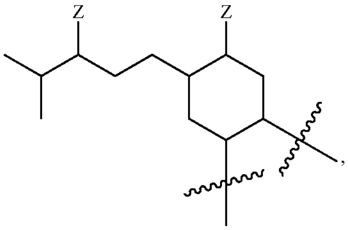, or

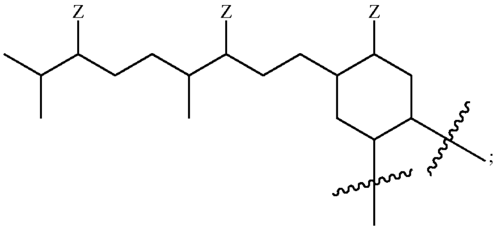;

each Z is —S—$R_1$;

each $R_1$ is independently a group having a formula selected from:

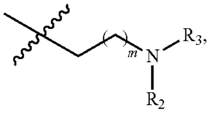, 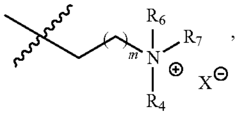,

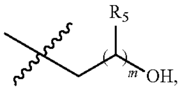, or 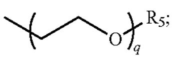;

each $R_2$ or $R_3$ is independently selected from hydrogen, $C_1$-$C_6$ alkyl, $C_1$-$C_6$ alkenyl, aralkyl, or hydroxyalkyl;

each $R_4$, $R_6$ or $R_7$ is independently selected from $C_1$-$C_6$ alkyl, $C_1$-$C_6$ alkenyl, or hydroxyalkyl;

each $R_5$ is independently hydrogen or $C_1$-$C_6$ alkyl;

each X is independently halogen;

each m is independently an integer independently selected from 1-10;

each q is independently an integer independently selected from 1-200;

each B is independently selected from:

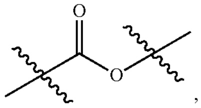, 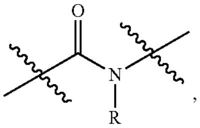,

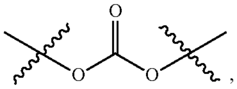, 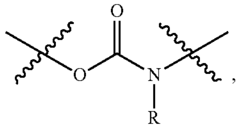, or

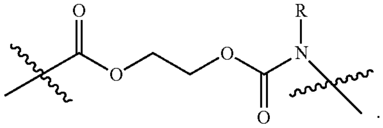.

wherein each R is independently selected from hydrogen or $C_1$-$C_6$ alkyl; and C is:

a. a $C_2$-$C_{100}$ hydrocarbon chain optionally containing one or more S atoms;

b. $Cyc^A$-L-$Cyc^B$, wherein $Cyc^A$ and $Cyc^B$ are each independently a 5-8 membered cycloalkyl and L is $C_1$-$C_3$ alkylene;

c. a polyalkylene oxide or polyalkylene oxide block copolymers of 200-5,000 molecular weight;

d. an aliphatic or aromatic polyester of 200-5,000 molecular weight;

e. an aliphatic or aromatic polyurethane of 200-5,000 molecular weight; or

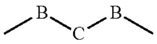

together form:

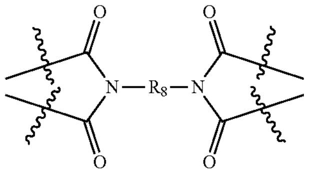

wherein each $R_8$ is independently selected from $C_2$-$C_6$ alkyl, aryl,

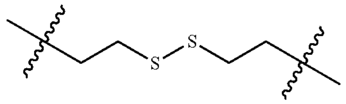

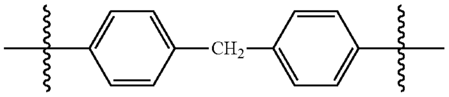

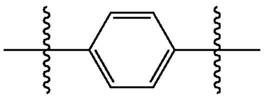

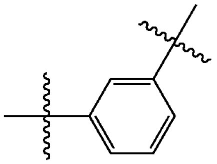

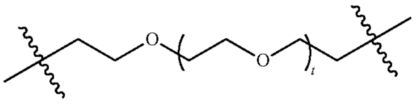

t is an integer selected from 1-10.

In some aspects, the multivalent bolaform amphiphilic lipid is of Formula (I):

Formula (I)

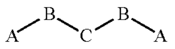

or a salt thereof, wherein:

each A is independently

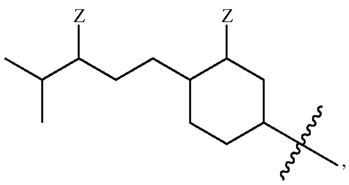
,

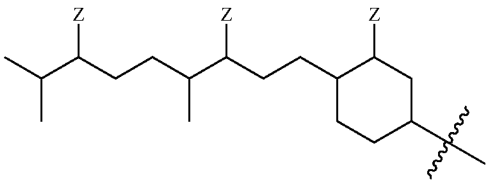
,

-continued

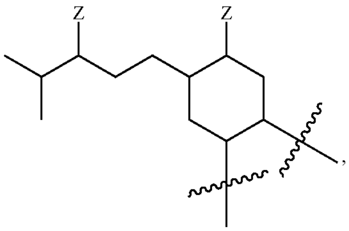
, or

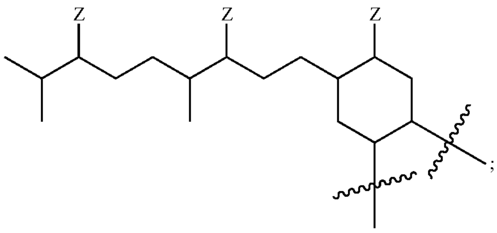
;

each Z is —S—$R_1$;

each $R_1$ is

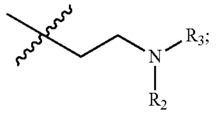

each $R_2$ or $R_3$ is independently selected from hydrogen or $C_1$-$C_6$ alkyl;

each B is

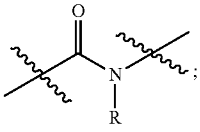

each R is independently selected from hydrogen or $C_1$-$C_6$ alkyl; and

C is a C2-C100 hydrocarbon chain, or $Cyc^A$-L-$Cyc^B$, wherein $Cyc^A$ and $Cyc^B$ are each independently a 5-8 membered cycloalkyl and L is $C_1$-$C_3$ alkylene; or

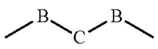

together form,

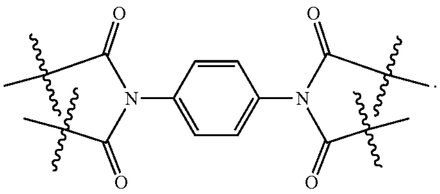 [SMILES: *C(=O)N(C(*)=O)c1ccc(N(C(*)=O)C(*)=O)cc1]
.

In some aspects, each A segment is:
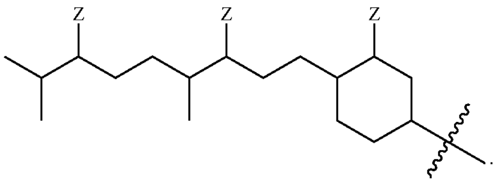
In some aspects, each A segment is:
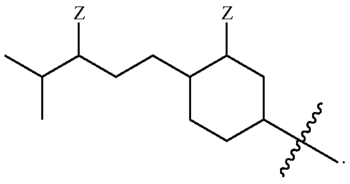
In some aspects, each A segment is:
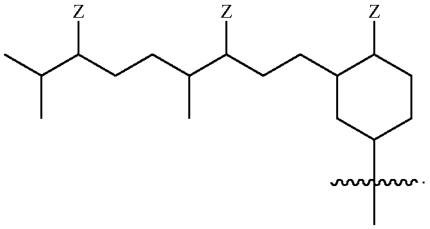
In some aspects, each A segment is:
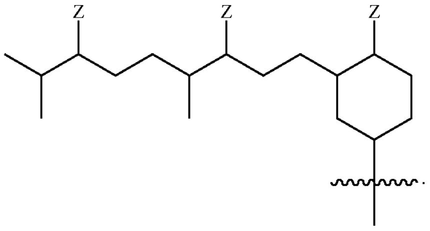
In some aspects, each A segment is:
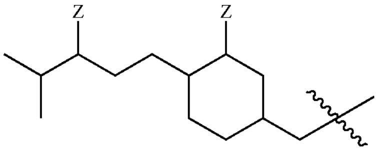
In some aspects, each A segment is:
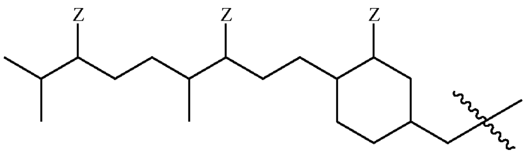
In some aspects, each A segment is:
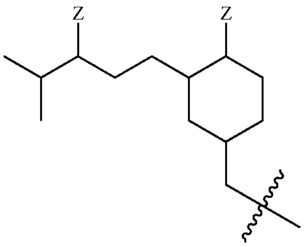
In some aspects, each A segment is:
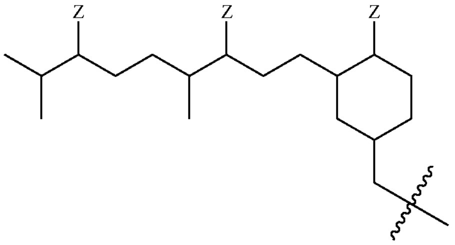
In some aspects, each A segment is:
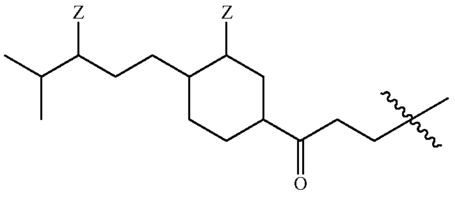
In some aspects, each A segment is:
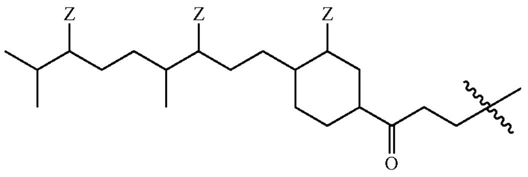

In some aspects, each A segment is:

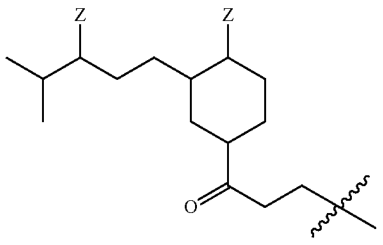

In some aspects, each A segment is:

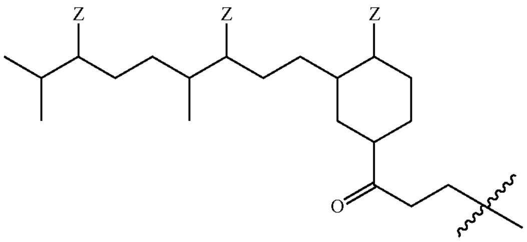

In some aspects, each A segment is:

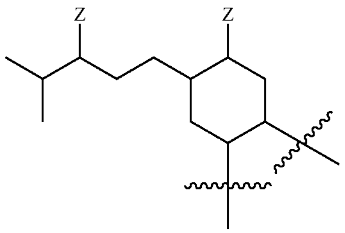

In some aspects, each A segment is:

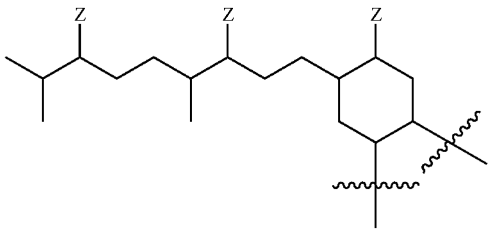

In some aspects, at least one, at least two, or at least three, or at least four or more Z groups of the A segment is —S—$R_1$, wherein $R_1$ is:

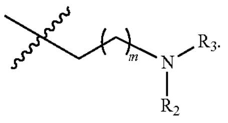

In one such embodiment, m is one and $R_2$, and $R_3$ are each independently $C_1$-$C_6$ alkyl. In one embodiment, each of the $C_1$-$C_6$ alkyl groups is methyl. In this embodiment, 2-(dimethylamino)ethanethiol or 2-(dimethylamino)ethanethiol hydrochloride can be used as the derivatizing agent.

In some aspects, each Z of the A segment is —S—$R_1$, wherein $R_1$ is:

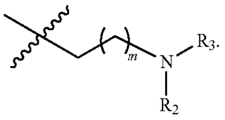

In one such embodiment, m is one and $R_2$, and $R_3$ are each independently $C_1$-$C_6$ alkyl. In one embodiment, each of the $C_1$-$C_6$ alkyl groups is ethyl. In the case where each of the $C_1$-$C_6$ alkyl groups are ethyl, 2-diethylaminoethane thiol or 2-diethylaminoethane thiol hydrochloride can be used as the derivatizing agent.

In some embodiments, each Z of the A segment is:

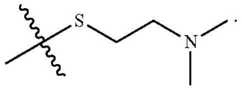 [SMILES: *SCCN(C)C]

In some aspects, at least one, at least two, or at least three, or at least four or more Z groups of the A segment is —S—$R_1$, wherein $R_1$ is:

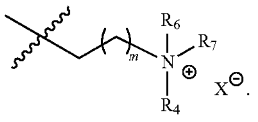

In one such embodiment, m is one and each $R_4$, $R_6$ or $R_7$ is independently $C_1$-$C_6$ alkyl. In one embodiment, each of the $C_1$-$C_6$ alkyl groups is methyl. In one embodiment, X is chlorine or bromine. In one embodiment, X is chlorine. In one embodiment, X is bromine. When X is bromine and C1-C6 is methyl, for example, (2-mercaptoethyl)-N,N,N-trimethylammonium bromide can be used as the derivatizing agent.

In some aspects, each Z of the A segment is —S—$R_1$, wherein $R_1$ is:

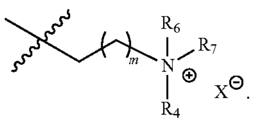

In one such embodiment, m is one and each $R_4$, $R_6$ or $R_7$ is independently $C_1$-$C_6$ alkyl. In one embodiment, each of the $C_1$-$C_6$ alkyl groups is methyl. In one embodiment, X is chlorine or bromine. In one embodiment, X is chlorine. In one embodiment, X is bromine. When X is bromine and C1-C6 is methyl, for example, (2-mercaptoethyl)-N,N,N-trimethylammonium bromide can be used as the derivatizing agent.

In some aspects, each Z is —S—$R_1$, wherein at least one, at least two, or at least three, or at least four or more $R_1$ is:

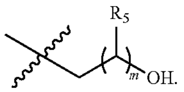

In one embodiment, m is one and $R_5$ is hydrogen.

In some aspects, each Z is —S—$R_1$, wherein at least one, at least two, or at least three, or at least four or more $R_1$ is:

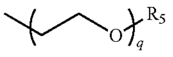

In one embodiment, q is one and $R^5$ is methyl.

In some aspects, each B segment is:

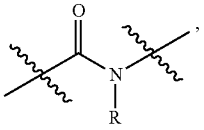

wherein each R is hydrogen and the carbonyl of the amide of each B segment is attached to each A segment.

In one embodiment, each B segment is:

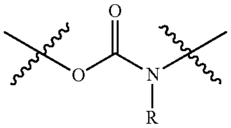

wherein each R is hydrogen and the oxygen of the carbamate group of each B segment is attached to each A segment.

In some aspects, each B segment is:

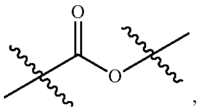 [SMILES: *OC(*)=O]

In some aspects, each B segment is:

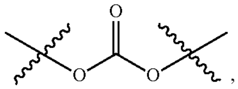 [SMILES: *OC(=O)O*]

In some aspects, each B segment is:

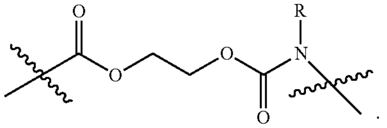

In some aspects, the C segment is a C2-C100 hydrocarbon chain. In one embodiment, the C2-C100 hydrocarbon chain is ethylene, propylene, isopropylene, butylene, isobutylene, sec-butylene, tert-butylene, pentylene, hexylene, heptanylene, octanylene, nonanylene, decanylene, undecanylene, dodecanylene, tridecanylene, icosanylene, triacontanylene, and tetracontanylene. In some aspects, the C segment is derived from the corresponding C2-C100 diamine or dialcohol depending on the desired B linkage.

In one embodiment, the C segment is a C6 hydrocarbon chain. In one embodiment, the C6 hydrocarbon chain is hexylene. In one embodiment, the C segment is a C12 hydrocarbon chain. In one embodiment, the C12 hydrocarbon chain is dodecanylene.

In one embodiment, the C segment is a C20 hydrocarbon chain. In one embodiment, the C20 hydrocarbon chain is icosanylene.

In one embodiment, the C2-C100 hydrocarbon chain includes one or more S atoms. In one embodiment, the C2-C100 hydrocarbon chain includes two S atoms.

In one embodiment, the C2-C100 hydrocarbon chain is:

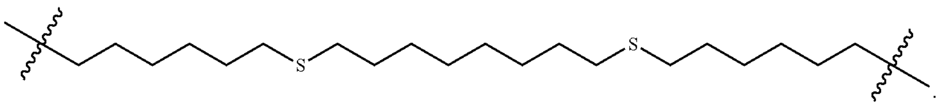 [SMILES: *CCCCCCSCCCCCCCCSCCCCCC*]

In one embodiment, the C segment is a C2-C12 hydrocarbon chain derived from well-known diisocyanates such as 1,4-diisocyanatobutane, hexamethylene diisocyanate, 1,8-Diisocyanatooctane, or 1,12-Diisocyanatododecane.

In one embodiment, the C segment is $Cyc^A$-L-$Cyc^B$, wherein $Cyc^A$ and $Cyc^B$ are each independently a 5-8 membered cycloalkyl chain and L is $C_1$-$C_3$ alkylene. In one embodiment, $Cyc^A$ and $Cyc^B$ are each cyclohexyl and L is methylene.

In one embodiment, the C segment is

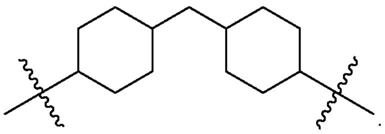 [SMILES: *C1CCC(CC2CCC(*)CC2)CC1]

In some aspects, the C segment is a polyalkylene oxide or polyalkylene oxide block copolymers of 200-5,000 molecular weight. In one embodiment, the polyalkylene oxide or polyalkylene oxide block copolymers of 200-5,000 molecular weight is, for example, poly(ethylene oxide) or poly (propylene oxide). Suitable random or block copolymers of poly(ethylene oxide) and/or poly(propylene oxide) include polylactide (PLA) [usually called poly(lactic acid)], polyglycolide (PGA), poly(ε-caprolactone) (PCL), and poly (γ-valerolactone) (PVL).

In some aspects, the C segment is an aliphatic or aromatic polyester of 200-5,000 molecular weight. Aliphatic polyesters have been used as polymers for drug delivery applications due to their biodegradable and biocompatible nature. Suitable aliphatic polyesters of appropriate molecular weight for use as C segment precursors herein include polylactide (PLA) [usually called poly(lactic acid)], polyglycolide (PGA), poly(F-caprolactone) (PCL), and poly (γ-valerolactone) (PVL).

In addition, a wide variety of aromatic polyesters of desired molecular weight may be used to prepare the C segment precursors. Aliphatic-aromatic polyesters may be obtained, for example, by condensing aliphatic diols, aliphatic dicarboxylic acids, and aromatic dicarboxylic acids/esters. The aliphatic-aromatic copolyesters are synthetically polymerized. Well known biodegradable aliphatic-aromatic copolyesters are poly(ethylene terephthalate) (PET), poly (butylene succinate-co-terephthalate) (PBST) and, poly (butylene adipate-co-terephthalate) (PBAT). Various representative industrial methods for producing aliphatic-co-aromatic copolyesters are described in U.S. Pat. No. 5,171,308 A (1992, DU PONT), WO9514740 A1 (1995, DU PONT), WO9625446 A1 (1996, BASE AG), E-P1108737 A2 (2001, IRE CHEMICAL LTD), and EP1106640 A2 (2001, IRE CHEMICAL LTD). In one embodiment, the aliphatic or aromatic polyester of 200-5,000 molecular weight is, for example, PBAT.

In some aspects, the C segment is an aliphatic or aromatic polyurethane of 200-5,000 molecular weight. Difunctionalized aliphatic diisocyanates may be used in preparation of degradable polyurethanes to circumvent any potential toxicity concerns. Suitable aliphatic diisocyanates for use herein include 1,4-butane diisocyanate, 1,6-hexamethylene diisocyanate, and lysine diisocyanates. Lysine diisocyanate has gained popularity in recent years due to the assumption that its lysine-based chemistry will yield safe carboxylic by-products. Butane diisocyanate is also considered to have biocompatible degradation products, as the hydrolyzed product, putrescine, is naturally occurring in the body.

Commercial aromatic isocyanates are toluenediisocyanate (TDI), diphenylmethane diisocyanate (MI), and naphthalene diisocyanate (NDI) and their polymeric forms.

In one embodiment, the aliphatic or aromatic polyurethane of 200-5,000 molecular weight is, for example, polyurethanes derived from biocompatible hydroxyl-terminated diols such as polylactide (PLA) [usually called poly(lactic acid)], polyglycolide (PGA), poly(s-caprolactone) (PCL), poly(ethyleneterpthalate, poly(ethyleneadipate), and poly(γ-valerolactone) (PVL)), polyether diols combined with diisocyanates such as lysine diisocyanate.

In some aspects, together form:

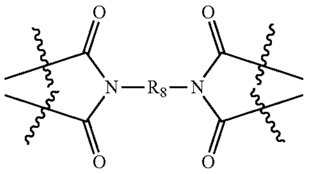

wherein each $R_8$ is independently selected from C2-C6 alkyl, aryl,

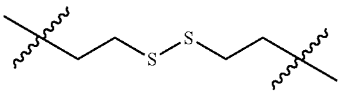

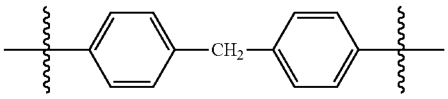

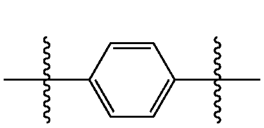

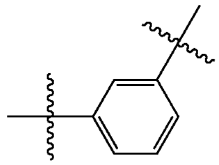

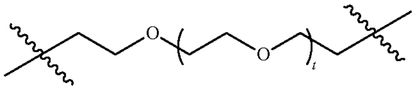

and wherein each t is an integer independently selected from 1-10.

In some embodiments, together form
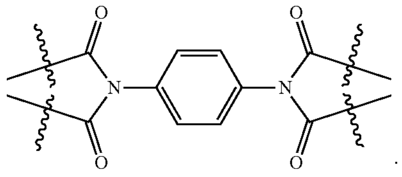 [SMILES: *C(=O)N(C(*)=O)c1ccc(N(C(*)=O)C(*)=O)cc1]
In some aspects, the multivalent bolaform amphiphilic compound of Formula (I) is:
COMPOUND 1
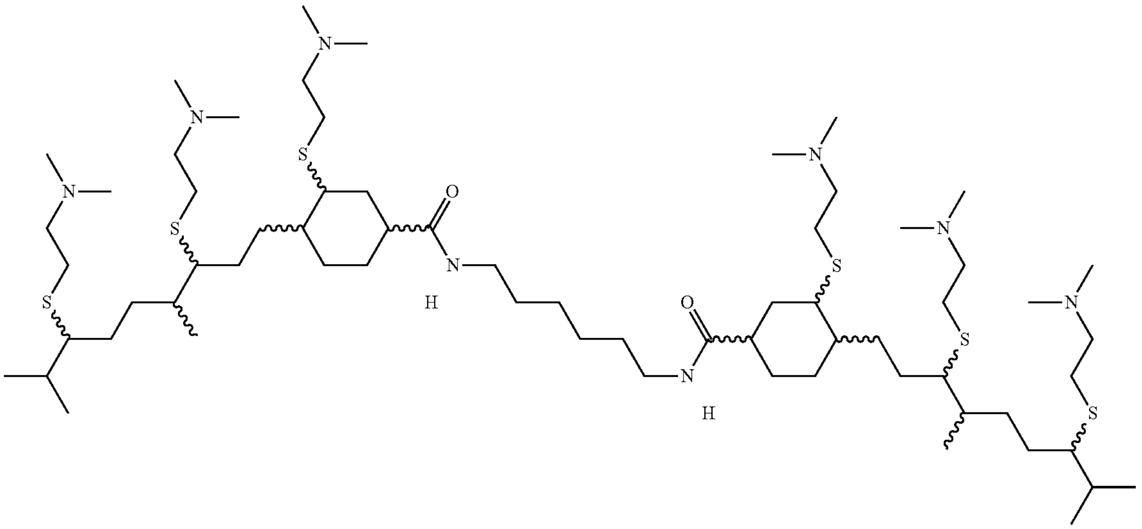
COMPOUND 2
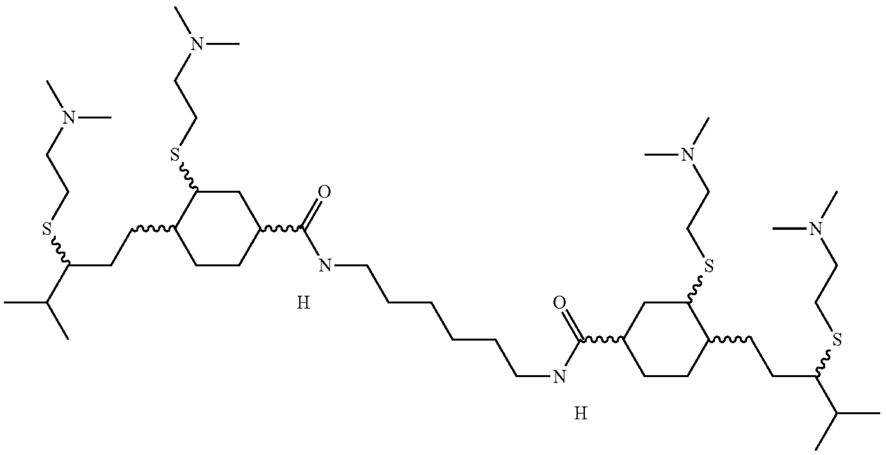

-continued
COMPOUND 3
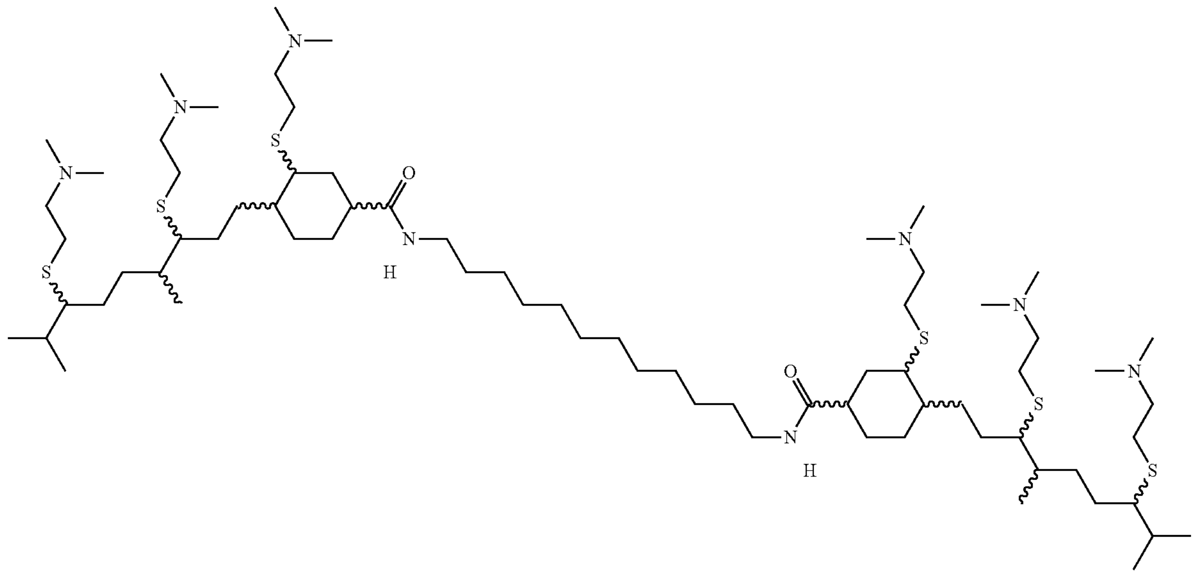
COMPOUND 4
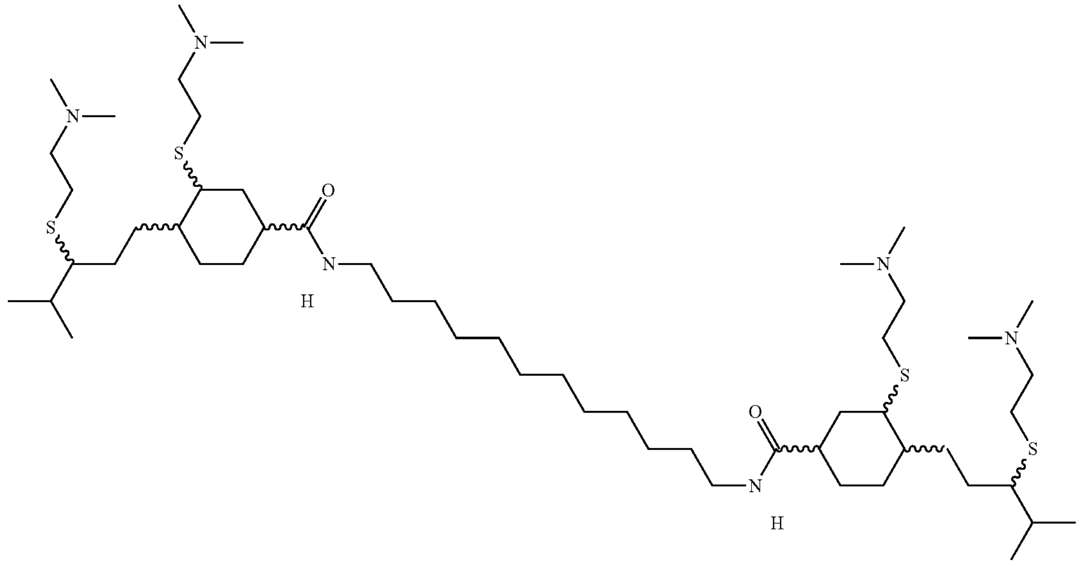

-continued
COMPOUND 5
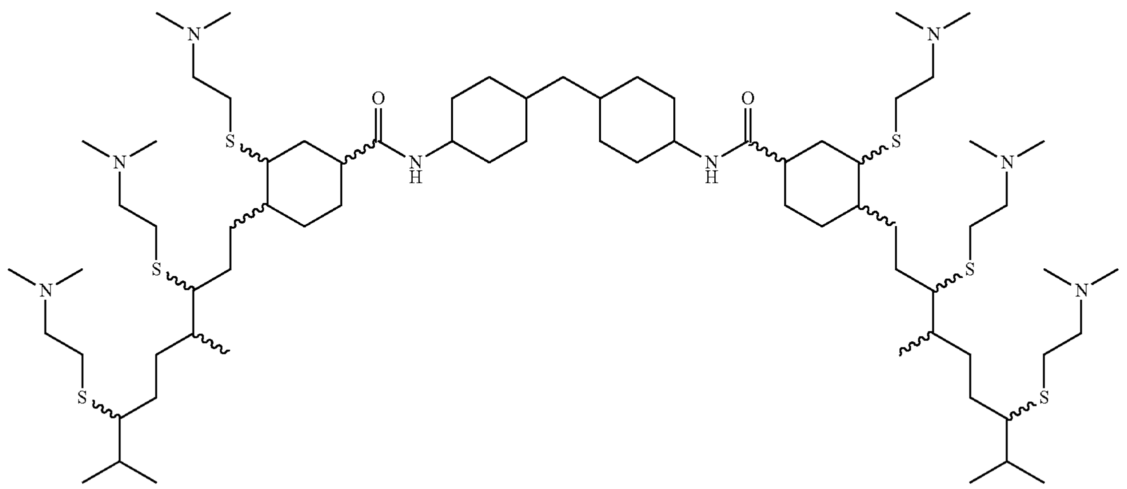
COMPOUND 6
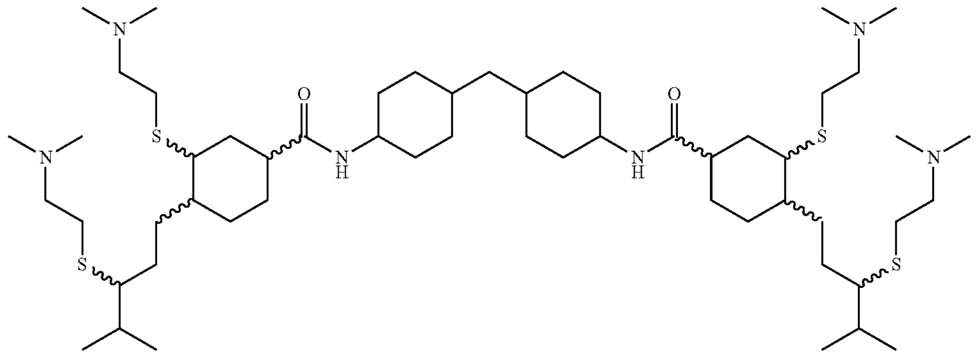
COMPOUND 7
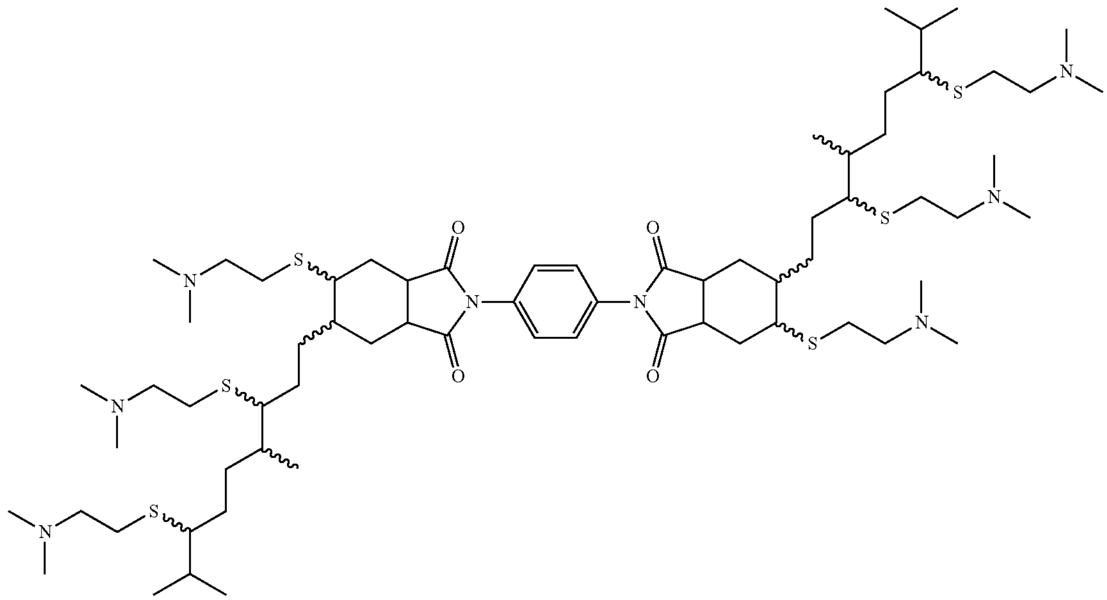

-continued
COMPOUND 8
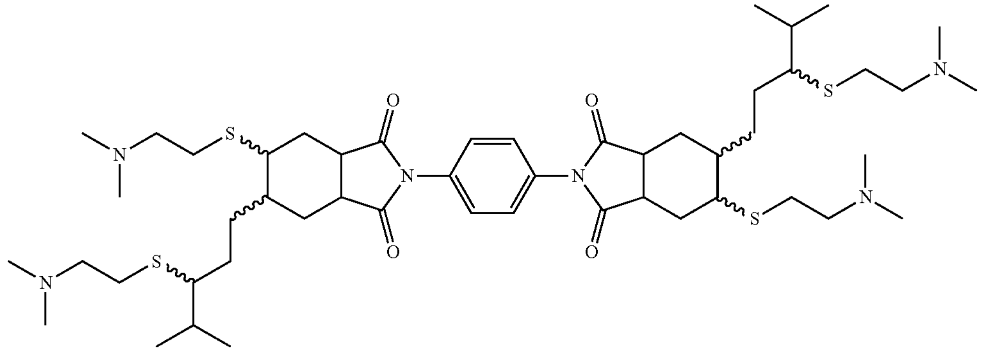
COMPOUND 9
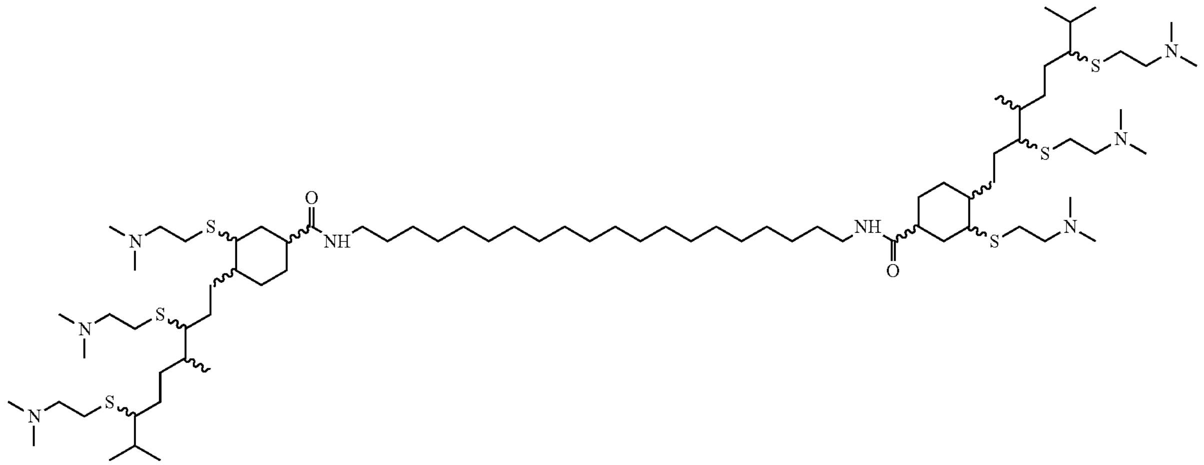
COMPOUND 10
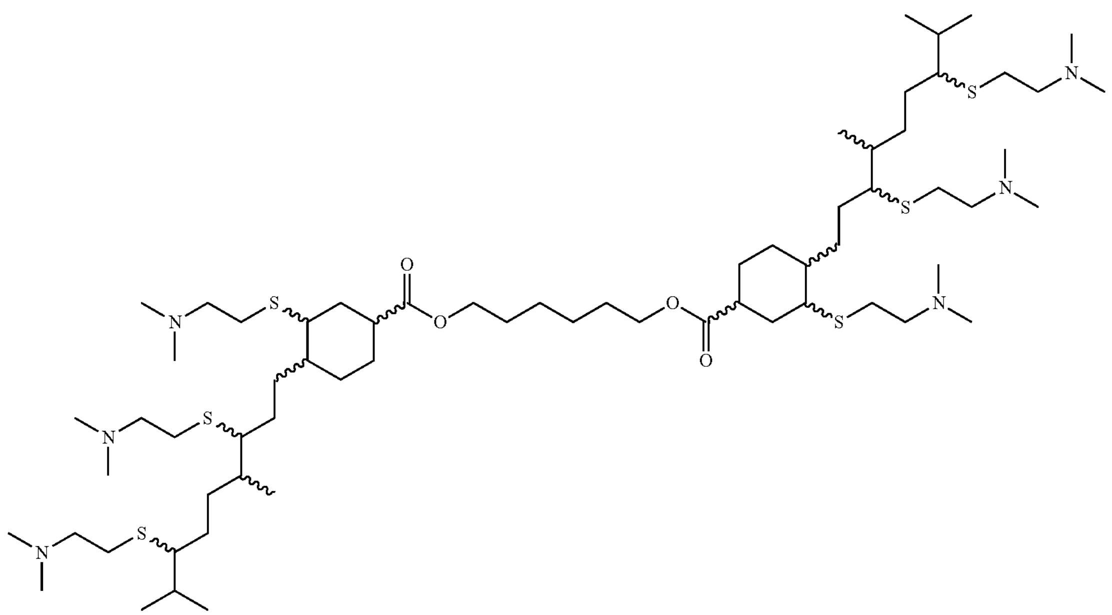

-continued
COMPOUND 11
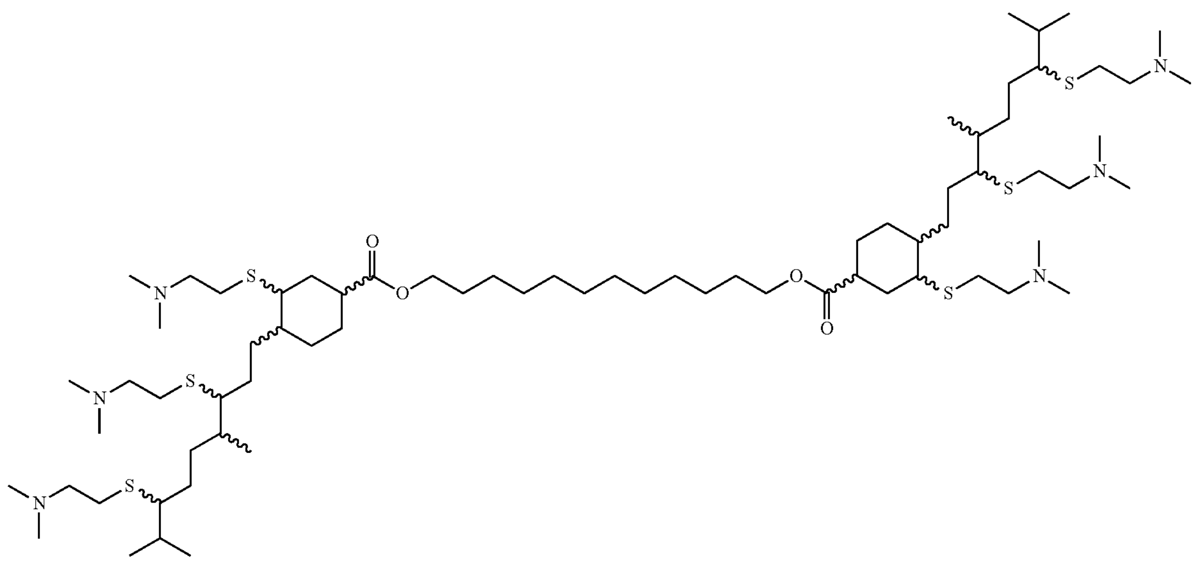
COMPOUND 12
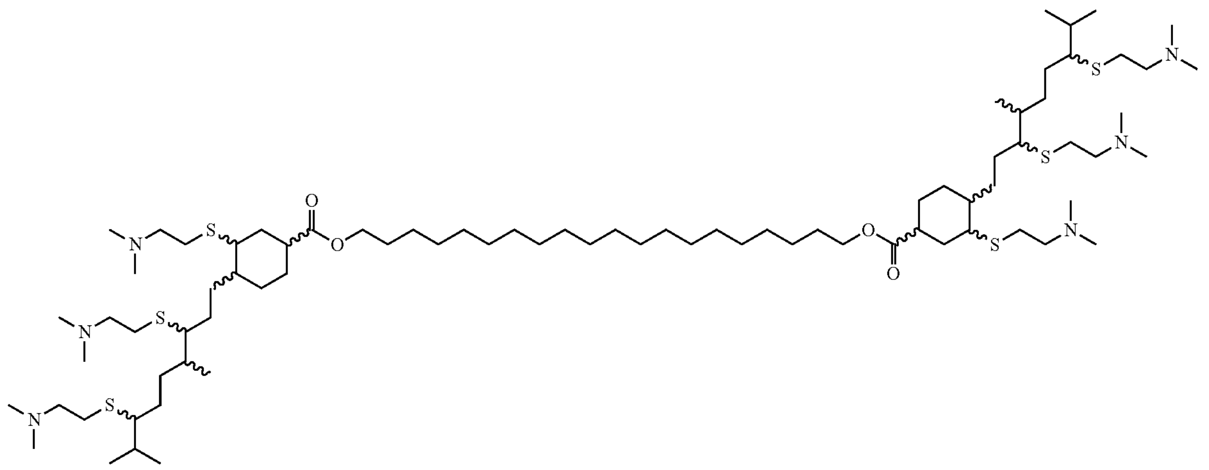
COMPOUND 13
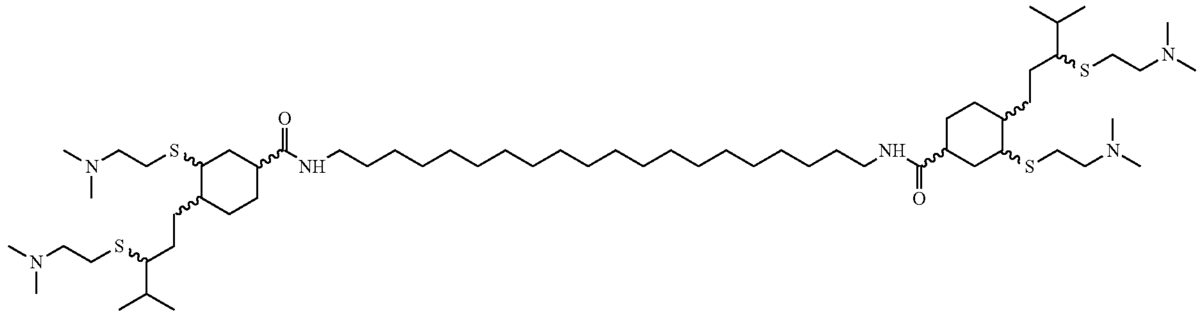

-continued
COMPOUND 14
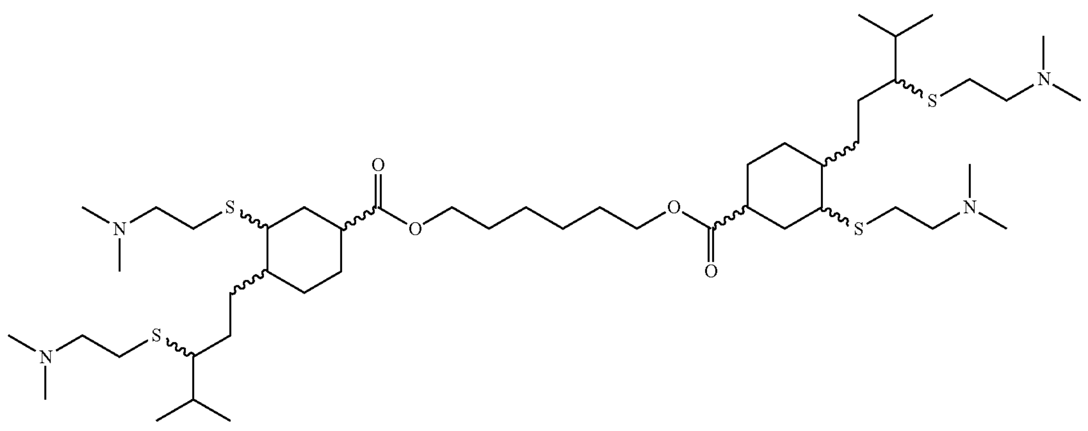
COMPOUND 15
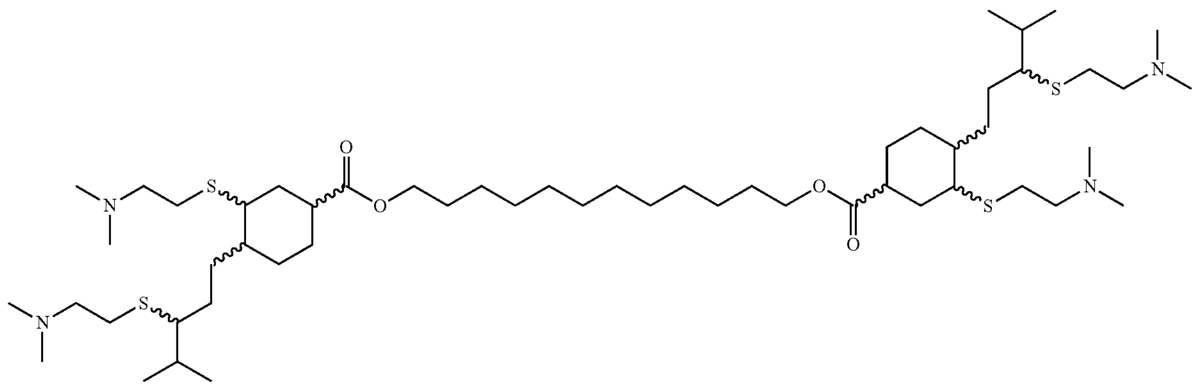
COMPOUND 16
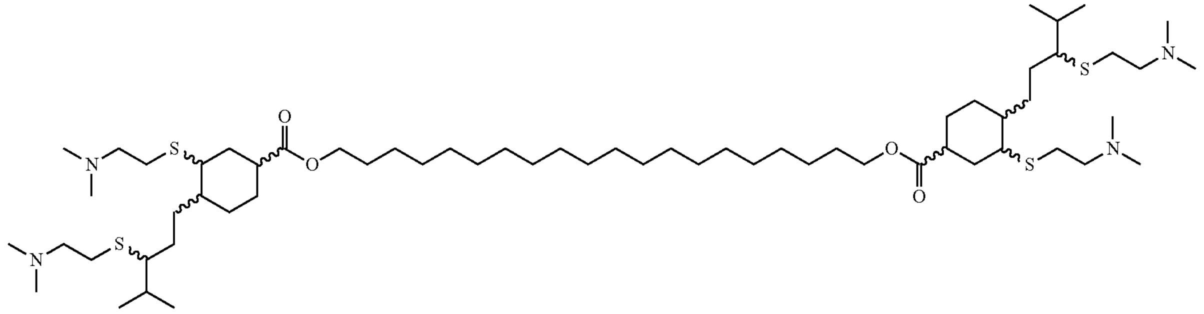

-continued
COMPOUND 17
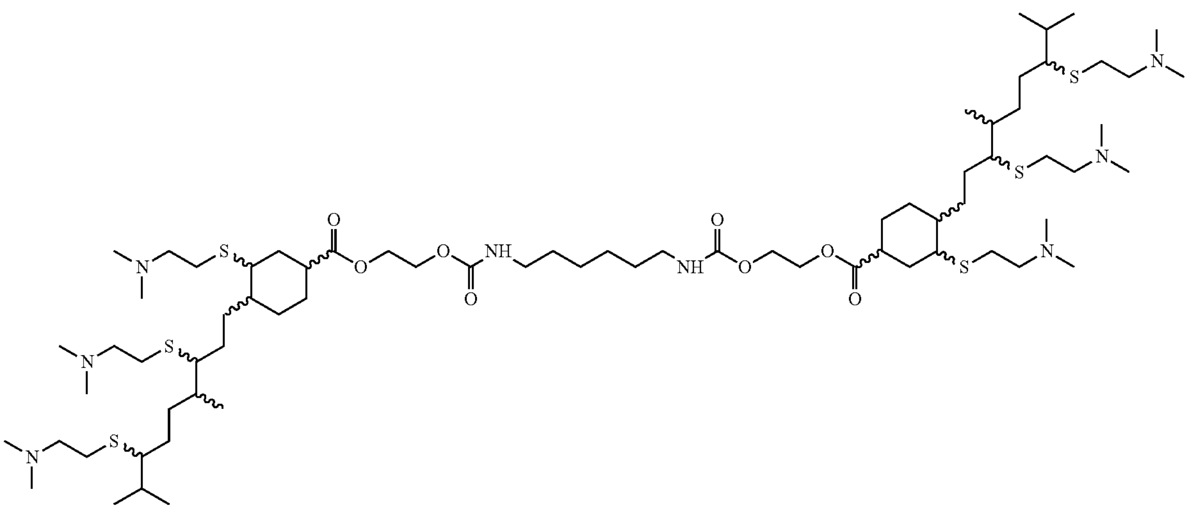
COMPOUND 18
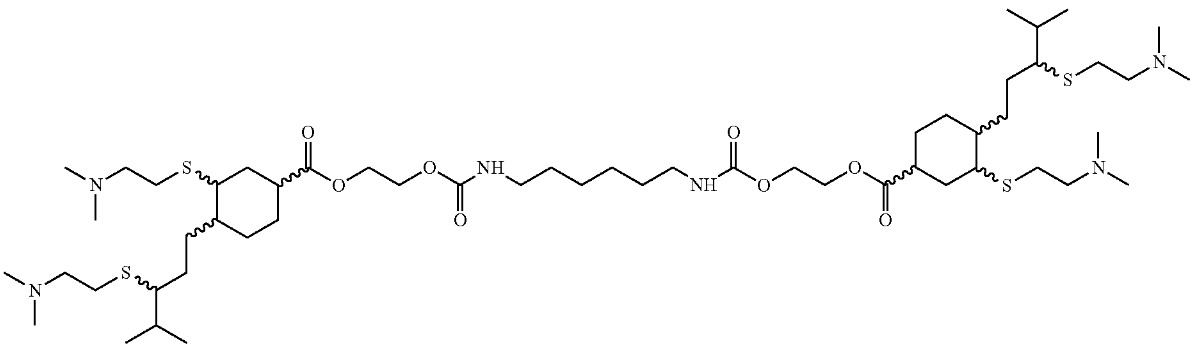
COMPOUND 19
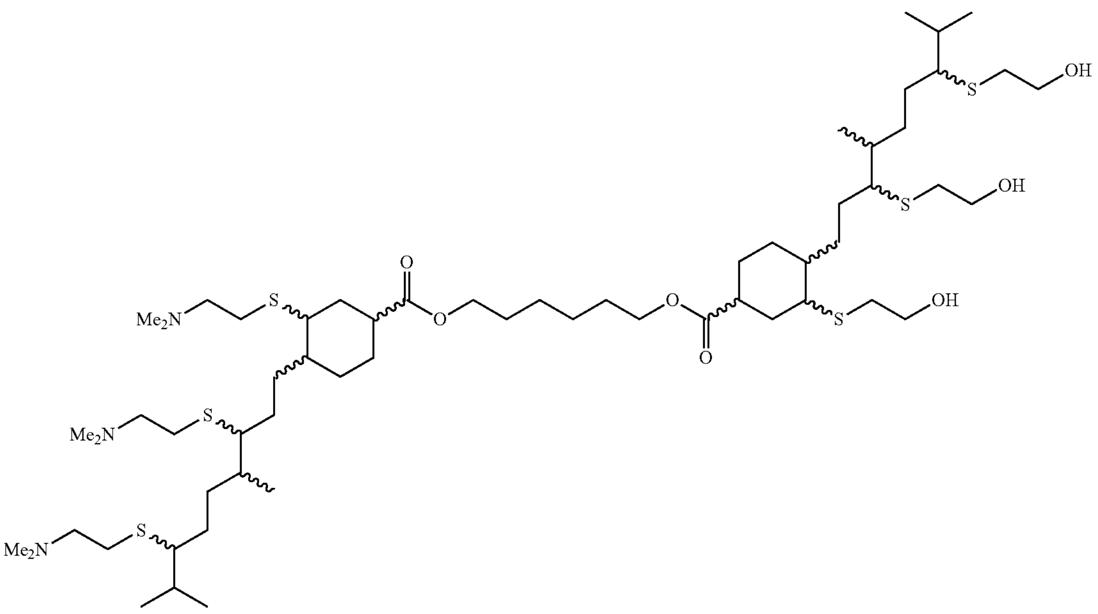

-continued

COMPOUND 20

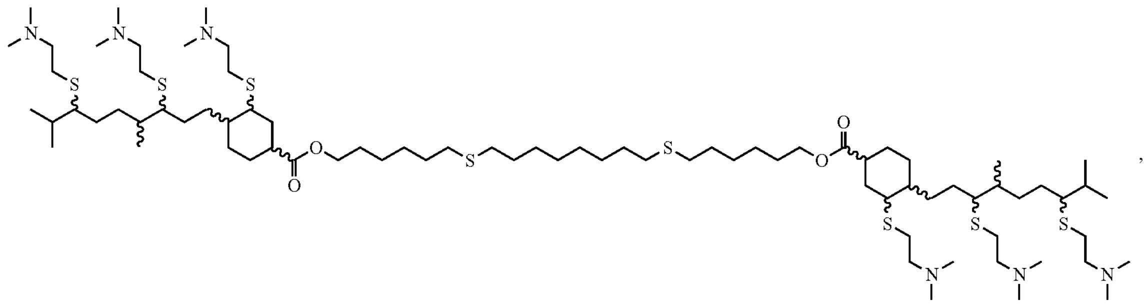

, and

COMPOUND 21

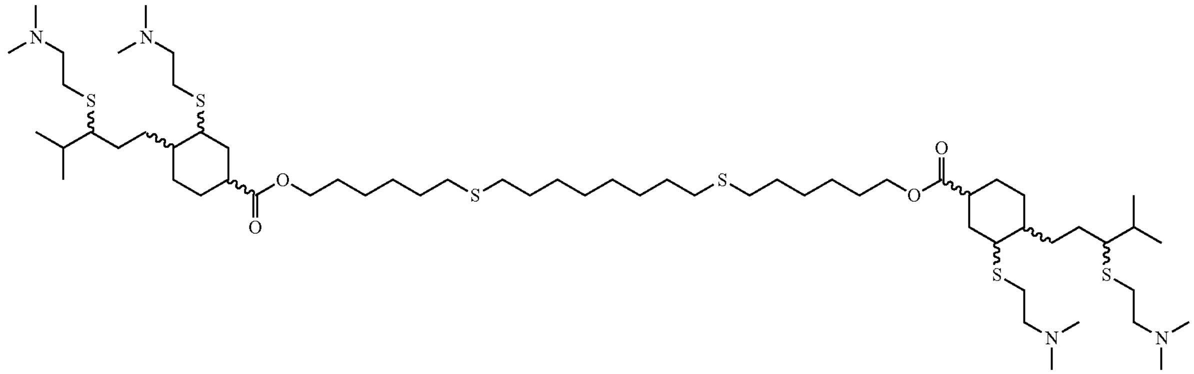

General Methods for the Preparation of Compounds of Formula (I) of the Present Disclosure Compounds of Formula (I) may be prepared using the reagents, intermediates, precursors and methods disclosed herein or using other commercially available reagents and methods known to those skilled in the art.

In general, the first step in preparation of multivalent cationic bolaform amphiphilic compounds of Formula (I) of the present disclosure is the election of appropriate terpene, e.g., trans-beta farnesene, beta myrcene or other suitable biorenewable terpene, to prepare the multivalent "A" segment precursor. For example, trans-beta farnesene may be reacted with a suitable unsaturated carboxylic acid derivative, e.g., ethyl acrylate, which serves as a dieneophile forming a suitable Diels-Alder adduct:

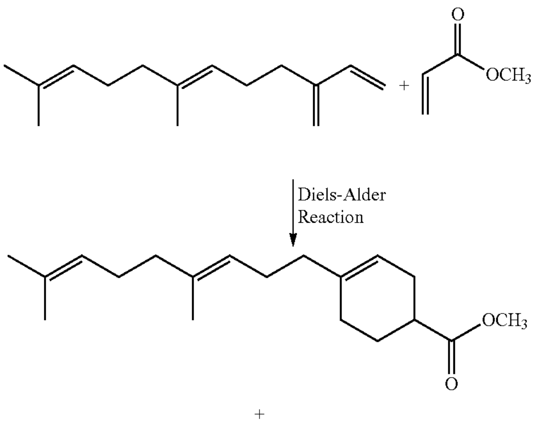

-continued

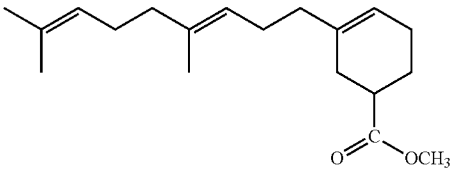

Suitable Diels-Alder products for use in the methods herein include:

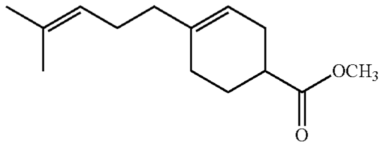

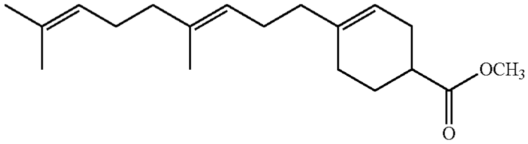

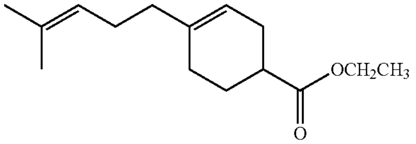

-continued

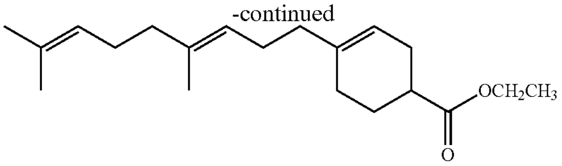

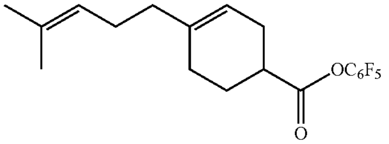

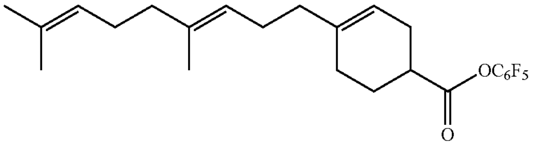

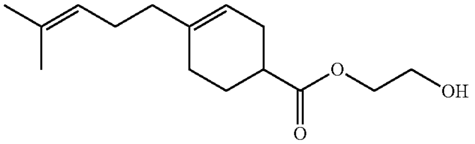

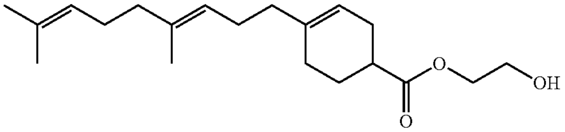

In general, the Diels-Alder product, the "A" segment precursor, was added to a heavy walled vial along with the selected diamine (1 molar equivalent) and a stir bar. 1,5,6-triazabicyclo[4.4.0]dec-5-ene (TBD) was added (20 mol % based on the terpene Diels-Alder adduct) and the reaction heated to 130° C. for 15 h. Upon cooling to room temperature, the reaction solidified into a tan semi-solid. The solid was first washed with multiple portions of hexanes (to remove excess terpene), water (to remove catalyst and unreacted diamine), and finally isolated by filtration. After drying under vacuum the isolated yields were all>90%.

In one instance, the "A" segment precursor, is reacted with a suitable difunctional nucleophile "C" segment precursor, e.g., C2-C100 hydrocarbon chain functionalized with an amine at each end position of the chain, wherein nucleophilic substitution reaction described above at each position links the two "A" segment precursors to the "C" segment precursor while simultaneously forming the two "B" segments:

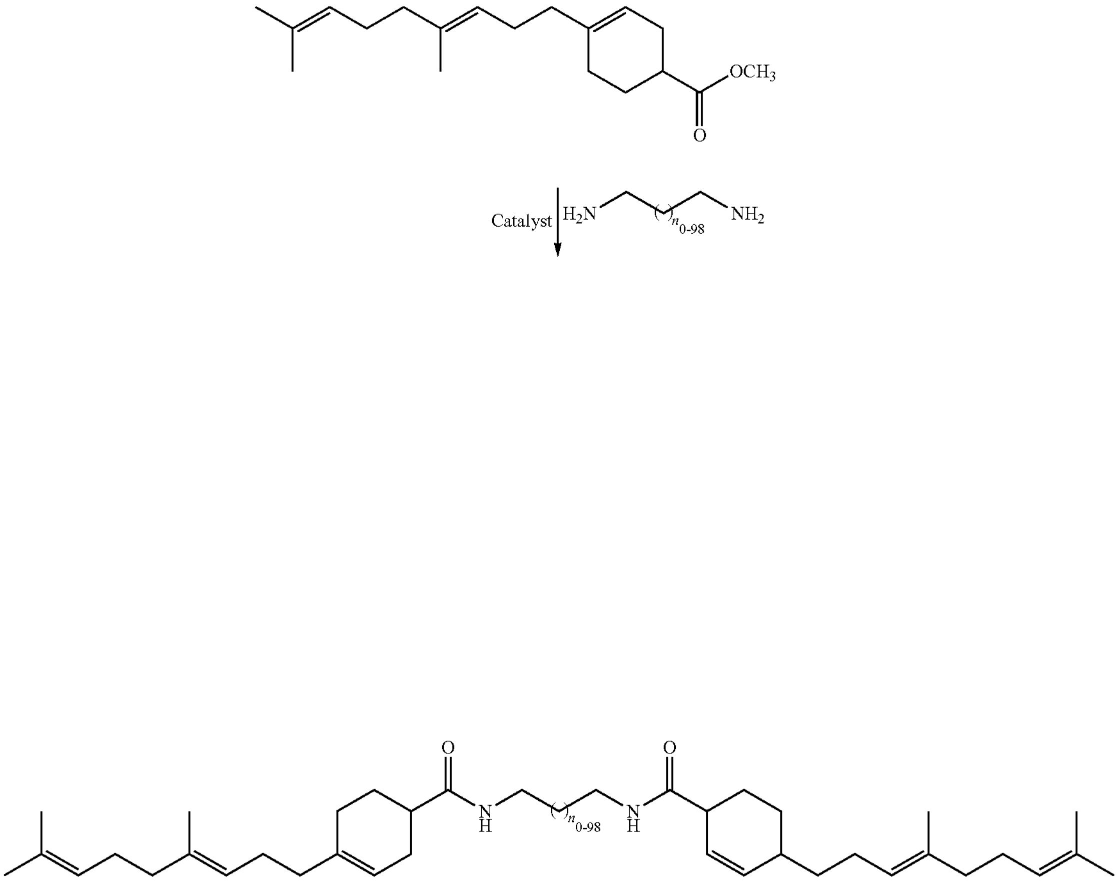

Similarly, in another instance, the “A” segment precursor, is reacted with a suitable difunctional nucleophile “C” segment precursor, e.g., C2-C100 hydrocarbon chain functionalized with a diol at each end position of the chain, wherein nucleophilic substitution reaction described above at each position links the two “A” segment precursors to the “C” segment precursor while simultaneously forming the two “B” segments:

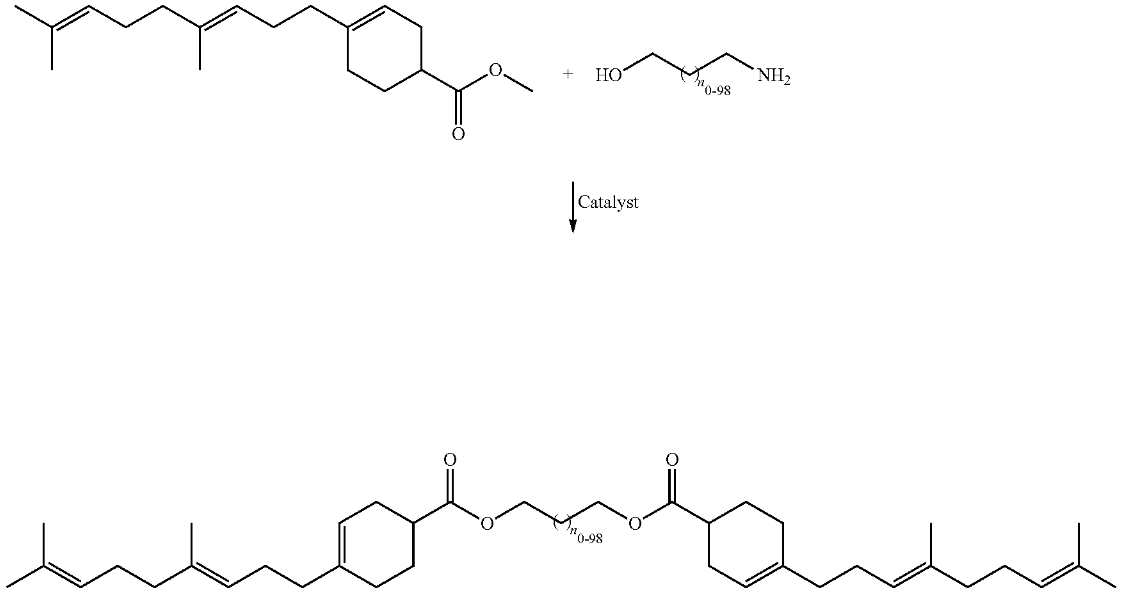

The compounds of Formula (I) can be prepared by the addition of “Z” to the assembled A-B-C-B-A precursor using a suitable $R_1$ group thiol precursor, e.g., amine, hydroxyl, or poly(alkeneoxide) functional thiol, individually or as mixtures, by photochemical or thermal means.

For instance, reacting the A-B-C-B-A precursor above with a suitable photochemical thiol, e.g., 1-(dimethylamino) ethanethiol hydrochloride, in the presence 2,2-dimethoxy-2-phenylacetophenone, and irradiating at room temperature with 370 nm light from OLED lights positioned at both sides at an appropriate distance, e.g., 5 cm or 14 cm, for a defined period, e.g., 12 hr or 4 hrs, respectively. The chloroform-methanol solution was evaporated and the resulting yellow solid washed with ethyl acetate before being redissolved in a minimal amount of water. The aqueous solution was dialyzed (100-500 D molecular weight cut off cellulose ester) against deionized water. The water was changed twice (4 hour intervals) and then left overnight. The final product was isolated by lyophilization affording compounds of Formula (I):

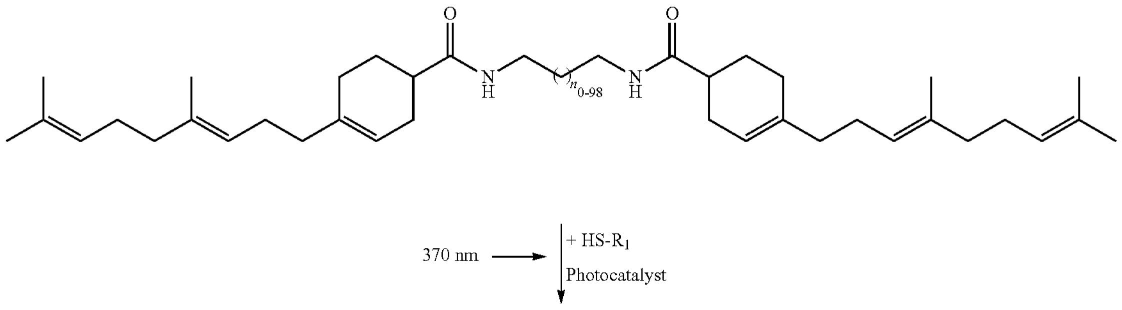

-continued

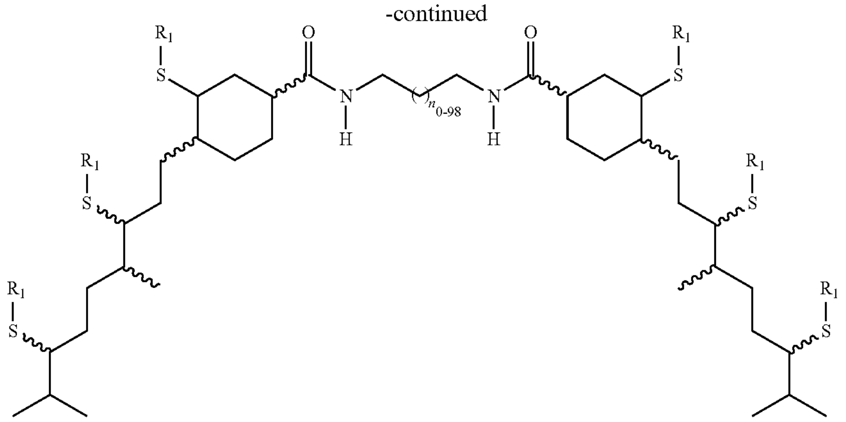

Alternatively, compounds of Formula (I) may be prepared by first coupling Z to the A chain precursor. In one embodiment, the methyl esters of trans-beta-farnesene may be subject to similar conditions above to generate A precursors preloaded with one or more Z (i.e., —SH-$R_1$) groups which is then coupled to the C precursors using methods analogous to those described above.

In another aspect, compounds of Formula (I) can be prepared by linear polymerization using bis-maleimides by Michael addition. The maleimide carbon-carbon double bond is highly electrophilic and can react with nucleophilic reagents, such as amines or thiol derivatives of the A segment, to afford compounds of Formula (I).

For example, such compounds of Formula (I) can be prepared as shown in Scheme 1.

Scheme 1

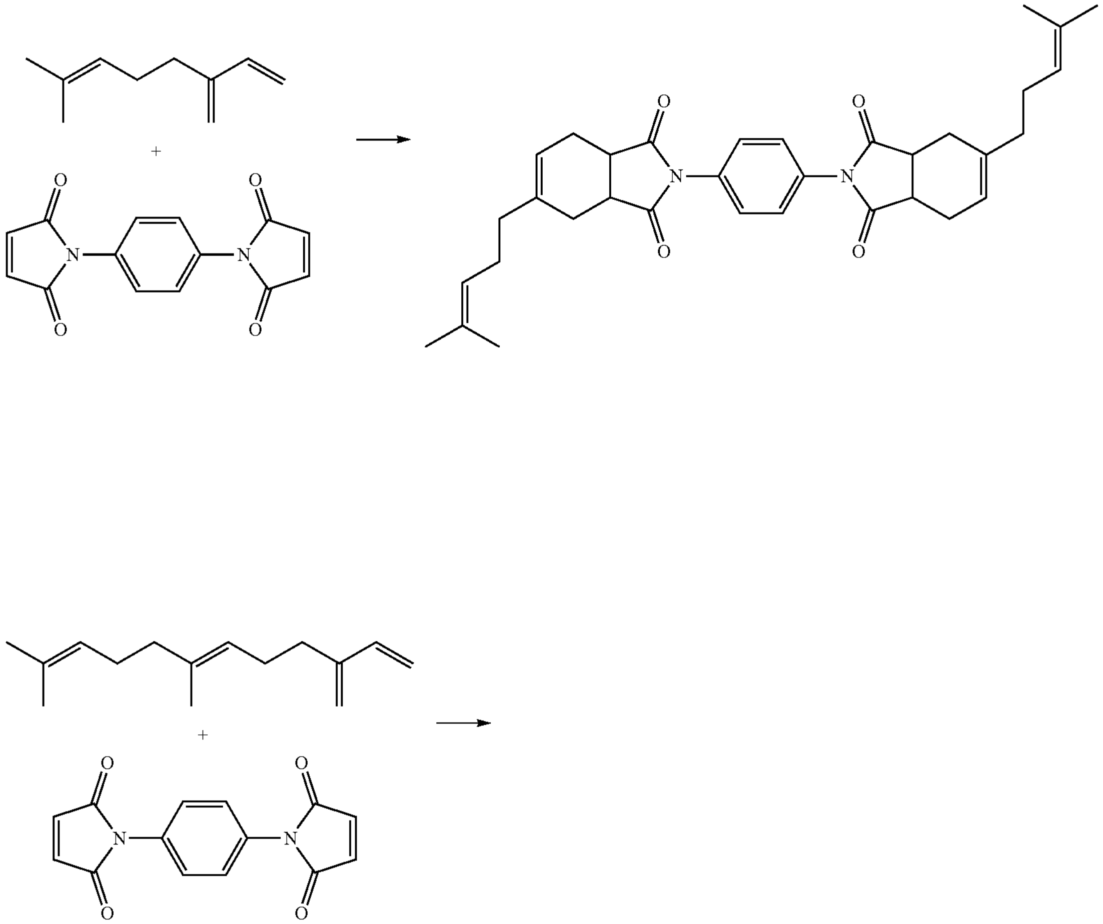

-continued

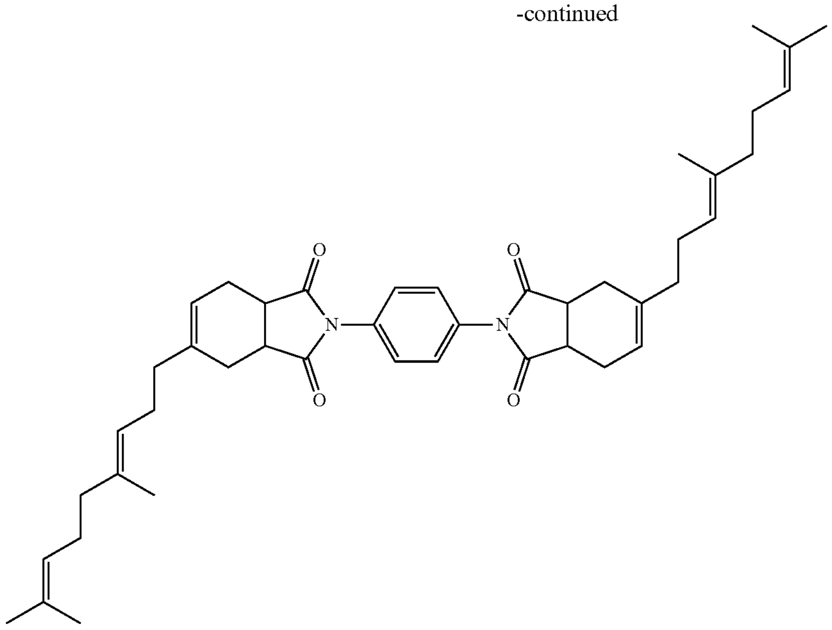

Farnesene or myrcene (3 molar equivalents) was added to a heavy walled vial along with N,N'-(1,4-phenylene)dimaleimide (1 molar equivalent). The vial was sealed and heated to 130° C. Within 30 minutes the reaction solidified yielding the crude product. The crude solid was removed from the reaction vessel, suspended in hexanes, and stirred. The mixture was subject to centrifugation and the hexane supernatant decanted away from the product.

The product was dried in a vacuum oven at 40° C.

The compounds of Formula (I) can be prepared by the addition of "Z" to the assembled A-B-C-B-A precursor using a suitable $R_1$ group thiol precursor, e.g., amine, hydroxyl, or poly(alkeneoxide) functional thiol, individually or as mixtures, by photochemical or thermal means.

In one embodiment, the suitable $R_1$ group thiol precursor is 2-(dimethylamino)ethanethiol hydrochloride as shown:

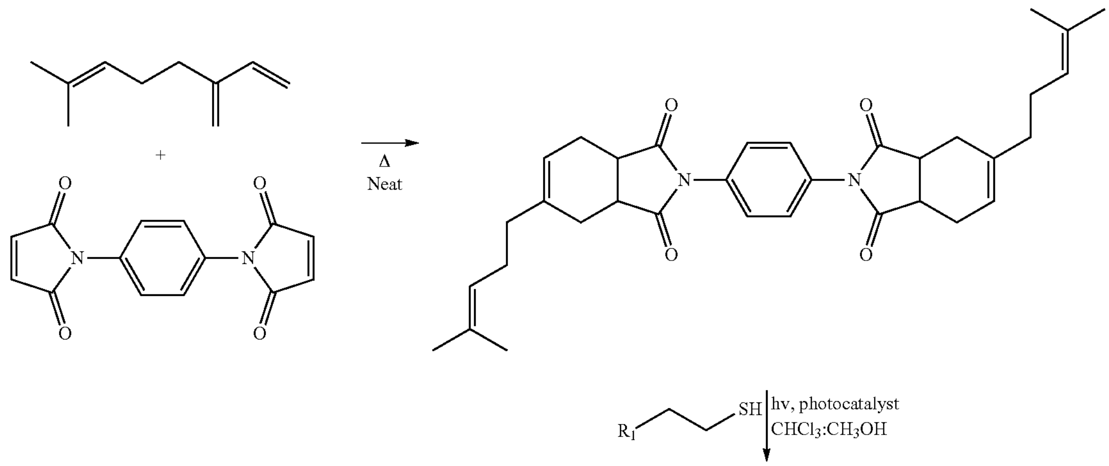

-continued

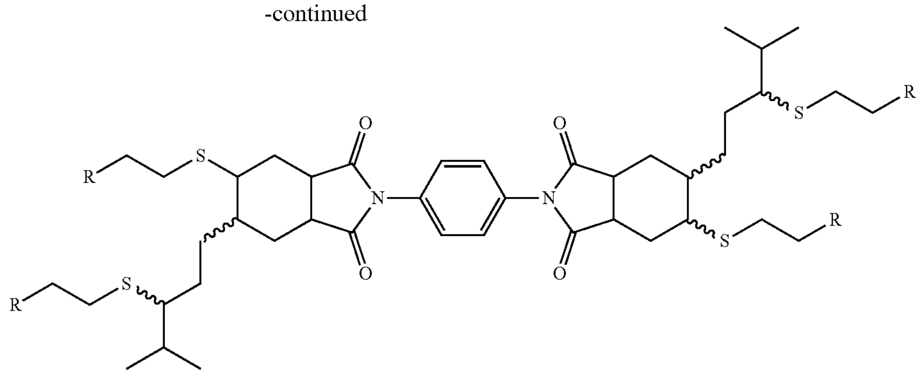

$R_1$=N$(CH_3)_2$

In yet another embodiment, compounds of the invention may be prepared as follows.

First, a bola base was prepared by the following general protocol:

A. General Protocol for Bolabase Preparation

In a 4 mL sealable glass tube, methyl ester (farnesene methyl ester (FME) or myrcene methyl ester (MME)) (4.0 eq) was added with the diamine or diol (1.0 eq) and a catalyst TBD (0.8 eq). The tube was sealed and stirred at 130° C. for 20 h (diamide series) or 48 h (diester series) without any solvent, except for $C_{20}$-diol and $C_{26}$-diol in which case 0.5 mL of DMSO was added for diol solubility. The reaction was cooled and purified by flash silica gel chromatography. In the case of $C_{20}$-diol and $C_{26}$-diol, the reaction mixture was added water and extracted with EtOAc (3×). All the EtOAc extracts were combined, washed with brine (3×), dried over $Na_2SO_4$, and evaporated. The crude was then purified by flash silica gel chromatography.

Purification conditions

Amide series:

Bola base of Compound 1: Silica gel column chromatography with 20-50% EtOAc:hexanes Bola base of Compound 3: Recrystallization with ethanol Ester series:

Bola bases of Compounds 11, 12, 17, & 20: Silica gel column chromatography with 5% EtOAc:hexanes Bola bases of Compounds 2, 4, & 21: Silica gel column chromatography with 50% toluene:hexanes B. General Protocol for Bolaamphiphiles Preparation Once the bola base was prepared, the bola base was used to make the final compounds as follows. In a 4 mL quartz tube, bola base (1.0 eq), thiol (1.5 eq per alkene), and photocatalyst, 2,2-Dimethoxy-2-phenylacetophenone (DMPA) (0.2 eq per alkene) were taken. A mixed solvent system of THF:MeOH (5:1) was added until all the reagents were dissolved and degassed with nitrogen for 10 mins before irradiating with 350 nm of UV light for 6 h at room temperature. The solvent was evaporated and the residue was passed through a silica gel column. Eluant 5% MeOH:DCM was used to remove nonpolar impurities and the compound was isolated with 10-50% MeOH:DCM. The off-white solid obtained was dissolved in a few mL of DI water and dialyzed against water in 100-500 daltons bag for 20 h. The dialyzed solution was lyophilized to get the bolaamphiphiles as off-white hygroscopic solids.

LNP Components

In some aspects, an LNP of the present disclosure can comprise at least about 2.5%, or at least about 5%, or at least about 7.5%, or at least about 10%, or at least about 12.5%, or at least about 15%, or at least about 17.5%, or at least about 20%, or at least about 22.5%, or at least about 25%, or at least about 27.5%, or at least about 30%, or at least about 32.5%, or at least about 35%, or at least about 37.5%, or at least about 40%, or at least about 42.5%, or at least about 45%, or at least about 47.5%, or at least about 50%, or at least about 52.5%, or at least about 55%, or at least about 57.5% or at least about 60%, or at least about 62.5%, or at least about 65%, or at least about 67.5%, or at least about 70% of at least one multivalent bolaform amphiphilic lipid of the present disclosure by moles. In some aspects, the at least one multivalent bolaform amphiphilic lipid is at least one compound of Formula (I), as described herein.

In some aspects, an LNP of the present disclosure can comprise about 2.5%, or about 5%, or about 7.5%, or about 10%, or about 12.5%, or about 15%, or about 17.5%, or about 20%, or about 22.5%, or about 25%, or about 27.5%, or about 30%, or about 32.5%, or about 35%, or about 37.5%, or about 40%, or about 42.5%, or about 45%, or about 47.5%, or about 50%, or about 52.5%, or about 55%, or about 57.5% or about 60%, or about 62.5%, or about 65%, or about 67.5%, or about 70% of at least one multivalent bolaform amphiphilic lipid of the present disclosure by moles. In some aspects, the at least one multivalent bolaform amphiphilic lipid is at least one compound of Formula (I), as described herein.

In some aspects, an LNP can further comprise at least about 2.5%, or at least about 5%, or at least about 7.5%, or at least about 10%, or at least about 12.5%, or at least about 15%, or at least about 17.5%, or at least about 20%, or at least about 22.5%, or at least about 25%, or at least about 27.5%, or at least about 30%, or at least about 32.5%, or at least about 35%, or at least about 37.5%, or at least about 40%, or at least about 42.5%, or at least about 45%, or at least about 47.5%, or at least about 50%, or at least about 52.5%, or at least about 55%, or at least about 57.5% or at least about 60%, or at least about 62.5%, or at least about 65%, or at least about 67.5%, or at least about 70% of at least one structural lipid by moles.

In some aspects, an LNP can further comprise at least about 2.5%, or about 5%, or about 7.5%, or about 10%, or about 12.5%, or about 15%, or about 17.5%, or about 20%, or about 22.5%, or about 25%, or about 27.5%, or about 30%, or about 32.5%, or about 35%, or about 37.5%, or about 40%, or about 42.5%, or about 45%, or about 47.5%, or about 50%, or about 52.5%, or about 55%, or about 57.5% or about 60%, or about 62.5%, or about 65%, or about 67.5%, or about 70% of at least one structural lipid by moles.

In some aspects, a LNP can further comprise at least about 2.5%, or at least about 5%, or at least about 7.5%, or at least about 10%, or at least about 12.5%, or at least about 15%, or at least about 17.5%, or at least about 20%, or at least about 22.5%, or at least about 25%, or at least about 27.5%, or at least about 30%, or at least about 32.5%, or at least about 35%, or at least about 37.5%, or at least about 40%, or at least about 42.5%, or at least about 45%, or at least about 47.5%, or at least about 50%, or at least about 52.5%, or at least about 55%, or at least about 57.5% or at least about 60%, or at least about 62.5%, or at least about 65%, or at least about 67.5%, or at least about 70% of at least one phospholipid by moles.

In some aspects, an LNP can further comprise at least about 2.5%, or about 5%, or about 7.5%, or about 10%, or about 12.5%, or about 15%, or about 17.5%, or about 20%, or about 22.5%, or about 25%, or about 27.5%, or about 30%, or about 32.5%, or about 35%, or about 37.5%, or about 40%, or about 42.5%, or about 45%, or about 47.5%, or about 50%, or about 52.5%, or about 55%, or about 57.5% or about 60%, or about 62.5%, or about 65%, or about 67.5%, or about 70% of at least one phospholipid by moles.

In some aspects, a LNP can further comprise at least about 0.25%, or at least about 0.5%, or at least about 0.75%, or at least about 1.0%, or at least about 2.5%, or at least about 5%, or at least about 7.5%, or at least about 10% PEGylated lipid by moles.

A. Multivalent Cationic Bolaform Amphiphilic Lipid of Formula (I)

As used herein, the terms "cationic bolaform amphiphilic lipid", "bolaform amphiphilic lipid", "multivalent cationic bolaform amphiphilic compound", "multivalent bolaform amphiphilic compound", "multivalent cationic bolaform amphiphilic lipid" and "multivalent bolaform amphiphilic lipid" are used interchangeably in their broadest sense to refer to any compound of Formula (I). That is, the terms refer to an amphiphilic molecule that comprises two units comprising at least one pH charge-dependent multivalent cationic head group, with the two units connected through a hydrophobic tail group connected by either stable or degradable linkages. In a non-limiting example, a cationic bolaform amphiphilic lipid includes those lipids and salts thereof having one, two, three, or more fatty acid or fatty alkyl chains and a pH-titratable amino head group (e.g., an alkylamino or dialkylamino head group). The multivalent cationic lipid can be protonated (i.e., positively charged) at a pH below the $pK_a$ of the cationic lipid and is substantially neutral at a pH above the $pK_a$ B. Structural Lipid In some aspects, a structural lipid can be a steroid. In some aspects, a structural lipid can be a sterol. In some aspects, a structural lipid can comprise cholesterol. In some aspects, a structural lipid can comprise ergosterol. In some aspects, a structural lipid can be a phytosterol.

C. Phospholipid

As used herein, the term "phospholipid" is used in its broadest sent to refer to any amphiphilic molecule that comprises a polar (hydrophilic) headgroup comprising phosphate and two hydrophobic fatty acid chains. In some aspects, a phospholipid can comprise dioleoylphosphatidylethanolamine (DOPE). In some aspects, a phospholipid can comprise DDPC (1,2-Didecanoyl-sn-glycero-3-phosphocholine), DEPA-NA (1,2-Dierucoyl-sn-glycero-3-phosphate (Sodium Salt)), DEPC (1,2-Dierucoyl-sn-glycero-3-phosphocholine), DEPE (1,2-Dierucoyl-sn-glycero-3-phosphoethanolamine), DEPG-NA (1,2-Dierucoyl-sn-glycero-3 [Phospho-rac-(1-glycerol) (Sodium Salt)), DLOPC (1,2-Dilinoleoyl-sn-glycero-3-phosphocholine), DLPA-NA (1,2-Dilauroyl-sn-glycero-3-phosphate (Sodium Salt)), DLPC (1,2-Dilauroyl-sn-glycero-3-phosphocholine), DLPE (1,2-Dilauroyl-sn-glycero-3-phosphoethanolamine), DLPG-NA (1,2-Dilauroyl-sn-glycero-3[Phospho-rac-(1-glycerol) (Sodium Salt)), DLPG-NH4 (1,2-Dilauroyl-sn-glycero-3[Phospho-rac-(1-glycerol) (Ammonium Salt)), DLPS-NA (1,2-Dilauroyl-sn-glycero-3-phosphoserine (Sodium Salt)), DMPA-NA (1,2-Dimyristoyl-sn-glycero-3-phosphate (Sodium Salt)), DMPC (1,2-Dimyristoyl-sn-glycero-3-phosphocholine), DMPE (1,2-Dimyristoyl-sn-glycero-3-phosphoethanolamine), DMPG-NA (1,2-Dimyristoyl-sn-glycero-3[Phospho-rac-(1-glycerol) (Sodium Salt)), DMPG-NH4 (1,2-Dimyristoyl-sn-glycero-3[Phospho-rac-(1-glycerol) (Ammonium Salt)), DMPG-NH4/NA (1,2-Dimyristoyl-sn-glycero-3[Phospho-rac-(1-glycerol) (Sodium/Ammonium Salt)), DMPS-NA (1,2-Dimyristoyl-sn-glycero-3-phosphoserine (Sodium Salt)), DOPA-NA (1,2-Dioleoyl-sn-glycero-3-phosphate (Sodium Salt)), DOPC (1,2-Dioleoyl-sn-glycero-3-phosphocholine), DOPE (1,2-Dioleoyl-sn-glycero-3-phosphoethanolamine), DOPG-NA (1,2-Dioleoyl-sn-glycero-3[Phospho-rac-(1-glycerol) (Sodium Salt)), DOPS-NA (1,2-Dioleoyl-sn-glycero-3-phosphoserine (Sodium Salt)), DPPA-NA (1,2-Dipalmitoyl-sn-glycero-3-phosphate (Sodium Salt)), DPPC (1,2-Dipalmitoyl-sn-glycero-3-phosphocholine), DPPE (1,2-Dipalmitoyl-sn-glycero-3-phosphoethanolamine), DPPG-NA (1,2-Dipalmitoyl-sn-glycero-3[Phospho-rac-(1-glycerol) (Sodium Salt)), DPPG-NH4 (1,2-Dipalmitoyl-sn-glycero-3[Phospho-rac-(1-glycerol) (Ammonium Salt)), DPPS-NA (1,2-Dipalmitoyl-sn-glycero-3-phosphoserine (Sodium Salt)), DSPA-NA (1,2-Distearoyl-sn-glycero-3-phosphate (Sodium Salt)), DSPC (1,2-Distearoyl-sn-glycero-3-phosphocholine), DSPE (1,2-Distearoyl-sn-glycero-3-phosphoethanolamine), DSPG-NA (1,2-Distearoyl-sn-glycero-3[Phospho-rac-(1-glycerol) (Sodium Salt)), DSPG-NH4 (1,2-Distearoyl-sn-glycero-3[Phospho-rac-(1-glycerol) (Ammonium Salt)), DSPS-NA (1,2-Distearoyl-sn-glycero-3-phosphoserine (Sodium Salt)), EPC (Egg-PC), HEPC (Hydrogenated Egg PC), HSPC (Hydrogenated Soy PC), LYSOPC MYRISTIC (1-Myristoyl-sn-glycero-3-phosphocholine), LYSOPC PALMITIC (1-Palmitoyl-sn-glycero-3-phosphocholine), LYSOPC STEARIC (1-Stearoyl-sn-glycero-3-phosphocholine), Milk Sphingomyelin (MPPC; 1-Myristoyl-2-palmitoyl-sn-glycero 3-phosphocholine), MSPC (1-Myristoyl-2-stearoyl-sn-glycero-3-phosphocholine), PMPC (1-Palmitoyl-2-myristoyl-sn-glycero-3-phosphocholine), POPC (1-Palmitoyl-2-oleoyl-sn-glycero-3-phosphocholine), POPE (1-Palmitoyl-2-oleoyl-sn-glycero-3-phosphoethanolamine), POPG-NA (1-Palmitoyl-2-oleoyl-sn-glycero-3[Phospho-rac-(1-glycerol)] (Sodium Salt)), PSPC (1-Palmitoyl-2-stearoyl-sn-glycero-3-phosphocholine), SMPC (1-Stearoyl-2-myristoyl-sn-glycero-3-phosphocholine), SOPC (1-Stearoyl-2-oleoyl-sn-glycero-3-phosphocholine), SPPC (1-Stearoyl-2-palmitoyl-sn-glycero-3-phosphocholine), or any combination thereof.

D. PEGylated Lipid

As used herein, the term "PEGylated lipid" is used to refer to any lipid that is modified (e.g. covalently linked to) at least one polyethylene glycol molecule. In some aspects, a PEGylated lipid can comprise 1,2-dimyristoyl-rac-glycero-3-methoxypolyethylene glycol-2000, hereafter referred to as DMG-PEG2000.

LNP Compositions

In some aspects, a lipid nanoparticle can comprise at least one nucleic acid molecule, at least one bolaform amphiphilic lipid, and at least one structural lipid.

In some aspects, a lipid nanoparticle can comprise at least one nucleic acid molecule, at least one bolaform amphiphilic lipid, and at least one PEGylated lipid.

In some aspects, the at least one structural lipid is a mixture of two structural lipids.

In some aspects, the at least one PEGylated lipid is a mixture of two PEGylated lipids.

In some aspects, a lipid nanoparticle can comprise at least one nucleic acid molecule, at least one bolaform amphiphilic lipid, at least one structural lipid, at least one PEGylated lipid or any combination thereof.

In some aspects, a lipid nanoparticle can comprise at least one nucleic acid, at least one cationic bolaform amphiphilic lipid, at least one structural lipid, and at least one PEGylated lipid.

In some aspects, a lipid nanoparticle can comprise at least one nucleic acid molecule, at least one cationic bolaform amphiphilic lipid, at least one structural lipid, at least one phospholipid, at least one PEGylated lipid or any combination thereof.

In some aspects, a lipid nanoparticle can comprise at least one nucleic acid, at least one cationic bolaform amphiphilic lipid, at least one structural lipid, at least one phospholipid and at least one PEGylated lipid.

In some aspects, the at least one bolaform amphiphilic lipid or the at least one cationic bolaform amphiphilic lipid is a compound of Formula (I).

In some aspects, the at least one bolaform amphiphilic lipid or the at least one cationic bolaform amphiphilic lipid is a mixture of two or more compounds of Formula (I).

In some aspects, a lipid nanoparticle comprising at least one nucleic acid can comprise about 10% of at least one compound of Formula (I) by moles, about 35% of at least one structural lipid by moles, about 50% of at least one phospholipid by moles, and about 5% of at least one PEGylated lipid by moles. In some aspects, a lipid nanoparticle comprising at least one nucleic acid can comprise about 1% to about 20% of at least one compound of Formula (I) by moles, about 25% to about 45% of at least one structural lipid by moles, about 40% to about 60% of at least one phospholipid by moles, and about 1% to about 15% of at least one PEGylated lipid by moles. In some aspects, a lipid nanoparticle comprising at least one nucleic acid can comprise about 5% to about 15% of at least one compound of Formula (I) by moles, about 30% to about 40% of at least one structural lipid by moles, about 45% to about 55% of at least one phospholipid by moles, and about 2.5% to about 10% of at least one PEGylated lipid by moles.

In some aspects, a lipid nanoparticle comprising at least one nucleic acid can comprise about 10% of at least one compound of Formula (I) by moles, about 39.5% of at least one structural lipid by moles, about 50% of at least one phospholipid by moles, and about 0.5% of at least one PEGylated lipid by moles. In some aspects, a lipid nanoparticle comprising at least one nucleic acid can comprise about 1% to about 20% of at least one compound of Formula (I) by moles, about 29.5% to about 49.5% of at least one structural lipid by moles, about 40% to about 60% of at least one phospholipid by moles, and about 0.1% to about 10.5% of at least one PEGylated lipid by moles. In some aspects, a lipid nanoparticle comprising at least one nucleic acid can comprise about 5% to about 15% of at least one compound of Formula (I) by moles, about 34.5% to about 44.5% of at least one structural lipid by moles, about 45% to about 55% of at least one phospholipid by moles, and about 0.25% to about 5.5% of at least one PEGylated lipid by moles.

In some aspects, a lipid nanoparticle comprising at least one nucleic acid can comprise about 32.4% of at least one compound of Formula (I) by moles, about 32.4% of at least one structural lipid by moles, about 32.4% of at least one phospholipid by moles, and about 2.8% of at least one PEGylated lipid by moles. In some aspects, a lipid nanoparticle comprising at least one nucleic acid can comprise about 22.4% to about 42.4% of at least one compound of Formula (I) by moles, about 22.4% to about 42.4% of at least one structural lipid by moles, about 22.4% to about 42.4% of at least one phospholipid by moles, and about 0.1% to about 12.8% of at least one PEGylated lipid by moles. In some aspects, a lipid nanoparticle comprising at least one nucleic acid can comprise about 27.4% to about 37.4% of at least one compound of Formula (I) by moles, about 27.4% to about 37.4% of at least one structural lipid by moles, about 27.4% to about 37.4% of at least one phospholipid by moles, and about 0.25% to about 7.8% of at least one PEGylated lipid by moles.

In some aspects, a lipid nanoparticle comprising at least one nucleic acid can comprise about 35% of at least one compound of Formula (I) by moles, about 50% of at least one structural lipid by moles, about 10% of at least one phospholipid by moles, and about 5% of at least one PEGylated lipid by moles. In some aspects, a lipid nanoparticle comprising at least one nucleic acid can comprise about 25% to about 45% of at least one compound of Formula (I) by moles, about 40% to about 60% of at least one structural lipid by moles, about 1% to about 20% of at least one phospholipid by moles, and about 1% to about 15% of at least one PEGylated lipid by moles. In some aspects, a lipid nanoparticle comprising at least one nucleic acid can comprise about 30% to about 40% of at least one compound of Formula (I) by moles, about 45% to about 55% of at least one structural lipid by moles, about 5% to about 15% of at least one phospholipid by moles, and about 2.5% to about 10% of at least one PEGylated lipid by moles.

In some aspects, a lipid nanoparticle comprising at least one nucleic acid can comprise about 39.5% of at least one compound of Formula (I) by moles, about 50% of at least one structural lipid by moles, about 10% of at least one phospholipid by moles, and about 0.5% of at least one PEGylated lipid by moles. In some aspects, a lipid nanoparticle comprising at least one nucleic acid can comprise about 29.5% to about 49.5% of at least one compound of Formula (I) by moles, about 40% to about 60% of at least one structural lipid by moles, about 1% to about 20% of at least one phospholipid by moles, and about 0.1% to about 10.5% of at least one PEGylated lipid by moles. In some aspects, a lipid nanoparticle comprising at least one nucleic acid can comprise about 34.5% to about 44.5% of at least one compound of Formula (I) by moles, about 45% to about 55% of at least one structural lipid by moles, about 5% to about 15% of at least one phospholipid by moles, and about 0.25% to about 5.5% of at least one PEGylated lipid by moles.

In some aspects, a lipid nanoparticle comprising at least one nucleic acid can comprise about 50% of at least one compound of Formula (I) by moles, about 10% of at least one structural lipid by moles, about 35% of at least one phospholipid by moles, and about 5% of at least one PEGylated lipid by moles. In some aspects, a lipid nanoparticle comprising at least one nucleic acid can comprise about 40% to about 60% of at least one compound of Formula (I) by moles, about 1% to about 20% of at least one structural lipid by moles, about 25% to about 45% of at least one phospholipid by moles, and about 1% to about 15% of at least one PEGylated lipid by moles. In some aspects, a lipid nanoparticle comprising at least one nucleic acid can comprise about 45% to about 55% of at least one compound of Formula (I) by moles, about 5% to about 15% of at least one structural lipid by moles, about 30% to about 40% of at least one phospholipid by moles, and about 2.5% to about 10% of at least one PEGylated lipid by moles.

In some aspects, a lipid nanoparticle comprising at least one nucleic acid can comprise about 50% of at least one compound of Formula (I) by moles, about 10% of at least one structural lipid by moles, about 39.5% of at least one phospholipid by moles, and about 0.5% of at least one PEGylated lipid by moles. In some aspects, a lipid nanoparticle comprising at least one nucleic acid can comprise about 40% to about 60% of at least one compound of Formula (I) by moles, about 1% to about 20% of at least one structural lipid by moles, about 29.5% to about 49.5% of at least one phospholipid by moles, and about 0.1% to about 10.5% of at least one PEGylated lipid by moles. In some aspects, a lipid nanoparticle comprising at least one nucleic acid can comprise about 45% to about 55% of at least one compound of Formula (I) by moles, about 5% to about 15% of at least one structural lipid by moles, about 34.5% to about 44.5% of at least one phospholipid by moles, and about 0.25% to about 5.5% of at least one PEGylated lipid by moles.

In some aspects, a lipid nanoparticle comprising at least one nucleic acid can comprise about 41.4% of at least one compound of Formula (I) by moles, about 10% of at least one structural lipid by moles, about 45.9% of at least one phospholipid by moles, and about 2.7% of at least one PEGylated lipid by moles. In some aspects, a lipid nanoparticle comprising at least one nucleic acid can comprise about 31.4% to about 51.4% of at least one compound of Formula (I) by moles, about 1% to about 20% of at least one structural lipid by moles, about 35.9% to about 55.9% of at least one phospholipid by moles, and about 0.1% to about 12.7% of at least one PEGylated lipid by moles. In some aspects, a lipid nanoparticle comprising at least one nucleic acid can comprise about 36.4% to about 46.4% of at least one compound of Formula (I) by moles, about 5% to about 15% of at least one structural lipid by moles, about 40.9% to about 50.9% of at least one phospholipid by moles, and about 1% to about 7.7% of at least one PEGylated lipid by moles.

In some aspects, a lipid nanoparticle comprising at least one nucleic acid can comprise about 33.5% of at least one compound of Formula (I) by moles, about 33.5% of at least one structural lipid by moles, about 32% of at least one phospholipid by moles, and about 1% of at least one PEGylated lipid by moles. In some aspects, a lipid nanoparticle comprising at least one nucleic acid can comprise about 23.5% to about 43.5% of at least one compound of Formula (I) by moles, about 23.5% to about 43.5% of at least one structural lipid by moles, about 22% to about 42% of at least one phospholipid by moles, and about 0.1% to about 11% of at least one PEGylated lipid by moles. In some aspects, a lipid nanoparticle comprising at least one nucleic acid can comprise about 28.5% to about 38.5% of at least one compound of Formula (I) by moles, about 28.5% to about 38.5% of at least one structural lipid by moles, about 27% to about 37% of at least one phospholipid by moles, and about 0.5% to about 6% of at least one PEGylated lipid by moles.

In some aspects, a lipid nanoparticle comprising at least one nucleic acid can comprise about 38% of at least one compound of Formula (I) by moles, about 10% of at least one structural lipid by moles, about 50% of at least one phospholipid by moles, and about 2% of at least one PEGylated lipid by moles. In some aspects, a lipid nanoparticle comprising at least one nucleic acid can comprise about 28% to about 48% of at least one compound of Formula (I) by moles, about 1% to about 20% of at least one structural lipid by moles, about 40% to about 60% of at least one phospholipid by moles, and about 0.1% to about 12% of at least one PEGylated lipid by moles. In some aspects, a lipid nanoparticle comprising at least one nucleic acid can comprise about 33% to about 43% of at least one compound of Formula (I) by moles, about 5% to about 15% of at least one structural lipid by moles, about 45% to about 55% of at least one phospholipid by moles, and about 1% to about 6% of at least one PEGylated lipid by moles.

In some aspects of the preceding LNPs, the compound of Formula (I) comprised in the LNP composition is one of COMPOUNDS 1-8.

In some aspects of the preceding LNPs, the compound of Formula (I) comprised in the LNP composition is one of COMPOUNDS 1-21.

In some aspects of the preceding LNPs, the structural lipid can be cholesterol. In some aspects of the preceding LNPs, the phospholipid can be DOPE. In some aspects of the preceding LNPs, the PEGylated lipid can be DMG-PEG2000.

In some aspects of the preceding LNPs, the structural lipid can be cholesterol, the phospholipid can be DOPE and the PEGylated lipid can be DMG-PEG2000.

In some aspects of the preceding LNPs, the at least one nucleic acid molecule is a DNA molecule. In one aspect, the at least one DNA molecule is a DoggyBone DNA molecule. In some aspects, the at least one DNA molecule is a DNA nanoplasmid.

In some aspects, a lipid nanoparticle comprising at least one nucleic acid can comprise at least one nucleic acid molecule. In some aspects, a lipid nanoparticle can comprise a plurality of nucleic acid molecules. In some aspects, the at least one nucleic acid molecule or the plurality of nucleic acid molecules can be formulated in a lipid nanoparticle.

In some aspects, a lipid nanoparticle can comprise lipid and nucleic acid at a specified ratio (weight/weight).

In some aspects, a lipid nanoparticle comprising at least one nucleic acid can comprise lipid and nucleic acid at a ratio of about 5:1 to about 15:1, or about 10:1 to about 20:1, or about 15:1 to about 25:1, or about 20:1 to about 30:1, or about 25:1 to about 35:1 or about 30:1 to about 40:1, or about 35:1 to about 45:1, or about 40:1 to about 50:1, or about 45:1 to about 55:1, or about 50:1 to about 60:1, or about 55:1 to about 65:1, or about 60:1 to about 70:1, or about 65:1 to about 75:1, or about 70:1 to about 80:1, or about 75:1 to about 85:1, or about 80:1 to about 90:1, or about 85:1 to about 95:1, or about 90:1 to about 100:1, or about 95:1 to about 105:1, or about 100:1 to about 110:1, or about 105:1 to about 115:1, or about 110:1 to about 120:1, or about 115:1 to about 125:1, or about 120:1 to about 130:1, or about 125:1 to about 135:1, or about 130:1 to about 140:1, or about 135:1 to about 145:1, or about 140:1 to about 150:1, lipid:nucleic acid, weight/weight.

In some aspects, a lipid nanoparticle comprising at least one nucleic acid can comprise lipid and nucleic acid at a ratio of about 5:1, or about 10:1, or about 15:1, or about 20:1, or about 25:1, or about 30:1, or about 35:1, or about 40:1, or about 45:1, or about 50:1, or about 55:1, or about 60:1, or about 65:1, or about 70:1, or about 75:1, or about 80:1, or about 85:1, or about 90:1, or about 95:1, or about 100:1, or about 105:1, or about 110:1, or about 115:1, or about 120:1, or about 125:1, or about 130:1, or about 135:1, or about 140:1, or about 145:1, or about 150:1, lipid:nucleic acid, weight/weight.

In some aspects, a lipid nanoparticle comprising at least one nucleic acid can comprise lipid and nucleic acid at a ratio of about 10:1, or about 25:1, or about 40:1, lipid: nucleic acid, weight/weight.

In some aspects of the preceding LNPs, the at least one nucleic acid molecule is an RNA molecule. In some aspects, the RNA molecule is an mRNA molecule. In some aspects, the mRNA molecule further comprises a 5'-CAP.

Thus, the present disclosure provides a lipid nanoparticle comprising about 10% of at least one compound of Formula (I) by moles, about 35% of at least one structural lipid by moles, about 50% of at least one phospholipid by moles, and about 5% of at least one PEGylated lipid by moles, wherein the lipid nanoparticle further comprises at least one RNA molecule (e.g. mRNA molecule). In some aspects, the present disclosure provides a lipid nanoparticle comprising about 1% to about 20% of at least one compound of Formula (I) by moles, about 25% to about 45% of at least one structural lipid by moles, about 40% to about 60% of at least one phospholipid by moles, and about 1% to about 15% of at least one PEGylated lipid by moles, wherein the lipid nanoparticle further comprises at least one RNA molecule (e.g. mRNA molecule). In some aspects, the present disclosure provides a lipid nanoparticle comprising about 5% to about 15% of at least one compound of Formula (I) by moles, about 30% to about 40% of at least one structural lipid by moles, about 45% to about 55% of at least one phospholipid by moles, and about 2.5% to about 10% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 15:1 to about 35:1 (w/w), or about 20:1 to about 30:1 (w/w). In some aspects, the ratio of lipid to nucleic acid in the nanoparticle can be about 25:1 (w/w).

In some aspects, a lipid nanoparticle is provided comprising about 10% of at least one compound of Formula (I) by moles, about 39.5% of at least one structural lipid by moles, about 50% of at least one phospholipid by moles, and about 0.5% of at least one PEGylated lipid by moles, wherein the lipid nanoparticle further comprises at least one RNA molecule (e.g. mRNA molecule). In some aspects, the present disclosure provides a lipid nanoparticle comprising about 1% to about 20% of at least one compound of Formula (I) by moles, about 29.5% to about 49.5% of at least one structural lipid by moles, about 40% to about 60% of at least one phospholipid by moles, and about 0.1% to about 10.5% of at least one PEGylated lipid by moles, wherein the lipid nanoparticle further comprises at least one RNA molecule (e.g. mRNA molecule). In some aspects, the present disclosure provides a lipid nanoparticle comprising about 5% to about 15% of at least one compound of Formula (I) by moles, about 34.5% to about 44.5% of at least one structural lipid by moles, about 45% to about 55% of at least one phospholipid by moles, and about 0.25% to about 5.5% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 5:1 to about 15:1 (w/w) or about 35:1 to about 45:1 (w/w). In some aspects, the ratio of lipid to nucleic acid in the nanoparticle can be about 10:1 (w/w) or about 40:1 (w/w).

In some aspects, a lipid nanoparticle is provided comprising about 32.4% of at least one compound of Formula (I) by moles, about 32.4% of at least one structural lipid by moles, about 32.4% of at least one phospholipid by moles, and about 2.8% of at least one PEGylated lipid by moles, wherein the lipid nanoparticle further comprises at least one RNA molecule (e.g. mRNA molecule). In some aspects, the present disclosure provides a lipid nanoparticle comprising about 22.4% to about 42.4% of at least one compound of Formula (I) by moles, about 22.4% to about 42.4% of at least one structural lipid by moles, about 22.4% to about 42.4% of at least one phospholipid by moles, and about 0.1% to about 12.8% of at least one PEGylated lipid by moles, wherein the lipid nanoparticle further comprises at least one RNA molecule (e.g. mRNA molecule). In some aspects, the present disclosure provides a lipid nanoparticle comprising about 27.4% to about 37.4% of at least one compound of Formula (I) by moles, about 27.4% to about 37.4% of at least one structural lipid by moles, about 27.4% to about 37.4% of at least one phospholipid by moles, and about 0.25% to about 7.8% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 15:1 to about 35:1 (w/w) or about 20:1 to about 30:1 (w/w). In some aspects, the ratio of lipid to nucleic acid in the nanoparticle can be about 25:1 (w/w).

In some aspects, a lipid nanoparticle is provided comprising about 35% of at least one compound of Formula (I) by moles, about 50% of at least one structural lipid by moles, about 10% of at least one phospholipid by moles, and about 5% of at least one PEGylated lipid by moles, wherein the lipid nanoparticle further comprises at least one RNA molecule (e.g. mRNA molecule). In some aspects, the present disclosure provides a lipid nanoparticle comprising about 25% to about 45% of at least one compound of Formula (I) by moles, about 40% to about 60% of at least one structural lipid by moles, about 1% to about 20% of at least one phospholipid by moles, and about 1% to about 15% of at least one PEGylated lipid by moles, wherein the lipid nanoparticle further comprises at least one RNA molecule (e.g. mRNA molecule). In some aspects, the present disclosure provides a lipid nanoparticle comprising about 30% to about 40% of at least one compound of Formula (I) by moles, about 45% to about 55% of at least one structural lipid by moles, about 5% to about 15% of at least one phospholipid by moles, and about 2.5% to about 10% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 30:1 to about 50:1 (w/w), or about 35:1 to about 45:1 (w/w). In some aspects, the ratio of lipid to nucleic acid in the nanoparticle can be about 40:1 (w/w).

In some aspects, a lipid nanoparticle is provided comprising about 39.5% of at least one compound of Formula (I) by moles, about 50% of at least one structural lipid by moles, about 10% of at least one phospholipid by moles, and about 0.5% of at least one PEGylated lipid by moles, wherein the lipid nanoparticle further comprises at least one RNA molecule (e.g. mRNA molecule). In some aspects, the present disclosure provides a lipid nanoparticle comprising about 29.5% to about 49.5% of at least one compound of Formula (I) by moles, about 40% to about 60% of at least one structural lipid by moles, about 1% to about 20% of at least one phospholipid by moles, and about 0.1% to about 10.5% of at least one PEGylated lipid by moles, wherein the lipid nanoparticle further comprises at least one RNA molecule (e.g. mRNA molecule). In some aspects, the present disclosure provides a lipid nanoparticle comprising about 34.5% to about 44.5% of at least one compound of Formula (I) by moles, about 45% to about 55% of at least one structural lipid by moles, about 5% to about 15% of at least one phospholipid by moles, and about 0.25% to about 5.5% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic in the nanoparticle can be about 20:1 to about 30:1 (w/w), or about 5:1 to about 15:1 (w/w). In some aspects, the ratio of lipid to nucleic acid in the nanoparticle can be about 25:1 (w/w) or about 10:1 (w/w).

In some aspects, a lipid nanoparticle is provided comprising about 50% of at least one compound of Formula (I) by moles, about 10% of at least one structural lipid by moles, about 35% of at least one phospholipid by moles, and about 5% of at least one PEGylated lipid by moles, wherein the lipid nanoparticle further comprises at least one RNA molecule (e.g. mRNA molecule). In some aspects, the present disclosure provides a lipid nanoparticle comprising about 40% to about 60% of at least one compound of Formula (I) by moles, about 1% to about 20% of at least one structural lipid by moles, about 25% to about 45% of at least one phospholipid by moles, and about 1% to about 15% of at least one PEGylated lipid by moles, wherein the lipid nanoparticle further comprises at least one RNA molecule (e.g. mRNA molecule). In some aspects, the present disclosure provides a lipid nanoparticle comprising about 45% to about 55% of at least one compound of Formula (I) by moles, about 5% to about 15% of at least one structural lipid by moles, about 30% to about 40% of at least one phospholipid by moles, and about 2.5% to about 10% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 1:1 to about 20:1 (w/w), or about 5:1 to about 15:1 (w/w). In some aspects, the ratio of lipid to nucleic acid in the nanoparticle can be about 10:1 (w/w).

In some aspects, a lipid nanoparticle is provided comprising at least one nucleic acid can comprise about 50% of at least one compound of Formula (I) by moles, about 10% of at least one structural lipid by moles, about 39.5% of at least one phospholipid by moles, and about 0.5% of at least one PEGylated lipid by moles, wherein the lipid nanoparticle further comprises at least one RNA molecule (e.g. mRNA molecule). In some aspects, the present disclosure provides a lipid nanoparticle comprising about 40% to about 60% of at least one compound of Formula (I) by moles, about 1% to about 20% of at least one structural lipid by moles, about 29.5% to about 49.5% of at least one phospholipid by moles, and about 0.1% to about 10.5% of at least one PEGylated lipid by moles, wherein the lipid nanoparticle further comprises at least one RNA molecule (e.g. mRNA molecule). In some aspects, the present disclosure provides a lipid nanoparticle comprising about 45% to about 55% of at least one compound of Formula (I) by moles, about 5% to about 15% of at least one structural lipid by moles, about 34.5% to about 44.5% of at least one phospholipid by moles, and about 0.25% to about 5.5% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 35:1 to about 45:1 (w/w), or about 20:1 to about 30:1 (w/w). In some aspects, the ratio of lipid to nucleic acid in the nanoparticle can be about 40:1 (w/w) or about 25:1 (w/w).

In some aspects, a lipid nanoparticle is provided comprising about 32.4% of at least one compound of Formula (I) by moles, about 32.4% of at least one structural lipid by moles, about 32.4% of at least one phospholipid by moles, and about 2.8% of at least one PEGylated lipid by moles, wherein the lipid nanoparticle further comprises at least one RNA molecule (e.g. mRNA molecule). In some aspects, the present disclosure provides a lipid nanoparticle comprising about 22.4% to about 42.4% of at least one compound of Formula (I) by moles, about 22.4% to about 42.4% of at least one structural lipid by moles, about 22.4% to about 42.4% of at least one phospholipid by moles, and about 0.1% to about 12.8% of at least one PEGylated lipid by moles, wherein the lipid nanoparticle further comprises at least one RNA molecule (e.g. mRNA molecule). In some aspects, the present disclosure provides a lipid nanoparticle comprising about 27.4% to about 37.4% of at least one compound of Formula (I) by moles, about 27.4% to about 37.4% of at least one structural lipid by moles, about 27.4% to about 37.4% of at least one phospholipid by moles, and about 0.25% to about 7.8% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 15:1 to about 35:1 (w/w) or about 20:1 to about 30:1 (w/w). In some aspects, the ratio of lipid to nucleic acid in the nanoparticle can be about 25:1 (w/w). In some aspects, the mRNA molecule further comprises a 5'-CAP. In some aspects, the ratio of lipid to nucleic acid in the nanoparticle can be about 45:1 to about 55:1 (w/w), or about 20:1 to about 30:1 (w/w). In some aspects, the ratio of lipid to nucleic acid in the nanoparticle can be about 50:1 (w/w) or about 25:1 (w/w).

In some aspects, a lipid nanoparticle is provided comprising about 33.5% of at least one compound of Formula (I) by moles, about 33.5% of at least one structural lipid by moles, about 32% of at least one phospholipid by moles, and about 1% of at least one PEGylated lipid by moles, wherein the lipid nanoparticle further comprises at least one RNA molecule (e.g. mRNA molecule). In some aspects, the present disclosure provides a lipid nanoparticle comprising about 23.5% to about 43.5% of at least one compound of Formula (I) by moles, about 23.5% to about 43.5% of at least one structural lipid by moles, about 22% to about 42% of at least one phospholipid by moles, and about 0.1% to about 11% of at least one PEGylated lipid by moles, wherein the lipid nanoparticle further comprises at least one RNA molecule (e.g. mRNA molecule). In some aspects, the present disclosure provides a lipid nanoparticle comprising about 28.5% to about 38.5% of at least one compound of Formula (I) by moles, about 28.5% to about 38.5% of at least one structural lipid by moles, about 27% to about 37% of at least one phospholipid by moles, and about 0.5% to about 6% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 15:1 to about 35:1 (w/w), or about 20:1 to about 30:1 (w/w). In some aspects, the ratio of lipid to nucleic acid in the nanoparticle can be about 25:1 (w/w).

In some aspects, a lipid nanoparticle is provided comprising about 38% of at least one compound of Formula (I) by moles, about 10% of at least one structural lipid by moles, about 50% of at least one phospholipid by moles, and about 2% of at least one PEGylated lipid by moles, wherein the lipid nanoparticle further comprises at least one RNA molecule (e.g. mRNA molecule). In some aspects, the present disclosure a lipid nanoparticle comprising about 28% to about 48% of at least one compound of Formula (I) by moles, about 1% to about 20% of at least one structural lipid by moles, about 40% to about 60% of at least one phospholipid by moles, and about 0.1% to about 12% of at least one PEGylated lipid by moles, wherein the lipid nanoparticle further comprises at least one RNA molecule (e.g. mRNA molecule). In some aspects, the present disclosure provides a lipid nanoparticle comprising about 33% to about 43% of at least one compound of Formula (I) by moles, about 5% to about 15% of at least one structural lipid by moles, about 45% to about 55% of at least one phospholipid by moles, and about 1% to about 6% of at least one PEGylated lipid by moles, wherein the lipid nanoparticle further comprises at least one RNA molecule (e.g. mRNA molecule). In some aspects, the mRNA molecule further comprises a 5'-CAP.

In some aspects, a lipid nanoparticle is provided comprising about 41.4% of at least one compound of Formula (I) by moles, about 45.9% of at least one structural lipid by moles, about 10% of at least one phospholipid by moles, and about 2.7% of at least one PEGylated lipid by moles, wherein the lipid nanoparticle further comprises at least one RNA molecule (e.g. mRNA molecule). In some aspects, the present disclosure provides a lipid nanoparticle comprising about 31.4% to about 51.4% of at least one compound of Formula (I) by moles, about 1% to about 20% of at least one structural lipid by moles, about 35.9% to about 55.9% of at least one phospholipid by moles, and about 0.1% to about 12.7% of at least one PEGylated lipid by moles, wherein the lipid nanoparticle further comprises a at least one RNA molecule (e.g. mRNA molecule). In some aspects, the present disclosure provides a lipid nanoparticle comprising about 36.4% to about 46.4% of at least one compound of Formula (I) by moles, about 5% to about 15% of at least one structural lipid by moles, about 40.9% to about 50.9% of at least one phospholipid by moles, and about 1% to about 7.7% of at least one PEGylated lipid by moles, wherein the lipid nanoparticle further comprises at least one RNA molecule (e.g. mRNA molecule). In some aspects, the mRNA molecule further comprises a 5'-CAP. In some aspects, the ratio of lipid to nucleic acid in the nanoparticle can be about 30:1 to about 50:1 (w/w), or about 35:1 to about 45:1 (w/w). In some aspects, the ratio of lipid to nucleic acid in the nanoparticle can be about 40:1 (w/w).

In some aspects, the nucleic acid molecule is a DNA molecule. Thus, the present disclosure provides, a lipid nanoparticle comprising about 38% of at least one compound of Formula (I) by moles, about 10% of at least one structural lipid by moles, about 50% of at least one phospholipid by moles, and about 2% of at least one PEGylated lipid by moles, wherein the at least one nucleic acid comprises at least one DNA molecule. In some aspects, the present disclosure provides a lipid nanoparticle comprising about 28% to about 48% of at least one compound of Formula (I) by moles, about 1% to about 20% of at least one structural lipid by moles, about 40% to about 60% of at least one phospholipid by moles, and about 0.1% to about 12% of at least one PEGylated lipid by moles, wherein the at least one nucleic acid comprises at least one DNA molecule. In some aspects, the present disclosure provides a lipid nanoparticle comprising about 33% to about 43% of at least one compound of Formula (I) by moles, about 5% to about 15% of at least one structural lipid by moles, about 45% to about 55% of at least one phospholipid by moles, and about 1% to about 6% of at least one PEGylated lipid by moles, wherein the at least one nucleic acid comprises at least one DNA molecule. In one aspect, the at least one DNA molecule is a DoggyBone DNA molecule. In some aspects, the at least one DNA molecule is a DNA nanoplasmid. In some aspects, the ratio of lipid to nucleic acid in the nanoparticle can be about 35:1 to about 55:1 (w/w), or about 40:1 to about 50:1 (w/w). In some aspects, the ratio of lipid to nucleic acid in the nanoparticle can be about 45:1 (w/w). In some aspects, the ratio of lipid to nucleic acid in the nanoparticle can be about 40:1 (w/w).

In some aspects, the compound of Formula (I) comprised in the LNP composition is one of COMPOUNDS 1-8.

In some aspects, the compound of Formula (I) comprised in the LNP composition is one of COMPOUNDS 1-21.

In some aspects of the preceding LNPs, the structural lipid can be cholesterol. In some aspects of the preceding LNPs, the phospholipid can be DOPE. In some aspects of the preceding LNPs, the PEGylated lipid can be DMG-PEG2000.

In some aspects of the preceding LNPs, the structural lipid can be cholesterol, the phospholipid can be DOPE and the PEGylated lipid can be DMG-PEG2000.

Compositions of the Present Disclosure-Lipoplex Nanoparticles

The present disclosure provides a composition comprising at least one lipoplex nanoparticle comprising a multivalent cationic bolaform amphiphilic lipid of Formula (I) and at least one nucleic acid molecule. In some aspects, a lipoplex nanoparticle can be prepared as described in Example 12. The lipoplex nanoparticles may be used as described in Example 13 or in other any of the methods described for the LNP compositions of the present disclosure, e.g., the modification of liver cells or T-cells in vitro, ex vivo or in vivo.

In some aspects, the multivalent cationic bolaform amphiphilic lipid of Formula (I) comprised in the lipoplex nanoparticle is one of COMPOUNDS 1-8.

In some aspects, the multivalent cationic bolaform amphiphilic lipid of Formula (I) comprised in the lipoplex nanoparticle is one of COMPOUNDS 1-21.

In some aspects, a lipoplex nanoparticle can comprise at least one multivalent cationic bolaform amphiphilic lipid of Formula (I) and at least one nucleic acid molecule. In some aspects, a lipoplex nanoparticle can comprise at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 1:1, or about 2:1, or about 3:1, or about 4:1, or about 5:1, or about 6:1, or about 7:1, or at about 8:1, or about 9:1, or about 10:1, or about 11:1, or about 12:1, or about 13:1, or about 14:1, or about 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1.

In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 5:1. In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 10:1. In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 20:1. In some aspects of the preceding lipoplex nanoparticles, the at least one nucleic acid molecule can be DNA (e.g. plasmid DNA, nanoplasmid DNA, or doggybone DNA).

In some aspects, a lipoplex nanoparticle can comprise at least one multivalent cationic bolaform amphiphilic lipid of Formula (I), at least one phospholipid, and at least one nucleic acid molecule. In some aspects, a lipoplex nanoparticle can comprise at least one multivalent cationic bolaform amphiphilic lipid of Formula (I), at least one phospholipid, and at least one nucleic acid molecule such that the molar ratio of protonable amino groups in the at least one multivalent cationic bolaform amphiphilic lipid of Formula (I) and the phosphate groups in the nucleic acid molecule is about 1:1, or about 2:1, or about 3:1, or about 4:1, or about 5:1, or about 6:1, or about 7:1, or at about 8:1, or about 9:1, or about 10:1, or about 11:1, or about 12:1, or about 13:1, or about 14:1, or about 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1 and the molar ratio of the at least one phospholipid to the at least one multivalent cationic bolaform amphiphilic lipid of Formula (I) is about 5:1, or about 4:1, or about 3:1, or about 2:1, or about 1:1, or about 1:2, or about 1:3, or about 1:4 or about 1:5.

In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 5:1 and the molar ratio of the at least one phospholipid to the at least one multivalent cationic bolaform amphiphilic lipid of Formula (I) is about 1:1. In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 10:1 and the molar ratio of the at least one phospholipid to the at least one multivalent cationic bolaform amphiphilic lipid of Formula (I) is about 1:1. In some aspects, the present disclosure provides a lipoplex nanoparticle comprising at least one multivalent cationic bolaform amphiphilic lipid of Formula (I) and at least one nucleic acid molecule such that the molar ratio of protonable amino groups in the at least one multivalent cationic bolaform amphiphilic lipid of Formula (I) and the phosphate groups in the nucleic acid molecule is about 20:1 and the molar ratio of the at least one phospholipid to the at least one multivalent cationic bolaform amphiphilic lipid of Formula (I) is 1:1. In some aspects of the preceding lipoplex nanoparticles, the at least one nucleic acid molecule can be DNA (e.g. plasmid DNA, nanoplasmid DNA, or doggybone DNA). In some aspects of the preceding lipoplex nanoparticles, the at least one phospholipid can be DOPE.

Pharmaceutical Compositions of the Present Disclosure

In some aspects, the present disclosure provides a pharmaceutical composition comprising at least one lipoplex nanoparticle of the present disclosure.

In some aspects, the present disclosure provides a pharmaceutical composition comprising at least one lipid nanoparticle of the present disclosure. In some aspects, the present disclosure provides a pharmaceutical composition comprising at least one first nanoparticle of the present disclosure and at least one second nanoparticle of the present disclosure, wherein the at least one first nanoparticle comprises at least one nucleic acid molecule encoding at least one transposase, wherein the at least one second nanoparticle comprises at least one nucleic acid molecule encoding at least one transposon. In some aspects, the at least one nucleic acid molecule encoding at least one transposase can be an RNA molecule (e.g. mRNA molecule) and the at least one nucleic acid molecule encoding at least one transposon can be a DNA molecule (e.g. a DoggyBone DNA molecule or a DNA nanoplasmid).

In some aspects, the present disclosure provides a composition comprising at least one cell that has been contacted by at least one nanoparticle of the present disclosure. In some aspects, the present disclosure provides a composition comprising at least one cell that has been genetically modified using at least one nanoparticle of the present disclosure. In some aspects, the present disclosure provides a composition comprising at least one cell that has been genetically modified using any method of the present disclosure.

In some aspects, the present disclosure provides a pharmaceutical composition comprising at least one cell that has been contacted by at least one nanoparticle of the present disclosure. In some aspects, the present disclosure provides a pharmaceutical composition comprising at least one cell that has been genetically modified using at least one nanoparticle of the present disclosure. In some aspects, the present disclosure provides a pharmaceutical composition comprising at least one cell that has been genetically modified using any method of the present disclosure.

Methods of the Present Disclosure

The present disclosure provides a method of delivering at least one nucleic acid to at least one cell comprising contacting the at least one cell with at least one composition of the present disclosure. The present disclosure provides a method of delivering at least one nucleic acid to at least one cell comprising contacting the at least one cell with at least one nanoparticle of the present disclosure.

In all methods, compositions and kits of the present disclosure, an at least one cell can be a liver cell. A liver cell can include, but is not limited to, a hepatocyte, a hepatic stellate cell, Kupffer cell or a liver sinusoidal endothelial cell. In all methods, compositions and kits of the present disclosure, an at least one cell can be a T-cell. A T-cell can be a resting T-cell, an activated T-cell, stem memory T cells ($T_{SCM}$ cells), central memory T cells ($T_{CM}$), or stem cell-like T cells.

In some aspects of any methods of the present disclosure, a cell can be in vivo, ex vivo or in vitro. In some aspects, any of the methods of the present disclosure can be applied in vivo, ex vivo or in vitro.

The present disclosure provides a method of genetically modifying at least one cell comprising contacting the at least one cell with at least one composition of the present disclosure. The present disclosure provides a method of genetically modifying at least one cell comprising contacting the at least one cell with at least one nanoparticle of the present disclosure.

In some aspects, genetically modifying a cell can comprise delivering at least one exogenous nucleic acid to the cell such that the cell expresses at least one protein that the cell otherwise would not normally express, or such that the at least one cell expresses at least one protein at a level that is higher than the level that the cell would otherwise normally express the at least one protein, or such that the cell expresses at least one protein at a level that is lower than the level that the cell would otherwise normally express. In some aspects, genetically modifying a cell can comprise delivering at least one exogenous nucleic to the cell such that at least one exogenous nucleic acid is integrated into the genome of the at least one cell.

In all methods of the present disclosure, T-cells can be activated prior to, concurrently with, or after contacting the T-cells with at least one composition or at least one nanoparticle of the present disclosure. In some aspects, T-cells can be activated using standard techniques known in the art, including, but not limited to, contacting the T-cells with CD3/CD28/CD2 activator solution, anti-CD3 antibody beads, anti-CD28 antibody bead, anti-CD2 antibody beads, anti-CD3 and anti-CD28 antibody beads, tetrameric antibody complexes that bind CD3, CD28 and CD2 cell surface ligands, or any combination thereof.

In some aspects, T-cells can be activated at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at least 24 hours, or at least 36 hours, or at least 48 hours, or at least 60 hours, or at least 72 hours prior to be contacted with at least one composition or nanoparticle of the present disclosure.

In some aspects, T-cells can be activated at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at least 24 hours, or at least 36 hours, or at least 48 hours, or at least 60 hours, or at least 72 hours after being contacted with at least one composition or nanoparticle of the present disclosure.

In some aspects of the preceding methods, step c) can be performed at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at least 24 hours, or at least 36 hours, or at least 48 hours, or at least 60 hours, or at least 72 hours after step b).

In some aspects of the preceding methods, step a) can be performed at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at least 24 hours, or at least 36 hours, or at least 48 hours, or at least 60 hours, or at least 72 hours prior to step b).

In some aspects, the methods of the present disclosure can yield a plurality of cells, wherein at least about 1%, or at least about 2%, or at least about 3%, or at least about 4%, or at least about 5%, or at least 10%, or at least 15%, or at least 20%, or at least 25%, or at least 30%, or at least 35%, or at least 40%, or at least 45%, or at least 50%, or at least 55%, or at least 60%, or at least about 65%, or at least about 70%, or at least about 75%, or at least about 80%, or at least about 85%, or at least about 90%, or at least about 95%, or at least about 99% of the cell in the plurality express at least one protein that was encoded in at least one nucleic acid that was delivered to the plurality of cells via a nanoparticle of the present disclosure.

In some aspects, the methods of the present disclosure can yield a plurality of cells, wherein at least about 1%, or at least about 2%, or at least about 3%, or at least about 4%, or at least about 5%, or at least 10%, or at least 15%, or at least 20%, or at least 25%, or at least 30%, or at least 35%, or at least 40%, or at least 45%, or at least 50%, or at least 55%, or at least 60%, or at least about 65%, or at least about 70%, or at least about 75%, or at least about 80%, or at least about 85%, or at least about 90%, or at least about 95%, or at least about 99% of the cells in the plurality are stem memory T cells.

In some aspects, the methods of the present disclosure can yield a plurality of cells, wherein at least about 1%, or at least about 2%, or at least about 3%, or at least about 4%, or at least about 5%, or at least 10%, or at least 15%, or at least 20%, or at least 25%, or at least 30%, or at least 35%, or at least 40%, or at least 45%, or at least 50%, or at least 55%, or at least 60%, or at least about 65%, or at least about 70%, or at least about 75%, or at least about 80%, or at least about 85%, or at least about 90%, or at least about 95%, or at least about 99% of the cells are express one or more cell-surface marker(s) of a stem memory T cell ($T_{SCM}$) or a $T_{SCM}$-like cell and wherein the one or more cell-surface marker(s) comprises CD62L and CD45RA.

The present disclosure provides a method of treating at least one disease in a subject, the method comprising administering to the subject at least one therapeutically effective amount of at least one composition of the present disclosure comprising at least one nucleic acid encoding a therapeutic protein.

The present disclosure provides a method of treating at least one disease in a subject, the method comprising administering at least one therapeutically effective amount of at least one nanoparticle of the present disclosure comprising at least one nucleic acid encoding a therapeutic protein.

The present disclosure provides a method of treating at least one disease in a subject, the method comprising administering at least one therapeutically effective amount of cells, wherein the cells have been contacted by at least one nanoparticle of the present disclosure comprising at least one nucleic acid encoding a therapeutic protein. The present disclosure provides a method of treating at least one disease in a subject, the method comprising administering at least one therapeutically effective amount of cells, wherein the cells have been genetically modified using the compositions and/or methods of the present disclosure.

In some aspects, the at least one disease can be a malignant disease, including, but not limited to, cancer. In some aspects, the at least one disease can be a metabolic liver disorder (MLD). In some aspects, the at least one disease can be a urea cycle disorder (UCD). An MLD and/or UCD can include, but is not limited to, N-Acetylglutamate Synthetase (NAGS) Deficiency, Carbamoylphosphate Synthetase I Deficiency (CPSI Deficiency), Ornithine Transcarbamylase (OTC) Deficiency, Argininosuccinate Synthetase Deficiency (ASSD) (Citrullinemia I), Citrin Deficiency (Citrullinemia II), Argininosuccinate Lyase Deficiency (Argininosuccinic Aciduria), Arginase Deficiency (Hyperargininemia), Ornithine Translocase Deficiency (HHH Syndrome), methylmalonic acidemia (MMA) or any combination thereof.

In some aspects, the at least one disease can be hemophilia A.

Accordingly, the present disclosure provides a method of treating hemophilia A in a subject in need thereof comprising administering to the subject at least one composition comprising at least one lipid nanoparticle of the present disclosure, wherein the lipid nanoparticle comprises a nucleic acid encoding a FVIII polypeptide.

According, the present disclosure provides a method of treating Ornithine Transcarbamylase (OTC) Deficiency in a subject in need thereof comprising administering to the subject at least one composition comprising at least one lipid nanoparticle of the present disclosure, wherein the lipid nanoparticle comprises a nucleic acid encoding an ornithine transcarbamylase (OTC) polypeptide.

According, the present disclosure provides a method of treating methylmalonic acidemia (MMA) in a subject in need thereof comprising administering to the subject at least one composition comprising at least one lipid nanoparticle of the present disclosure, wherein the lipid nanoparticle comprises a nucleic acid encoding a methylmalonyl-CoA mutase (MUT1) polypeptide.

Nucleic Acid Molecules

In some aspects, a nucleic acid molecule can be an RNA molecule. Thus, in some aspects, a lipid nanoparticle can comprise at least one RNA molecule. The at least one RNA molecule can be encapsulated within the lipid nanoparticle. In some aspects, an RNA molecule can be an mRNA molecule. In some aspects, a lipid nanoparticle can comprise at least one mRNA molecule. The mRNA molecule can be encapsulated within the lipid nanoparticle.

In some aspects, a nucleic acid molecule can be a synthetic nucleic acid molecule. In some aspects, a nucleic acid molecule can be a non-naturally occurring nucleic acid molecule. In some aspects, a non-naturally occurring nucleic acid molecule can comprise at least one non-naturally occurring nucleotide. The at least one non-naturally occurring nucleotide can be any non-naturally occurring nucleotide known in the art. In some aspects, a nucleic acid molecule can be a modified nucleic acid molecule. In some aspects, a modified nucleic acid molecule can comprise at least one modified nucleotide. The at least one modified nucleotide can be any modified nucleic acid known in the art.

In some aspects, an mRNA molecule can be capped using any method and/or capping moiety known in the art. An mRNA molecule can be capped with m7G(5')ppp(5')G moiety.

A m7G(5')ppp(5')G moiety is also referred to herein as a "Cap0". An mRNA molecule can be capped with a CleanCap® moiety. A CleanCap® moiety can comprise a m7G(5')ppp(5')(2'OMeA) (CleanCap® AG) moiety. A CleanCap® moiety can comprise a m7G(5')ppp(5')(2'OMeG) (CleanCap® GG) moiety. An mRNA molecule can be capped with an anti-reverse cap analog (ARCA®) moiety. An ARCA® moiety can comprise a m7(3'-O-methyl)G(5')ppp(5')G moiety. An mRNA molecule can be capped with a CleanCap® 3'OMe moiety (CleanCap®+ARCA®).

In some aspects, an mRNA molecule can comprise at least one modified nucleic acid.

The at least one modified nucleic acid can comprise 5-methoxyuridine (5 moU). In some aspects, at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, at least about 90%, or at least about 95%, or at least about 99% of the uridine bases in an mRNA molecule are 5-methoxyuridine bases. In some aspects, all of the uridine bases in an mRNA molecule are 5-methoxyuridine bases. Without wishing to be bound by theory, 5-methoxyuridine can improve protein expression and reduce immunogenicity (see Li et al., *Bioconjugate Chem.* 2016, 27, 3, 849-853 and Vaidyanathan et al. *Molecular Therapy Nucleic Acids,* 2018, 12, 530-542).

In some aspects, an mRNA molecule can comprise at least one modified nucleic acid.

The at least one modified nucleic acid can comprise $N_1$-methylpseudouridine ($me^1\Psi$). In some aspects, at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, at least about 90%, or at least about 95%, or at least about 99% of the uridine bases in an mRNA $N_1$-methylpseudouridine bases. In some aspects, all of the uridine bases in an mRNA molecule are $N_1$-methylpseudouridine bases. Without wishing to be bound by theory, $N_1$-methylpseudouridine can improve protein expression (see Li et al., *Bioconjugate Chem.* 2016, 27, 3, 849-853).

In some aspects, an mRNA molecule can comprise at least one modified nucleic acid.

The at least one modified nucleic acid can comprise pseudouridine (Ψ). In some aspects, at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, at least about 90%, or at least about 95%, or at least about 99% of the uridine bases in an mRNA pseudouridine bases. In some aspects, all of the uridine bases in an mRNA molecule are pseudouridine bases. Without wishing to be bound by theory, pseudouridine can improve protein expression and reduce immunogenicity (see Li et al., *Bioconjugate Chen.* 2016, 27, 3, 849-853 and Vaidyanathan et al. *Molecular Therapy—Nucleic Acids,* 2018, 12, 530-542).

In some aspects, an mRNA molecule can comprise at least one modified nucleic acid.

The at least one modified nucleic acid can comprise 5-methylcytidine (5-MeC). In some aspects, at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, at least about 90%, or at least about 95%, or at least about 99% of the cytidine bases in an mRNA 5-MeC bases. In some aspects, all of the cytidine bases in an mRNA molecule are 5-MeC bases.

In some aspects, a nucleic acid molecule can comprise a DNA molecule. Thus, in some aspects, a lipid nanoparticle can comprise a DNA molecule. In some aspects, the DNA molecule can be a circular DNA molecule, such as, but not limited to, a DNA plasmid or DNA nanoplasmid. Thus, in some aspects, a lipid nanoparticle can comprise a circular DNA molecule. In some aspects, a lipid nanoparticle can comprise a Doggybone DNA molecule. In some aspects, a lipid nanoparticle can comprise a DNA plasmid. In some aspects, a lipid nanoparticle can comprise a DNA nanoplasmid. In some aspects, a DNA molecule can be a linearized DNA molecule, such as, but not limited to, a linearized DNA plasmid or a linearized DNA nanoplasmid.

A DNA plasmid or DNA nanoplasmid can comprise can be at least about 0.25 kb, or at least about 0.5 kb, or at least about 0.75 kb, or at least about 1.0 kb, or at least about 1.25 kb, or at least about 1.5 kb, or at least about 1.75 kb, or at least about 2.0 kb, or at least about 2.25 kb, or at least about 2.5 kb, or at least about 2.75 kb, or at least about 3.0 kb, or at least about 3.25 kb, or at least about 3.5 kb, or at least about 3.75 kb, or at least about 4.0 kb, or at least about 4.25 kb, or at least about 4.5 kb, or at least about 4.75 kb, or at least about 5.0 kb, or at least about 5.25 kb, or at least about 5.5 kb, or at least about 5.75 kb, or at least about 6.0 kb, or at least about 6.25 kb, or at least about 6.5 kb, or at least about 6.75 kb, or at least about 7.0 kb, or at least about 7.25 kb, or at least about 7.5 kb, or at least about 7.75 kb, or at least about 8.0 kb, or at least about 8.25 kb, or at least about 8.5 kb, or at least about 8.75 kb, or at least about 9.0 kb, or at least about 9.25 kb, or at least about 9.5 kb, or at least about 9.75 kb, or at least about 10.0 kb, or at least about 10.25 kb, or at least about 10.5 kb, or at least about 10.75 kb, or at least about 11.0 kb, or at least about 11.25 kb, or at least about 11.5 kb, or at least about 11.75 kb, or at least about 12 kb, or at least about 12.25 kb, or at least about 12.5 kb, or at least about 12.75 kb, or at least about 13.0 kb, or at least about 13.25 kb, or at least about 13.5 kb, or at least about 13.75 kb, or at least about 14.0 kb, or at least about 14.25 kb, or at least about 14.5 kb, or at least about 14.75 kb or at least about 15.0 kb in length.

In some aspects, a nucleic acid molecule formulated in a lipid nanoparticle of the present disclosure can comprise at least one transgene sequence. In some aspects, a transgene sequence can comprise a nucleotide sequence encoding at least one therapeutic protein. In some aspects, a transgene sequence can comprise a nucleotide sequence encoding at least one transposase. In some aspects, a transgene sequence can comprise a nucleotide sequence encoding at least one transposon. In some aspects, a transposon can comprise a nucleotide sequence encoding at least one therapeutic protein. In some aspects, a transposon can comprise a nucleotide sequence encoding at least one therapeutic protein and at least one protomer sequence, wherein the at least one therapeutic protein is operatively linked to the at least one promoter sequence.

In some aspects, a therapeutic protein can be an ornithine transcarbamylase (OTC) polypeptide, a methylmalonyl-CoA mutase (MUT1) polypeptide, a chimeric antigen receptor, or a Factor VIII (FVIII) polypeptide.

In some aspects, the lipid nanoparticles of the present disclosure can be produced using a microfluidic-mixing platform. In some aspects, the microfluidic-mixing platform can be a non-turbulent microfluidic mixing platform.

In some aspects, a microfluidic-mixing platform can produce the lipid nanoparticles of the present invention by combining a miscible solvent phase comprising the lipid components of the nanoparticle and an aqueous phase comprising the lipid nanoparticle cargo (e.g. nucleic acid, DNA, mRNA, etc.) using a microfluidic device. In some aspects, the miscible solvent phase and the aqueous phase are mixed in the microfluidic device under laminar flow conditions that do not allow for immediate mixing of the two phases. As the two phases move under laminar flow in a microfluidic channel, microscopic features in the channel can allow for controlled, homogenous mixing to produce the lipid nanoparticles of the present disclosure.

In some aspects, the microfluidic-mixing platform can include, but are not limited to the NanoAssemblr® Spark (Precision NanoSystems), the NanoAssemblr® Ignite™ (Precision NanoSystems), the NanoAssemblr® Benchtop (Precision NanoSystems), the NanoAssemblr® Blaze (Precision NanoSystems) or the NanoAssemblr® GMP System (Precision NanoSystems).

In some aspects, the lipid nanoparticles of the present disclosure can be produced using a microfluidic-mixing platform, wherein the microfluidic mixing platform mixes at a rate of at least about 2.5 ml/min, or at least about 5 ml/min, or at least about 7.5 ml/min, or at least about 10 ml/min, or at least about 12.5 ml/min, or at least about 15 ml/min, or at least about 17.5 ml/min, or at least about 20 ml/min, or at least about 22.5 ml/min, or at least about 25 ml/min, or at least about 27.5 ml/min, or at least about 30 ml/min.

In some aspects, the lipid nanoparticles of the present disclosure can be produced using a microfluidic-mixing platform, wherein the microfluidic mixing platform mixes a miscible solvent phase and an aqueous phase at a ratio of about 10:1, or about 9:1, or about 8:1, or about 7:1, or about 6:1, or about 5:1, or about 4:1, or about 3:1, or about 2:1, or about 1:1, or about 1:2, or about 1:3, or about 1:4, or about 1:5, or about 1:6, or about 1:7, or about 1:8, or about 1:9, or about 1:10, solvent: aqueous, v:v.

piggyBac ITR Sequences

In some aspects, a nucleic acid can comprise a piggBac ITR sequence. In some aspects, a nucleic acid can comprise a first piggyBac ITR sequence and a second piggBac ITR sequence.

In some aspects, a piggyBac ITR sequence can comprise any piggyBac ITR sequence known in the art.

In some aspects of the methods of the present disclosure, a piggyBac ITR sequence, such as a first piggyBac ITR sequence and/or a second piggyBac ITR sequence in an AAV piggyBac transposon can comprise, consist essentially of, or consist of a Sleeping Beauty transposon ITR, a Helraiser transposon ITR, a Tol2 transposon ITR, a TcBuster transposon ITR or any combination thereof.

Promoter Sequences

In some aspects, a nucleic acid can comprise a promoter sequence. In some aspects, a promoter sequence can comprise any promoter sequence known in the art. In some aspects, a promoter sequence can comprise any liver-specific promoter sequence known in the art.

In some aspects, a promoter sequence can comprise a hybrid liver promoter (HLP). In some aspects, a promoter sequence can comprise an LP1 promoter. In some aspects, a promoter sequence can comprise a leukocyte-specific expression of the pp52 (LSP1) long promoter. In some aspects, a promoter sequence can comprise a thyroxine binding globulin (TBG) promoter.

In some aspects, a promoter sequence can comprise a wTBG promoter. In some aspects, a promoter sequence can comprise a hepatic combinatorial bundle (HCB) promoter. In some aspects, a promoter sequence can comprise a 2×ApoE-hAAT promoter. In some aspects, a promoter sequence can comprise a leukocyte-specific expression of the pp52 (LSP1) plus chimeric intron promoter. In some aspects, a promoter sequence can comprise a cytomegalovirus (CMV) promoter.

Transgene Sequences

In some aspects, a transgene sequence can comprise a nucleic acid sequence that encodes for a methylmalonyl-CoA mutase (MUT1) polypeptide. The MUT1 polypeptide can be any MUT1 polypeptide known in the art.

In some aspects, a transgene sequence can comprise a nucleic acid sequence that encodes for an ornithine transcarbamylase (OTC) polypeptide. The OTC polypeptide can be any OTC polypeptide known in the art.

In some aspects, a transgene sequence can comprise a nucleic acid sequence that encodes for a Factor VIII (FVIII) polypeptide. The FVIII polypeptide can be any FVIII polypeptide known in the art.

In some aspects, a transgene sequence can comprise a nucleic acid sequence that encodes for an iCAS9 polypeptide.

In some aspects, a transgene sequence can be codon optimized according to methods known in the art.

In some aspects, an at least one transgene sequence can be operatively linked to at least one promoter sequence present in the same polynucleotide.

polyA Sequences

In some aspects, a nucleic acid can comprise a polyA sequence. In some aspects, a polyA sequence can comprise any polyA sequence known in the art.

Self-Cleaving Peptide Sequence

In some aspects, a nucleic acid can comprise a self-cleaving peptide sequence. In some aspects, a self-cleaving peptide sequence can comprise any self-cleaving peptide sequence known in the art. In some aspects, a self-cleaving peptide sequence can comprise an 2A self-cleaving peptide sequence known in the art. Non-limiting examples of self-cleaving peptides include a T2A peptide, GSG-T2A peptide, an E2A peptide, a GSG-E2A peptide, an F2A peptide, a GSG-F2A peptide, a P2A peptide, or a GSG-P2A peptide.

In some aspects, a self-cleaving peptide sequence can comprise a nucleic acid sequence that encodes for a T2A peptide.

In some aspects, a self-cleaving peptide sequence can comprise a nucleic acid sequence that encodes for a GSG-T2A peptide.

In some aspects, a self-cleaving peptide sequence can comprise a nucleic acid sequence that encodes for an E2A peptide.

In some aspects, a self-cleaving peptide sequence can comprise a nucleic acid sequence that encodes for a GSG-E2A peptide.

In some aspects, a self-cleaving peptide sequence can comprise a nucleic acid sequence that encodes for a F2A peptide.

In some aspects, a self-cleaving peptide sequence can comprise a nucleic acid sequence that encodes for a GSG-F2A peptide.

In some aspects, a self-cleaving peptide sequence can comprise a nucleic acid sequence that encodes for a P2A peptide.

In some aspects, a self-cleaving peptide sequence can comprise a nucleic acid sequence that encodes for a GSG-P2A peptide.

Chimeric Antigen Receptor (CAR)

A transgene sequence can comprise a nucleic acid sequence encoding a CAR, wherein the CAR comprises an ectodomain comprising at least one antigen recognition region; a transmembrane domain, and an endodomain comprising at least one costimulatory domain. The CAR can further comprise a hinge region between the antigen recognition domain and the transmembrane domain.

The antigen recognition region can comprise at least one single chain variable fragment (scFv), Centyrin, single domain antibody, or a combination thereof. In an aspect, the at least one single domain antibody is a VHH. In an aspect, the at least one single domain antibody is a VH.

scFv

In some aspects, the antigen recognition region of the CAR can comprise one or more scFv compositions to recognize and bind to a specific target protein/antigen. The antigen recognition region can comprise at least two scFvs. The antigen recognition region can comprise at least three scFvs. In an aspect, a CAR of the disclosure is a bi-specific CAR comprising at least two scFvs that specifically bind two distinct antigens.

The scFv compositions can comprise a heavy chain variable region and a light chain variable region of an antibody. An scFv is a fusion protein of the variable regions of the heavy (VH) and light (VL) chains of immunoglobulins, and the VH and VL domains are connected with a short peptide linker. An scFv can retain the specificity of the original immunoglobulin, despite removal of the constant regions and the introduction of the linker.

Centyrin

In some aspects, the antigen recognition region of the CAR can comprise one or more Centyrin compositions to recognize and bind to a specific target protein/antigen. Centyrins that specifically bind an antigen may be used to direct the specificity of a cell, (e.g., a cytotoxic immune cell) towards the specific antigen. A CAR comprising a Centyrin is referred to herein as a CARTyrin.

Centyrins of the disclosure may comprise a protein scaffold, wherein the scaffold is capable of specifically binding an antigen. Centyrins of the disclosure may comprise a protein scaffold comprising a consensus sequence of at least one fibronectin type III (FN3) domain, wherein the scaffold is capable of specifically binding an antigen. The at least one fibronectin type III (FN3) domain may be derived from a human protein. The human protein may be Tenascin-C.

The consensus sequence can be modified at one or more positions within (a) a A-B loop at positions 13-16 of the consensus sequence; (b) a B-C loop at positions 22-28 of the consensus sequence; (c) a C-D at positions 38-43 of the consensus sequence; (d) a D-E loop at positions 51-54 of the consensus sequence; (e) a E-F loop at positions 60-64 of the consensus sequence; (f) a F-G loop at positions 75-81 of the consensus sequence; or (g) any combination of (a)-(f). Centyrins of the disclosure may comprise a consensus sequence of at least 5 fibronectin type III (FN3) domains, at least 10 fibronectin type III (FN3) domains or at least 15 fibronectin type III (FN3) domains.

The term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Antibody mimetics may provide superior properties over antibodies including, but not limited to, superior solubility, tissue penetration, stability towards heat and enzymes (e.g., resistance to enzymatic degradation), and lower production costs. Exemplary antibody mimetics include, but are not limited to, an affibody, an afflilin, an affimer, an affitin, an alphabody, an anticalin, and avimer (also known as avidity multimer), a DARPin (Designed Ankyrin Repeat Protein), a Fynomer, a Kunitz domain peptide, and a monobody.

In some aspects, a transgene sequence can comprise a nucleic acid sequence encoding at least one affibody molecule. Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

In some aspects, a transgene sequence can comprise a nucleic acid sequence encoding at least one affilin molecule. In Affilin molecules of the disclosure comprise a protein scaffold produced by modification of exposed amino acids of, for example, either gamma-B crystallin or ubiquitin. Affilin molecules functionally mimic an antibody's affinity to antigen, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target sequence or antigen.

In some aspects, a transgene sequence can comprise a nucleic acid sequence encoding at least one affimer molecule. Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

In some aspects, a transgene sequence can comprise a nucleic acid sequence encoding at least one affitin molecule. Affitin molecules of the disclosure comprise an artificial protein scaffold, the structure of which may be derived, for example, from a DNA binding protein (e.g., the DNA binding protein Sac7d). Affitins of the disclosure selectively bind a target sequence, which may be the entirety or part of an antigen. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In some aspects, an affitin molecule may be used as a specific inhibitor of an enzyme. Affitin molecules of the disclosure may include heat-resistant proteins or derivatives thereof.

In some aspects, a transgene sequence can comprise a nucleic acid sequence encoding at least one Alphabody molecule. Alphabody molecules of the disclosure may also be referred to as Cell-Penetrating Alphabodies (CPAB). Alphabody molecules of the disclosure comprise small proteins (typically of less than 10 kDa) that bind to a variety of target sequences (including antigens). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

In some aspects, a transgene sequence can comprise a nucleic acid sequence encoding at least one Anticalin molecule. Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In some aspects, anticalin molecules of the disclosure comprise a barrel structure comprising eight antiparallel beta-strands pairwise connected by loops and an attached alpha helix.

In some aspects, a transgene sequence can comprise a nucleic acid sequence encoding at least one Avimer molecule. Avimer molecules of the disclosure comprise an artificial protein that specifically binds to a target sequence (which may also be an antigen). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

In some aspects, a transgene sequence can comprise a nucleic acid sequence encoding at least one DARPin. DARPins (Designed Ankyrin Repeat Proteins) of the disclosure comprise genetically-engineered, recombinant, or chimeric proteins having high specificity and high affinity for a target sequence. In some aspects, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

In some aspects, a transgene sequence can comprise a nucleic acid sequence encoding at least one Fynomer. Fynomers of the disclosure comprise small binding proteins (about 7 kDa) derived from the human Fyn SH3 domain and engineered to bind to target sequences and molecules with equal affinity and equal specificity as an antibody.

In some aspects, a transgene sequence can comprise a nucleic acid sequence encoding at least one Kunitz domain peptide. Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

In some aspects, a transgene sequence can comprise a nucleic acid sequence encoding at least one monobody. Monobodies of the disclosure are small proteins (comprising about 94 amino acids and having a mass of about 10 kDa) comparable in size to a single chain antibody. These genetically engineered proteins specifically bind target sequences including antigens. Monobodies of the disclosure may specifically target one or more distinct proteins or target sequences. In some aspects, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof, contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Multispecific monobodies may be optimized by modifying the loops BC and FG. Monobodies of the disclosure may comprise an adnectin.

VHH

In some aspects, the antigen recognition region of the CAR can comprise at least one single domain antibodies (SdAb) to recognize and bind to a specific target protein/antigen. In an aspect, the single domain antibody is a VHH. A VHH is a heavy chain antibody found in camelids. A VHH that specifically binds an antigen may be used to direct the specificity of a cell, (e.g., a cytotoxic immune cell) towards the specific antigen. The antigen recognition region can comprise at least two VHHs. The antigen recognition region can comprise at least three VHHs. In an aspect, a CAR of the disclosure is a bi-specific CAR comprising at least two VHHs that specifically bind two distinct antigens. A CAR comprising a VHH is referred to herein as a VCAR.

At least one VHH protein or VCAR of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino acids from a VHH protein can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, VHH proteins can be engineered with retention of high affinity for the antigen and other favorable biological properties. To achieve this goal, the VHH proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif). Inspection of these displays permits analysis of the likely role of the residues in the functioning of the candidate sequence, i.e., the analysis of residues that influence the ability of the candidate VHH protein to bind its antigen. In this way, residues can be selected and combined from the parent and reference sequences so that the desired characteristic, such as affinity for the target antigen(s), is achieved. Alternatively, or in addition to, the above procedures, other suitable methods of engineering can be used. Screening VHH for specific binding to similar proteins or fragments can be conveniently achieved using nucleotide (DNA or RNA display) or peptide display libraries, for example, in vitro display. Competitive assays can be performed with the VHH or VCAR of the disclosure in order to determine what proteins, antibodies, and other antagonists compete for binding to a target protein with the VHH or VCAR of the present disclosure and/or share the epitope region. These assays as readily known to those of ordinary skill in the art evaluate competition between antagonists or ligands for a limited number of binding sites on a protein

VH

In some aspects, the antigen recognition region of the CAR can comprise at least one single domain antibodies (SdAb) to recognize and bind to a specific target protein/antigen. In an aspect, the single domain antibody is a VH. A VH is a single domain binder derived from common IgG. A VH that specifically binds an antigen may be used to direct the specificity of a cell, (e.g., a cytotoxic immune cell) towards the specific antigen. The antigen recognition region can comprise at least two VHs. The antigen recognition region can comprise at least three VHs. In an aspect, a CAR of the disclosure is a bi-specific CAR comprising at least two VHs that specifically bind two distinct antigens.

The VH can be isolated or derived from a human sequence. The VH can comprise a human CDR sequence and/or a human framework sequence and a non-human or humanized sequence (e.g., a rat Fc domain). In some aspects, the VH is a fully humanized VH. In some aspects, the VH is neither a naturally occurring antibody nor a fragment of a naturally occurring antibody. In some aspects, the VH is not a fragment of a monoclonal antibody. In some aspects, the VH is a UniDab antibody (TeneoBio). In some aspects, the VH is be modified to remove an Fe domain or a portion thereof. In some aspects, a framework sequence of the VH is modified to, for example, improve expression, decrease immunogenicity or to improve function.

The VH can be fully engineered using the UniRat (TeneoBio) system and "NGS-based Discovery" to produce the VH. Using this method, the specific VH are not naturally-occurring and are generated using fully engineered systems.

The VH are not derived from naturally-occurring monoclonal antibodies (mAbs) that were either isolated directly from the host (for example, a mouse, rat or human) or directly from a single clone of cells or cell line (hybridoma). These VHs were not subsequently cloned from said cell lines. Instead, VH sequences are fully-engineered using the UniRat system as transgenes that comprise human variable regions (VH domains) with a rat Fc domain, and are thus human/rat chimeras without a light chain and are unlike the standard mAb format. The native rat genes are knocked out and the only antibodies expressed in the rat are from transgenes with VH domains linked to a Rat Fc (UniAbs). These are the exclusive Abs expressed in the UniRat. Next generation sequencing (NGS) and bioinformatics are used to identify the full antigen-specific repertoire of the heavy-chain antibodies generated by UniRat after immunization. Then, a unique gene assembly method is used to convert the antibody repertoire sequence information into large collections of fully-human heavy-chain antibodies that can be screened in vitro for a variety of functions. In some aspects, fully humanized VH are generated by fusing the human VH domains with human Fcs in vitro (to generate a non-naturally occurring recombinant VH antibody). In some aspects, the VH are fully humanized, but they are expressed in vivo as human/rat chimera (human VH, rat Fc) without a light chain. Fully humanized VHs are expressed in vivo as human/rat chimera (human VH, rat Fc) without a light chain are about 80 kDa (vs 150 kDa).

A CAR of the present disclosure may bind human antigen with at least one affinity selected from a $K_D$ of less than or equal to $10^{-9}$M, less than or equal to $10^{-10}$M, less than or equal to $10^{-11}$M, less than or equal to $10^{-12}$M, less than or equal to $10^{-13}$M, less than or equal to $10^{-14}$M, and less than or equal to $10^{-15}$. The $K_D$ may be determined by any means, including, but not limited to, surface plasmon resonance.

In an aspect, the antigen recognition region of the disclosed CAR comprises at least one anti-BCMA Centyrin. A CAR comprising the anti-BCMA Centyrin is referred to as a BCMA CARTyrin herein.

In some aspects, a nanoparticle of the present disclosure can comprise a nucleic acid sequence encoding a BCMA CARTyrin.

In an aspect, the antigen recognition region of the disclosed CAR comprises at least one anti-PSMA Centyrin. A CAR comprising the anti-PSMA Centyrin is referred to as a PSMA CARTyrin herein.

In some aspects, a nanoparticle of the present disclosure can comprise a nucleic acid sequence encoding a PSMA CARTyrin.

In an aspect, the antigen recognition region of the disclosed CAR comprises at least one anti-BCMA VH. A CAR comprising the anti-BCMA VH is referred to as a BCMA VCAR herein.

In some aspects, a nanoparticle of the present disclosure can comprise a nucleic acid sequence encoding a BCMA VCAR.

The ectodomain can comprise a signal peptide. The signal peptide can comprise a sequence encoding a human CD2, CD3δ, CD3ε, CD3γ, CD3ζ, CD4, CD8α, CD19, CD28, 4-1BB or GM-CSFR signal peptide. In a preferred aspect, the signal peptide comprises, consists essentially of, or consists of: a human CD8 alpha (CD8α) signal peptide (SP) or a portion thereof.

The hinge domain or hinge region can comprise a human CD8α, IgG4, CD4 sequence, or a combination thereof. In a preferred aspect, the hinge can comprise, consist essentially of, or consist of a human CD8 alpha (CD8α) hinge or a portion thereof.

The transmembrane domain can comprise, consist essentially of, or consist of a sequence encoding a human CD2, CD3δ, CD3ε, CD3γ, CD3ζ, CD4, CD8α, CD19, CD28, 4-1BB or GM-CSFR transmembrane domain. Preferably, the transmembrane domain can comprise, consist essentially of, or consist of a human CD8 alpha (CD8α) transmembrane domain, or a portion thereof.

The at least one costimulatory domain can comprise, consist essentially of, or consist of a human 4-1BB, CD28, CD3 zeta (CD3ζ), CD40, ICOS, MyD88, OX-40 intracellular domain, or any combination thereof. Preferably, the at least one costimulatory domain comprises a CD3ζ, a 4-1 in costimulatory domain, or a combination thereof.

Transposition Systems

In some aspects, a nucleic acid can comprise a transposon or a nanotransposon comprising: a first nucleic acid sequence comprising: (a) a first inverted terminal repeat (ITR) or a sequence encoding a first ITR, (b) a second ITR or a sequence encoding a second ITR, and (c) an intra-ITR sequence or a sequence encoding an intra-ITR, wherein the intra-ITR sequence comprises a transposon sequence or a sequence encoding a transposon.

In some aspects, a nucleic acid can comprise a transposon or a nanotransposon comprising: a first nucleic acid sequence comprising: (a) a first inverted terminal repeat (ITR) or a sequence encoding a first ITR, (b) a second ITR or a sequence encoding a second ITR, and (c) an intra-ITR sequence or a sequence encoding an intra-ITR, wherein the intra-ITR sequence comprises a transposon sequence or a sequence encoding a transposon, and a second nucleic acid sequence comprising an inter-ITR sequence or a sequence encoding an inter-ITR, wherein the length of the inter-ITR sequence is equal to or less than 700 nucleotides.

The transposon or nanotransposon of the disclosure comprises a protein scaffold (e.g., a CAR comprising at least one scFv, single domain antibody or Centyrin). The transposon or nanotransposon can be a plasmid DNA transposon comprising a sequence encoding a protein scaffold (e.g., a CAR comprising at least one scFv, single domain antibody or Centyrin) flanked by two cis-regulatory insulator elements. The transposon or nanotransposon can further comprises a plasmid comprising a sequence encoding a transposase. The sequence encoding the transposase may be a DNA sequence or an RNA sequence. Preferably, the sequence encoding the transposase is an mRNA sequence.

The transposon or nanotransposon of the present disclosure can be a piggyBac™ (PB) transposon. In some aspects when the transposon is a PB transposon, the transposase is a piggyBac™ (PB) transposase a piggyBac-like (PBL) transposase or a Super piggyBac™ (SPB) transposase. Preferably, the sequence encoding the SPB transposase is an mRNA sequence.

Non-limiting examples of PB transposons and PB, PBL and SPB transposases are described in detail in U.S. Pat. Nos. 6,218,182; 6,962,810; 8,399,643 and PCT Publication No. WO 2010/099296.

The PB, PBL and SPB transposases recognize transposon-specific inverted terminal repeat sequences (ITRs) on the ends of the transposon, and inserts the contents between the ITRs at the sequence 5'-TTAT-3' within a chromosomal site (a TTAT target sequence) or at the sequence 5'-TTAA-3' within a chromosomal site (a TTAA target sequence). The target sequence of the PB or PBL transposon can comprise or consist of 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. The PB or PBL transposon system has no payload limit for the genes of interest that can be included between the ITRs.

Exemplary amino acid sequence for one or more PB, PBL and SPB transposases are disclosed in U.S. Pat. Nos. 6,218,185; 6,962,810 and 8,399,643. In a preferred aspect, the PB transposase comprises or consists of an amino acid sequence at least 75%, 80%, 85%, 90%, 95%, 96%, 97%, 98%, 99% or 100% (or any percentage in between) identical to SEQ ID NO: 1.

The PB or PBL transposase can comprise or consist of an amino acid sequence having an amino acid substitution at two or more, at three or more or at each of positions 30, 165, 282, or 538 of the sequence of SEQ ID NO: 1. The transposase can be a SPB transposase that comprises or consists of the amino acid sequence of the sequence of SEQ ID NO: 1 wherein the amino acid substitution at position 30 can be a substitution of a valine (V) for an isoleucine (I), the amino acid substitution at position 165 can be a substitution of a serine (S) for a glycine (G), the amino acid substitution at position 282 can be a substitution of a valine (V) for a methionine (M), and the amino acid substitution at position 538 can be a substitution of a lysine (K) for an asparagine (N).

In certain aspects wherein the transposase comprises the above-described mutations at positions 30, 165, 282 and/or 538, the PB, PBL and SPB transposases can further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 are described in more detail in PCT Publication No. WO 2019/173636 and PCT/US2019/049816.

The PB, PBL or SPB transposases can be isolated or derived from an insect, vertebrate, crustacean or urochordate as described in more detail in PCT Publication No. WO 2019/173636 and PCT/US2019/049816. In preferred aspects, the PB, PBL or SPB transposases is be isolated or derived from the insect *Trichoplusia ni* (GenBank Accession No. AAA87375) or *Bombyx mori* (GenBank Accession No. BAD11135).

A hyperactive PB or PBL transposase is a transposase that is more active than the naturally occurring variant from which it is derived. In a preferred aspect, a hyperactive PB or PBL transposase is isolated or derived from *Bombyx mori* or *Xenopus tropicalis*. Examples of hyperactive PB or PBL transposases are disclosed in U.S. Pat. Nos. 6,218,185; 6,962,810, 8,399,643 and WO 2019/173636. A list of hyperactive amino acid substitutions is disclosed in U.S. Pat. No. 10,041,077.

In some aspects, the PB or PBL transposase is integration deficient. An integration deficient PB or PBL transposase is a transposase that can excise its corresponding transposon, but that integrates the excised transposon at a lower frequency than a corresponding wild type transposase. Examples of integration deficient PB or PBL transposases are disclosed in U.S. Pat. Nos. 6,218,185; 6,962,810, 8,399,643 and WO 2019/173636. A list of integration deficient amino acid substitutions is disclosed in U.S. Pat. No. 10,041,077.

In some aspects, the PB or PBL transposase is fused to a nuclear localization signal. Examples of PB or PBL transposases fused to a nuclear localization signal are disclosed in U.S. Pat. Nos. 6,218,185; 6,962,810, 8,399,643 and WO 2019/173636.

A transposon or nanotransposon of the present disclosure can be a Sleeping Beauty transposon. In some aspects, when the transposon is a Sleeping Beauty transposon, the transposase is a Sleeping Beauty transposase (for example as disclosed in U.S. Pat. No. 9,228,180) or a hyperactive Sleeping Beauty (SB100X) transposase.

A transposon or nanotransposon of the present disclosure can be a Helraiser transposon. An exemplary Helraiser transposon includes Helibat1. In some aspects, when the transposon is a Helraiser transposon, the transposase is a Helitron transposase (for example, as disclosed in WO 2019/173636).

A transposon or nanotransposon of the present disclosure can be a Tol2 transposon. In some aspects, when the transposon is a Tol2 transposon, the transposase is a Tol2 transposase (for example, as disclosed in WO 2019/173636).

A transposon or nanotransposon of the present disclosure can be a TcBuster transposon. In some aspects, when the transposon is a TcBuster transposon, the transposase is a TcBuster transposase or a hyperactive TcBuster transposase (for example, as disclosed in WO 2019/173636). The TcBuster transposase can comprise or consist of a naturally occurring amino acid sequence or a non-naturally occurring amino acid sequence. The polynucleotide encoding a TcBuster transposase can comprise or consist of a naturally occurring nucleic acid sequence or a non-naturally occurring nucleic acid sequence.

In some aspects, a mutant TcBuster transposase comprises one or more sequence variations when compared to a wild type TcBuster transposase as described in more detail in PCT Publication No. WO 2019/173636 and PCT/US2019/049816.

The cell delivery compositions (e.g., transposons) disclosed herein can comprise a nucleic acid molecule encoding a therapeutic protein or therapeutic agent. Examples of therapeutic proteins include those disclosed in PCT Publication No. WO 2019/173636 and PCT/US2019/049816.

Cells and Modified Cells of the Disclosure

Cells and modified cells of the disclosure can be mammalian cells. Preferably, the cells and modified cells are human cells. Cells and modified cells of the disclosure can be immune cells. The immune cells of the disclosure can comprise lymphoid progenitor cells, natural killer (NK) cells, T lymphocytes (T-cell), stem memory T cells ($T_{SCM}$ cells), central memory T cells ($T_{CM}$), stem cell-like T cells, B lymphocytes (B-cells), antigen presenting cells (APCs), cytokine induced killer (CIK) cells, myeloid progenitor cells, neutrophils, basophils, eosinophils, monocytes, macrophages, platelets, erythrocytes, red blood cells (RBCs), megakaryocytes or osteoclasts.

The immune precursor cells can comprise any cells which can differentiate into one or more types of immune cells. The immune precursor cells can comprise multipotent stem cells that can self-renew and develop into immune cells. The immune precursor cells can comprise hematopoietic stem cells (HSCs) or descendants thereof. The immune precursor cells can comprise precursor cells that can develop into immune cells. The immune precursor cells can comprise hematopoietic progenitor cells (HPCs).

Hematopoietic stem cells (HSCs) are multipotent, self-renewing cells. All differentiated blood cells from the lymphoid and myeloid lineages arise from HSCs. HSCs can be found in adult bone marrow, peripheral blood, mobilized peripheral blood, peritoneal dialysis effluent and umbilical cord blood.

HSCs can be isolated or derived from a primary or cultured stem cell. HSCs can be isolated or derived from an embryonic stem cell, a multipotent stem cell, a pluripotent stem cell, an adult stem cell, or an induced pluripotent stem cell (iPSC).

Immune precursor cells can comprise an HSC or an HSC descendent cell. Non-limiting examples of HSC descendent cells include multipotent stem cells, lymphoid progenitor cells, natural killer (NK) cells, T lymphocyte cells (T-cells), B lymphocyte cells (B-cells), myeloid progenitor cells, neutrophils, basophils, eosinophils, monocytes and macrophages.

HSCs produced by the disclosed methods can retain features of "primitive" stem cells that, while isolated or derived from an adult stem cell and while committed to a single lineage, share characteristics of embryonic stem cells. For example, the "primitive" HSCs produced by the disclosed methods retain their "sternness" following division and do not differentiate. Consequently, as an adoptive cell therapy, the "primitive" HSCs produced by the disclosed methods not only replenish their numbers, but expand in vivo. "Primitive" HSCs produced by disclosed the methods can be therapeutically-effective when administered as a single dose.

Primitive HSCs can be CD34+. Primitive HSCs can be CD34+ and CD38−. Primitive HSCs can be CD34+, CD38− and CD90+. Primitive HSCs can be CD34+, CD38−, CD90+ and CD45RA−. Primitive HSCs can be CD34+, CD38−, CD90+, CD45RA−, and CD49f+. Primitive HSCs can be CD34+, CD38−, CD90+, CD45RA−, and CD49f+.

Primitive HSCs, HSCs, and/or HSC descendent cells can be modified according to the disclosed methods to express an exogenous sequence (e.g., a chimeric antigen receptor or therapeutic protein). Modified primitive HSCs, modified HSCs, and/or modified HSC descendent cells can be forward differentiated to produce a modified immune cell including, but not limited to, a modified T cell, a modified natural killer cell and/or a modified B-cell.

The modified immune or immune precursor cells can be NK cells. The NK cells can be cytotoxic lymphocytes that differentiate from lymphoid progenitor cells. Modified NK cells can be derived from modified hematopoietic stem and progenitor cells (HSPCs) or modified HSCs. In some aspects, non-activated NK cells are derived from CD3-depleted leukapheresis (containing CD14/CD19/CD56+ cells).

The modified immune or immune precursor cells can be B cells. B cells are a type of lymphocyte that express B cell receptors on the cell surface. B cell receptors bind to specific antigens. Modified B cells can be derived from modified hematopoietic stem and progenitor cells (HSPCs) or modified HSCs.

Modified T cells of the disclosure may be derived from modified hematopoietic stem and progenitor cells (HSPCs) or modified HSCs. Unlike traditional biologics and chemotherapeutics, the disclosed modified-T cells the capacity to rapidly reproduce upon antigen recognition, thereby potentially obviating the need for repeat treatments. To achieve this, in some aspects, modified-T cells not only drive an initial response, but also persist in the patient as a stable population of viable memory T cells to prevent potential relapses. Alternatively, in some aspects, when it is not desired, the modified-T cells do not persist in the patient.

Intensive efforts have been focused on the development of antigen receptor molecules that do not cause T cell exhaustion through antigen-independent (tonic) signaling, as well as of a modified-T cell product containing early memory T cells, especially stem cell memory ($T_{SCM}$) or stem cell-like T cells. Stem cell-like modified-T cells of the disclosure exhibit the greatest capacity for self-renewal and multipotent capacity to derive central memory ($T_{CM}$) T cells or $T_{CM}$ like cells, effector memory ($T_{EM}$) and effector T cells ($T_E$), thereby producing better tumor eradication and long-term modified-T cell engraftment. A linear pathway of differentiation may be responsible for generating these cells: Naïve T cells (TN)>$T_{SCM}$>$T_{CM}$>$T_{EM}$>$T_E$>$T_{TE}$, whereby $T_N$ is the parent precursor cell that directly gives rise to $T_{SCM}$, which then, in turn, directly gives rise to $T_{CM}$, etc. Compositions of T cells of the disclosure can comprise one or more of each parental T cell subset with $T_{SCM}$ cells being the most abundant (e.g., $T_{SCM}$>$T_{CM}$>$T_{EM}$>$T_E$>$T_{TE}$).

The immune cell precursor can be differentiated into or is capable of differentiating into an early memory T cell, a stem cell like T-cell, a Naïve T cells ($T_N$), a $T_{SCM}$, a $T_{CM}$, a $T_{EM}$, a $T_E$, or a $T_{TE}$. The immune cell precursor can be a primitive HSC, an HSC, or a HSC descendent cell of the disclosure. The immune cell can be an early memory T cell, a stem cell like T-cell, a Naïve T cells ($T_N$), a $T_{SCM}$, a $T_{CM}$, a $T_{EM}$, a $T_E$, or a $T_{TE}$.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of a plurality of modified T cells in the population expresses one or more cell-surface marker(s) of an early memory T cell. The population of modified early memory T cells comprises a plurality of modified stem cell-like T cells. The population of modified early memory T cells comprises a plurality of modified $T_{SCM}$ cells. The population of modified early memory T cells comprises a plurality of modified $T_{CM}$ cells.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a stem cell-like T cell. The population of modified stem cell-like T cells comprises a plurality of modified $T_{SCM}$ cells. The population of modified stem cell-like T cells comprises a plurality of modified $T_{CM}$ cells.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% or any percentage in between of the plurality of modified T cells in the population expresses one or more cell-surface marker(s) of a stem memory T cell ($T_{SCM}$) or a $T_{SCM}$-like cell; and wherein the one or more cell-surface marker(s) comprise CD45RA and CD62L. The cell-surface markers can comprise one or more of CD62L, CD45RA, CD28, CCR7, CD127, CD45RO, CD95, CD95 and IL-2Rβ. The cell-surface markers can comprise one or more of CD45RA, CD95, IL-2Rβ, CCR7, and CD62L.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the plurality of modified T cells in the population expresses one or more cell-surface marker(s) of a central memory T cell ($T_{CM}$) or a $T_{CM}$-like cell; and wherein the one or more cell-surface marker(s) comprise CD45RO and CD62L. The cell-surface markers can comprise one or more of CD45RO, CD95, IL-2Rβ, CCR7, and CD62L.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a naïve T cell ($T_N$). The cell-surface markers can comprise one or more of CD45RA, CCR7 and CD62L.

The methods of the disclosure can modify and/or produce a population of modified T cells, wherein at least 2%, 5%0, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of an effector T-cell (modified $T_{EFF}$). The cell-surface markers can comprise one or more of CD45RA, CD95, and IL-2Rβ.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells of the population expresses one or more cell-surface marker(s) of a stem cell-like T cell, a stem memory T cell ($T_{SCM}$) or a central memory T cell ($T_{CM}$).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 or wherein at least about 70% to about 99%, about 75% to about 95% or about 85% to about 95% of the population of modified cells express one or more cell-surface marker(s) comprising CD34 (e.g., comprise the cell-surface marker phenotype CD34+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and do not express one or more cell-surface marker(s) comprising CD38, or wherein at least about 45% to about 90%, about 50% to about 80% or about 65% to about 75% of the population of modified cells express one or more cell-surface marker(s) comprising CD34 and do not express one or more cell-surface marker(s) comprising CD38 (e.g., comprise the cell-surface marker phenotype CD34+ and CD38−).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 (e.g., comprise the cell-surface marker phenotype CD34+, CD38− and CD90+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38 and CD45RA, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 and CD45RA (e.g., comprise the cell-surface marker phenotype CD34+, CD38−, CD90+, CD45RA−).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34, CD90 and CD49f and do not express one or more cell-surface marker(s) comprising CD38 and CD45RA, or wherein at least about 0.02% to about 30%, about 0.02% to about 2%, about 0.04% to about 2% or about 0.04% to about 1% of the population of modified cells express one or more cell-surface marker(s) comprising CD34, CD90 and CD49f and do not express one or more cell-surface marker(s) comprising CD38 and CD45RA (e.g., comprise the cell-surface marker phenotype CD34+, CD38−, CD90+, CD45RA- and CD49f+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD45RA, or wherein at least about 0.2% to about 5%, about 0.2% to about 3% or about 0.4% to about 3% of the population of modified cells express one or more cell-surface marker(s) comprising CD34 and CD90 and do not express one or more cell-surface marker(s) comprising CD45RA (e.g., comprise the cell-surface marker phenotype CD34+, CD90+ and CD45RA−).

Compositions and methods of producing and/or expanding the immune cells or immune precursor cells (e.g., the disclosed modified T-cells) and buffers for maintaining or enhancing a level of cell viability and/or a stem-like phenotype of the immune cells or immune precursor cells (e.g., the disclosed modified T-cells) are disclosed elsewhere herein and are disclosed in more detail in U.S. Pat. No. 10,329,543 and PCT Publication No. WO 2019/173636.

Cells and modified cells of the disclosure can be somatic cells. Cells and modified cells of the disclosure can be differentiated cells. Cells and modified cells of the disclosure can be autologous cells or allogenic cells. Allogeneic cells are engineered to prevent adverse reactions to engraftment following administration to a subject. Allogeneic cells may be any type of cell. Allogenic cells can be stem cells or can be derived from stem cells. Allogeneic cells can be differentiated somatic cells.

Methods of Expressing a Chimeric Antigen Receptor

The disclosure provides methods of expressing a CAR on the surface of a cell. The method comprises (a) obtaining a cell population; (b) contacting the cell population to a composition of the present disclosure comprising a CAR or a sequence encoding the CAR, under conditions sufficient to transfer the CAR across a cell membrane of at least one cell in the cell population, thereby generating a modified cell population; (c) culturing the modified cell population under conditions suitable for integration of the sequence encoding the CAR; and (d) expanding and/or selecting at least one cell from the modified cell population that express the CAR on the cell surface.

In some aspects, the cell population can comprise leukocytes and/or CD4+ and CD8+ leukocytes. The cell population can comprise CD4+ and CD8+ leukocytes in an optimized ratio. The optimized ratio of CD4+ to CD8+ leukocytes does not naturally occur in vivo. The cell population can comprise a tumor cell.

In some aspects, the conditions sufficient to transfer the CAR or the sequence encoding the CAR, transposon, or vector across a cell membrane of at least one cell in the cell population comprises at least one of an application of one or more pulses of electricity at a specified voltage, a buffer, and one or more supplemental factor(s). In some aspects, the conditions suitable for integration of the sequence encoding the CAR comprise at least one of a buffer and one or more supplemental factor(s).

The buffer can comprise PBS, HBSS, OptiMEM, BTXpress, Amaxa Nucleofector, Human T cell nucleofection buffer or any combination thereof. The one or more supplemental factor(s) can comprise (a) a recombinant human cytokine, a chemokine, an interleukin or any combination thereof; (b) a salt, a mineral, a metabolite or any combination thereof; (c) a cell medium; (d) an inhibitor of cellular DNA sensing, metabolism, differentiation, signal transduction, one or more apoptotic pathway(s) or combinations thereof, and (e) a reagent that modifies or stabilizes one or more nucleic acids. The recombinant human cytokine, the chemokine, the interleukin or any combination thereof can comprise IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L or any combination thereof. The salt, the mineral, the metabolite or any combination thereof can comprise HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, antibiotics, pH adjusters, Earle's Salts, 2-Mercaptoethanol, Human transferrin, Recombinant human insulin, Human serum albumin, Nucleofector PLUS Supplement, KCL, $MgCl_2$, $Na_2HPO_4$, $NAH_2PO_4$, Sodium lactobionate, Mannitol, Sodium succinate, Sodium Chloride, CINa, Glucose, $Ca(NO_3)_2$, Tris/HCl, $K_2HPO_4$, $KH_2PO_4$, Polyethylenimine, Poly-ethylene-glycol, Poloxamer 188, Poloxamer 181, Poloxamer 407, Poly-vinylpyrrolidone, Pop313, Crown-5, or any combination thereof. The cell medium can comprise PBS, HBSS, OptiMEM, DMEM, RPMI 1640, AIM-V, X-VIVO 15, CellGro DC Medium, CTS OpTimizer T Cell Expansion SFM, TexMACS Medium, PRIME-XV T Cell Expansion Medium, ImmunoCult-XF T Cell Expansion Medium or any combination thereof. The inhibitor of cellular DNA sensing, metabolism, differentiation, signal transduction, one or more apoptotic pathway(s) or combinations thereof comprise inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspase1, Pro-IL1B, PI3K, Akt, Wnt3A, inhibitors of glycogen synthase kinase-3β (GSK-3β) (e.g. TWS119), or any combination thereof. Examples of such inhibitors can include Bafilomycin, Chloroquine, Quinacrine, AC-YVAD-CMK, Z-VAD-FMK, Z-IETD-FMK or any combination thereof. The reagent that modifies or stabilizes one or more nucleic acids comprises a pH modifier, a DNA-binding protein, a lipid, a phospholipid, $CaPO_4$, a net neutral charge DNA binding peptide with or without a NLS sequence, a TREX1 enzyme or any combination thereof.

The expansion and selection steps can occur concurrently or sequentially. The expansion can occur prior to selection. The expansion can occur following selection, and, optionally, a further (i.e. second) selection can occur following expansion. Concurrent expansion and selection can be simultaneous. The expansion and/or selection steps can proceed for a period of 10 to 14 days, inclusive of the endpoints.

The expansion can comprise contacting at least one cell of the modified cell population with an antigen to stimulate the at least one cell through the CAR, thereby generating an expanded cell population. The antigen can be presented on the surface of a substrate. The substrate can have any form, including, but not limited to a surface, a well, a bead or a plurality thereof, and a matrix. The substrate can further comprise a paramagetic or magnetic component. The antigen can be presented on the surface of a substrate, wherein the substrate is a magnetic bead, and wherein a magnet can be used to remove or separate the magnetic beads from the modified and expanded cell population. The antigen can be presented on the surface of a cell or an artificial antigen presenting cell. Artificial antigen presenting cells can include, but are not limited to, tumor cells and stem cells.

In some aspects wherein the transposon or vector comprises a selection gene, the selection step comprises contacting at least one cell of the modified cell population with a compound to which the selection gene confers resistance, thereby identifying a cell expressing the selection gene as surviving the selection and identifying a cell failing to express the selection gene as failing to survive the selection step.

The disclosure provides a composition comprising the modified, expanded and selected cell population of the methods described herein.

A more detailed description of methods for expressing a CAR on the surface of a cell is disclosed in PCT Publication No. WO 2019/049816 and PCT/US2019/049816.

The present disclosure provides a cell or a population of cells wherein the cell comprises a composition comprising (a) an inducible transgene construct, comprising a sequence encoding an inducible promoter and a sequence encoding a transgene, and (b) a receptor construct, comprising a sequence encoding a constitutive promoter and a sequence encoding an exogenous receptor, such as a CAR, wherein, upon integration of the construct of (a) and the construct of (b) into a genomic sequence of a cell, the exogenous receptor is expressed, and wherein the exogenous receptor, upon binding a ligand or antigen, transduces an intracellular signal that targets directly or indirectly the inducible promoter regulating expression of the inducible transgene (a) to modify gene expression.

The composition can modify gene expression by decreasing gene expression. The composition can modify gene expression by transiently modifying gene expression (e.g., for the duration of binding of the ligand to the exogenous receptor). The composition can modify gene expression acutely (e.g., the ligand reversibly binds to the exogenous receptor). The composition can modify gene expression chronically (e.g., the ligand irreversibly binds to the exogenous receptor).

In some aspects, a nucleic acid can comprise a transgene comprising a nucleic acid molecule encoding at least one exogenous receptor. The exogenous receptor can comprise an endogenous receptor with respect to the genomic sequence of the cell. Exemplary receptors include, but are not limited to, intracellular receptors, cell-surface receptors, transmembrane receptors, ligand-gated ion channels, and G-protein coupled receptors.

The exogenous receptor can comprise a non-naturally occurring receptor. The non-naturally occurring receptor can be a synthetic, modified, recombinant, mutant or chimeric receptor. The non-naturally occurring receptor can comprise one or more sequences isolated or derived from a T-cell receptor (TCR). The non-naturally occurring receptor can comprise one or more sequences isolated or derived from a scaffold protein. In some aspects, including those wherein the non-naturally occurring receptor does not comprise a transmembrane domain, the non-naturally occurring receptor interacts with a second transmembrane, membrane-bound and/or an intracellular receptor that, following contact with the non-naturally occurring receptor, transduces an intracellular signal. The non-naturally occurring receptor can comprise a transmembrane domain. The non-naturally occurring receptor can interact with an intracellular receptor that transduces an intracellular signal. The non-naturally occurring receptor can comprise an intracellular signaling domain. The non-naturally occurring receptor can be a chimeric ligand receptor (CLR). The CLR can be a chimeric antigen receptor (CAR).

The sequence encoding the inducible promoter of comprises a sequence encoding an NFκB promoter, a sequence encoding an interferon (IFN) promoter or a sequence encoding an interleukin-2 promoter. In some aspects, the IFN promoter is an IFNγ promoter. The inducible promoter can be isolated or derived from the promoter of a cytokine or a chemokine. The cytokine or chemokine can comprise IL2, IL3, IL4, IL5, IL6, IL10, IL12, IL13, IL17A/F, IL21, IL22, IL23, transforming growth factor beta (TGFβ), colony stimulating factor 2 (GM-CSF), interferon gamma (IFNγ), Tumor necrosis factor alpha (TNFα), LTα, perforin, Granzyme C (Gzmc), Granzyme B (Gzmb), C-C motif chemokine ligand 5 (CCL5), C-C motif chemokine ligand 4 (Ccl4), C-C motif chemokine ligand 3 (Ccl3), X-C motif chemokine ligand 1 (Xcl1) or LIF interleukin 6 family cytokine (Lif).

The inducible promoter can be isolated or derived from the promoter of a gene comprising a surface protein involved in cell differentiation, activation, exhaustion and function. In some aspects, the gene comprises CD69, CD71, CTLA4, PD-1, TIGIT, LAG3, TIM-3, GITR, MHCII, COX-2, FASL or 4-1BB.

The inducible promoter can be isolated or derived from the promoter of a gene involved in CD metabolism and differentiation. The inducible promoter can be isolated or derived from the promoter of Nr4a1, Nr4a3, Tnfrsf9 (4-1BB), Sema7a, Zfp3612, Gadd45b, Dusp5, Dusp6 and Neto2.

In some aspects, the inducible transgene construct comprises or drives expression of a signaling component downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of which are disclosed in PCT Publication No. WO 2019/173636 and PCT Application No. PCT/US2019/049816.

Armored Cells

The modified cells of disclosure (e.g., CAR T-cells) can be further modified to enhance their therapeutic potential. Alternatively, or in addition, the modified cells may be further modified to render them less sensitive to immunologic and/or metabolic checkpoints. Modifications of this type "armor" the cells, which, following the modification, may be referred to here as "armored" cells (e.g., armored T-cells). Armored cells may be produced by, for example, blocking and/or diluting specific checkpoint signals delivered to the cells (e.g., checkpoint inhibition) naturally, within the tumor immunosuppressive microenvironment.

An armored cell of the disclosure can be derived from any cell, for example, a T cell, a NK cell, a hematopoietic progenitor cell, a peripheral blood (PB) derived T cell (including a T cell isolated or derived from G-CSF-mobilized peripheral blood), or an umbilical cord blood (UCB) derived T cell. An armored cell (e.g., armored T-cell) can comprise one or more of a chimeric ligand receptor (CLR comprising a protein scaffold, an antibody, an ScFv, or an antibody mimetic)/chimeric antigen receptor (CAR comprising a protein scaffold, an antibody, an ScFv, or an antibody mimetic), a CARTyrin (a CAR comprising a Centyrin), and/or a VCAR (a CAR comprising a camelid VHH or a single domain VH). An armored cell (e.g., armored T-cell) can comprise an inducible proapoptotic polypeptide as disclosed herein. An armored cell (e.g., armored T-cell) can comprise an exogenous sequence. The exogenous sequence can comprise a sequence encoding a therapeutic protein. Exemplary therapeutic proteins may be nuclear, cytoplasmic, intracellular, transmembrane, cell-surface bound, or secreted proteins. Exemplary therapeutic proteins expressed by the armored cell (e.g., armored T-cell) may modify an activity of the armored cell or may modify an activity of a second cell. An armored cell (e.g., armored T-cell) can comprise a selection gene or a selection marker. An armored cell (e.g., armored T-cell) can comprise a synthetic gene expression cassette (also referred to herein as an inducible transgene construct).

The modified cells of disclosure (e.g., CAR T-cells) can be further modified to silence or reduce expression one or more gene(s) encoding receptor(s) of inhibitory checkpoint signals to produce an armored cell (e.g., armored CAR T-cell). Receptors of inhibitory checkpoint signals are expressed on the cell surface or within the cytoplasm of a cell. Silencing or reducing expressing of the gene encoding the receptor of the inhibitory checkpoint signal results a loss of protein expression of the inhibitory checkpoint receptors on the surface or within the cytoplasm of an armored cell. Thus, armored cells having silenced or reduced expression of one or more genes encoding an inhibitory checkpoint receptor is resistant, non-receptive or insensitive to checkpoint signals. The resistance or decreased sensitivity of the armored cell to inhibitory checkpoint signals enhances the therapeutic potential of the armored cell in the presence of these inhibitory checkpoint signals. Non-limiting examples of inhibitory checkpoint signals (and proteins that induce immunosuppression) are disclosed in PCT Publication No. WO 2019/173636. Preferred examples of inhibitory checkpoint signals that may be silenced include, but are not limited to, PD-1 and TGFβRII.

The modified cells of disclosure (e.g., CAR T-cells) can be further modified to silence or reduce expression of one or more gene(s) encoding intracellular proteins involved in checkpoint signaling to produce an armored cell (e.g., armored CAR T-cell). The activity of the modified cells may be enhanced by targeting any intracellular signaling protein involved in a checkpoint signaling pathway, thereby achieving checkpoint inhibition or interference to one or more checkpoint pathways. Non-limiting examples of intracellular signaling proteins involved in checkpoint signaling are disclosed in PCT Publication No. WO 2019/173636.

The modified cells of disclosure (e.g., CAR T-cells) can be further modified to silence or reduce expression of one or more gene(s) encoding a transcription factor that hinders the efficacy of a therapy to produce an armored cell (e.g., armored CAR T-cell). The activity of modified cells may be enhanced or modulated by silencing or reducing expression (or repressing a function) of a transcription factor that hinders the efficacy of a therapy. Non-limiting examples of transcription factors that may be modified to silence or reduce expression or to repress a function thereof include, but are not limited to, the exemplary transcription factors are disclosed in PCT Publication No. WO 2019/173636.

The modified cells of disclosure (e.g., CAR T-cells) can be further modified to silence or reduce expression of one or more gene(s) encoding a cell death or cell apoptosis receptor to produce an armored cell (e.g., armored CAR T-cell). Interaction of a death receptor and its endogenous ligand results in the initiation of apoptosis. Disruption of an expression, an activity, or an interaction of a cell death and/or cell apoptosis receptor and/or ligand render a modified cell less receptive to death signals, consequently, making the armored cell more efficacious in a tumor environment. Non-limiting examples of cell death and/or cell apoptosis receptors and ligands are disclosed in PCT Publication No. WO 2019/173636. A preferred example of cell death receptor which may be modified is Fas (CD95).

The modified cells of disclosure (e.g., CAR T-cells) can be further modified to silence or reduce expression of one or more gene(s) encoding a metabolic sensing protein to produce an armored cell (e.g., armored CAR T-cell). Disruption to the metabolic sensing of the immunosuppressive tumor microenvironment (characterized by low levels of oxygen, pH, glucose and other molecules) by a modified cell leads to extended retention of T-cell function and, consequently, more tumor cells killed per cell. Non-limiting examples of metabolic sensing genes and proteins are disclosed in PCT Publication No. WO 2019/173636. A preferred example, HIF1a and VHL play a role in T-cell function while in a hypoxic environment. An armored T-cell may have silenced or reduced expression of one or more genes encoding HIF1a or VHL.

The modified cells of disclosure (e.g., CAR T-cells) can be further modified to silence or reduce expression of one or more gene(s) encoding proteins that that confer sensitivity to a cancer therapy, including a monoclonal antibody, to produce an armored cell (e.g., armored CAR T-cell). Thus, an armored cell can function and may demonstrate superior function or efficacy whilst in the presence of a cancer therapy (e.g., a chemotherapy, a monoclonal antibody therapy, or another anti-tumor treatment). Non-limiting examples of proteins involved in conferring sensitivity to a cancer therapy are disclosed in PCT Publication No. WO 2019/173636.

The modified cells of disclosure (e.g., CAR T-cells) can be further modified to silence or reduce expression of one or more gene(s) encoding a growth advantage factor to produce an armored cell (e.g., armored CAR T-cell). Silencing or reducing expression of an oncogene can confer a growth advantage for the cell. For example, silencing or reducing expression (e.g., disrupting expression) of a TET2 gene during a CAR T-cell manufacturing process results in the generation of an armored CAR T-cell with a significant capacity for expansion and subsequent eradication of a tumor when compared to a non-armored CAR T-cell lacking this capacity for expansion. This strategy may be coupled to a safety switch (e.g., an iC9 safety switch described herein), which permits the targeted disruption of an armored CAR T-cell in the event of an adverse reaction from a subject or uncontrolled growth of the armored CAR T-cell. Non-limiting examples of growth advantage factors are disclosed in PCT Publication No. WO 2019/173636.

The modified cells of disclosure (e.g., CAR T-cells) can be further modified to express a modified/chimeric checkpoint receptor to produce an armored T-cell of the disclosure.

The modified/chimeric checkpoint receptor can comprise a null receptor, decoy receptor or dominant negative receptor. A null receptor, decoy receptor or dominant negative receptor can be modified/chimeric receptor/protein. A null receptor, decoy receptor or dominant negative receptor can be truncated for expression of the intracellular signaling domain. Alternatively, or in addition, a null receptor, decoy receptor or dominant negative receptor can be mutated within an intracellular signaling domain at one or more amino acid positions that are determinative or required for effective signaling. Truncation or mutation of null receptor, decoy receptor or dominant negative receptor can result in loss of the receptor's capacity to convey or transduce a checkpoint signal to the cell or within the cell.

For example, a dilution or a blockage of an immunosuppressive checkpoint signal from a PD-L1 receptor expressed on the surface of a tumor cell may be achieved by expressing a modified/chimeric PD-1 null receptor on the surface of an armored cell (e.g., armored CAR T-cell), which effectively competes with the endogenous (non-modified) PD-1 receptors also expressed on the surface of the armored cell to reduce or inhibit the transduction of the immunosuppressive checkpoint signal through endogenous PD-1 receptors of the armored cell. In this non-limiting example, competition between the two different receptors for binding to PD-L1 expressed on the tumor cell reduces or diminishes a level of effective checkpoint signaling, thereby enhancing a therapeutic potential of the armored cell expressing the PD-1 null receptor.

The modified/chimeric checkpoint receptor can comprise a null receptor, decoy receptor or dominant negative receptor that is a transmembrane receptor, a membrane-associated or membrane-linked receptor/protein or an intracellular receptor/protein. Exemplary null, decoy, or dominant negative intracellular receptors/proteins include, but are not limited to, signaling components downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of cytokines, cytokine receptors, chemokines and chemokine receptors are disclosed in PCT Publication No. WO 2019/173636.

The modified/chimeric checkpoint receptor can comprise a switch receptor. Exemplary switch receptors comprise a modified/chimeric receptor/protein wherein a native or wild type intracellular signaling domain is switched or replaced with a different intracellular signaling domain that is either non-native to the protein and/or not a wild-type domain. For example, replacement of an inhibitory signaling domain with a stimulatory signaling domain would switch an immunosuppressive signal into an immunostimulatory signal. Alternatively, replacement of an inhibitory signaling domain with a different inhibitory domain can reduce or enhance the level of inhibitory signaling. Expression or overexpression, of a switch receptor can result in the dilution and/or blockage of a cognate checkpoint signal via competition with an endogenous wild-type checkpoint receptor (not a switch receptor) for binding to the cognate checkpoint receptor expressed within the immunosuppressive tumor microenvironment. Armored cells (e.g., armored CAR T-cells) can comprise a sequence encoding a switch receptor, leading to the expression of one or more switch receptors, and consequently, altering an activity of an armored cell. Armored cells (e.g., armored CAR T-cells) can express a switch receptor that targets an intracellularly expressed protein downstream of a checkpoint receptor, a transcription factor, a cytokine receptor, a death receptor, a metabolic sensing molecule, a cancer therapy, an oncogene, and/or a tumor suppressor protein or gene.

Exemplary switch receptors can comprise or can be derived from a protein including, but are not limited to, the signaling components downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene.

The modified cells of disclosure (e.g., CAR T-cells) can be further modified to express a CLR/CAR that mediates conditional gene expression to produce an armored T-cell. The combination of the CLR/CAR and the condition gene expression system in the nucleus of the armored T-cell constitutes a synthetic gene expression system that is conditionally activated upon binding of cognate ligand(s) with CLR or cognate antigen(s) with CAR. This system may help to 'armor' or enhance therapeutic potential of modified T-cells by reducing or limiting synthetic gene expression at the site of ligand or antigen binding, at or within the tumor environment for example.

The present disclosure provides a gene editing composition and/or a cell comprising the gene editing composition. The gene editing composition can comprise a nanoparticle comprising a nucleic acid, wherein the nucleic acid comprises a sequence encoding a DNA binding domain and a sequence encoding a nuclease protein or a nuclease domain thereof. The sequence encoding a nuclease protein or the sequence encoding a nuclease domain thereof can comprise a DNA sequence, an RNA sequence, or a combination thereof. The nuclease or the nuclease domain thereof can comprise one or more of a CRISPR/Cas protein, a Transcription Activator-Like Effector Nuclease (TALEN), a Zinc Finger Nuclease (ZFN), and an endonuclease.

The nuclease or the nuclease domain thereof can comprise a nuclease-inactivated Cas (dCas) protein and an endonuclease. The endonuclease can comprise a Clo051 nuclease or a nuclease domain thereof. The gene editing composition can comprise a fusion protein. The fusion protein can comprise a nuclease-inactivated Cas9 (dCas9) protein and a Clo051 nuclease or a Clo051 nuclease domain. The gene editing composition can further comprise a guide sequence. The guide sequence comprises an RNA sequence.

A transgene can comprise a nucleic sequence encoding a small, Cas9 (Cas9) operatively-linked to an effector. The disclosure provides a fusion protein comprising, consisting essentially of or consisting of a DNA localization component and an effector molecule, wherein the effector comprises a small, Cas9 (Cas9). A small Cas9 construct of the disclosure can comprise an effector comprising a type IIS endonuclease.

A transgene can comprise a nucleic sequence encoding an inactivated, small, Cas9 (dSaCas9) operatively-linked to an effector. A transgene can comprise a nucleic sequence encoding a fusion protein comprising, consisting essentially of or consisting of a DNA localization component and an effector molecule, wherein the effector comprises a small, inactivated Cas9 (dSaCas9). A small, inactivated Cas9 (dSaCas9) construct of the disclosure can comprise an effector comprising a type IIS endonuclease.

A transgene can comprise a nucleic sequence encoding an inactivated Cas9 (dCas9) operatively-linked to an effector. A transgene can comprise a nucleic sequence encoding a fusion protein comprising, consisting essentially of or consisting of a DNA localization component and an effector molecule, wherein the effector comprises an inactivated Cas9 (dCas9). An inactivated Cas9 (dCas9) construct of the disclosure can comprise an effector comprising a type IIS endonuclease.

The dCas9 can be isolated or derived from *Streptoccocus pyogenes*. The dCas9 can comprise a dCas9 with substitutions at amino acid positions 10 and 840, which inactivate the catalytic site. In some aspects, these substitutions are D10A and H840A.

A cell comprising the gene editing composition can express the gene editing composition stably or transiently. Preferably, the gene editing composition is expressed transiently. The guide RNA can comprise a sequence complementary to a target sequence within a genomic DNA sequence. The target sequence within a genomic DNA sequence can be a target sequence within a safe harbor site of a genomic DNA sequence.

Gene editing compositions, including Cas-CLOVER, and methods of using these compositions for gene editing are described in detail in U.S. Patent Publication Nos. 2017/0107541, 2017/0114149, 2018/0187185 and U.S. Pat. No. 10,415,024.

Chimeric Stimulator Receptors and Recombinant HLA-E Polypeptides

Adoptive cell compositions that are "universally" safe for administration to any patient requires a significant reduction or elimination of alloreactivity. Towards this end, cells of the disclosure (e.g., allogenic cells) can be modified to interrupt expression or function of a T-cell Receptor (TCR) and/or a class of Major Histocompatibility Complex (MHC). The TCR mediates graft vs host (GvH) reactions whereas the MHC mediates host vs graft (HvG) reactions. In preferred aspects, any expression and/or function of the TCR is eliminated to prevent T-cell mediated GvH that could cause death to the subject. Thus, in a preferred aspect, the disclosure provides a pure TCR-negative allogeneic T-cell composition (e.g., each cell of the composition expresses at a level so low as to either be undetectable or non-existent).

Expression and/or function of MHC class I (MHC-I, specifically, HLA-A, HLA-B, and HLA-C) is reduced or eliminated to prevent HvG and, consequently, to improve engraftment of cells in a subject. Improved engraftment results in longer persistence of the cells, and, therefore, a larger therapeutic window for the subject. Specifically, expression and/or function of a structural element of MHC-I, Beta-2-Microglobulin (B2M), is reduced or eliminated.

The above strategies induce further challenges. T Cell Receptor (TCR) knockout (KO) in T cells results in loss of expression of CD3-zeta (CD3z or CD3$\zeta$), which is part of the TCR complex. The loss of CD3$\zeta$ in TCR-KO T-cells dramatically reduces the ability of optimally activating and expanding these cells using standard stimulation/activation reagents, including, but not limited to, agonist anti-CD3 mAb. When the expression or function of any one component of the TCR complex is interrupted, all components of the complex are lost, including TCR-alpha (TCR$\alpha$), TCR-beta (TCR$), CD3-gamma (CD3$\gamma$), CD3-epsilon (CD3$\varepsilon$), CD3-delta (CD3$\delta$), and CD3-zeta (CD3$\zeta$). Both CD3$\varepsilon$ and CD3$\zeta$ are required for T cell activation and expansion. Agonist anti-CD3 mAbs typically recognize CD3$\varepsilon$ and possibly another protein within the complex which, in turn, signals to CD3$\zeta$. CD3$\zeta$ provides the primary stimulus for T cell activation (along with a secondary co-stimulatory signal) for optimal activation and expansion. Under normal conditions, full T-cell activation depends on the engagement of the TCR in conjunction with a second signal mediated by one or more co-stimulatory receptors (e.g., CD28, CD2, 4-1BBL) that boost the immune response. However, when the TCR is not present, T cell expansion is severely reduced when stimulated using standard activation/stimulation reagents, including agonist anti-CD3 mAb. In fact, T cell expansion is reduced to only 20-40% of the normal level of expansion when stimulated using standard activation/stimulation reagents, including agonist anti-CD3 mAb.

Thus, the present disclosure provides a non-naturally occurring chimeric stimulatory receptor (CSR) comprising: (a) an ectodomain comprising a activation component, wherein the activation component is isolated or derived from a first protein; (b) a transmembrane domain; and (c) an endodomain comprising at least one signal transduction domain, wherein the at least one signal transduction domain is isolated or derived from a second protein; wherein the first protein and the second protein are not identical.

In some aspects, a transgene sequence can comprise a nucleic acid sequence encoding a non-naturally occurring chimeric stimulatory receptor (CSR) comprising: (a) an ectodomain comprising a activation component, wherein the activation component is isolated or derived from a first protein; (b) a transmembrane domain; and (c) an endodomain comprising at least one signal transduction domain, wherein the at least one signal transduction domain is isolated or derived from a second protein; wherein the first protein and the second protein are not identical.

The activation component can comprise a portion of one or more of a component of a T-cell Receptor (TCR), a component of a TCR complex, a component of a TCR co-receptor, a component of a TCR co-stimulatory protein, a component of a TCR inhibitory protein, a cytokine receptor, and a chemokine receptor to which an agonist of the activation component binds. The activation component can comprise a CD2 extracellular domain or a portion thereof to which an agonist binds.

The signal transduction domain can comprise one or more of a component of a human signal transduction domain, T-cell Receptor (TCR), a component of a TCR complex, a component of a TCR co-receptor, a component of a TCR co-stimulatory protein, a component of a TCR inhibitory protein, a cytokine receptor, and a chemokine receptor. The signal transduction domain can comprise a CD3 protein or a portion thereof. The CD3 protein can comprise a CD3ζ protein or a portion thereof.

The endodomain can further comprise a cytoplasmic domain. The cytoplasmic domain can be isolated or derived from a third protein. The first protein and the third protein can be identical. The ectodomain can further comprise a signal peptide. The signal peptide can be derived from a fourth protein. The first protein and the fourth protein can be identical. The transmembrane domain can be isolated or derived from a fifth protein. The first protein and the fifth protein can be identical.

In some aspects, the activation component does not bind a naturally-occurring molecule. In some aspects, the activation component binds a naturally-occurring molecule but the CSR does not transduce a signal upon binding of the activation component to a naturally-occurring molecule. In some aspects, the activation component binds to a non-naturally occurring molecule. In some aspects, the activation component does not bind a naturally-occurring molecule but binds a non-naturally occurring molecule. The CSR can selectively transduces a signal upon binding of the activation component to a non-naturally occurring molecule.

In a preferred aspect, the present disclosure provides a non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds; (b) a transmembrane domain, wherein the transmembrane domain comprises a CD2 transmembrane domain or a portion thereof, and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof.

The present disclosure also provides a non-naturally occurring chimeric stimulatory receptor (CSR) wherein the ectodomain comprises a modification. The modification can comprise a mutation or a truncation of the amino acid sequence of the activation component or the first protein when compared to a wild type sequence of the activation component or the first protein. The mutation or a truncation of the amino acid sequence of the activation component can comprise a mutation or truncation of a CD2 extracellular domain or a portion thereof to which an agonist binds. The mutation or truncation of the CD2 extracellular domain can reduce or eliminate binding with naturally occurring CD58.

In a preferred aspect, the present disclosure provides non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds and wherein the CD2 extracellular domain or a portion thereof to which an agonist binds comprises a mutation or truncation; (b) a transmembrane domain, wherein the transmembrane domain comprises a CD2 transmembrane domain or a portion thereof, and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof.

The present disclosure provides a nucleic acid sequence encoding any CSR disclosed herein. The present disclosure provides a transposon or a vector comprising a nucleic acid sequence encoding any CSR disclosed herein.

The present disclosure provides a cell comprising any CSR disclosed herein. The present disclosure provides a cell comprising a nucleic acid sequence encoding any CSR disclosed herein. The present disclosure provides a cell comprising a vector comprising a nucleic acid sequence encoding any CSR disclosed herein. The present disclosure provides a cell comprising a transposon comprising a nucleic acid sequence encoding any CSR disclosed herein.

A modified cell disclosed herein can be an allogeneic cell or an autologous cell. In some preferred aspects, the modified cell is an allogeneic cell. In some aspects, the modified cell is an autologous T-cell or a modified autologous CAR T-cell. In some preferred aspects, the modified cell is an allogeneic T-cell or a modified allogeneic CAR T-cell.

The present disclosure provides a composition comprising any CSR disclosed herein. The present disclosure provides a composition comprising a nucleic acid sequence encoding any CSR disclosed herein. The present disclosure provides a composition comprising a vector comprising a nucleic acid sequence encoding any CSR disclosed herein. The present disclosure provides a composition comprising a transposon comprising a nucleic acid sequence encoding any CSR disclosed herein. The present disclosure provides a composition comprising a modified cell disclosed herein or a composition comprising a plurality of modified cells disclosed herein.

The present disclosure provides a modified T lymphocyte (T-cell), comprising: (a) a modification of an endogenous sequence encoding a T-cell Receptor (TCR), wherein the modification reduces or eliminates a level of expression or activity of the TCR; and (b) a chimeric stimulatory receptor (CSR) comprising: (i) an ectodomain comprising an activation component, wherein the activation component is isolated or derived from a first protein; (ii) a transmembrane domain; and (iii) an endodomain comprising at least one signal transduction domain, wherein the at least one signal transduction domain is isolated or derived from a second protein; wherein the first protein and the second protein are not identical.

The modified T-cell can further comprise an inducible proapoptotic polypeptide. The modified T-cell can further comprise a modification of an endogenous sequence encoding Beta-2-Microglobulin (B2M), wherein the modification reduces or eliminates a level of expression or activity of a major histocompatibility complex (MHC) class I (MHC-I).

The modified T-cell can further comprise a non-naturally occurring polypeptide comprising an HLA class I histocompatibility antigen, alpha chain E (HLA-E) polypeptide. The non-naturally occurring polypeptide comprising a HLA-E polypeptide can further comprise a B2M signal peptide. The non-naturally occurring polypeptide comprising a HLA-E polypeptide can further comprise a B2M polypeptide. The non-naturally occurring polypeptide comprising an HLA-E polypeptide can further comprise a linker, wherein the linker is positioned between the B2M polypeptide and the HLA-E polypeptide. The non-naturally occurring polypeptide comprising an HLA-E polypeptide can further comprise a peptide and a B2M polypeptide. The non-naturally occurring polypeptide comprising an HLA-E can further comprise a first linker positioned between the B2M signal peptide and the peptide, and a second linker positioned between the B2M polypeptide and the peptide encoding the HLA-E.

The modified T-cell can further comprise a non-naturally occurring antigen receptor, a sequence encoding a therapeutic polypeptide, or a combination thereof. The non-naturally occurring antigen receptor can comprise a chimeric antigen receptor (CAR).

The CSR can be transiently expressed in the modified T-cell. The CSR can be stably expressed in the modified T-cell. The polypeptide comprising the HLA-E polypeptide can be transiently expressed in the modified T-cell. The polypeptide comprising the HLA-E polypeptide can be stably expressed in the modified T-cell. The inducible proapoptotic polypeptide can be transiently expressed in the modified T-cell. The inducible proapoptotic polypeptide can be stably expressed in the modified T-cell. The non-naturally occurring antigen receptor or a sequence encoding a therapeutic protein can be transiently expressed in the modified T-cell. The non-naturally occurring antigen receptor or a sequence encoding a therapeutic protein can be stably expressed in the modified T-cell.

Gene editing compositions, including but not limited to, RNA-guided fusion proteins comprising dCas9-Clo051, as described in detail herein, can be used to target and decrease or eliminate expression of an endogenous T-cell receptor. In preferred aspects, the gene editing compositions target and delete a gene, a portion of a gene, or a regulatory element of a gene (such as a promoter) encoding an endogenous T-cell receptor. Non-limiting examples of primers (including a T7 promoter, genome target sequence, and gRNA scaffold) for the generation of guide RNA (gRNA) templates for targeting and deleting TCR-alpha (TCR-α), targeting and deleting TCR-beta (TCR-β), and targeting and deleting beta-2-microglobulin (β2M) are disclosed in PCT Application No. PCT/US2019/049816.

Gene editing compositions, including but not limited to, RNA-guided fusion proteins comprising dCas9-Clo051, can be used to target and decrease or eliminate expression of an endogenous MHCI, MHCII, or MHC activator. In preferred aspects, the gene editing compositions target and delete a gene, a portion of a gene, or a regulatory element of a gene (such as a promoter) encoding one or more components of an endogenous MHCI, MHCII, or MHC activator. Non-limiting examples of guide RNAs (gRNAs) for targeting and deleting MHC activators are disclosed in PCT Application No. PCT/US2019/049816.

A detailed description of non-naturally occurring chimeric stimulatory receptors, genetic modifications of endogenous sequences encoding TCR-alpha (TCR-α), TCR-beta (TCR-δ), and/or Beta-2-Microglobulin (p2M), and non-naturally occurring polypeptides comprising an HLA class I histocompatibility antigen, alpha chain E (HLA-E) polypeptide is disclosed in PCT Application No. PCT/US2019/049816.

Formulations, Dosages and Modes of Administration

The present disclosure provides formulations, dosages and methods for administration of the compositions described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the composition as well known in the art or as described herein.

For example, the disclosed LNP compositions of the present invention can further comprise a diluent. In some compositions, the diluent can be phosphate buffered saline ("PBS").

Non-limiting examples of pharmaceutical excipients and additives suitable for use include proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

The compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers are organic acid salts, such as citrate.

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intravesical, oral, parenteral, rectal, sublingual, subcutaneous, transdermal or vaginal means.

A composition of the disclosure can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994,), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

For parenteral administration, any composition disclosed herein can be formulated as a solution, suspension, emulsion, particle, powder, or lyophilized powder in association, or separately provided, with a pharmaceutically acceptable parenteral vehicle. Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

For pulmonary administration, preferably, a composition or pharmaceutical composition described herein is delivered in a particle size effective for reaching the lower airways of the lung or sinuses. The composition or pharmaceutical composition can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers (e.g., jet nebulizer, ultrasonic nebulizer), dry powder generators, sprayers, and the like. All such devices can use formulations suitable for the administration for the dispensing of a composition or pharmaceutical composition described herein in an aerosol. Such aerosols can be comprised of either solutions (both aqueous and non-aqueous) or solid particles. Additionally, a spray including a composition or pharmaceutical composition described herein can be produced by forcing a suspension or solution of at least one protein scaffold through a nozzle under pressure. In a metered dose inhaler (MDI), a propellant, a composition or pharmaceutical composition described herein, and any excipients or other additives are contained in a canister as a mixture including a liquefied compressed gas.

Actuation of the metering valve releases the mixture as an aerosol. A more detailed description of pulmonary administration, formulations and related devices is disclosed in PCT Publication No. WO 2019/049816.

For absorption through mucosal surfaces, compositions include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the disclosure can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695). A more detailed description of mucosal administration and formulations is disclosed in PCT Publication No. WO 2019/049816.

For transdermal administration, a composition or pharmaceutical composition disclosed herein is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599). A more detailed description of transdermal administration, formulations and suitable devices is disclosed in PCT Publication No. WO 2019/049816.

It can be desirable to deliver the disclosed compounds to the subject over prolonged periods of time, for example, for periods of one week to one year from a single administration. Various slow release, depot or implant dosage forms can be utilized.

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J. Preferred doses can optionally include about 0.1-99 and/or 100-500 mg/kg/administration, or any range, value or fraction thereof, or to achieve a serum concentration of about 0.1-5000 μg/ml serum concentration per single or multiple administration, or any range, value or fraction thereof. A preferred dosage range for the compositions or pharmaceutical compositions disclosed herein is from about 1 mg/kg, up to about 3, about 6 or about 12 mg/kg of body weight of the subject.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired.

As a non-limiting example, treatment of humans or animals can be provided as a one-time or periodic dosage of the compositions or pharmaceutical compositions disclosed herein about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

In aspects where the compositions to be administered to a subject in need thereof are modified cells as disclosed herein, the cells can be administered between about $1\times10^3$ and $1\times10^{15}$ cells; $1\times10^3$ and $1\times10^{15}$ cells, about $1\times10^4$ and $1\times10^{12}$ cells; about $1\times10^5$ and $1\times10^{10}$ cells; about $1\times10^6$ and $1\times10^9$ cells; about $1\times10^6$ and $1\times10^8$ cells; about $1\times10^6$ and $1\times10^7$ cells; or about $1\times10^6$ and $25\times10^6$ cells. In an aspect the cells are administered between about $5\times10^6$ and $25\times10^6$ cells.

A more detailed description of pharmaceutically acceptable excipients, formulations, dosages and methods of administration of the disclosed compositions and pharmaceutical compositions is disclosed in PCT Publication No. WO 2019/04981.

The disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In an aspect, the subject is a mammal. Preferably, the subject is human. The terms "subject" and "patient" are used interchangeably herein.

The disclosure provides a method for modulating or treating at least one malignant disease or disorder in a cell, tissue, organ, animal or subject. Preferably, the malignant disease is cancer. Non-limiting examples of a malignant disease or disorder include leukemia, acute leukemia, acute lymphoblastic leukemia (ALL), acute lymphocytic leukemia, B-cell, T-cell or FAB ALL, acute myeloid leukemia (AML), acute myelogenous leukemia, chronic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

In preferred aspects, the treatment of a malignant disease or disorder comprises adoptive cell therapy. For example, in an aspect, the disclosure provides modified cells that express at least one disclosed protein scaffold and/or CAR comprising a protein scaffold (e.g., scFv, single domain antibody, Centyrin, delivered to the cell with a composition of the disclosure) that have been selected and/or expanded for administration to a subject in need thereof. Modified cells can be formulated for storage at any temperature including room temperature and body temperature. Modified cells can be formulated for cryopreservation and subsequent thawing. Modified cells can be formulated in a pharmaceutically acceptable carrier for direct administration to a subject from sterile packaging. Modified cells can be formulated in a pharmaceutically acceptable carrier with an indicator of cell viability and/or CAR expression level to ensure a minimal level of cell function and CAR expression. Modified cells can be formulated in a pharmaceutically acceptable carrier at a prescribed density with one or more reagents to inhibit further expansion and/or prevent cell death.

Any can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one chemotherapeutic agent (e.g., an alkylating agent, an a mitotic inhibitor, a radiopharmaceutical).

In some aspects, the subject does not develop graft vs. host (GvH) and/or host vs. graft (HvG) following administration. In an aspect, the administration is systemic. Systemic administration can be any means known in the art and described in detail herein. Preferably, systemic administration is by an intravenous injection or an intravenous infusion. In an aspect, the administration is local. Local administration can be any means known in the art and described in detail herein. Preferably, local administration is by intratumoral injection or infusion, intraspinal injection or infusion, intracerebroventricular injection or infusion, intraocular injection or infusion, or intraosseous injection or infusion.

In some aspects, the therapeutically effective dose is a single dose. In some aspects, the single dose is one of at least 2, 5, 10, 15, 20, 25, 30, 35, 40, 45, 50, 55, 60, 65, 70, 75, 80, 85, 90, 95, 100 or any number of doses in between that are manufactured simultaneously. In some aspects, where the composition is autologous cells or allogeneic cells, the dose is an amount sufficient for the cells to engraft and/or persist for a sufficient time to treat the disease or disorder.

In one example, the disclosure provides a method of treating cancer in a subject in need thereof, comprising administering to the subject a composition comprising a protein scaffold or a CAR comprising a protein scaffold (e.g., e.g., scFv, single domain antibody, Centyrin) the antibody or CAR specifically binds to an antigen on a tumor cell. In aspects where the composition comprises a modified cell or cell population, the cell or cell population may be autologous or allogeneic.

In some aspects of the methods of treatment described herein, the treatment can be modified or terminated. Specifically, in aspects where the composition used for treatment comprises an inducible proapoptotic polypeptide, apoptosis may be selectively induced in the cell by contacting the cell with an induction agent. A treatment may be modified or terminated in response to, for example, a sign of recovery or a sign of decreasing disease severity/progression, a sign of disease remission/cessation, and/or the occurrence of an adverse event. In some aspects, the method comprises the step of administering an inhibitor of the induction agent to inhibit modification of the cell therapy, thereby restoring the function and/or efficacy of the cell therapy (for example, when a sign or symptom of the disease reappear or increase in severity and/or an adverse event is resolved).

Protein Scaffold Production, Screening and Purification

At least one protein scaffold (e.g., monoclonal antibody, a chimeric antibody, a single domain antibody, a VHH, a VH, a single chain variable fragment (scFv), a Centyrin, an antigen-binding fragment (Fab) or a Fab fragment) of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino acids from a protein scaffold can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, a protein scaffold can be engineered with retention of high affinity for the antigen and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif). Inspection of these displays permits analysis of the likely role of the residues in the functioning of the candidate sequence, i.e., the analysis of residues that influence the ability of the candidate protein scaffold to bind its antigen. In this way, residues can be selected and combined from the parent and reference sequences so that the desired characteristic, such as affinity for the target antigen (s), is achieved. Alternatively, or in addition to, the above procedures, other suitable methods of engineering can be used.

Screening of a protein scaffold for specific binding to similar proteins or fragments can be conveniently achieved using nucleotide (DNA or RNA display) or peptide display libraries, for example, in vitro display. This method involves the screening of large collections of peptides for individual members having the desired function or structure. The displayed nucleotide or peptide sequences can be from 3 to 5000 or more nucleotides or amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. WO 91/17271, WO 91/18980, WO 91/19818, and WO 93/08278.

Other systems for generating libraries of peptides have aspects of both in vitro chemical synthesis and recombinant methods. See, PCT Patent Publication Nos. WO 92/05258, WO 92/14843, and WO 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge Antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra.

A protein scaffold of the disclosure can bind human or other mammalian proteins with a wide range of affinities (KD). In a preferred aspect, at least one protein scaffold of the present disclosure can optionally bind to a target protein with high affinity, for example, with a KD equal to or less than about $10^{-7}$ M, such as but not limited to, 0.1-9.9 (or any range or value therein)$\times10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art.

The affinity or avidity of a protein scaffold for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular protein scaffold-antigen interaction can vary if measured under different conditions (e.g., salt concentration, pH). Thus, measurements of affinity and other antigen-binding parameters (e.g., KD, Kon, Koff) are preferably made with standardized solutions of protein scaffold and antigen, and a standardized buffer, such as the buffer described herein.

Competitive assays can be performed with a protein scaffold in order to determine what proteins, antibodies, and other antagonists compete for binding to a target protein with the protein scaffold and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to the target protein is separated from the unbound sample, for example, by decanting (where the protein/antibody was pre-insolubilized) or by centrifuging (where the protein/antibody was precipitated after the competitive reaction). Also, the competitive binding may be determined by whether function is altered by the binding or lack of binding of the protein scaffold to the target protein, e.g., whether the protein scaffold inhibits or potentiates the enzymatic activity of, for example, a label. ELISA and other functional assays may be used, as well known in the art.

Nucleic Acid Molecules

Nucleic acid molecules of the disclosure encoding a protein scaffold can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one protein scaffold; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold as described herein and/or as known in the art. Of course, the genetic code is well known in the art. Thus, it would be routine for one skilled in the art to generate such degenerate nucleic acid variants that code for a specific protein scaffold of the present disclosure. See, e.g., Ausubel, et al., supra, and such nucleic acid variants are included in the present disclosure.

As indicated herein, nucleic acid molecules of the disclosure which comprise a nucleic acid molecule encoding a protein scaffold can include, but are not limited to, those encoding the amino acid sequence of a protein scaffold fragment, by itself, the coding sequence for the entire protein scaffold or a portion thereof; the coding sequence for a protein scaffold, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold can be fused to a marker sequence, such as a sequence encoding a peptide that facilitates purification of the fused protein scaffold comprising a protein scaffold fragment or portion.

Polynucleotides Selectively Hybridizing to a Polynucleotide as Described Herein

The disclosure provides isolated nucleic acids that hybridize under selective hybridization conditions to a polynucleotide disclosed herein. Thus, the polynucleotides can be used for isolating, detecting, and/or quantifying nucleic acids comprising such polynucleotides. For example, polynucleotides of the present disclosure can be used to identify, isolate, or amplify partial or full-length clones in a deposited library. The polynucleotides can be genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of a protein scaffold encoded by the polynucleotides described herein. The polynucleotides embrace nucleic acid sequences that can be employed for selective hybridization to a polynucleotide encoding a protein scaffold of the present disclosure. See, e.g., Ausubel, supra; Colligan, supra, each entirely incorporated herein by reference.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise sequences in addition to a polynucleotide of the present disclosure. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some aspects, oligonucleotide probes that selectively hybridize, under stringent conditions, to the polynucleotides of the present disclosure are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the disclosure can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid of the disclosure. A nucleic acid sequence of the disclosure, for example, a cDNA or a genomic sequence encoding a protein scaffold of the disclosure, can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some aspects, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Expression Vectors and Host Cells

The disclosure also relates to vectors that include isolated nucleic acid molecules of the disclosure, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), DIFR (encoding Dihydrofolate Reductase and conferring resistance to Methotrexate), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one protein scaffold of the disclosure can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid molecule encoding a protein of the disclosure. Alternatively, nucleic acids of the disclosure can be expressed in a host cell by turning on (by manipulation) in a host cell that contains endogenous DNA encoding a protein scaffold of the disclosure. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a preferred aspect, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present disclosure are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Protein Scaffold Purification

A protein scaffold can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

A protein scaffold of the disclosure include purified products, products of chemical synthetic procedures, and products produced by recombinant techniques from a prokaryotic or eukaryotic host, including, for example, *E. coli*, yeast, higher plant, insect and mammalian cells. Depending upon the host employed in a recombinant production procedure, the protein scaffold of the disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Amino Acid Codes

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the disclosure can include one or more amino acid substitutions, deletions or additions, from spontaneous or mutations and/or human manipulation, as specified herein. Amino acids in a protein scaffold of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

As those of skill will appreciate, the disclosure includes at least one biologically active protein scaffold of the disclosure. Biologically active protein scaffolds have a specific activity at least 20%, 30%, or 40%, and, preferably, at least 50%, 60%, or 70%, and, most preferably, at least 80%, 90%, or 95%-99% or more of the specific activity of the native (non-synthetic), endogenous or related and known protein scaffold. Methods of assaying and quantifying measures of enzymatic activity and substrate specificity are well known to those of skill in the art.

In another aspect, the disclosure relates to protein scaffolds and fragments, as described herein, which are modified by the covalent attachment of an organic moiety. Such modification can produce a protein scaffold fragment with improved pharmacokinetic properties (e.g., increased in vivo serum half-life). The organic moiety can be a linear or branched hydrophilic polymeric group, fatty acid group, or fatty acid ester group. In particular aspect, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified protein scaffolds and fragments of the disclosure can comprise one or more organic moieties that are covalently bonded, directly or indirectly, to the antibody. Each organic moiety that is bonded to a protein scaffold or fragment of the disclosure can independently be a hydrophilic polymeric group, a fatty acid group or a fatty acid ester group. As used herein, the term “fatty acid” encompasses mono-carboxylic acids and di-carboxylic acids. A “hydrophilic polymeric group,” as the term is used herein, refers to an organic polymer that is more soluble in water than in octane. For example, polylysine is more soluble in water than in octane. Thus, a protein scaffold modified by the covalent attachment of polylysine is encompassed by the disclosure. Hydrophilic polymers suitable for modifying protein scaffolds of the disclosure can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the protein scaffold of the disclosure has a molecular weight of about 800 to about 150,000 Daltons as a separate molecular entity. For example, PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying protein scaffolds of the disclosure can be saturated or can contain one or more units of unsaturation. Fatty acids that are suitable for modifying protein scaffolds of the disclosure include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-A9-octadecanoate (C18, oleate), all cis-A5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified protein scaffolds and fragments can be prepared using suitable methods, such as by reaction with one or more modifying agents. A “modifying agent” as the term is used herein, refers to a suitable organic group (e.g., hydrophilic polymer, a fatty acid, a fatty acid ester) that comprises an activating group. An “activating group” is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —(CH2)3-, —NH—(CH2)6-NH—, —(CH2)2-NH— and —CH2-O-CH2-CH2-O-CH2-CH2O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified protein scaffolds of the disclosure can be produced by reacting a protein scaffold or fragment with a modifying agent. For example, the organic moieties can be bonded to the protein scaffold in a non-site specific manner by employing an amine-reactive modifying agent, for example, an NHS ester of PEG. Modified protein scaffolds and fragments comprising an organic moiety that is bonded to specific sites of a protein scaffold of the disclosure can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "alkyl" refers to straight and, when applicable, branched chain aliphatic groups having from 1 to 12 carbon atoms, As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. For instance, a $C_1$-$C_6$ alkyl group includes alkyl groups having 1 to 6 carbons. Examples of alkyl groups include, without limitation, methyl, ethyl, propyl, isopropyl, butyl, isobutyl, sec-butyl, tert-butyl, pentyl, and hexyl.

As used herein, the term "alkylene" is an alkyl, as defined hereinabove, that is positioned between and serves to connect two other chemical groups. Examples of alkylene groups include, without limitation, methylene, ethylene, propylene, butylene, pentylene and hexylene.

As used herein, the term "alkenyl" refers to an unsaturated straight or, when applicable, branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

As used herein, the term "aralkyl" group comprises an aryl group covalently linked to an alkyl group, either of which may independently be optionally substituted or unsubstituted.

An example of an aralkyl group is —($C_1$-$C_6$)alkyl($C_6$-$C_{10}$)aryl, including, without limitation, benzyl, phenethyl, and naphthylmethyl.

As used herein, the term "aryl" group is a $C_6$-$C_{14}$ aromatic moiety comprising one to three aromatic rings, which is optionally substituted. As such, "aryl" includes $C_6$, $C_7$, $C_8$, $C_9$, $C_{10}$, $C_{11}$, $C_{12}$ $C_{13}$, and $C_{14}$ cyclic hydrocarbon groups. An exemplary aryl group is a C.sub.6-C.sub.10 aryl group. Particular aryl groups include, without limitation, phenyl, naphthyl, anthracenyl, and fluorenyl.

As used herein, the term "C2-C100 hydrocarbon chain" refers to straight or branched chain, saturated or unsaturated comprising 2 to 100 carbon atoms. Examples of C2-C100 hydrocarbon chains groups include methyl, ethyl, propyl, isopropyl, butyl, isobutyl, sec-butyl, tert-butyl, pentyl, hexyl, heptanyl, octanyl, nonanyl, decanyl, undecanyl, dodecanyl, tridecanyl, icosanyl, triacontanyl, and tetracontanyl, and unsaturated counterparts thereof, e.g., propenyl and propynyl.

As used herein, the term "cycloalkyl" as employed herein includes saturated and partially unsaturated cyclic hydrocarbon groups having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Representative cycloalkyl groups include, without limitation, cyclopropyl, cyclobutyl, cyclopentyl, cyclopentenyl, cyclohexyl, cyclohexenyl, cycloheptyl, and cyclooctyl.

As used herein, the term "hydroxyalkyl" refers to -alkyl-OH or an alkyl chain substituted with at least one —OH.

As used herein, the term "halo" or "halogen" refers to fluoro, chloro, bromo and iodo.

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

It will be understood that in any of the Formulae described herein, when a "-" is used to indicate linkage between two variables (e.g., A-B), the linkage could be one or more covalent bonds. For example, in Formula (I) below, the adjacent variables A and B could be linked by one covalent bond, or by more than one (e.g., two) covalent bonds.

(I)

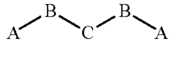

For another example, when variable A is presented as a moiety having two attachment points (e.g.,

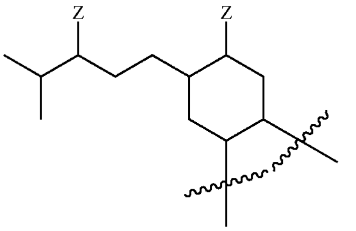

or

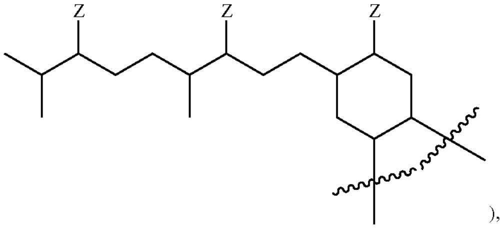

), both of the two attachment points in the variable A could be attached to its adjacent variable B (e.g., when

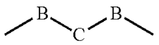

together form

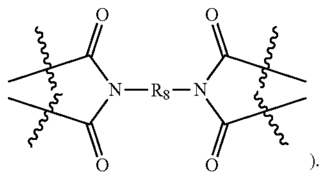

).

The disclosure provides isolated or substantially purified polynucleotide or protein compositions. An “isolated” or “purified” polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an “isolated” polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term “fragment” refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term “antibody” is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as “analogs”) of the antibodies hereof as defined herein. Thus, according to an aspect hereof, the term “antibody hereof” in its broadest sense also covers such analogs. Generally, in such analogs, one or more amino acid residues may have been replaced, deleted and/or added, compared to the antibodies hereof as defined herein.

“Antibody fragment”, and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a “single-chain antibody fragment” or “single chain polypeptide”), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g., CHI in the IgG isotype)

found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Aspects defined by each of these transition terms are within the scope of this disclosure.

The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A method for directing proteins to a specific locus in a genome of an organism is disclosed. The method may comprise the steps of providing a DNA localization component and providing an effector molecule, wherein the DNA localization component and the effector molecule are capable of operatively linking via a non-covalent linkage.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In some aspects, a specific binding interaction will discriminate between desirable and undesirable antigens in a sample. In some aspects, more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

A "target site" or "target sequence" is a nucleic acid sequence that defines a portion of a nucleic acid to which a binding molecule will bind, provided sufficient conditions for binding exist.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Probes of the disclosure may comprise a single stranded nucleic acid that can hybridize to a target sequence under stringent hybridization conditions. Thus, nucleic acids of the disclosure may refer to a probe that hybridizes under stringent hybridization conditions.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, EF-1 Alpha promoter, CAG promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. A vector may comprise a combination of an amino acid with a DNA sequence, an RNA sequence, or both a DNA and an RNA sequence.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In an aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some aspects, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table 1.

TABLE 1

| Conservative Substitutions I | | |
|---|---|---|
| Side chain characteristics | | Amino Acid |
| Aliphatic | Non-polar | G A P I L V F |
| | Polar-uncharged | C S T M N Q |
| | Polar-charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table 2.

TABLE 2

| Conservative Substitutions II | | |
|---|---|---|
| Side Chain Characteristic | | Amino Acid |
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table 3.

TABLE 3

| Conservative Substitutions III | |
|---|---|
| Original Residue | Exemplary Substitution |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the cell the polynucleotide construct in such a manner that the construct gains access to the interior of the host cell. The methods of the disclosure do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

Example 1 Preparation of Multivalent Bolaform Amphiphilic Compositions by Photochemical Thiol-Ene Reaction

COMPOUND 1

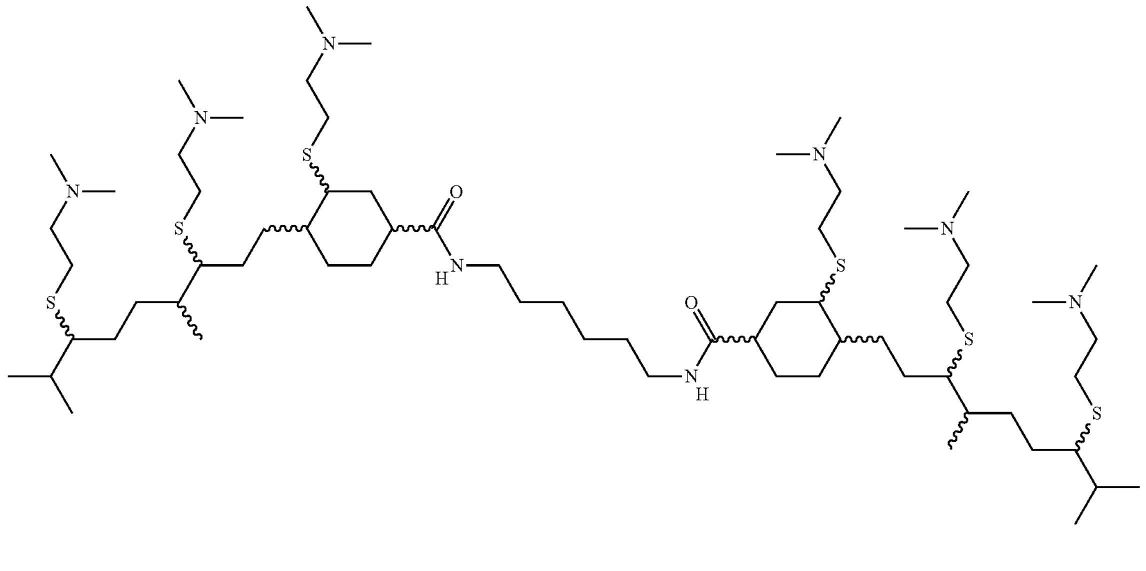

This compound was prepared two separate ways.

Synthesis 1 a. Preparation of Methyl Ester Diels-Alder Adduct from Trans-β-Farnesene and Methyl Acrylate To a 20 mL sealable vessel was added trans-β-farnesene (1.00 g, 4.89 mmol), 0.5 wt % (relative to farnesene) p-methoxyphenol (0.005 g, 0.02 mmol), methyl acrylate (0.42 g, 4.98 mmol), and a stir bar. The mixture was heated at 130° C. for 4 h and then cooled to room temperature. The resulting oil was chromatographed on silica gel (95:5 hexanes/ethyl acetate) to give a colorless oil. The isolated product was a mixture of both meta- and para-Diels-Alder regioisomers (0.78 g, 55% yield). $C_{19}H_{30}O_2$ $^1$H NMR (500 MHz, CDCl3) δ: 5.40 (s, CHCR2, 1H), 5.10 (s, CHCR2, 2H), 3.69 (s, C(O)OCH3, 3H), 2.51 (m, CHR2, 1H), 2.24 (m, aliphatic, 1H), 2.02 (m, aliphatic, 12H), 1.68 (s, CH3, 3H), 1.60 (s, (CH3)2, 6H). 13C NMR (500 MHz, CDCl3) δ:176.4 (C(O)OCH3), 137.4, 136.0, 135.1, 131.2, 124.4, 124.0, 120.3, 118.9, 51.5 (C(O)OCH3), 47.5, 39.8, 39.7, 39.4, 37.7, 37.5, 30.7, 27.7, 26.7, 26.3, 25.7, 25.6, 25.1, 24.6.

b. Preparation of Multivalent Cationic Bolaform Amphiphile Precursor

The Diels-Alder adduct of methyl acrylate and trans-ß-farnesene (10 g, 34 mmol) was added to an 8 mL vessel along with hexamethylenediamine (1.34 g, 11.5 mmol) and a stir bar. The reaction was heated to 130° C. and TBD (0.96 g, 6.9 mmol) was added. Heating was continued overnight. Upon cooling, the reaction solidified into a tan solid. The solid was washed rigorously with hexanes and water and before isolating by filtration (7.28 g, 99% isolated yield). $C_{42}H_{68}N_2O_2$. $C_{42}H_{68}N_2O_2$.

$^1$H NMR (500 MHz, CDCl3) δ: 5.80 (s, —NHR2, 2H) 5.39 (s, —CH═CR$_2$, 2H), 5.09 (s, —CH═CR$_2$, 4H), 3.23 (s, —CH$_2$—NHR, 4H), 2.64 (s, —CO—CHR$_2$, 2H), 2.19 (m, aliphatic, 24H), 1.67 (s, —CH$_3$, 6H), 1.59 (s, —(CH$_3$)$_2$, 12H), 1.49 (s, —NCH—CH$_2$R, 4H), 1.32 (s, —CH$_2$—CH$_2$R, 4H).

c. Preparation of Multivalent Cationic Bolaform Amphiphilic Compound of Formula (I) Using a Photochemical Thiol-Ene Reaction In a 4 mL sealable vessel, 2-(dimethylamino)ethanthiol hydrochloride (453 mg, 3.2 mmol) was dissolved in 0.12 mL methanol and 1.88 mL chloroform. Compound from step b above (200 mg, 0.32 mmol) was added along with 20 mol % 2,4-diethyl-9H-thioxanthen-9-one relative to the thiol (172 mg, 0.64 mmol) along with a stir bar. The solution was stirred at room temperature and irradiated using two 370 nm light emitting diodes from 5 cm away for 4 hours. The chloroform-methanol solution was removed by rotary evaporation and the resulting yellow solid was washed using three portions of ethyl acetate. The washed solid was redissolved in 6 mL water, placed in 100-500 D molecular weight cut off cellulose ester tubing and dialyzed against deionized water. The water was changed twice in the first 8 hours before being left overnight. The final product was isolated by lyophilization as a light yellow solid (220 mg). $C_{66}H_{134}N_8O_2S_6$ $^1$H NMR (500 MHz, d$_6$-DMSO) δ: 3.16 (s (br)), 2.99 (br), 2.73 (s), 2.22-1.18 (m (br)), 0.95 (s), 0.89 (s).

Synthesis 2

First, bola base was prepared according to Protocol A. The bola base has the following structure:

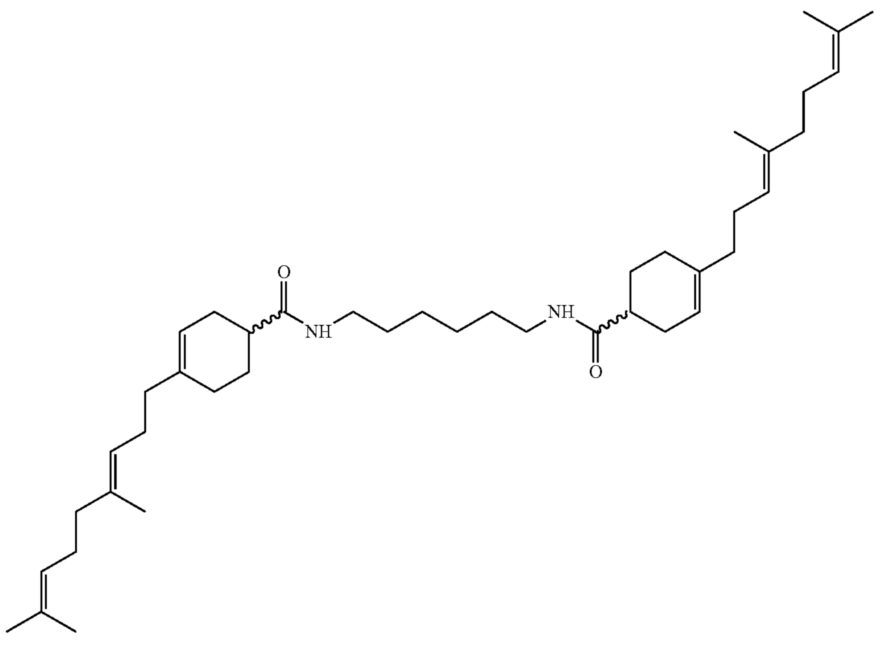 [SMILES: CC(C)=CCC/C(C)=C/CCC1=CCC(C(=O)NCCCCCCNC(=O)C2CC=C(CC/C=C(\C)CCC=C(C)C)CC2)CC1]

The results were:

74% yield, off-white solid. 1H NMR (400 MHz, CDCl3) δ 5.91 (p, J=6.5, 5.7 Hz, 2H), 5.43-5.32 (m, 2H), 5.16-4.98 (m, 4H), 3.27-3.16 (m, 4H), 2.39-1.78 (m, 28H), 1.74-1.53 (m, 18H), 1.48 (d, J=7.7 Hz, 5H), 1.30 (tt, J=7.7, 3.8 Hz, 5H). 13C NMR (101 MHz, CDCl3) δ 176.25, 176.24, 137.61, 136.30, 135.24, 135.21, 131.38, 124.37, 124.08, 124.05, 120.35, 119.10, 41.96, 41.49, 39.79, 38.87, 38.84, 37.82, 37.62, 31.43, 29.60, 29.59, 28.46, 27.92, 26.79, 26.36, 26.29, 26.00, 25.98, 25.96, 25.80, 24.83, 17.79, 16.12, 16.09.

Then, Protocol B was followed. The results were:

1H NMR (500 MHz, DMSO-d6) δ 3.38-3.30 (m, 8H), 3.24-3.10 (m, 22H), 2.86-2.70 (m, 62H), 1.94-1.84 (m, 2H), 1.78-1.54 (m, 8H), 1.41-1.14 (m, 16H), 1.00-0.57 (m, 18H).

COMPOUND 2

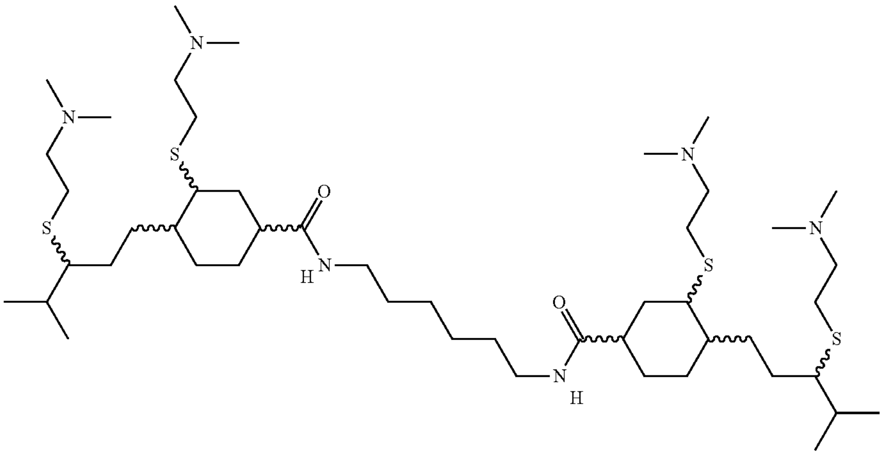

Compound 2 was prepared in the exact same manner as Compound 1 except the initial (step a) Diels-Alder reaction was conducted with beta-myrcene instead of trans-beta-farnesene. Molar ratios and reaction conditions for step b (transamidation) and step c (photochemical thiolation) were identical to that of Compound 1. $C_{48}H_{96}N_6O_2S_4$.

$^{1}H$ NMR (500 MHz, $d_6$-DMSO) δ: 3.37 (m), 3.18 (m (br)), 2.99 (br), 2.85 (br), 2.77 (s), 2.74 (m (br)), 2.03-1.16 (m (br)), 0.94 (s), 0.88 (s).

COMPOUND 3

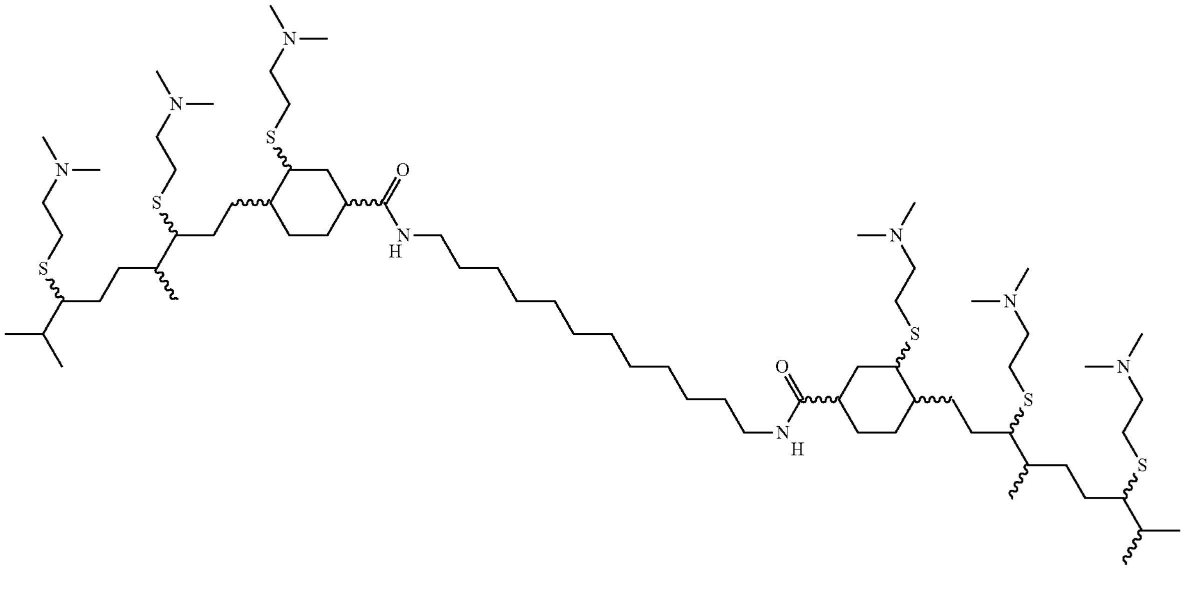

This compound was prepared two separate ways.

Synthesis 1

Compound 3 was prepared in the exact same manner as Compound 1 except 1,12-daminododecane was substituted for hexamethylenediamine. Molar ratios and reaction conditions for Compound 3's three step synthetic sequence were identical to that of Compound 1. $C_{72}H_{146}N_8O_2S_6$.

$^1$H NMR (500 MHz, $d_6$-DMSO) δ: 3.25 (m), 3.16 (m (br)), 3.00 (br), 2.85 (br), 2.69 (s), 2.21-1.32 (m (br)), 1.22 (m (br)), 0.94 (s), 0.88 (s).

Synthesis 2

First, bola base was prepared according to Protocol A. The bola base had the following structure:

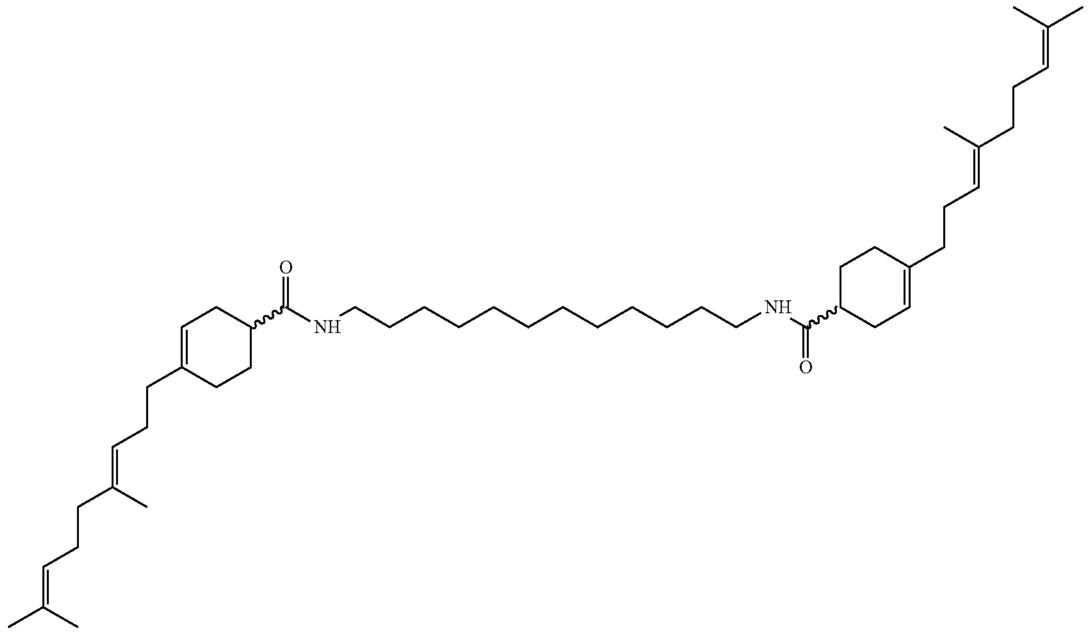 [SMILES: CC(C)=CCC/C(C)=C/CCC1=CCC(C(=O)NCCCCCCCCCCCCNC(=O)C2CC=C(CC/C=C(\C)CCC=C(C)C)CC2)CC1]

The results were:

75% yield, off-white solid. 1H NMR (500 MHz, CDCl3) δ 5.66 (s, 2H), 5.39 (s, 2H), 5.13-5.02 (m, 4H), 3.27-3.18 (m, 4H), 2.38-2.13 (m, 6H), 2.12-1.80 (m, 23H), 1.77-1.65 (m, 8H), 1.63-1.56 (m, 11H), 1.52-1.42 (m, 4H), 1.34-1.20 (m, 16H). 13C NMR (126 MHz, CDCl3) δ 175.99, 137.73, 136.35, 135.29, 135.25, 131.41, 124.40, 124.10, 124.07, 120.45, 119.13, 42.03, 41.53, 39.82, 39.53, 39.50, 37.84, 37.64, 31.46, 29.78, 29.59, 29.37, 28.48, 27.91, 26.99, 26.82, 26.37, 26.33, 26.29, 25.96, 25.83, 24.83, 17.81, 16.15, 16.12.

Then, Protocol B was followed. The results were:

1H NMR (500 MHz, DMSO-d6) δ 3.25-3.06 (m, 14H), 3.03-2.79 (m, 15H), 2.78-2.64 (m, 38H), 1.97-1.46 (m, 23H), 1.42-1.06 (m, 38H), 1.02-0.64 (m, 18H).

COMPOUND 4

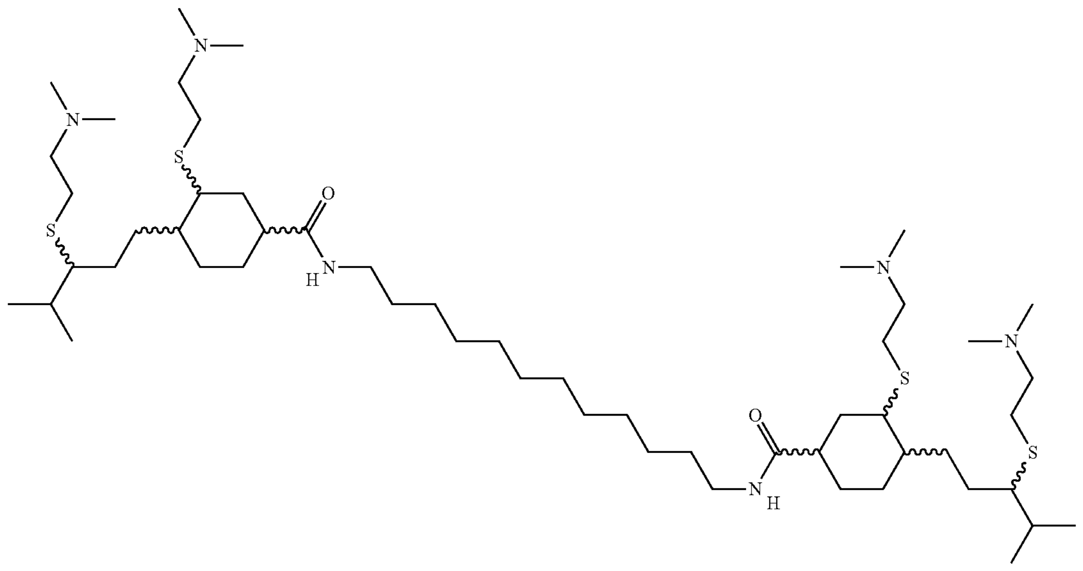

Compound 4 was prepared in the exact same manner as Compound 1 except beta-myrcene was used in the initial Diels-Alder reaction (step a) instead of trans-beta-farnesene and 1,12-daminododecane was substituted for hexamethylenediamine (step b). Molar ratios and reaction conditions for steps a-c were identical to that of Compound 1. $C_{48}H_{96}N_6O_2S_4$.

$^1H$ NMR (500 MHz, $d_6$-DMSO) δ: 3.18 (m (br)), 2.99 (br), 2.85 (br), 2.77 (s), 2.74 (m (br)), 2.03-1.16 (m (br)), 0.94 (s), 0.88 (s).

COMPOUND 5

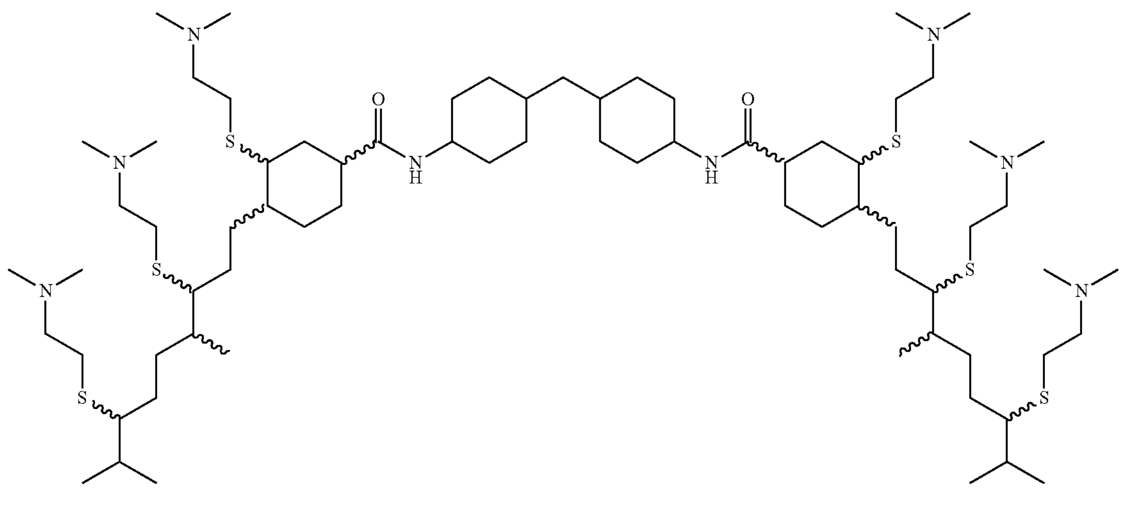

Compound 5 was prepared in the exact same manner as Compound 1 except 4,4'-methylenebis(cyclohexylamine) was substituted for hexamethylenediamine. Molar ratios and reaction conditions for Compound 5's three step synthetic sequence were identical to that of Compound 1. $C_{73}H_{144}N_8O_2S_6$.

$^1H$ NMR (500 MHz, $d_6$-DMSO) δ: 3.40-3.33 (m(br)), 3.18 (m), 2.77 (s), 1.91 (br), 1.71-1.55 (m (br)), 1.33-0.85 (m(br)).

COMPOUND 6

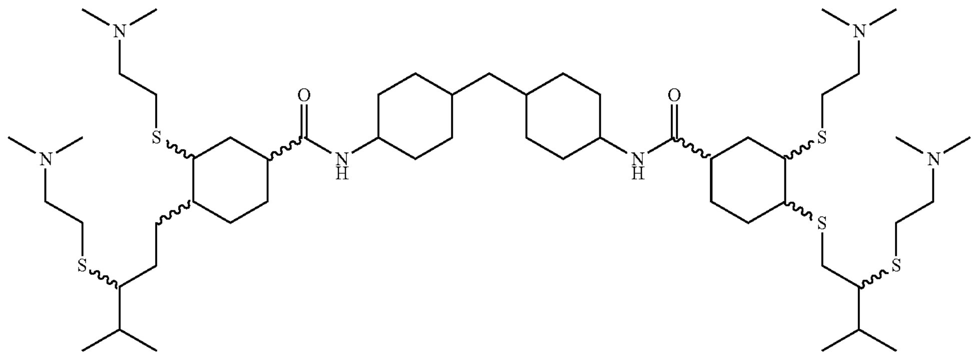

Compound 6 was prepared in the exact same manner as Compound 1 except beta-myrcene was used in the initial Diels-Alder reaction (step a) instead of trans-beta-farnesene and 4,4'-methylenebis(cyclohexylamine) was substituted for hexamethylenediamine (step b). Molar ratios and reaction conditions for steps a-c were identical to that of Compound 1. $C_{55}H_{106}N_6O_2S_4$.

$^1H$ NMR (500 MHz, $d_6$-DMSO) δ: 3.58-3.26 (m (br)), 3.25 (m), 3.01 (m), 2.86 (m), 2.68 (s), 2.19-0.84 (m (br)).

COMPOUND 7

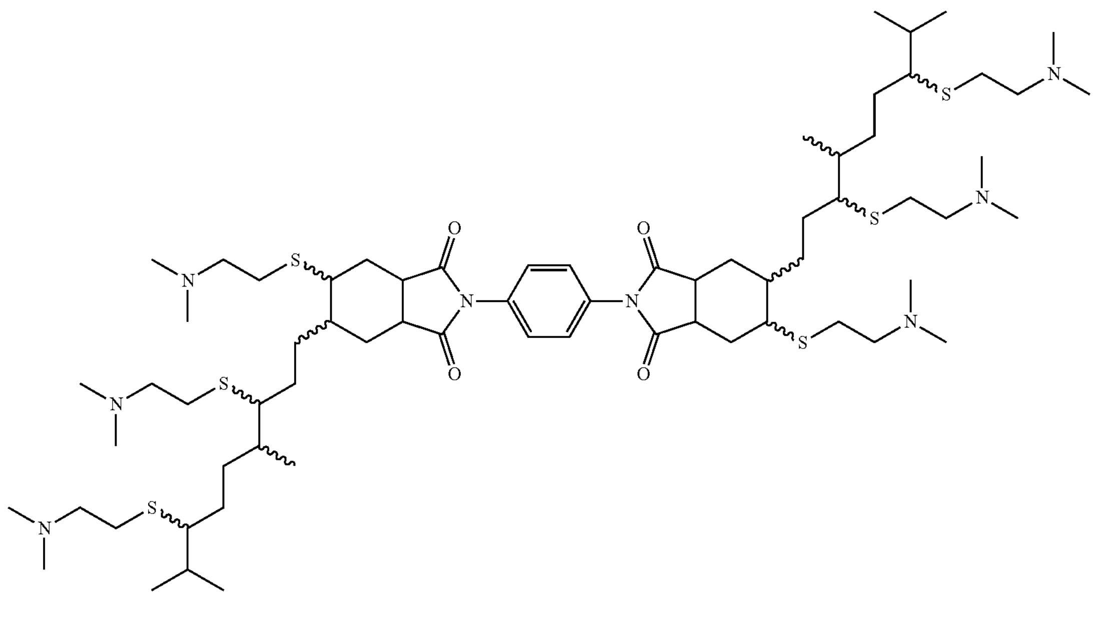

Step a. Preparation of Bolaamphiphilic Precursor Via Diels-Alder Reaction of Trans-beta-farnesene and N,N'-(1,4-Phenylene)dimaleimide.

Trans-beta-farnesene (3 molar equivalents) was added to a heavy walled vial along with N,N'-(1,4-phenylene)dimaleimide (1 molar equivalent). The vial was sealed and heated to 130° C. After 30 minutes the reaction solidified yielding the crude product. The crude solid was removed from the reaction vessel, suspended in hexanes, and stirred. The mixture was centrifuged and the hexane supernatant decanted away from the product. The product was dried in a vacuum oven at 40° C.

Step b. Preparation of Multivalent Cationic Bolaamphiphilic Compound of Formula (I) Using a Photochemical Thiol-Ene Reaction.

In a 4 mL sealable vessel, 2-(dimethylamino)ethanthiol hydrochloride (198 mg, 1.4 mmol) was dissolved in 0.06 mL methanol and 0.94 mL chloroform. Compound from step a above (100 mg, 0.14 mmol) was added along with 20 mol % 2,4-diethyl-9H-thioxanthen-9-one relative to the thiol along with a stir bar. The solution was stirred at room temperature and irradiated using two 370 nm light emitting diodes from 5 cm away overnight. The chloroform-methanol solution was removed by rotary evaporation and the resulting yellow solid was washed using three portions of ethyl acetate. The washed solid was redissolved in water, placed in 100-500 D molecular weight cut off cellulose ester tubing and dialyzed against deionized water. The water was changed twice in the first 8 hours before being left overnight. The final product was isolated by lyophilization (37 mg). $C_{68}H_{122}N_8O_4S_6$.

$^1H$ NMR (500 MHz, $d_6$-DMSO) 7.30 (br), 3.24 (m), 3.16 (m), 2.82 (br), 2.69 (s), 2.00-1.55 (m (br)), 1.19 (br), 0.94 (s), 0.88 (s).

COMPOUND 8

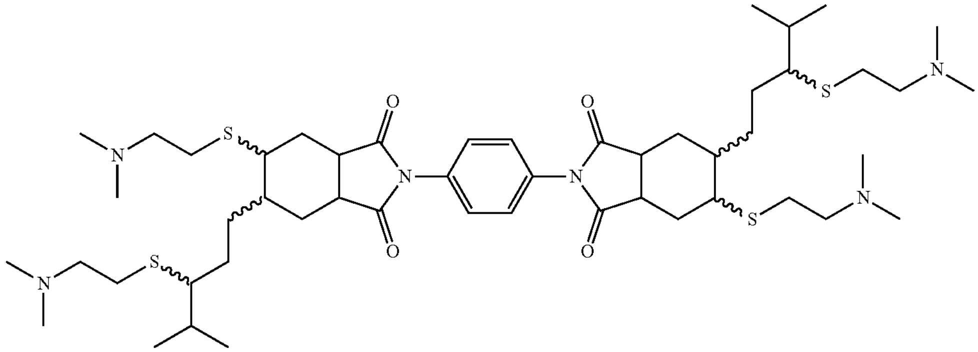

Compound 8 was prepared in the exact same manner as Compound 7 except beta-myrcene was used in the initial Diels-Alder reaction (step a) instead of trans-beta-farnesene. Molar ratios and reaction conditions for steps a-b were identical to that of Compound 7. $C_{50}H_{84}N_6O_4S_6$.

$^1H$ NMR (500 MHz, $d_6$-DMSO) 7.28 (br), 3.31 (m), 3.14-3.07 (m), 2.77 (br), 2.62 (s), 2.24-1.84 (m (br)), 1.18 (br), 0.86 (m).

COMPOUND 9

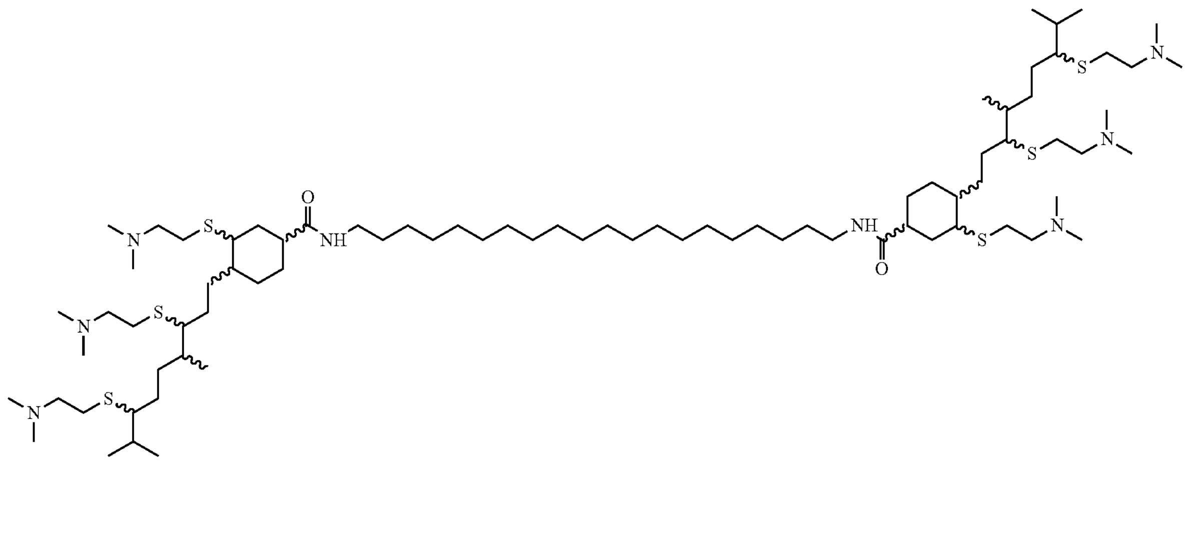

This compound can be prepared by following Protocol A for bola base preparation, to yield bola base of the following structure:
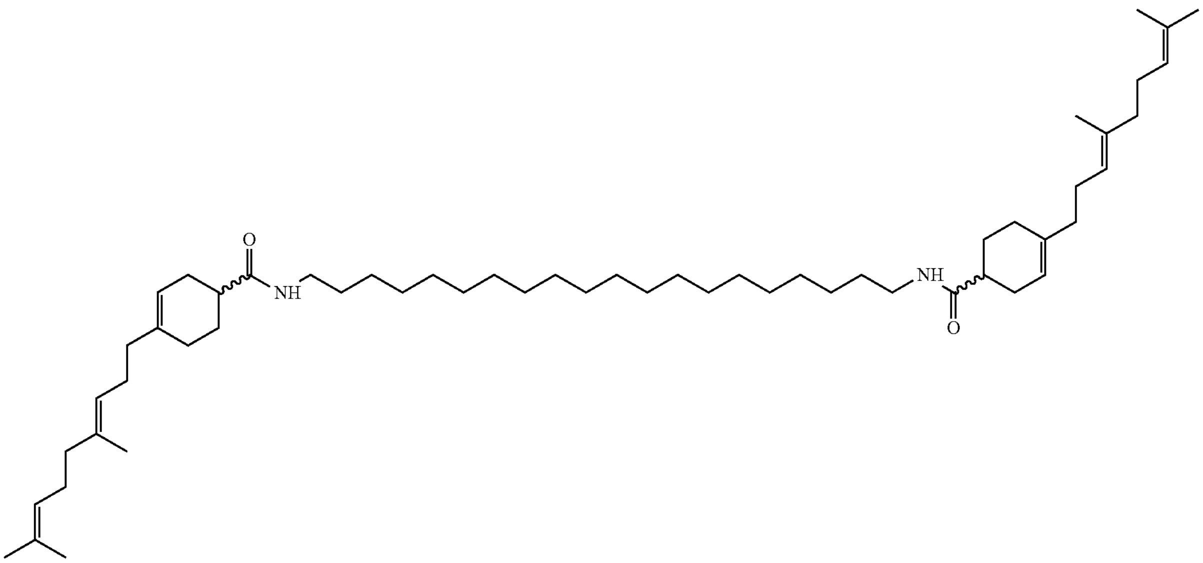 [SMILES: CC(C)=CCC/C(C)=C/CCC1=CCC(C(=O)NCCCCCCCCCCCCCCCCCCCCNC(=O)C2CC=C(CC/C=C(\C)CCC=C(C)C)CC2)CC1]
and then Protocol B for bolaamphiphile preparation.
COMPOUND 10
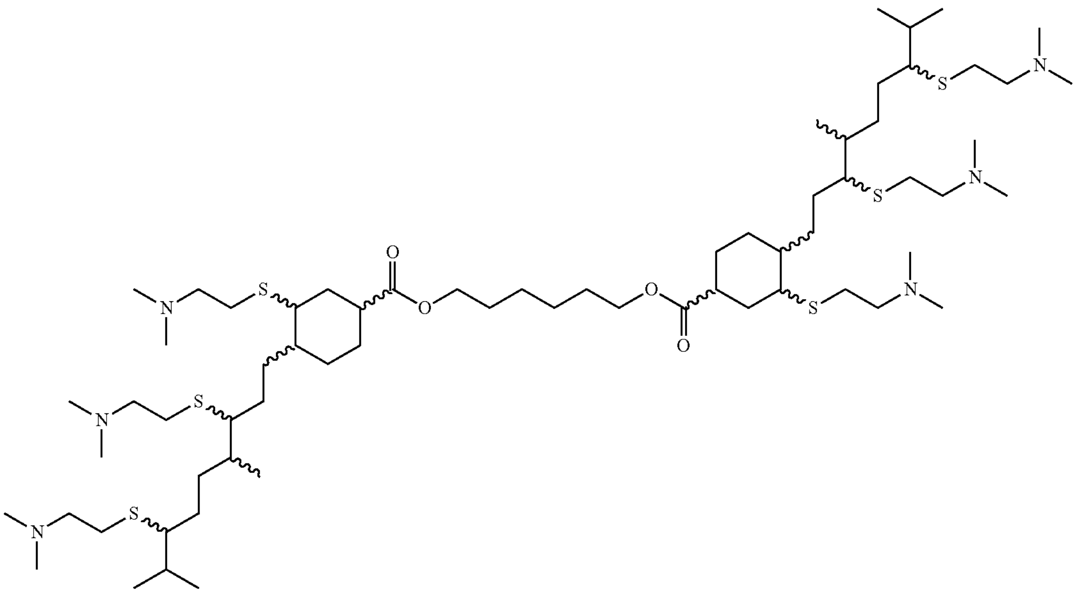

Synthesis of Compound 10
First, bola base was prepared according to Protocol A. The bola base had the following structure:
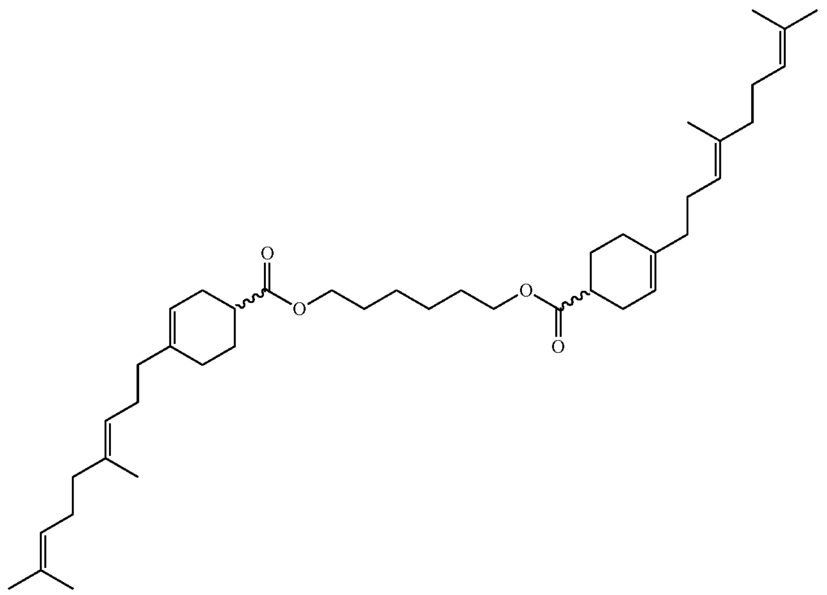
The results were:
44% yield, pale yellow oil. 1H NMR (500 MHz, CDCl3) δ 5.43-5.35 (m, 2H), 5.14-5.05 (m, 4H), 4.12-4.03 (m, 4H), 2.59-2.43 (m, 2H), 2.30-1.91 (m, 26H), 1.75-1.54 (m, 24H), 1.46-1.31 (m, 4H). 13C NMR (126 MHz, CDCl3) δ 176.23, 176.19, 137.48, 136.11, 135.24, 135.22, 131.41, 124.45, 124.17, 124.14, 120.38, 119.03, 64.35, 64.30, 40.06, 39.83, 39.64, 37.81, 37.64, 30.76, 28.69, 27.88, 27.83, 26.94, 26.84, 26.38, 26.35, 25.84, 25.75, 25.70, 25.32, 24.69, 17.83, 16.15.
Then, Protocol B procedure was followed. The results were:
1H NMR (500 MHz, DMSO-d6) δ 4.04-3.94 (m, 4H), 3.33-3.11 (m, 14H), 2.90-2.79 (m, 10H), 2.75 (d, J=3.4 Hz, 38H), 2.70-2.54 (m, 6H), 2.12-2.05 (m, 4H), 1.94-1.06 (m, 42H), 1.00-0.79 (m, 18H).
COMPOUND 11
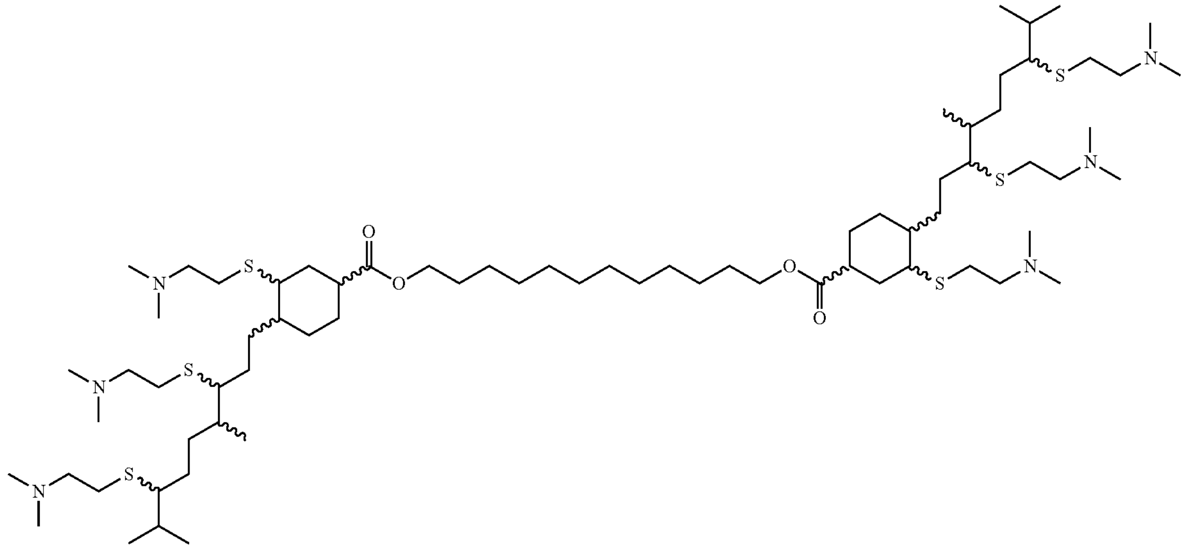

Synthesis of Compound 11
First, bola base was prepared according to Protocol A. The bola base had the following structure:
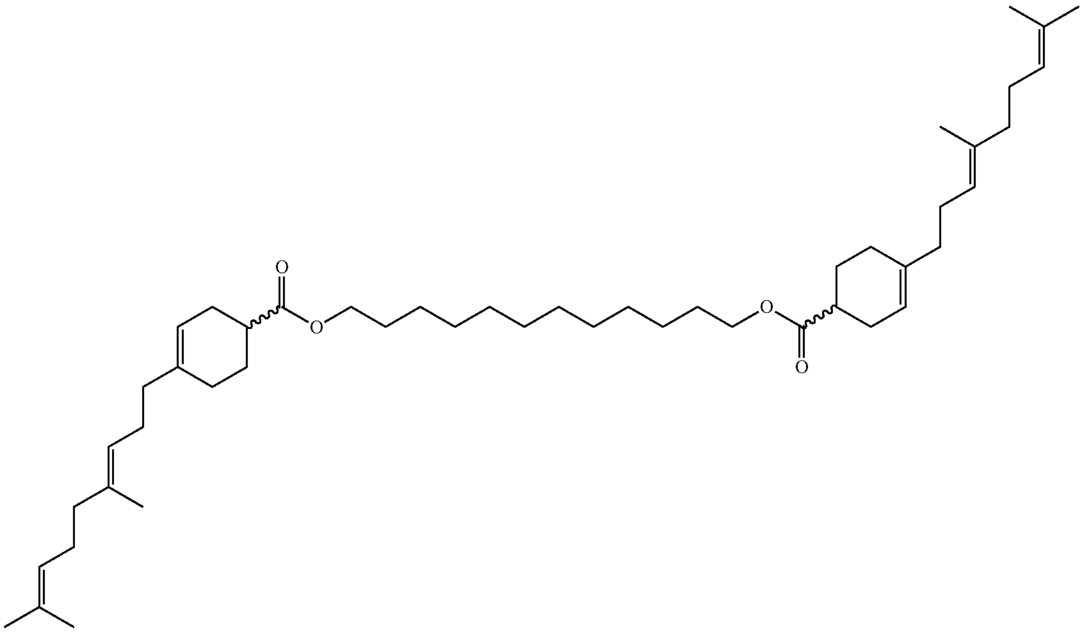 [SMILES: CC(C)=CCC/C(C)=C/CCC1=CCC(C(=O)OCCCCCCCCCCCCOC(=O)C2CC=C(CC/C=C(\C)CCC=C(C)C)CC2)CC1]
The results were:
45% yield, pale yellow oil. 1H NMR (500 MHz, CDCl3) δ 5.39 (bs, 2H), 5.09 (bs, 4H), 4.11-4.03 (m, 4H), 2.59-2.42 (m, 2H), 2.30-1.91 (m, 26H), 1.73-1.56 (m, 24H), 1.40-1.23 (m, 16H). 13C NMR (126 MHz, CDCl3) δ 176.24, 176.20, 137.44, 136.13, 135.21, 135.19, 131.38, 124.44, 124.17, 124.15, 120.37, 119.07, 64.56, 64.51, 40.06, 39.82, 39.64, 37.81, 37.64, 30.76, 29.67, 29.64, 29.38, 28.77, 27.83, 26.83, 26.37, 26.34, 26.04, 25.83, 25.68, 25.30, 24.69, 17.81, 16.13, 16.12.
Then, Protocol B procedure was followed. The results were:
1H NMR (400 MHz, DMSO-d6) δ 4.02-3.94 (m, 4H), 3.21-3.04 (m, 14H), 2.88-2.78 (m, 10H), 2.73 (s, 36H), 2.60-2.52 (m, 2H), 2.11-1.39 (m, 36H), 1.31-1.14 (m, 24H), 1.00-0.73 (m, 18H).
COMPOUND 12
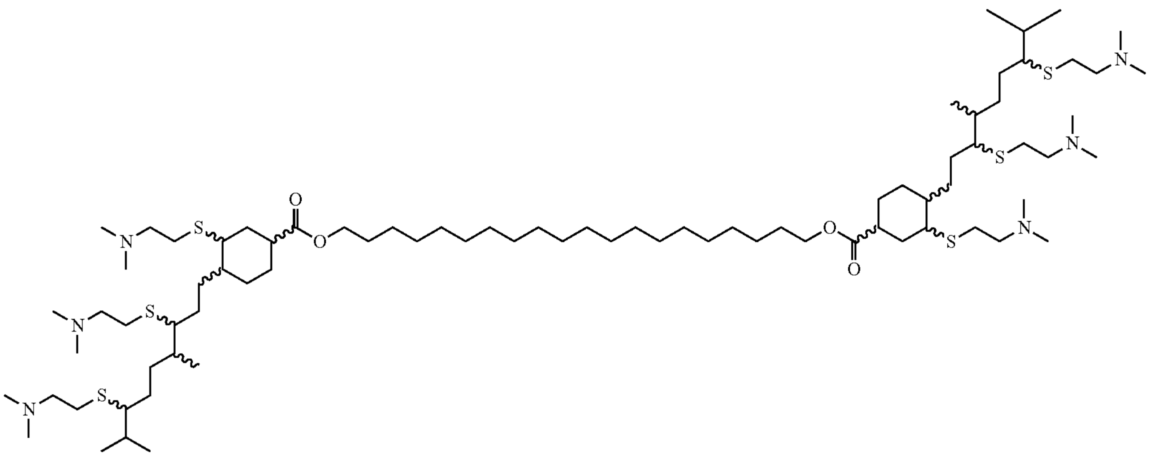

Synthesis of Compound 12

First, bola base was prepared according to Protocol A. The bola base had the following structure:

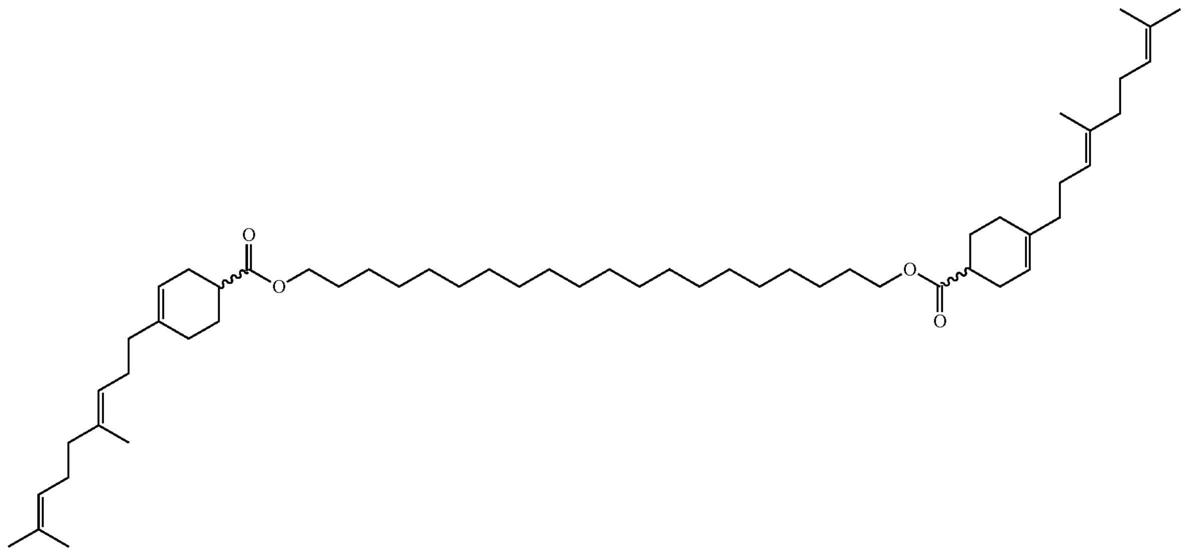 [SMILES: CC(C)=CCC/C(C)=C/CCC1=CCC(C(=O)OCCCCCCCCCCCCCCCCCCCCOC(=O)C2CC=C(CC/C=C(\C)CCC=C(C)C)CC2)CC1]

The results were:

49% yield; pale yellow oil; 1H NMR (400 MHz, CDCl3) δ 5.44-5.33 (m, 2H), 5.18-5.01 (m, 4H), 4.12-4.01 (m, 4H), 2.61-2.40 (m, 2H), 2.30-1.88 (m, 26H), 1.78-1.48 (m, 24H), 1.25 (d, J=4.8 Hz, 32H).

Then, Protocol B procedure was followed. The results were:

1H NMR (400 MHz, DMSO-d6) δ 4.05-3.94 (m, 4H), 3.30-3.27 (m, 12H), 3.17-3.13 (m, 12H), 2.91-2.80 (m, 2H), 2.73 (s, 36H), 1.99-1.82 (m, 9H), 1.78-1.50 (m, 21H), 1.24 (d, J=12.2 Hz, 46H), 1.03-0.64 (m, 18H).

COMPOUND 13

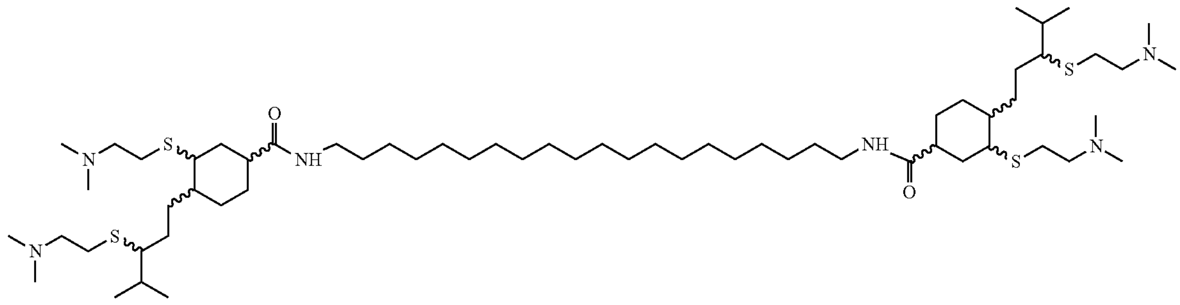

This compound can be prepared by following Protocol A for bola base preparation, resulting in preparation of the bola base of the following structure:

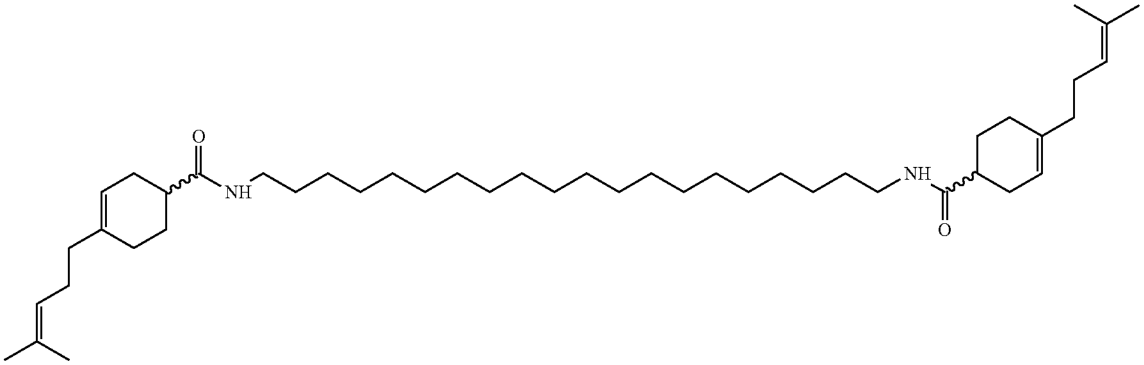 [SMILES: CC(C)=CCCC1=CCC(C(=O)NCCCCCCCCCCCCCCCCCCCCNC(=O)C2CC=C(CCC=C(C)C)CC2)CC1]
and then following Protocol B for bolaamphiphile preparation.
COMPOUND 14
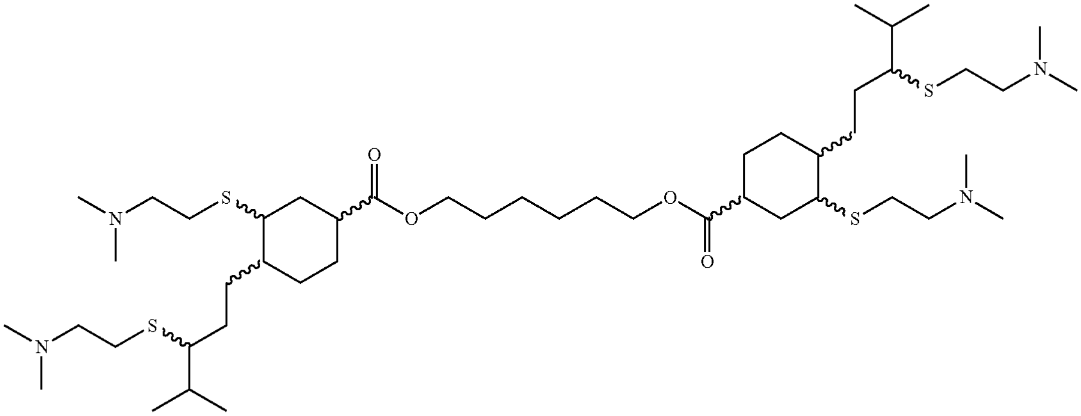
Synthesis of Compound 14
First, bola base was prepared according to Protocol A. The bola base had the following structure:
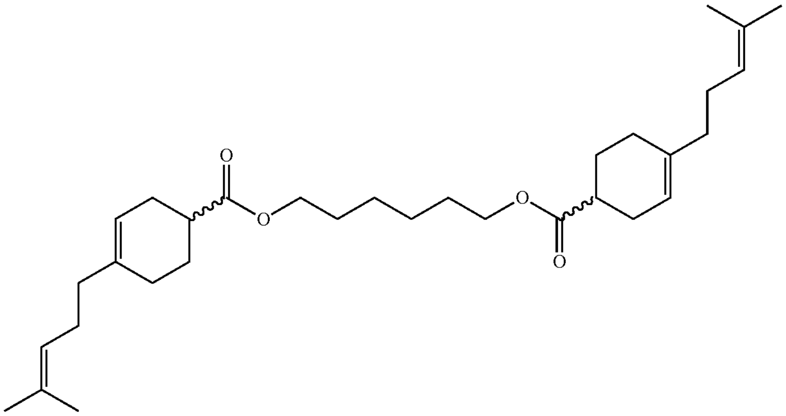 [SMILES: CC(C)=CCCC1=CCC(C(=O)OCCCCCCOC(=O)C2CC=C(CCC=C(C)C)CC2)CC1]

The results were:
21% yield; 1H NMR (500 MHz, CDCl3) δ 5.42-5.29 (m, 2H), 5.12-5.00 (m, 2H), 4.13-3.98 (m, 4H), 2.59-2.40 (m, 2H), 2.33-1.85 (m, 19H), 1.73-1.52 (m, 17H), 1.48-1.21 (m, 4H). 13C NMR (126 MHz, CDCl3) δ 176.12, 176.08, 137.41, 136.08, 131.52, 131.49, 124.24, 120.28, 118.95, 64.27, 64.22, 39.99, 39.57, 37.77, 37.61, 30.73, 28.64, 27.78, 27.76, 26.43, 25.77, 25.69, 25.62, 25.25, 24.62, 17.77, 17.76.
Then, Protocol B procedure was followed. The results were:
1H NMR (500 MHz, DMSO-d6) δ 4.03-3.93 (m, 4H), 3.25-3.17 (m, 8H), 3.16-3.03 (m, 8H), 2.85-2.76 (m, 4H), 2.73-2.64 (m, 24H), 2.54 (d, J=10.5 Hz, 2H), 2.17-1.18 (m, 32H), 1.00-0.73 (m, 12H).
COMPOUND 15
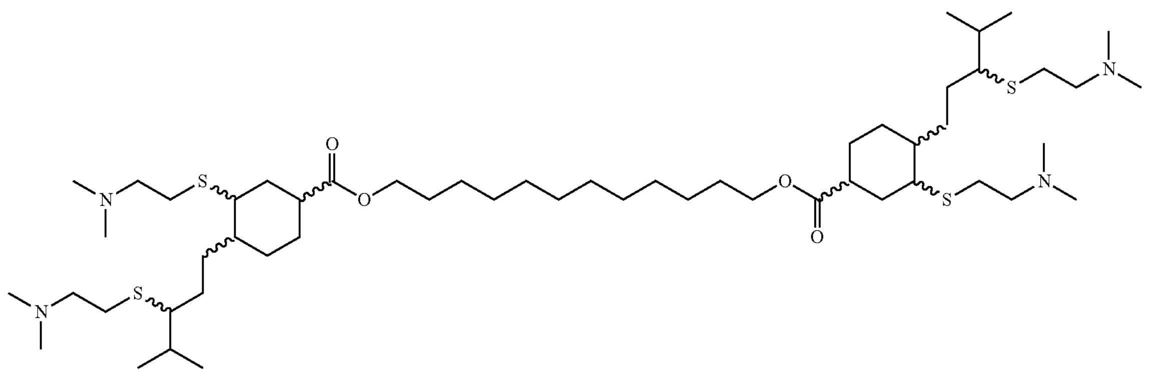
Synthesis of Compound 15
First, bola base was prepared according to Protocol A. The bola base had the following structure:
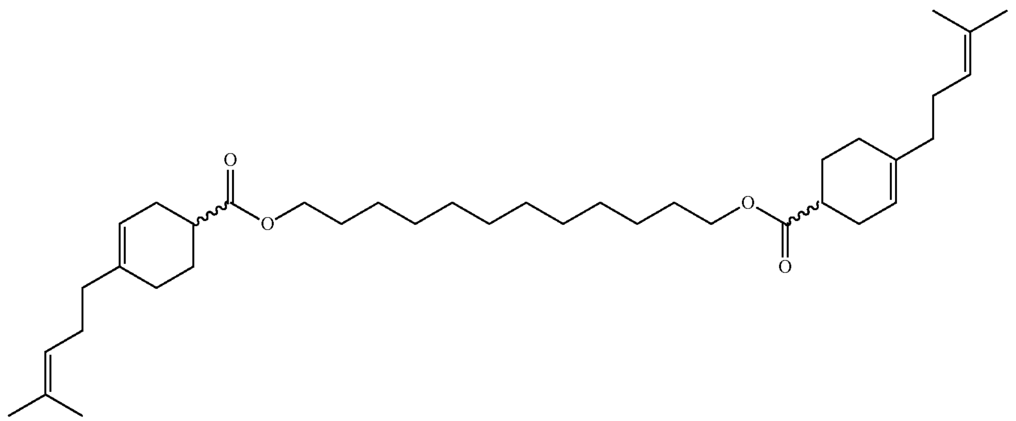 [SMILES: CC(C)=CCCC1=CCC(C(=O)OCCCCCCCCCCCCOC(=O)C2CC=C(CCC=C(C)C)CC2)CC1]

The results were:

28% yield, pale yellow oil. 1H NMR (500 MHz, CDCl3) δ 5.44-5.34 (m, 2H), 5.14-5.04 (m, 2H), 4.12-4.02 (m, 4H), 2.59-2.43 (m, 2H), 2.30-1.90 (m, 18H), 1.76-1.53 (m, 18H), 1.27 (s, 16H). 13C NMR (126 MHz, CDCl3) δ 176.28, 176.25, 137.50, 137.49, 136.19, 131.64, 131.62, 124.30, 120.35, 119.05, 64.59, 64.55, 40.09, 39.67, 37.85, 37.68, 30.80, 29.68, 29.66, 29.39, 28.79, 27.84, 26.51, 26.50, 26.06, 25.85, 25.69, 25.31, 24.70, 17.85, 17.84.

Then, Protocol B procedure was followed. The results were:

1H NMR (500 MHz, DMSO-d6) δ 4.06-3.89 (m, 4H), 3.40-3.29 (m, 8H), 3.26-3.08 (m, 8H), 2.95-2.53 (m, 32H), 2.20-1.13 (m, 42H), 1.00-0.78 (m, 12H).

COMPOUND 16

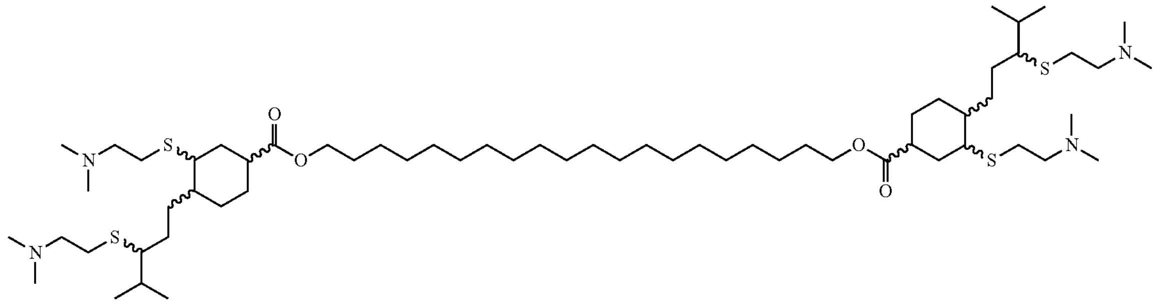

Synthesis of Compound 16

First, bola base was prepared according to Protocol A. The bola base had the following structure:

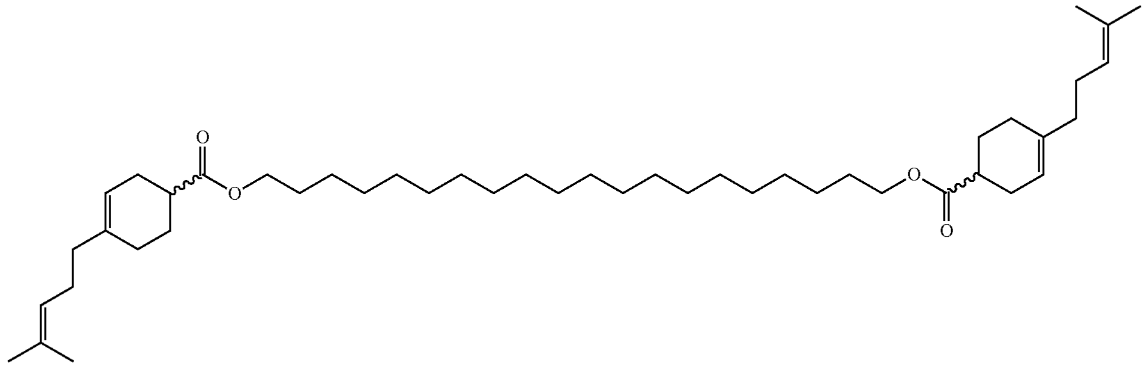 [SMILES: CC(C)=CCCC1=CCC(C(=O)OCCCCCCCCCCCCCCCCCCCCOC(=O)C2CC=C(CCC=C(C)C)CC2)CC1]

The results were:

59% yield; 1H NMR (500 MHz, CDCl3) δ 5.45-5.33 (m, 2H), 5.16-5.02 (m, 2H), 4.16-3.95 (m, 4H), 2.60-2.35 (m, 2H), 2.30-1.88 (m, 18H), 1.82-1.50 (m, 18H), 1.42-1.09 (m, 32H). 13C NMR (126 MHz, CDCl3) δ 176.29, 176.26, 137.50, 136.21, 131.64, 131.62, 124.31, 120.35, 119.05, 64.61, 64.57, 40.10, 39.67, 37.85, 37.69, 30.81, 29.86, 29.84, 29.80, 29.73, 29.68, 29.40, 28.80, 27.85, 26.51, 26.07, 25.85, 25.70, 25.32, 24.71, 17.86, 17.84.

Then, Protocol B procedure was followed. The results were:

1H NMR (500 MHz, DMSO-d6) δ 4.05-3.95 (m, 4H), 3.37-3.05 (m, 11H), 2.99-2.53 (m, 36H), 2.42-1.01 (m, 59H), 0.98-0.83 (m, 12H).

COMPOUND 17

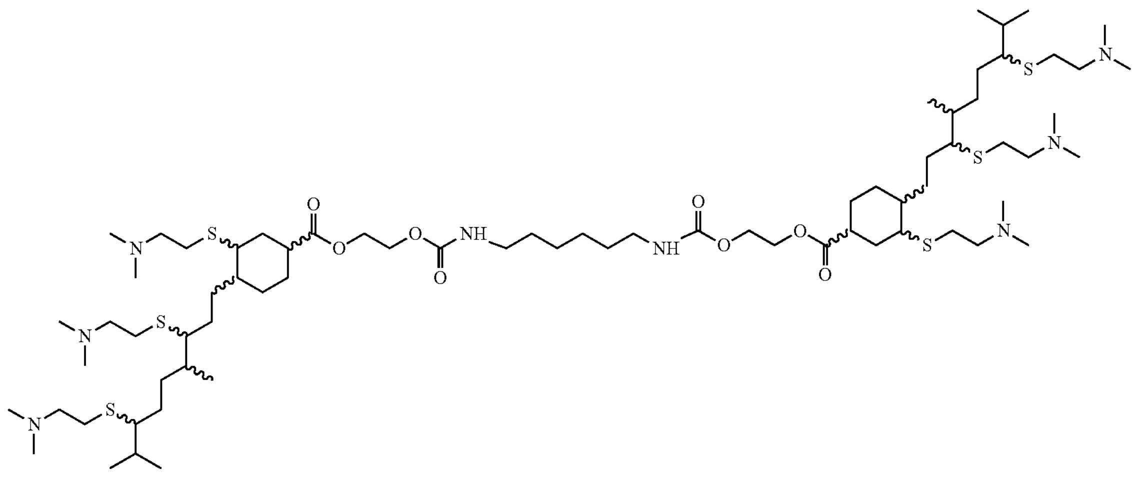

Synthesis of Compound 17

First, bola base was prepared as follows.

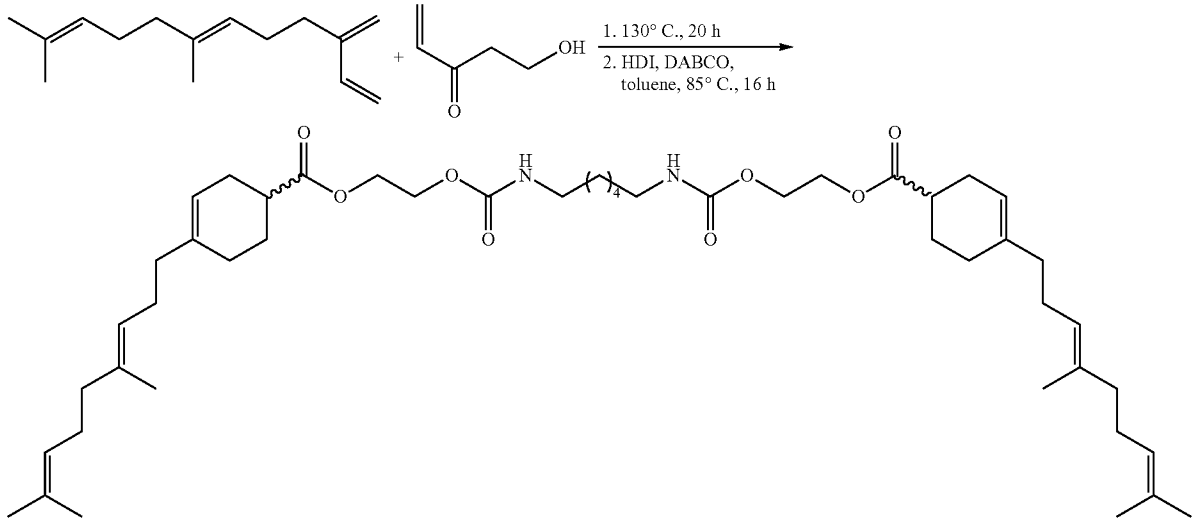

In a 4 mL sealable glass tube, trans-$-farnesene (1.02 g, 4.99 mmol, 1.0 eq) and hydroxyethyl acrylate (0.56 g, 4.99 mmol, 1.0 eq) were taken. The tube was sealed and stirred at 130° C. for 20 h. The reaction mixture was cooled and purified by silica gel chromatography with 20% EtOAc/hexane eluent to give the hydroxyl farnesene methyl ester.

86% yield, colorless oil; 1H NMR (500 MHz, CDCl3) δ 5.44-5.29 (m, 1H), 5.15-4.98 (m, 2H), 4.20 (q, J=4.7 Hz, 2H), 3.83-3.76 (m, 2H), 2.62-2.32 (m, 2H), 2.28-1.90 (m, 13H), 1.80-1.42 (m, 10H). 13C NMR (126 MHz, CDCl3) δ 176.57, 176.52, 137.46, 135.93, 135.22, 135.18, 131.32, 124.39, 124.07, 124.03, 120.34, 118.82, 66.02, 65.99, 61.26, 61.23, 39.91, 39.76, 39.47, 39.46, 37.71, 37.55, 30.68, 27.72, 27.69, 26.78, 26.30, 26.27, 25.76, 25.63, 25.24, 24.55, 17.75, 16.08, 16.06.

The hydroxyl compound (453 mg, 1.49 mmol, 2.5 eq) was mixed with hexamethylene diisocyanate, HDI (100 mg, 0.59 mmol, 1.0 eq), and DABCO (3 mg, 0.03 mmol, 5 mol %) in anhydrous toluene (2.0 mL). The resulting reaction mixture was stirred 85° C. for 16 h. Cooled, toluene was evaporated, the reaction mixture was partitioned between water (20 mL) and EtOAc (20 mL). Both layers were separated, aqueous layer was extracted with EtOAc (3x20 mL). Combined EtOAc extracts were washed with brine (20 mL), dried over Na2SO4, filtered and evaporated. The crude was purified by silica gel chromatography with 30% EtOAc:hexanes as eluents to give final bola base (330 mg, 68%) as a semi-solid.

56% yield; off-white solid; 1H NMR (500 MHz, CDCl3) δ 5.44-5.33 (m, 2H), 5.16-5.02 (m, 4H), 4.83-4.69 (m, 2H), 4.36-4.18 (m, 8H), 3.24-3.03 (m, 4H), 2.66-2.44 (m, 2H), 2.31-1.78 (m, 26H), 1.74-1.62 (m, 8H), 1.62-1.54 (m, 12H), 1.54-1.44 (m, 4H), 1.39-1.28 (m, 4H). 13C NMR (126 MHz, CDCl3) δ 175.94, 175.89, 156.24, 137.51, 136.02, 135.30, 135.26, 131.42, 124.45, 124.13, 124.11, 120.39, 118.92, 62.75, 62.67, 62.63, 40.98, 39.90, 39.83, 39.48, 37.80, 37.63, 30.67, 29.96, 27.78, 27.75, 26.85, 26.38, 26.36, 26.35, 25.83, 25.63, 25.24, 24.63, 17.83, 16.16, 16.14.

Then, Protocol B procedure was followed. The results were:
1H NMR (400 MHz, DMSO-d6) δ 4.26-4.05 (m, 8H), 3.37-3.10 (m, 22H), 3.07-2.79 (m, 16H), 2.75 (s, 36H), 2.62-2.53 (m, 4H), 2.21-1.12 (m, 42H), 1.00-0.74 (m, 18H).
COMPOUND 18
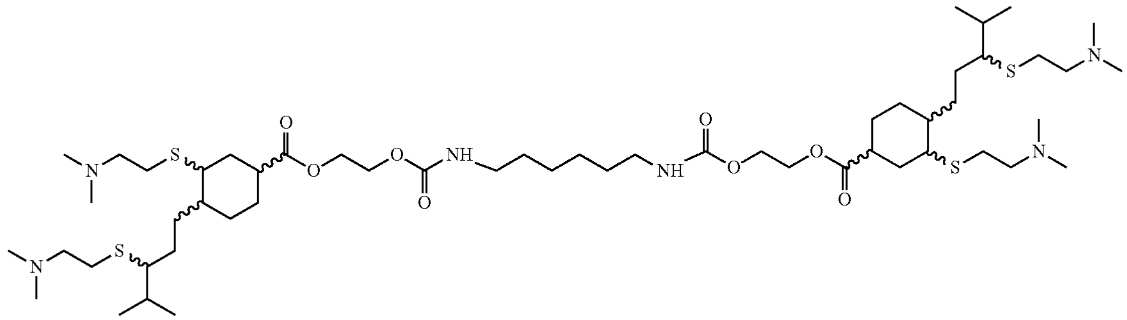
Compound 18 can be prepared by following the procedure described in the methods of preparation of Compound 17 for bola base preparation, and then following Protocol B for bolaamphiphile preparation.
COMPOUND 19
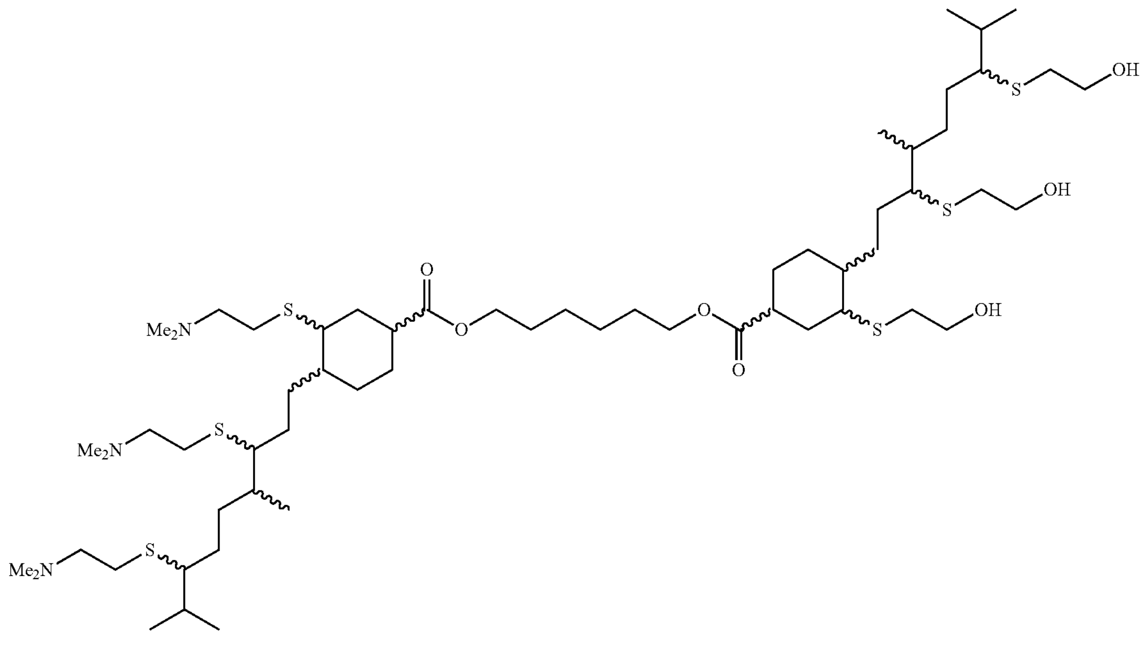

Synthesis of Compound 19

First, bola base was prepared according to Protocol A as follows:

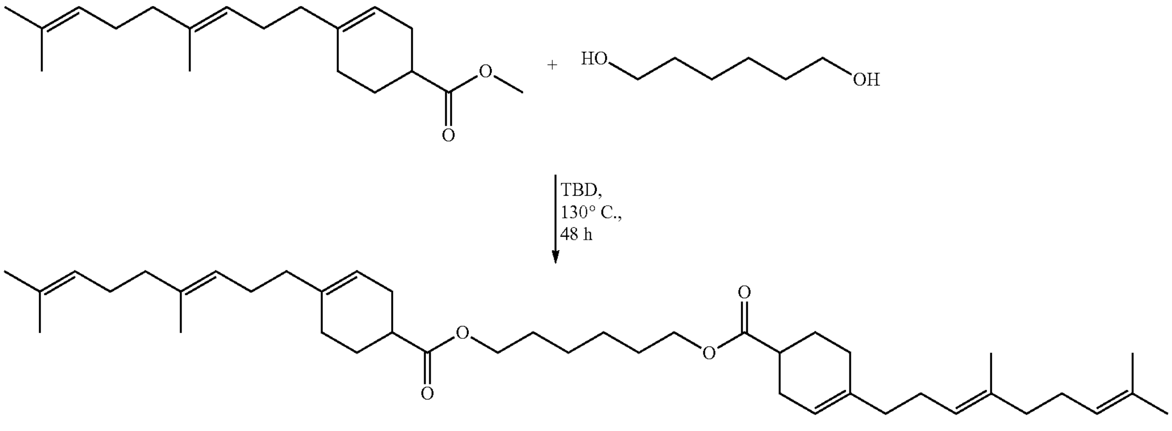

In a 4 mL sealable glass tube, farnesene methyl ester (FME) (4.9 g, 4.0 mmol, 4.0 eq) was added with the 1,6-hexanediol (0.5 g, 1.0 mmol, 1.0 eq) and a catalyst TBD (471 mg, 0.8 mmol, 0.8 eq). The tube was sealed and stirred at 130° C. for 20 h without any solvent. The reaction was cooled and purified by flash silica gel chromatography with 5-10% of EtOAc:hexanes as eluents.

The results were: 1.19 g (44%), pale yellow oil. 1H NMR (500 MHz, CDCl3) δ 5.43-5.35 (m, 2H), 5.14-5.05 (m, 4H), 4.12-4.03 (m, 4H), 2.59-2.43 (m, 2H), 2.30-1.91 (m, 26H), 1.75-1.54 (m, 24H), 1.46-1.31 (m, 4H). 13C NMR (126 MHz, CDCl3) δ 176.23, 176.19, 137.48, 136.11, 135.24, 135.22, 131.41, 124.45, 124.17, 124.14, 120.38, 119.03, 64.35, 64.30, 40.06, 39.83, 39.64, 37.81, 37.64, 30.76, 28.69, 27.88, 27.83, 26.94, 26.84, 26.38, 26.35, 25.84, 25.75, 25.70, 25.32, 24.69, 17.83, 16.15.

Then, Protocol B procedure was followed as follows:

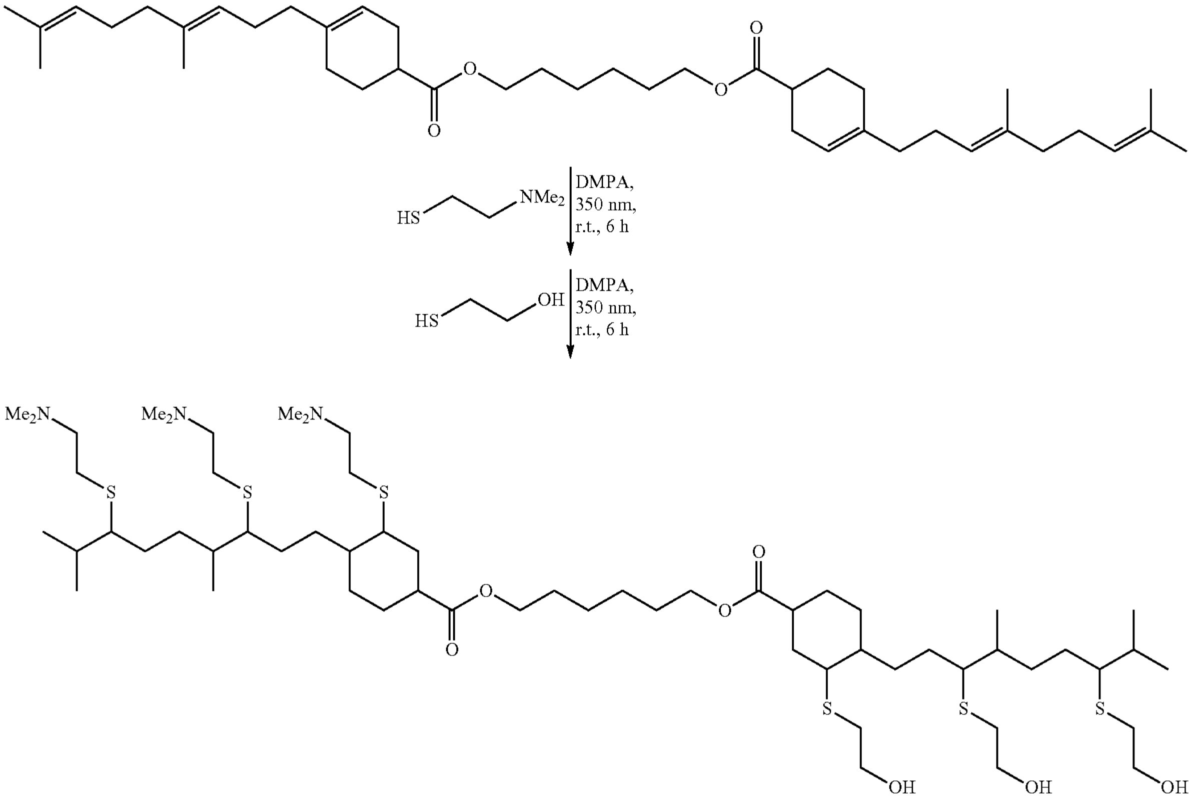

Comppound 19

In a 4 mL quartz tube, corresponding bola base (400 mg, 0.63 mmol), 2-mercaptoethanol (149 mg, 1.89 mmol), and photocatalyst, 2,2-dimethoxy-2-phenyl acetophenone (DMPA) (96 mg, 0.38 mmol) were taken. A mixed solvent system of THF:MeOH (4.0 mL, 5:1) was added until all the reagents were dissolved and degassed with nitrogen for 10 mins before irradiating with 350 nm of UV light for 6 h at room temperature. The solvent was evaporated and the residue was passed through a silica gel column. Eluant 5% MeOH:DCM was used to remove nonpolar impurities and the compound was isolated with $10^{-50}$% MeOH:DCM. The pale-yellow oil obtained (330 mg, 0.38 mmol) was added 2-(dimethylamino)ethanethiol hydrochloride (271 mg, 1.9 mmol) and DMPA (98 mg, 0.38 mmol) in a quartz tube. The contents were dissolved in THF:MeOH (4.0 mL, 5:1) and degassed with nitrogen for 10 mins. The resulting reaction mixture was irradiated with 350 nm for 6 h at room temperature. The solvent was evaporated and the residue was passed through a silica gel column. Eluant 5% MeOH:DCM was used to remove nonpolar impurities and the compound was isolated with $10^{-50}$% MeOH:DCM. The off-white solid obtained was dissolved in 2.0 mL of DI water and dialyzed against water in 100-500 daltons bag for 20 h. The dialyzed solution was lyophilized to get compound 19 as a hygroscopic off-white solid (121 mg, 16%).

The results were:

1H NMR (400 MHz, DMSO-d6) δ 4.02-3.96 (m, 4H), 3.53-3.44 (m, 8H), 3.28-3.09 (m, 8H), 2.87-2.73 (m, 26H), 2.58-2.53 (m, 4H), 1.96-1.80 (m, 8H), 1.70-1.22 (m, 41H), 1.03-0.68 (m, 18H).

COMPOUND 20

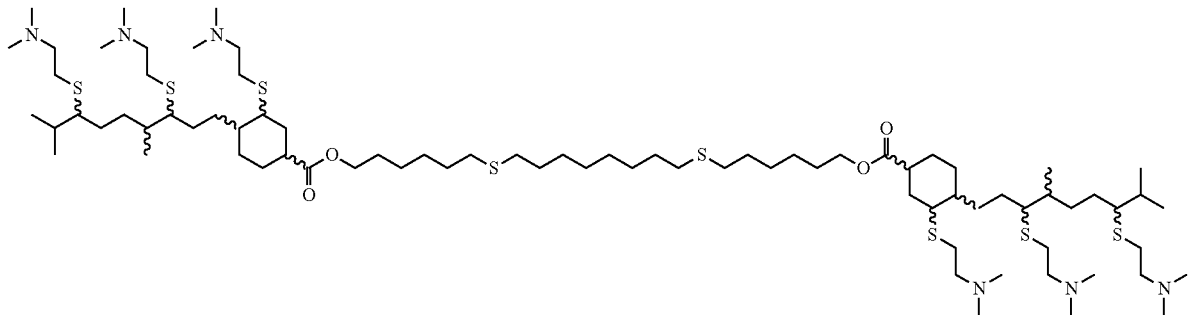

Synthesis of Compound 20

First, C20S2 diol-linker was prepared as follows.

In a 4 mL quartz tube, 1,7-octadiene (0.2 g, 1.8 mmol, 1.0 eq), 6-mercapto-1-hexanol (0.73 g, 5.4 mmol, 1.5 eq per alkene), and photocatalyst, 2,2-Dimethoxy-2-phenylacetophenone (DMPA) (0.19 g, 0.7 mmol, 0.2 eq per alkene) were taken. A mixed solvent system of CHCl3:MeOH (2.0 mL, 5:1) was added and degassed with nitrogen for 10 mins before irradiating with 350 nm of UV light for 6 h at room temperature. The solvent was evaporated completely and the resulting residue was recrystallized with ethanol (10 mL) to give C20S2 diol.

0.41 g, (60%); off-white solid; 1H NMR (400 MHz, CDCl3) δ 3.62 (td, J=6.6, 1.0 Hz, 4H), 2.54-2.42 (m, 8H), 1.69-1.64 (m, 2H), 1.63-1.47 (m, 12H), 1.45-1.23 (m, 16H). 13C NMR (101 MHz, CDCl3) δ 77.16, 62.92, 32.70, 32.22, 32.14, 29.73, 29.69, 29.20, 28.94, 28.76, 25.48.

Then Protocol A was followed to make a bola base of the following structure:

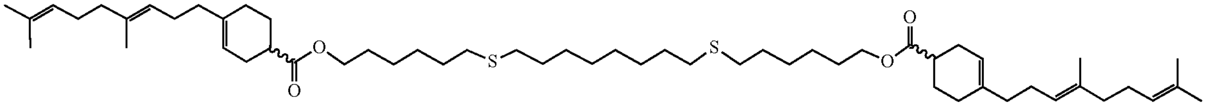

The results were as follows. 54% yield; $^{1}$H NMR (400 MHz, CDCl3) δ 5.42-5.27 (m, 2H), 5.13-4.95 (m, 4H), 4.11-3.92 (m, 4H), 2.56-2.35 (m, 10H), 2.25-1.83 (m, 27H), 1.72-1.47 (m, 31H), 1.44-1.18 (m, 16H). $^{13}$C NMR (101 MHz, CDCl3) δ 175.97, 175.94, 137.26, 135.94, 135.01, 134.98, 131.15, 124.32, 124.03, 124.01, 120.23, 118.93, 64.21, 64.16, 39.89, 39.69, 39.47, 37.68, 37.51, 32.13, 32.00, 30.62, 29.63, 29.52, 29.14, 28.86, 28.55, 28.50, 27.69, 26.70, 26.23, 26.20, 25.71, 25.59, 25.54, 25.16, 24.54, 17.69, 16.01, 15.99.

Then, Protocol B procedure was followed. The results were:

1H NMR (400 MHz, DMSO-d6) δ 4.04-3.94 (m, 4H), 3.40-3.28 (m, 12H), 3.26-3.08 (m, 18H), 2.91-2.55 (m, 46H), 2.48-2.37 (m, 6H), 2.21-1.19 (m, 56H), 1.01-0.74 (m, 18H).

COMPOUND 21

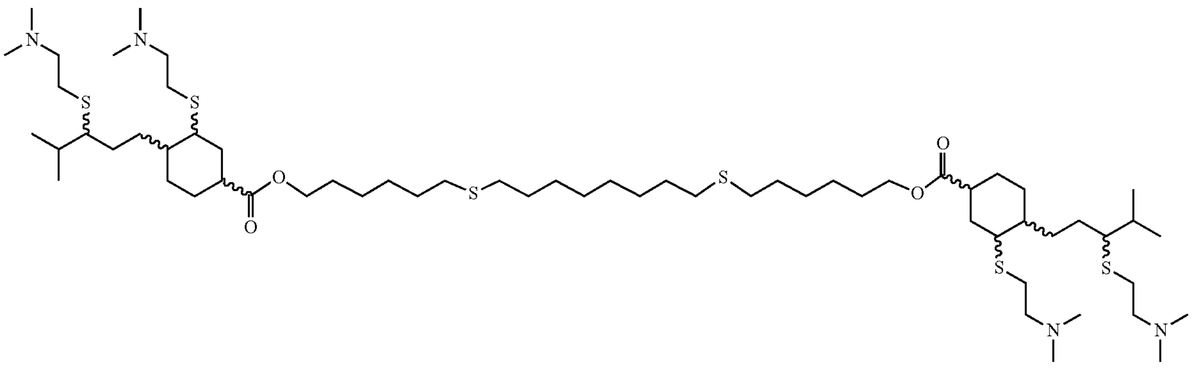

Synthesis of Compound 21

First, C20S2 diol-linker was prepared as described in the example of preparation of Compound 20.

Then, Protocol A was followed to make a bola base of the following structure:

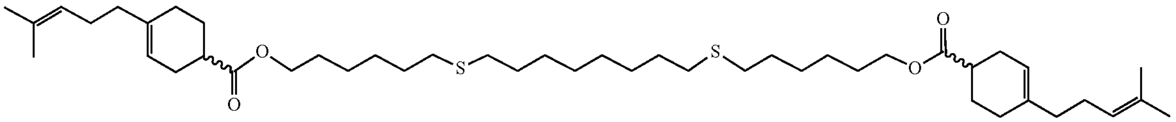 [SMILES: CC(C)=CCCC1=CCC(C(=O)OCCCCCCSCCCCCCCCSCCCCCCOC(=O)C2CC=C(CCC=C(C)C)CC2)CC1]

The results were as follows. 51% yield; 1H NMR (400 MHz, CDCl3) δ 5.38-5.28 (m, 2H), 5.09-4.97 (m, 2H), 4.06-3.97 (m, 4H), 2.53-2.36 (m, 10H), 2.21-1.83 (m, 19H), 1.64-1.48 (m, 25H), 1.40-1.22 (m, 16H). 13C NMR (101 MHz, CDCl3) δ 175.96, 175.93, 137.27, 135.97, 131.37, 131.34, 124.15, 120.18, 118.87, 64.21, 64.16, 39.87, 39.45, 37.69, 37.52, 32.13, 32.00, 32.00, 30.63, 29.63, 29.52, 29.13, 28.85, 28.54, 28.49, 27.68, 27.67, 26.35, 26.33, 25.70, 25.58, 25.52, 25.15, 24.53, 17.70, 17.68.

Then, Protocol B procedure was followed. The results were:

1H NMR (400 MHz, DMSO-d6) δ 4.06-3.91 (m, 4H), 3.29-3.03 (m, 14H), 2.92-2.75 (m, 6H), 2.75-2.60 (m, 24H), 2.47-2.30 (m, 10H), 2.21-1.16 (m, 52H), 1.00-0.75 (m, 12H).

Example 2—General Method for the Preparation of LNPs of Present Disclosure Comprising RNA The following is a nonlimiting example that provides a general method for effectively formulating a plurality of multi-component LNP compositions comprising exemplary compounds of Formula (I) and mRNA.

A series of ten multi-component LNP compositions of the present disclosure comprising exemplary compounds of Formula (I) was prepared by combining various percentages of an exemplary compound of Formula (I), the phospholipid DOPE, the structural lipid cholesterol (Chol) and 1,2-dimyristoyl-sn-glycerol methoxypolyethylene glycol (DMG-PEG2000; Avanti Polar Lipids, Alabaster, Alabama, USA).

Individual 25 mg/ml stock solutions were prepared by solubilizing the lipids in 200-proof HPLC-grade ethanol and stock solutions were stored at −80° C. until formulated. At the time of formulation, the lipid stock solutions were briefly allowed to equilibrate to room temp and then placed on a hot plate maintained at a temperature range of 50-55° C. Subsequently, the hot lipid stock solutions were combined to yield desired final mol % as shown in Table 4.

TABLE 4

| LNP ID | Formula (I) cpd | DOPE | Chol | PEG-DMG | Lipid Blend (mM) | Lipid:RNA (w/w) |
|---|---|---|---|---|---|---|
| 1 | 10 | 50 | 35 | 5 | 17.5 | 25 |
| 2 | 10 | 50 | 39.5 | 0.5 | 10 | 10 |
| 3 | 10 | 50 | 39.5 | 0.5 | 25 | 40 |
| 4 | 32.4 | 32.4 | 32.4 | 2.8 | 17.5 | 25 |
| 5 | 35 | 10 | 50 | 5 | 10 | 40 |
| 6 | 39.5 | 10 | 50 | 0.5 | 25 | 25 |

TABLE 4-continued

| LNP ID | Formula (I) cpd | DOPE | Chol | PEG-DMG | Lipid Blend (mM) | Lipid:RNA (w/w) |
|---|---|---|---|---|---|---|
| 7 | 39.5 | 10 | 50 | 0.5 | 17.5 | 10 |
| 8 | 50 | 35 | 10 | 5 | 10 | 10 |
| 9 | 50 | 39.5 | 10 | 0.5 | 25 | 25 |
| 10 | 50 | 39.5 | 10 | 0.5 | 17.5 | 40 |

A 1 mg/mi solution of the desired mRNA to be incorporated into the LNPs was added to 150 mM sodium acetate buffer (pH 5.2) to form a stock solution and kept on ice. The lipid phase was mixed with the aqueous m RNA phase inside a microfluidic chip using a NanoAssemblr® instrument (Precision Nanosystems, Vancouver, BC, Canada) according to the manufacturer's instructions to form LNP compositions comprising encapsulated mRNAs. Nanoassemblr process parameters for mRNA encapsulation are shown in the Table 5.

TABLE 5

| Total flow rate (ml/min) | Lipid phase: aqueous (RNA) phase (v/v) |
|---|---|
| 20 | 1:3 |

The resultant mRNA LNP compositions were then transferred to a Repligen Float-A-Lyzer dialysis device—having a molecular weight cut off (MWCO) of 8-10 kDa (Spectrum Chemical Mfg. Corp, CA, USA) and processed by dialysis against phosphate buffered saline (PBS) (dialysate:dialysis buffer volume at least 1:200 v/v), pH 7.4 overnight at 4° C. (or alternatively room temperature for at least 4 hours), to remove the 25% ethanol and achieve a complete buffer exchange. In some experiments the LNPs were further concentrated by in an Amicon® Ultra-4 centrifugal filter unit, MWCO-30 kDa (Millipore Sigma, USA) spun at ~4100×g in an ultracentrifuge. The mRNA LNPs were then stored at 4° C. until further use.

Example 3—Characterization of mRNA-Containing LNP Compositions Comprising Compounds 1-8

The following is a nonlimiting example demonstrating that a plurality of mRNA-containing LNP compositions may be effectively prepared comprising COMPOUNDS 1-8 of Example 1.

A series of multicomponent LNP compositions comprising one of COMPOUNDS 1-8 described in Example 1 and the mRNA encoding flue was prepared according to Example 2 and the physical characteristics of the resulting LNPs were analyzed.

Table 6 shows the results of the analysis of LNPs comprising COMPOUND 1 of Example 1.

TABLE 6

LNPs comprising COMPOUND 1

| LNP ID | Diameter (DLS; nm) | PDI | Diameter (NTA; nm) | Total Particles/ml | Zeta Potential (mV) |
|---|---|---|---|---|---|
| 1 | 168 | 0.07 | 157 | 6.40E+11 | −1.0 |
| 2 | 2800 | 0.6 | 154 | 1.09E+11 | −10.4 |
| 3 | 351 | 0.14 | 234 | 8.80E+10 | −0.6 |
| 4 | 137 | 0.16 | 117 | 5.40E+11 | −0.2 |
| 5 | 133 | 0.04 | 114 | 8.40E+11 | 1.6 |
| 6 | 3104 | 0.54 | 105 | 4.16E+10 | 0.4 |
| 7 | 3013 | 0.60 | 161 | 6.05E+10 | −1.3 |
| 8 | 154 | 0.29 | 150 | 4.14E+10 | −0.7 |
| 9 | 117 | 0.13 | 134 | 1.73E+11 | 3.8 |
| 10 | 122 | 0.18 | 125 | 2.21E+11 | 5.4 |

As shown in Table 6, COMPOUND 1 was, successfully formulated into a plurality of mRNA-containing LNP compositions with the average diameter ranging from about 100 to about 250 as measured by NTA.

The LNP compositions were analyzed to verify the presence of mRNA. An aliquot of each of the LNP compositions was loaded on to a 1% agarose gel with a size standard and naked mRNA control, subject to electrophoresis and the presence of mRNA was detected by exposure of ultraviolet light to excite the fluorophore (SYBR Safe) which is complexed with nucleic acid. The free mRNA migrated in the gel in accordance with its molecular weight whereas all of the mRNA-containing LNP compositions remained at the interface of the agarose gel and the well with little to no detectable free mRNA indicating the LNP compositions comprising COMPOUND 1 of Example 1 were capable of incorporating mRNA.

Table 7 shows the results of the analysis of LNPs comprising COMPOUND 2 of Example 1.

TABLE 7

LNPs comprising COMPOUND 2

| LNP ID | Diameter (DLS; nm) | PDI | Diameter (NTA; nm) | Total Particles/ml | Zeta Potential (mV) |
|---|---|---|---|---|---|
| 1 | 166 | 0.26 | 127 | 6.30E+11 | −2.69 |
| 2 | 726 | 0.34 | 246 | 7.55E+09 | −10.2 |
| 3 | 2007 | 0.56 | 126 | 3.34E+10 | −1.05 |
| 4 | 151 | 0.45 | 94 | 3.72E+11 | −0.66 |
| 5 | 175 | 0.20 | 140 | 8.70E+11 | −0.91 |
| 6 | 3479 | 0.58 | 127 | 3.27E+10 | −1.1 |
| 7 | 4246 | 0.66 | 199 | 1.68E+10 | −7.42 |
| 8 | 219 | 0.49 | 120 | 1.67E+11 | −3.20 |
| 9 | 328 | 0.20 | 168 | 8.40E+10 | 0.58 |
| 10 | 293 | 0.14 | 171 | 8.30E+10 | 0.88 |

As shown in Table 7, COMPOUND 2 was successfully formulated into a plurality of LNP compositions with the average diameter ranging from about 100 to about 250 nm as measured by NTA. The incorporation of mRNA encoding flue into the LNP compositions was confirmed by gel electrophoresis as described above for COMPOUND 1.

In a separate experiment, LNP compositions of the present disclosure comprising mRNA encoding firefly luciferase (hereafter “Fluc”; TriLink) and COMPOUNDS 1-8 were prepared as described in Example 2 by combining one of COMPOUNDS 1-8, the phospholipid DOPE, the structural lipid cholesterol (Chol) and 1,2-dimyristoyl-sn-glycerol methoxypolyethylene glycol (DMG-PEG2000) in the percentages presented in Table 8:

TABLE 8

| One of COMPOUND 1-8 | DOPE | Cholesterol | DMG-PEG2000 | Lipid Blend (mM) | Lipid:RNA (w/w) |
|---|---|---|---|---|---|
| 41.44 | 45.85 | 10 | 2.7 | 25 | 40:1 |

The LNP compositions were further characterized as shown in Table 9.

TABLE 9

| COMPOUND | Diameter (DLS; nm) | PDI | Diameter (NTA; nm) | Total Particles/ml | Zeta Potential (mV) |
|---|---|---|---|---|---|
| 1 | 155.1 | 0.174 | 126.5 | 1.66E+11 | 1.41 |
| 2 | 79.6 | 0.259 | 113.8 | 2.97E+10 | −0.19 |
| 3 | 94.0 | 0.482 | 87.9 | 3.68E+11 | 0.12 |
| 4 | 286.2 | 0.708 | 88.9 | 3.40E+11 | −0.27 |
| 5 | 91.8 | 0.389 | 84.4 | 7.03E+10 | 0.18 |
| 6 | 101.4 | 0.464 | 86.0 | 1.3E+11 | 0.48 |
| 7 | 123.5 | 0.113 | 108.4 | 5.10E+10 | −0.29 |
| 8 | 91.8 | 0.392 | 106.1 | 1.15E+11 | 0.25 |

As shown in Table 9, mRNA-containing LNP compositions comprising one of COMPOUNDS 1-8 were successfully formulated with the average diameter ranging from about 80 to about 130 nm as measured by NTA. The incorporation of mRNA encoding fluc into the LNP compositions was confirmed by gel electrophoresis as described above for COMPOUND 1.

Example 4—In Vitro LNP-Delivery of mRNA to Adherent Cells

The following is a nonlimiting example demonstrating that the lipid nanoparticle compositions of the present disclosure can be used to deliver mRNA to adherent cells in vitro and that following delivery of the mRNA, the encoded protein is expressed by the cells.

HEK293T cells were seeded in 96 well plates and grown to 70% confluence in DMEM+10% FBS] under a 5% $CO_2$ atmosphere at 37° C. A 0.125 µg amount of 5'-CleanCap-eGFP mRNA (TriLink Biotech) formulated with LNP compositions comprising COMPOUNDS 1-4 as prepared in Example 3 at the following percentages in Table 10 was added to each well.

TABLE 10

| One of COMPOUNDS 1-4 | DOPE | Cholesterol | DMG-PEG2000 | Lipid Blend (mM) | Lipid:RNA (w/w) |
|---|---|---|---|---|---|
| 41.44 | 45.85 | 10.0 | 2.7 | 25 | 40:1 |

After incubating for 24 hr, cells were imaged for GFP expression with a Leica fluorescence microscope and then detached from 96 well plate to quantitate expression by flow cytometry. The results are shown in Table 11.

TABLE 11

| LNPs comprising Compound # | % Viable GFP+ |
|---|---|
| 1 | 23.5 |
| 2 | 17.5 |
| 3 | 19.4 |
| 4 | 90.1 |

As shown in Table 11, the LNP compositions comprising COMPOUNDS 1-4 were successfully able to delivery mRNA to adherent HEK293T cells. Approximately 23.5%, 17.5%, 19.4% and 90.1% of HEK293T cells were positive for eGFP expression when incubated with LNPs comprising COMPOUNDS 1-4, respectively, whereas less than 0.29 percent of cells were positive for eGFP expression in untreated controls demonstrating the ability of the LNP compositions of the present disclosure to deliver RNA to adherent cells in vitro.

Example 5-Delivery of mRNA to Resting T-Cells Using the LNP Compositions and Methods of the Present Disclosure The following nonlimiting example demonstrates that the LNP compositions and methods of the present disclosure can be used to deliver mRNA to resting T-cells.

In one experiment, LNPs of the present disclosure comprising one of COMPOUNDS 1-4, DOPE, Cholesterol and DMG-PEG2000 at a molar ratio of 0.4144:0.4585:0.1:0.027 and further comprising Cleancap mRNA encoding eGFP were formed on a NanoAssemblr® (Precision Nanosystems). The eGFP mRNA LNPs had a lipid:nucleic acid ratio (w:w) of 40:1. Resting T-cells were treated with varying amounts of the four LNP composition and at 24 hrs, the cells were analyzed to determine the percentage of cells that were viable and that expressed luciferase. The results of the analysis are shown in Table 12 for a dose of 0.5 ug mRNA per well.

TABLE 12

| LNP comprising Compound # | % Viable GFP+ |
|---|---|
| 1 | 9.5 |
| 2 | 5.5 |
| 3 | 10.9 |
| 4 | 2.9 |

As shown in Table 13, the LNP compositions comprising COMPOUNDS 1-4 were able to deliver the mRNA and eGFP expression was observed in 9.5%, 5.5%, 10.9% and 2.9% of the treated primary, resting T-cells, respectively.

Example 6—In Vivo LNP-Delivery of mRNA to Liver

The following is a nonlimiting example demonstrating that the lipid nanoparticle compositions of the present disclosure can be used to deliver mRNA to liver cells in vivo and expression of the encoded protein.

Adult female BALB/C mice (n=2/group) were intravenously administered 0.5 mg/kg of 5'-CleanCap-fLuciferase mRNA (TriLink Biotech) formulated with LNP compositions Formulation ID Nos 1-10 for COMPOUND 1 and COMPOUND 2 described in Example 2. One group of mice was treated with vehicle (PBS, Thermo Fisher Scientific, USA) as a negative control.

The location and extent of luciferase expression in treated and control mice were determined at 4 hr by bioluminescent imaging (BLI) of anesthetized mice using an IVIS Lumina in vivo imaging system (Perkin Elmer) according to the manufacturer's instructions. Briefly, mice were anesthetized using isoflurane in oxygen, and placed supine on a heated stage. Mice were then administered D-luciferin (PerkinElmer #122799) IP, and BLI was performed. The results of this experiment for LNP ID Nos 1-10 comprising COMPOUND 1 are shown in Table 14.

TABLE 14

| LNP ID | Ave flux (p/s) n = 2 | Avg. flux (p/s) n = 2 |
|---|---|---|
| 1 | 2.66E+5 | 2.36E+5 |
| 2 | 1.93E+5 | 2.05E+5 |
| 3 | 2.71E+5 | 2.69E+5 |
| 4 | 2.54E+5 | 2.28E+5 |
| 5 | 3.16E+5 | 2.86E+5 |
| 6 | 2.20E+5 | 2.22E+5 |
| 7 | 3.17E+5 | 2.88E+5 |
| 8 | 2.72E+5 | 2.68E+5 |
| 9 | 3.16E+5 | 3.04E+5 |
| 10 | 2.84E+5 | 2.67E+5 |
| Vehicle | 2.14E+5 | 1.15E+5 |

The results of this experiment for LNP ID Nos 4, 5, 6 & 10 comprising COMPOUND 2 are shown in Table 15.

TABLE 15

| LNP ID | Ave flux (p/s) n = 2 |
|---|---|
| 4 | 4.65E+5 |
| 5 | 1.49E+5 |
| 6 | 1.30E+5 |
| 10 | 1.28E+5 |
| Vehicle | 1.15E+5 |

As shown in Tables 14 and 15, luciferase expression was detected in treated animals for each of the ten LNP compositions comprising COMPOUND 1 and the four LNP compositions comprising COMPOUND 2 of the present disclosure. Mice treated with each of the LNP compositions comprising COMPOUND 1 or COMPOUND 2 exhibited higher luciferase expression, predominantly in the liver as detected and quantified by BLI, than those mice treated with the PBS vehicle control.

Example 7—In Vivo Intramuscular LNP-Delivery of mRNA

The following is a nonlimiting example demonstrating that the lipid nanoparticle compositions of the present disclosure can be used for intramuscular (IM) deliver of mRNA in vivo and expression of the encoded protein.

Adult female BALB/C mice (n=2/group) were intramuscularly administered in the right hind limb of each mouse 20 μg of 5'-CleanCap-fLuciferase mRNA (TriLink Biotech) formulated with LNP composition comprising COMPOUND 2 as prepared according to Example 2 in the following percentages shown in Table 16:

TABLE 16

| COMPOUND 2 | DOPE | Cholesterol | DMG-PEG2000 | Lipid Blend (mM) | Lipid:RNA (w/w) |
|---|---|---|---|---|---|
| 32.411 | 32.411 | 32.411 | 2.77 | 17.5 | 25:1 or 50:1 |

One group of mice was treated with PBS, pH 7.4 (Thermo Fisher Scientific, USA) as a negative control.

The location and extent of luciferase expression in treated and untreated mice were determined at 4 hr and 24 hr by bioluminescent imaging (BLI) of anesthetized mice using an IVIS Lumina in vivo imaging system (Perkin Elmer) according to the manufacturer's instructions. Briefly, mice were anesthetized using isoflurane in oxygen, and placed supine on a heated stage. Mice were then administered D-luciferin (Perkin-Elmer #122799) IP, and BLI was performed. The results of this experiment are shown in Table 17.

TABLE 17

| | Ave flux (p/s) | | |
|---|---|---|---|
| Time (hr) | Lipid:RNA 25:1 | Lipid:RNA 50:1 | Vehicle (PBS, pH 7.4) |
| 4 | 4.58E+6 | 9.67E+5 | 1.13E+5 |
| 24 | 3.53E+6 | 8.09E+5 | 7.25E+4 |

As shown in Table 17, LNP compositions of the present disclosure comprising COMPOUND 2 can locally deliver nn RNA to muscle tissue and expression of the encoded luciferase gene product was detected by BLI predominantly at the injection site.

In another experiment, adult female BALB/C mice (n=2/group) were intramuscularly administered in the right hind limb of each mouse 20 μg of 5'-CleanCap-fLuciferase mRNA (TriLink Biotech) formulated with LNP composition comprising one of COMPOUNDS 3-8 as prepared according to Example 3 in the following percentages shown in Table 18:

TABLE 18

| One of COMPOUNDS 3-8 | DOPE | Cholesterol | DMG-PEG2000 | Lipid Blend (mM) | Lipid:RNA (w/w) |
|---|---|---|---|---|---|
| 33.5 | 32.0 | 33.5 | 1.0 | 40 | 25:1 |

One group of mice was treated with PBS, pH 7.4 (Thermo Fisher Scientific, USA) as a negative control.

The location and extent of luciferase expression in treated and untreated mice were determined at 4 hr by bioluminescent imaging (BLI) of anesthetized mice as described above. The results of this experiment are shown in Table 19.

TABLE 19

| LNPs comprising Compound # | Avg IM flux n = 2 |
|---|---|
| 3 | 5.8E+6 |
| 4 | 2.07E+6 |
| 5 | 2.12E+5 |
| 6 | 7.37E+4 |

TABLE 19-continued

| LNPs comprising Compound # | Avg IM flux n = 2 |
|---|---|
| 7 | 2.4E+5 |
| 8 | 8.31E+4 |
| Vehicle | 9.03E+4 |

As shown in Table 19, LNP compostions of the present disclosure comprising COMPOUNDS 3-5 and 7 deliver mRNA to muscle tissue and expression of the encoded luciferase gene product was detected predominantly at the local injection site.

Example 8—Preparation of LNP Compositions of the Present Disclosure Comprising DNA The following is a nonlinmiting example that demonstrates that a DNA nanoplasmid (a circular DNA) can be incorporated in LNP compositions of the present disclosure.

LNP compositions of the present disclosure comprising DNA, a nanoplasmid encoding a piggyBac transposon, wherein the piggyBac transposon comprised GFP under control of the EF1a promoter (herein referred to as the nano-pB-EF1a-GFP), and one of COMPOUNDS 1-8 were prepared as described in Example 3 by combining one of COMPOUNDS 1-8, the phospholipid DOPE, the structural lipid cholesterol (Chol) and 1,2-dimyristoyl-sn-glycerol methoxypolyethylene glycol (DMG-PEG2000) in the following percentages in Table 20:

TABLE 20

| One of COMPOUNDs 1-8 | DOPE | Cholesterol | DMG-PEG2000 | Lipid Blend (mM) | Lipid:DNA (w/w) |
|---|---|---|---|---|---|
| 38.0 | 50.0 | 10.0 | 2.0 | 12.5 | 45:1 |

The LNP compositions were further characterized as shown in Table 21.

TABLE 21

| LNPs comprising COMPOUND # | Diameter (DLS; nm) | PDI | Diameter (NTA; nm) | Total Particles/ml | Zeta Potential (mV) |
|---|---|---|---|---|---|
| 1 | 123.5 | 0.17 | 96.9 | 5.76E+11 | 0.67 |
| 2 | 80.6 | 0.221 | 105.0 | 4.58B+11 | −0.02 |
| 3 | 92.8 | 0.25 | 98.5 | 1.85E+11 | 0.5 |
| 4 | 254.9 | 1.0 | 132.5 | 8.01E+10 | −0.17 |
| 5 | 82.0 | 0.168 | 85.8 | 2.31E+11 | 0.21 |
| 6 | 78.2 | 0.241 | 81.8 | 3.30E+11 | 0.67 |
| 7 | 110.2 | 0.224 | 90.8 | 5.52E+11 | 0.96 |
| 8 | 92.9 | 0.237 | 122.1 | 2.43E+11 | 0.34 |

As shown in Table 21, DNA-containing LNP compositions comprising one of COMPOUNDS 1-8 were successfully formulated with the average diameter ranging from about 80 to about 135 nm as measured by NTA. The incorporation of DNA into the LNP compositions was confirmed by gel electrophoresis as described in Example 3.

Example 9—In Vitro LNP-Delivery of DNA to Adherent Cells

The following is a nonlimiting example demonstrating that the lipid nanoparticle compositions of the present disclosure can be used to deliver DNA to adherent cells in vitro and expression of the encoded protein.

HEK293T cells were seeded in 96 well plates and grown to 70% confluence in [DMEM+10% FBS] under a 5% $CO_2$ atmosphere at 37° C. A 0.5 μg amount of nano-pB-EF1a-GFP DNA formulated with LNP compositions comprising COMPOUNDS 1, 3 & 4 as prepared in Examples 3 and 8 was added to each well. Following treatment with the LNPs, the cells were imaged for GFP+expression with a Leica fluorescence microscope and then detached from 96 well plate to quantitate expression by flow cytometry. The results are shown in Table 22.

TABLE 22

| LNPs comprising Compound # | % Viable GFP+ |
|---|---|
| 1 | 48.6 |
| 3 | 97.1 |
| 4 | 17.1 |
| Untreated | <0.29 |

As shown in Table 22, the LNP compositions comprising COMPOUNDS 1, 3 & 4 were successfully able to deliver DNA to adherent HEK293T cells. Approximately 48.6%, 97.8% and 17.1% of HEK293T cells were positive for luciferase expression for LNPs comprising COMPOUNDS 1, 3 & 4, respectively, whereas less than 0.29 percent of cells were positive for eGFP expression in untreated controls demonstrating the ability to deliver DNA to adherent cells in vitro.

Example 10—Delivery of DNA to Resting T-Cells Using the LNP Compositions and Methods of the Present Disclosure The following nonlimiting example demonstrates that the LNP compositions and methods of the present disclosure can be used to deliver DNA to resting T-cells. The experiments described in this example used CD4/CD8 positive T-cells isolated from a leukapheresis product from a healthy donor.

In one experiment, LNPs of the present disclosure comprising one of COMPOUNDS 1-4, DOPE, Cholesterol and DMG-PEG2000 at a molar ratio of 0.38:0.5:0.1:0.02 and further comprising 0.125 μg amount of nano-pB-EF1a-GFP DNA were formed on a NanoAssemblr® (Precision Nanosystems. The nano-pB-EF1a-GFP DNA LNPs had a lipid: nucleic acid ratio (w:w) of 45:1. Resting T-cells were treated with varying amounts of the four LNP composition and at 24 hrs post treatment, the cells were analyzed to determine the percentage of cells that were viable and that expressed eGFP. The results of the analysis at 24 hr are shown in Table 23.

TABLE 23

| LNPs comprising Compound # | % Viable GFP+ |
|---|---|
| 1 | 35.2 |
| 2 | 4.4 |
| 3 | 18.0 |
| 4 | 2.3 |

As shown in Table 23, the LNP compositions comprising COMPOUNDS 1-4 were able to deliver the DNA and observe GFP expression in 35.2%, 4.4%, 18.0% and 2.3% of treated, viable primary T-cells, respectively.

Example 11 Genetic Modification of Suspension Cell Line Using the LNP Compositions and Methods of the Present Disclosure The following nonlimiting example demonstrates that the compositions and methods of the present disclosure can be used to genetically modify cells.

In general, TF1a cells (a suspension cell line) were engineered to stably express the SPB transposase. Cell were plated at 5e5/ml. LNP comprising a nanoplasmid transposon coding for eGFP under control of the EF1a protein were added to each well at a concentration of 1.25 mg/ml (0.125 ug total) of DNA per well. Medium was exchanged and cells were split by spinning cells down in a v-bottom plate and resuspending cells in fresh RPMI+10% FBS+2 ug/ml Puromycin media on D4 post LNP addition). Day=6, cells were assessed for GFP expression by epifluorescence microscopy and flow cytometry.

For example, LNP compositions comprising COMPOUND 3 were prepared comprising COMPOUND 3, DOPE, Cholesterol and DMG-PEG2000 at a molar ratio of 0.38:0.5:0.1:0.02 and the nanoplasmid transposon and cells were assessed at Day 6 for GFP expression by epifluorescence microscopy and flow cytometry. Approximately, 9.8% of cells were positive for GFP expression demonstrating that COMPOUND 3-containing LNPs can deliver DNA to cells and genetically modify cells by stable transposition of the nanoplasmid into the genome of the cell.

The results of the experiment described above demonstrate that the LNP compositions and methods of the present disclosure can be used to deliver genetic modification systems to cells and can be used to genetically modify cells.

Example 12 Preparation of Lipoplex Nanoparticles Comprising at Least One Multivalent Cationic Bolaform Amphiphilic Lipid and at Least One Nucleic Acid The following nonlimiting example demonstrates that multivalent cationic bolaform amphiphilic lipids can be formulated into lipoplex nanoparticles comprising at least one nucleic acid molecule.

Lipoplex nanoparticles were formulated using solvent injection method. In brief, a multivalent cationic bolaform amphiphilic lipid (4.0 mg) was dissolved in dimethyl sulfoxide (1 mL) to obtain 4 mg/mL solution. The solution was heated for 15 min at 40° C. to dissolve the lipid. DNA or mRNA (0.040 mg) was diluted with 50 mM Sodium acetate buffer (2 mL, pH 5.5) to obtained 0.02 mg/mL solution. Bolamphiphile lipid solution (0.4 mg, 100 p1) was injected in DNA or mRNA solution (0.04 mg, 2 mL) under constant sonication. The mass ratio of DNA or mRNA to bolamphiphile lipid was kept constant to 10 for all the bolamphiphile formulation. The sonication was continued for 5 min. The solution was dialyzed (MWCO 30 kDa) for 4-6 hours in PBS (1×, pH 7.4) at room temperature. Sample was concentrated using Amicon centrifuge tube (30 kDa) to get the desired concentration for subsequent in vivo or in vitro use.

Lipoplex nanoparticles were prepared comprising mRNA encoding eGFP using COMPOUND 1 according to the method above and the average diameter of the resulting nanoparticles was determined by DLS or NTA. Both methods yielded average diameters of about 120 nm and the presence of RNA in the nanoparticle was confirmed by gel electrophoresis as described in Example 3.

Example 13—In Vitro Lipoplex Nanoparticle-Delivery of mRNA to Adherent Cells The following nonlimiting example demonstrates that lipoplex nanoparticles of the present disclosure comprising COMPOUND 1 can deliver RNA to cells and express the encoded protein.

HEK293T cells were seeded in 96 well plates and grown to 70% confluence in [DMEM+10% FBS under a 5% $CO_2$ atmosphere at 37° C. Lipoplex nanoparticles comprising COMPOUND 1 and 0.007, 0.03, 0.125, and 0.50 μg mRNA encoding eGFP were added to the cells. Following incubation with the lipoplex nanoparticles, cells were assessed for GFP expression by epifluorescence microscopy and flow cytometry. The results are shown in Table 24

TABLE 24

| μg mRNA in Lipoplex Nanoparticle | % GFP |
|---|---|
| 0.007 | 0.99 |
| 0.03 | 7.37 |
| 0.125 | 30.1 |
| 0.50 | 56.1 |

As shown in Table 24, the number of GFP-positive cells increased linearly with increasing mRNA amounts demonstrating that the lipoplex nanoparticles can deliver mRNA to cells over a wide range of RNA concentrations.

Example 14—General Method for the Preparation of LNPs of Present Disclosure Comprising RNA or DNA The following is a nonlimiting example that provides a general method for effectively formulating a plurality of multi-component LNP compositions comprising exemplary compounds of Formula (I) and mRNA or DNA.

LNP compositions of the present disclosure comprising exemplary compounds of Formula (I) were prepared by combining various percentages of an exemplary compound of Formula (I), the phospholipid DOPE, the structural lipid cholesterol (Chol) and 1,2-dimyristoyl-sn-glycerol methoxypolyethylene glycol (DMG-PEG2000; Avanti Polar Lipids, Alabaster, Alabama, USA).

Individual 25 mg/ml stock solutions were prepared by solubilizing the lipids in 200-proof HPLC-grade ethanol and stock solutions were stored at −80° C. until formulated. At the time of formulation, the lipid stock solutions were briefly allowed to equilibrate to room temp and then placed on a hot plate maintained at a temperature range of 50-55° C. Subsequently, the hot lipid stock solutions were combined to yield desired final mol % as shown in Tables 25 and 26.

TABLE 25

| One of COMPOUNDS 9-21 | DOPE | Cholesterol | DMG-PEG2000 | Lipid Blend (mM) | Lipid:RNA (w/w) |
|---|---|---|---|---|---|
| 41.44 | 45.85 | 10 | 2.7 | 25 | 40:1 |

TABLE 26

| One of COMPOUNDS 9-21 | DOPE | Cholesterol | DMG-PEG2000 | Lipid Blend (mM) | Lipid:DNA (w/w) |
|---|---|---|---|---|---|
| 38 | 50 | 10.0 | 2.0 | 25 | 45:1 |

A 1 mg/ml solution of the desired mRNA or DNA to be incorporated into the LNPs was added to 150 mM sodium acetate buffer (pH 5.2) to form a stock solution and kept on ice. The aqueous mRNA or DNA was then added to the lipids as shown in Table 25 or 26 and hand-mixed vigorously with a single channel pipettor.

The resultant mRNA or DNA LNP compositions were then transferred to a Repligen Float-A-Lyzer dialysis device—having a molecular weight cut off (MWCO) of 8-10 kDa (Spectrum Chemical Mfg. Corp, CA, USA) and processed by dialysis against phosphate buffered saline (PBS) (dialysate:dialysis buffer volume at least 1:200 v/v), pH 7.4 overnight at 4° C. (or alternatively room temperature for at least 4 hours), to remove the 25% ethanol and achieve a complete buffer exchange. In some experiments the LNPs were further concentrated by in an Amicon® Ultra-4 centrifugal filter unit, MWCO-30 kDa (Millipore Sigma, USA) spun at ~4100×g in an ultracentrifuge. The mRNA and DNA LNPs were then stored at 4° C. until further use.

Example 15—Characterization of m RNA- and DNA-Containing LN P Compositions Comprising Compounds 9-21

The following is a nonlimiting example demonstrating that a plurality of mRNA- and DNA-containing LNP compositions may be effectively prepared comprising COMPOUNDS 9-21 of Example 1.

LNP compositions of the present disclosure comprising mRNA or DNA encoding firefly luciferase (hereafter "Flue"; TriLink) and COMPOUNDS 9-21 were prepared as described in Example 14 by combining one of COMPOUNDS 9-21, the phospholipid DOPE, the structural lipid cholesterol (Chol) and 1,2-dimyristoyl-sn-glycerol methoxypolyethylene glycol (DMG-PEG2000) in the percentages presented in Tables 27 and 28:

TABLE 27

| One of COMPOUNDS 9-21 | DOPE | Cholesterol | DMG-PEG2000 | Lipid Blend (mM) | Lipid:RNA (w/w) |
|---|---|---|---|---|---|
| 41.44 | 45.85 | 10 | 2.7 | 25 | 40:1 |

TABLE 28

| One of COMPOUNDS 9-21 | DOPE | Cholesterol | DMG-PEG2000 | Lipid Blend (mM) | Lipid:DNA (w/w) |
|---|---|---|---|---|---|
| 38 | 50 | 10.0 | 2.0 | 25 | 45:1 |

The physical characteristics of the resulting LNPs were analyzed. Table 29 shows the results of the analysis of LNPs comprising COMPOUNDS 10-12, 14-16, 20 and 21 of Example 1.

TABLE 29

| LNPs comprising COMPOUNDS 10-12, 14-15, 20 and 21 | | | | |
|---|---|---|---|---|
| COMPOUND # | Particle Size (nm) RNA | PDI RNA | Particle Size (nm) DNA | PDI DNA |
| 14 | 222.5 | 0.249 | 392.2 | 0.272 |
| 15 | 267.1 | 0.208 | 375.6 | 0.201 |
| 16 | 188.8 | 0.327 | 149.8 | 0.277 |
| 21 | 144.9 | 0.273 | 161.1 | 0.230 |
| 10 | 254.1 | 0.120 | 291.2 | 0.403 |
| 11 | 270.4 | 0.156 | 511.8 | 0.366 |
| 12 | 162.7 | 0.216 | 228.0 | 0.251 |
| 20 | 221.0 | 0.211 | 229.6 | 0.189 |

Example 16—In Vitro LNP-Delivery of mRNA or DNA to Suspension Cells

The following is a nonlimiting example demonstrating that the lipid nanoparticle compositions of the present disclosure can be used to deliver mRNA or DNA to suspension in vitro and that following delivery of the mRNA or DNA, the encoded protein is expressed by the cells.

TF1a cells were seeded in 96 well plates and grown to log confluency in RPMI+10% FBS] under a 500 $CO_2$ atmosphere at 37° C. A 0.125 µg amount of 5'-CleanCap-firefly luciferase mRNA or DNA (TriLink Biotech) formulated with LNP compositions comprising one of COMPOUNDS 9-21 as prepared in Example 14 at the following percentages in Tables 30 and 31 was added to each well. Cells were exposed to five different doses of mRNA or DNA.

TABLE 30

| One of COMPOUNDS 9-21 | DOPE | Cholesterol | DMG-PEG2000 | Lipid Blend (mM) | Lipid:RNA (w/w) |
|---|---|---|---|---|---|
| 41.44 | 45.85 | 10.0 | 2.7 | 25 | 40:1 |

TABLE 31

| One of COMPOUNDS 9-21 | DOPE | Cholesterol | DMG-PEG2000 | Lipid Blend (mM) | Lipid:DNA (w/w) |
|---|---|---|---|---|---|
| 38 | 50 | 10.0 | 2.0 | 25 | 45:1 |

After incubating for 24 hr, cells were incubated with non-lytic Promega RealTime-Glo® reagent for 1 hr and NanoLuc® luciferase was measured on a plate reader to assess viability. From the 5-point dosage response curve from a concentration of 0.03 ug/ml to 6 ug/ml, the Area under the Curve of measured relative NanoLuc luciferase is shown in Table 32. AUC RT-glo values are a metric of viable cellular return with a higher value associated with higher tolerability of the cationic material.

TABLE 32

| LNPs comprising Compound # | AUC RTglo mRNA | AUC RTglo DNA |
|---|---|---|
| 14 | 2390 | 3467 |
| 15 | 2685 | 3719 |
| 16 | 2740 | 2875 |

TABLE 32-continued

| LNPs comprising Compound # | AUC RTglo mRNA | AUC RTglo DNA |
|---|---|---|
| 21 | 4830 | 6553 |
| 10 | 904.7 | 1050 |
| 11 | 2040 | 20965 |
| 12 | 6420 | 6398 |
| 20 | 5076 | 4495 |

After reading out viability the cells were spun down, lysed, and read on the plate reader for firefly luciferase expression activity. From the 5-point dosage response curve from a concentration of 0.03 ug/ml to 6 ug/ml, the Area under the Curve of measured relative firefly luciferase is shown in Table 33. AUC firefly luciferase values are a metric of bulk protein expression and a higher value associated with higher delivery of the cationic material.

TABLE 33

| LNPs comprising Compound # | AUC Fluc mRNA | AUC Fluc DNA |
|---|---|---|
| 14 | 340.3 | 405.2 |
| 15 | 7967 | 648.6 |
| 16 | 89210 | 3489 |
| 21 | 79285 | 3648 |
| 10 | 126.5 | 82.94 |
| 11 | 11279 | 556.2 |
| 12 | 202152 | 4218 |
| 20 | 157428 | 3741 |

As shown in Tables 32 and 33, the LNP compositions comprising COMPOUNDS 9-21 were successfully able to delivery mRNA and DNA to suspension TF1a cells.

Example 17—Preparation of Lipoplex Nanoparticles

The following is a non-limiting example of lipoplexes formed using the multivalent cationic bolaform amphiphilic lipid of Formula (I).

Chemicals Used: Compounds 3 and 11; plasmid DNA (pDNA) (MW: 25382.8 KD, KiloDaltons); DOPE: 1,2-Dioleoyl-sn-glycero-3-phosphoethanolamine; PBS (phosphate buffered saline) buffer, pH 7.4.

Instrument: Zetasizer Nano (Malvern Instruments) for size measurements.

Lipoplex nanoparticles were prepared in PBS buffer at pH 7.4 by mixing both solutions of the pDNA and the corresponding multivalent cationic bolaform amphiphilic lipid. The multivalent cationic bolaform amphiphilic lipid solutions were prepared by adding aliquots of their stock solutions (in PBS at pH 7.4) to the buffer. Some of the lipoplex nanoparticles also included, DOPE, and in those instances, DOPE was added at a 1:1 molar ratio to multivalent cationic bolaform amphiphilic lipid concentration. The final DNA concentration was 20 µM, while the multivalent cationic bolaform amphiphilic lipid concentrations was adjusted according to a desired N/P (5, 10, 20) ratio. The N/P ratio between the multivalent cationic bolaform amphiphilic lipid and pDNA was expressed as the molar ratio between all the protonable amino groups of the multivalent cationic bolaform amphiphilic lipids and the phosphate groups of the DNA. The DLS experiments were performed after 10 min of incubation at room temperature. The average size of the complexes was determined with a Zetasizer Nano (Malvern Instruments) at a scattering angle of 1730 (temperature: 25° C.).

Results are shown in FIG. 1 and Table 34. FIG. 1 is a bar graph showing the size (Z-ave: average diameter) of the nanoparticle formed with various concentrations of individual components and lipoplex nanoparticles with and without DOPE. Compounds 3 & 11 were tested. (uM: micromolar, nM: nanomolar concentrations; N/P: molar ratio of amine content in bola to the phosphate content in pDNA; Comp: compound number)

Table 34 provides the size, diameter in nm (population %), of bolaplexes formulated with and without DOPE.

TABLE 34

| Composition | N/P 5 | N/P 10 | N/P 20 |
|---|---|---|---|
| Compound 3/DNA | 664 (87%) | 778 (69%) | 888 (85%) |
| Compound 3/DOPE/DNA | 810 (60%) | 245 (85%) | 240 (97%) |
| Compound 11/DNA | 645 (83%) | 566 (94%) | 707 (76%) |
| Compound 11/DOPE/DNA | 575 (88%) | 232 (86%) | 300 (95%) |

What is claimed is:
1. A composition comprising at least one lipid nanoparticle comprising at least one compound of Formula (I):
Formula (I)
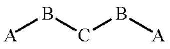
or a salt thereof, wherein:
each A is independently:
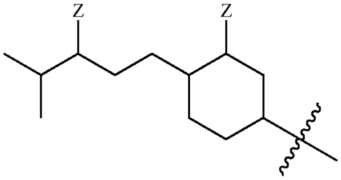
,
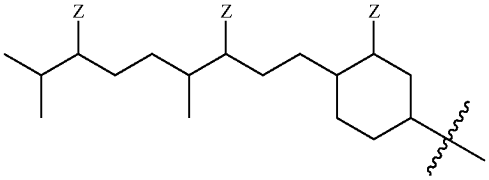
,
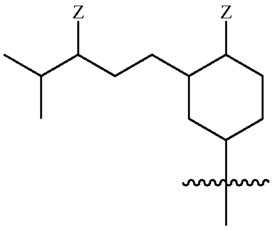
,
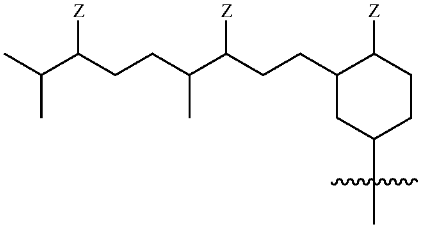
,
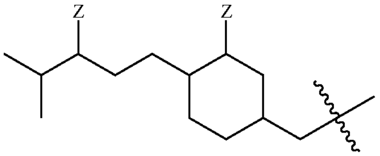
,
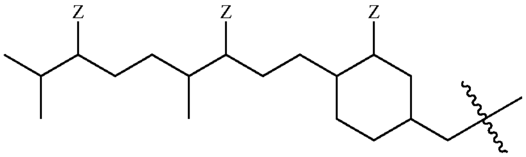
,
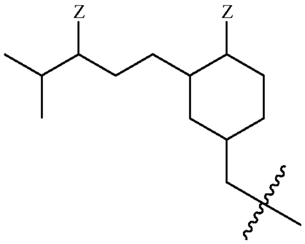
,
-continued
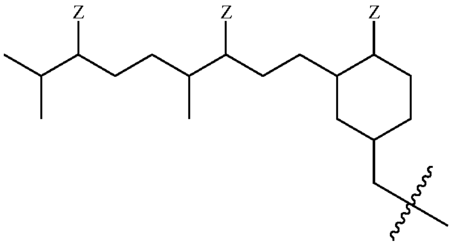
,
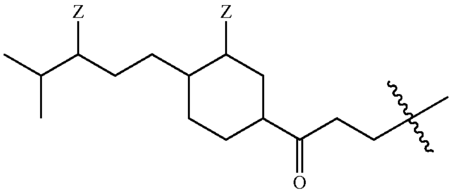
,
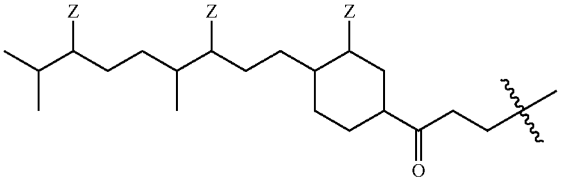
,
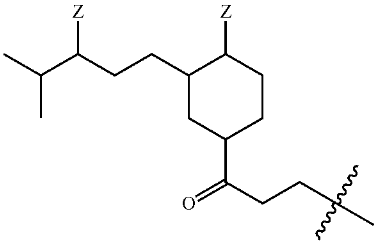
,
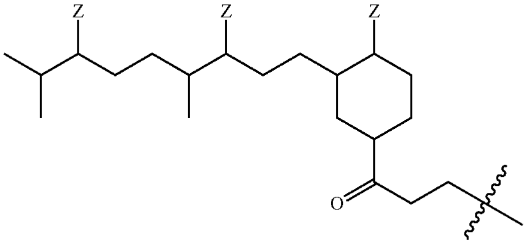
,
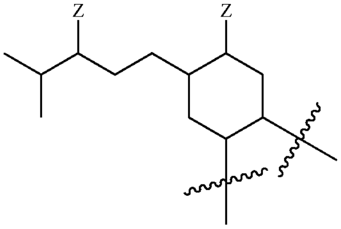
, or
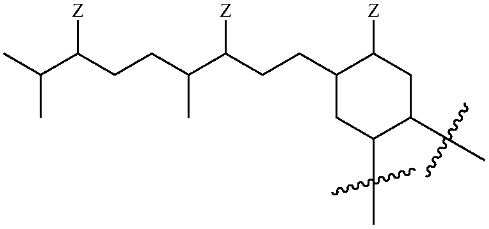
;

each Z is —S—$R_1$;

each $R_1$ is independently:

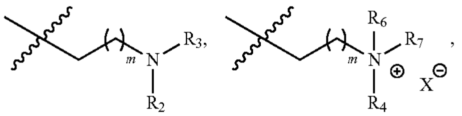

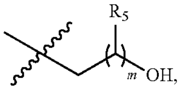

or

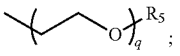

;

each $R_2$ or $R_3$ is independently selected from hydrogen, $C_1$-$C_6$ alkyl, $C_1$-$C_6$ alkenyl, aralkyl, or hydroxyalkyl;

each $R_4$, $R_6$ or $R_7$ is independently selected from $C_1$-$C_6$ alkyl, $C_1$-$C_6$ alkenyl, or hydroxyalkyl;

each $R_5$ is independently hydrogen or $C_1$-$C_6$ alkyl;

each X is independently halogen;

each m is independently an integer independently selected from 1-10;

each q is independently an integer independently selected from 1-200;

each B is independently selected from:

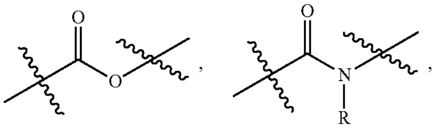

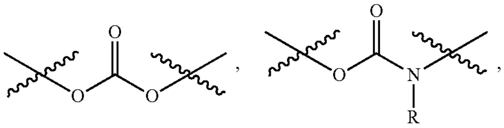

or

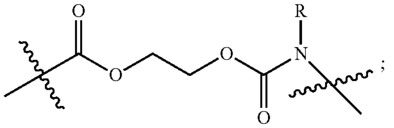

;

wherein each R is independently selected from hydrogen or $C_1$-$C_6$ alkyl; and C is:

a. a C2-C100 hydrocarbon chain optionally containing one or more S atoms, b. $Cyc^A$-L-$Cyc^B$, wherein $Cyc^A$ and $Cyc^B$ are each independently a 5-8 membered cycloalkyl and L is $C_1$-$C_3$ alkylene, c. a polyalkylene oxide or polyalkylene oxide block copolymers of 200-5,000 molecular weight, d. an aliphatic or aromatic polyester of 200-5,000 molecular weight, or e. an aliphatic or aromatic polyurethane of 200-5,000 molecular weight; or wherein

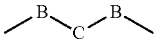

together form:

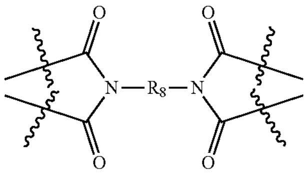

wherein $R_8$ is selected from C2-C6 alkyl, aryl,

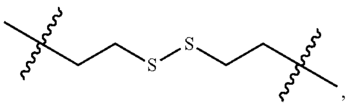

,

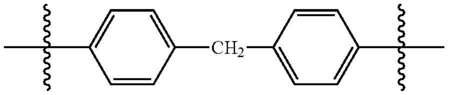

,

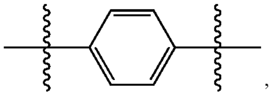

,

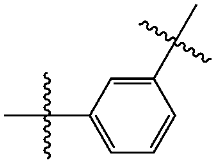

, or

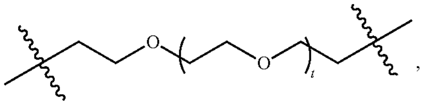

, wherein t is an integer selected from 1-10; and wherein the at least one lipid nanoparticle further comprises at least one nucleic acid molecule.

2. The composition of claim 1, wherein the at least one lipid nanoparticle comprises:

(i) about 10% of the at least one compound of Formula (I) by moles, wherein the at least one nucleic acid molecule comprises at least one RNA molecule, wherein the at least one lipid nanoparticle further comprises:

about 35% of cholesterol by moles, about 50% of DOPE by moles, and about 5% of DMG-PEG2000 by moles; and wherein the ratio of lipid to nucleic acid in the at least one nanoparticle is about 25:1 (w/w);

(ii) about 10% of the at least one compound of Formula (I) by moles, wherein the at least one nucleic acid molecule comprises at least one RNA molecule, wherein the at least one lipid nanoparticle further comprises:

about 39.5% of cholesterol by moles, about 50% of DOPE by moles, and about 0.5% of DMG-PEG2000 by moles; and wherein the ratio of lipid to nucleic acid in the at least one nanoparticle is about 10:1 or about 40:1 (w/w);

(iii) about 35% of the at least one compound of Formula (I) by moles, wherein the at least one nucleic acid molecule comprises at least one RNA molecule, wherein the at least one lipid nanoparticle further comprises:

about 50% of cholesterol by moles, about 10% of DOPE by moles, and about 5% of DMG-PEG2000 by moles; and wherein the ratio of lipid to nucleic acid in the at least one nanoparticle is about 40:1 (w/w);

(iv) about 50% of the at least one compound of Formula (I) by moles, wherein the at least one nucleic acid molecule comprises at least one RNA molecule, wherein the at least one lipid nanoparticle further comprises:

about 10% of cholesterol by moles, about 39.5% of DOPE by moles, and about 0.5% of DMG-PEG2000 by moles; and wherein the ratio of lipid to nucleic acid in the at least one nanoparticle is about 25:1 or about 40:1 (w/w);

(v) about 50% of the at least one compound of Formula (I) by moles, wherein the at least one nucleic acid molecule comprises at least one RNA molecule, wherein the at least one lipid nanoparticle further comprises:

about 10% of cholesterol by moles, about 35% of DOPE by moles, and about 5% of DMG-PEG2000 by moles; and wherein the ratio of lipid to nucleic acid in the at least one nanoparticle is about 10:1 (w/w);

(vi) about 41.4% of the at least one compound of Formula (I) by moles, wherein the at least one nucleic acid molecule comprises at least one RNA molecule, wherein the at least one lipid nanoparticle further comprises:

about 10% of cholesterol by moles, about 45.9% of DOPE by moles, and about 2.7% of DMG-PEG2000 by moles; and wherein the ratio of lipid to nucleic acid in the at least one nanoparticle is about 40:1 (w/w);

(vii) about 32.4% of the at least one compound of Formula (I) by moles, wherein the at least one nucleic acid molecule comprises at least one RNA molecule, wherein the at least one lipid nanoparticle further comprises:

about 32.4% of cholesterol by moles, about 32.4% of DOPE by moles, and about 2.8% of DMG-PEG2000 by moles; and wherein the ratio of lipid to nucleic acid in the at least one nanoparticle is about 25:1 w/w) or about 50:1 (w/w);

(viii) about 33.5% of the at least one compound of Formula (I) by moles, wherein the at least one nucleic acid molecule comprises at least one RNA molecule, wherein the at least one lipid nanoparticle further comprises:

about 33.5% of cholesterol by moles, about 32% of DOPE by moles, and about 1% of DMG-PEG2000 by moles; and wherein the ratio of lipid to nucleic acid in the at least one nanoparticle is about 25:1 (w/w);

(ix) about 39.5% of the at least one compound of Formula (I) by moles, wherein the at least one nucleic acid molecule comprises at least one RNA molecule, wherein the at least one lipid nanoparticle further comprises:

about 50% of cholesterol by moles, about 10% of DOPE by moles, and about 0.5% of DMG-PEG2000 by moles; and wherein the ratio of lipid to nucleic acid in the at least one nanoparticle is about 25:1 (w/w) or about 10:1 (w/w); or (x) about 38% of the at least one compound of Formula (I) by moles, wherein the at least one nucleic acid molecule comprises at least one DNA molecule, wherein the at least one lipid nanoparticle further comprises:

about 10% of cholesterol by moles, about 50% of DOPE by moles, and about 2% of DMG-PEG2000 by moles; and wherein the ratio of lipid to nucleic acid in the at least one nanoparticle is about 45:1 (w/w) or about 40:1 (w/w).

3. The composition of claim 1, wherein each A in the compound of Formula (I) is:

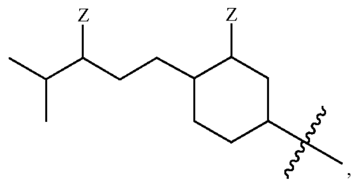

, or

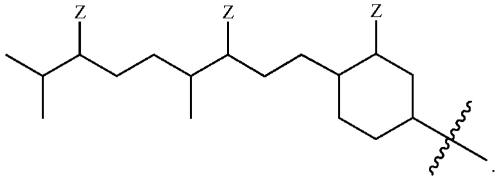

.

4. The composition of claim 3, wherein each Z is —S—$R_1$, and wherein at least one $R_1$ is:

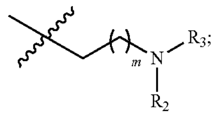

wherein m is 1, $R_2$ and $R_3$ are each $C_1$-$C_6$ alkyl, wherein each $C_1$-$C_6$ alkyl is methyl.

5. The composition claim 3, wherein each B in the compound of Formula (I) is:

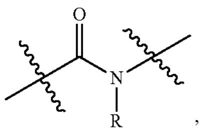

,

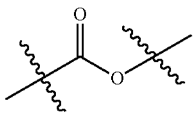

, or

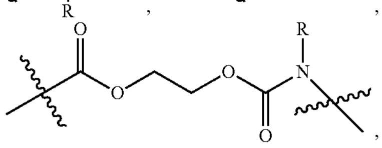

, wherein R is hydrogen;

wherein the carbonyl group of each B is linked to A in Formula (I).

6. The composition of claim 3, wherein C in the compound of Formula (I) is a C2-C100 hydrocarbon chain;

wherein the C2-C100 hydrocarbon chain is C6 hydrocarbon chain, a C12 hydrocarbon chain, or a C20 hydrocarbon chain; and wherein the C6 hydrocarbon chain is hexanylene, the C12 hydrocarbon chain is dodecanylene, and the C20 hydrocarbon chain is icosanylene.

7. The composition of claim 3, wherein C in the compound of Formula (I) is:

(i) $Cyc^A$-L-$Cyc^B$, wherein $Cyc^A$ and $Cyc^B$ are each independently a 5-8 membered cycloalkyl chain and L is $C_1$-$C_3$ alkylene, wherein $Cyc^A$ and $Cyc^B$ are each cyclohexyl and L is methylene; or (ii)

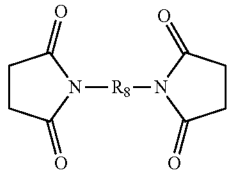

wherein $R_8$ is selected from C2-C6 alkyl, aryl,

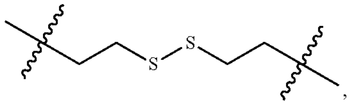

,

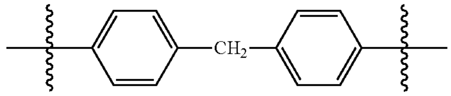

,

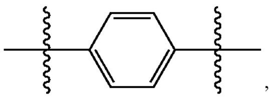

,

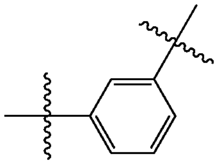

, or

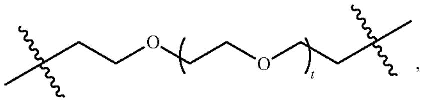

, and wherein each t is an integer independently selected from 1-10.

8. The composition of claim 1, wherein the compound of Formula (I) is:

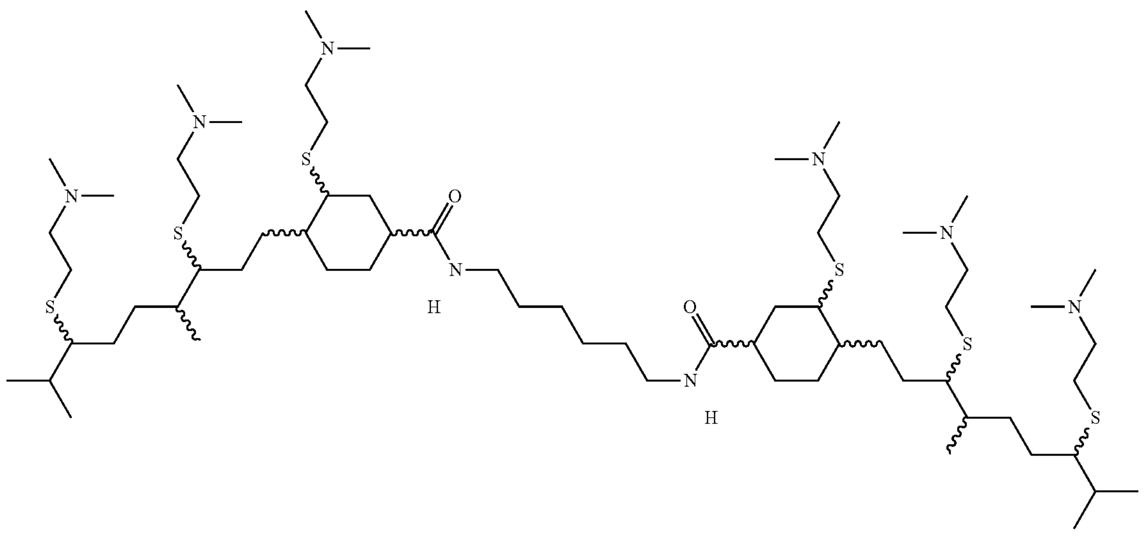

,

-continued
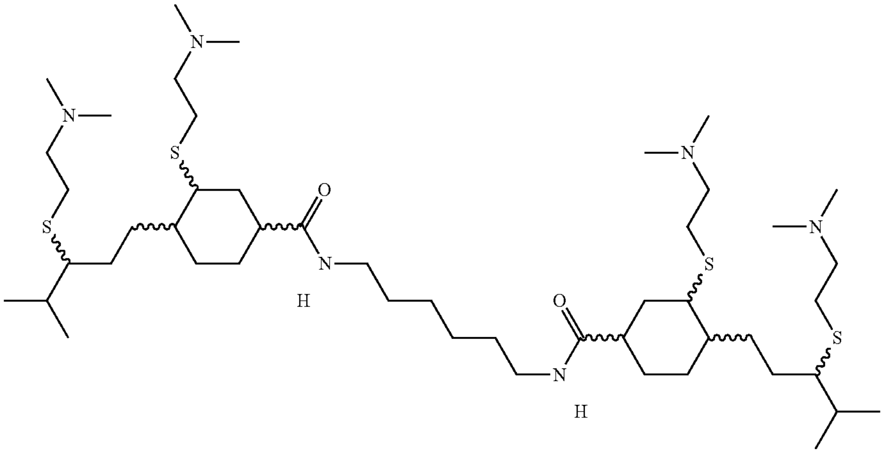
,
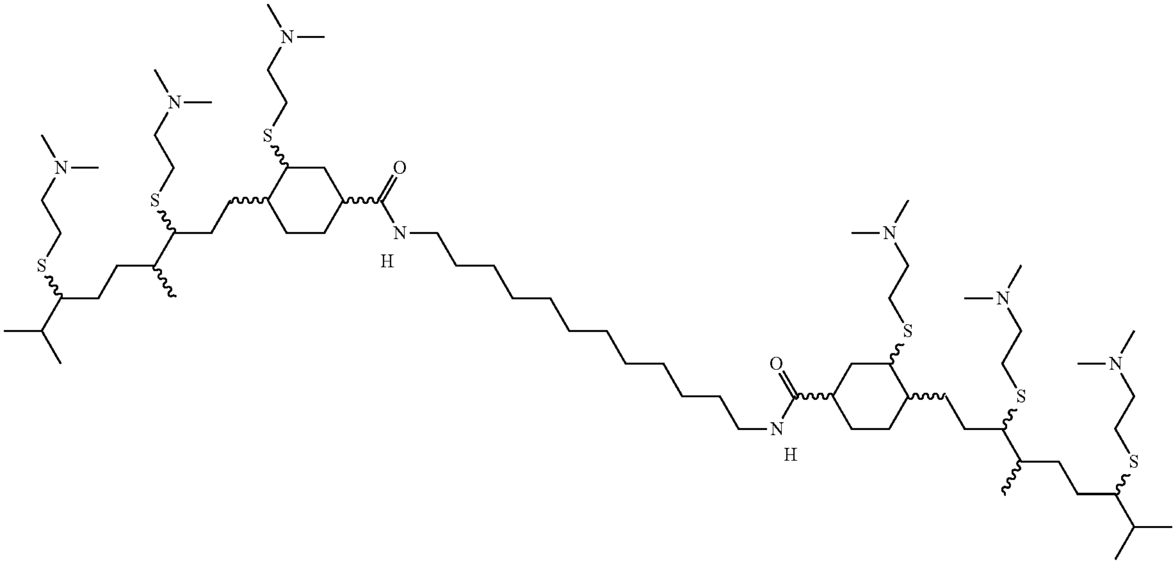
,
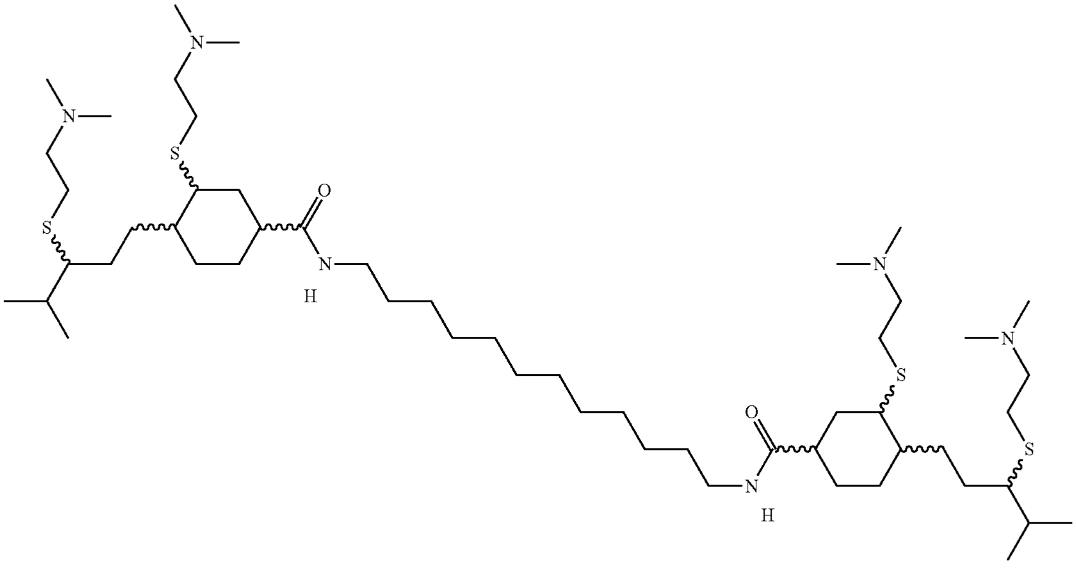
,

-continued
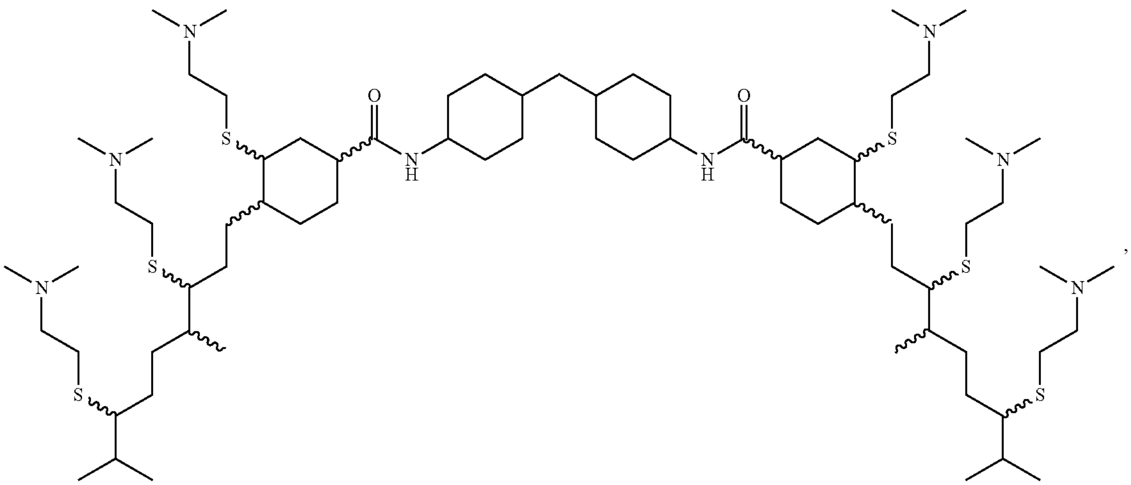
,
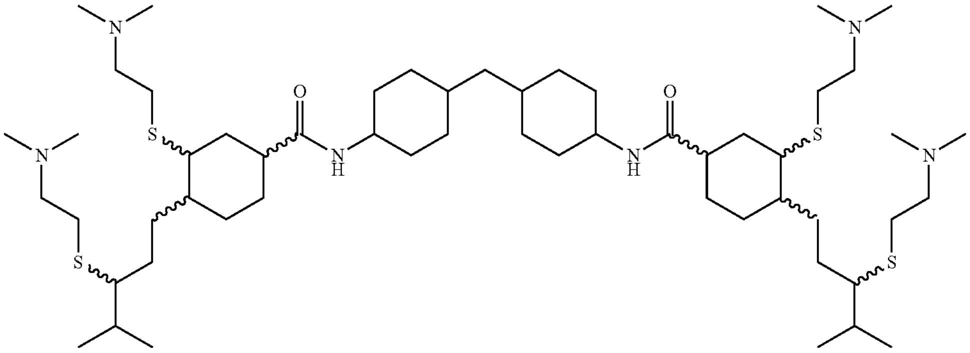
,
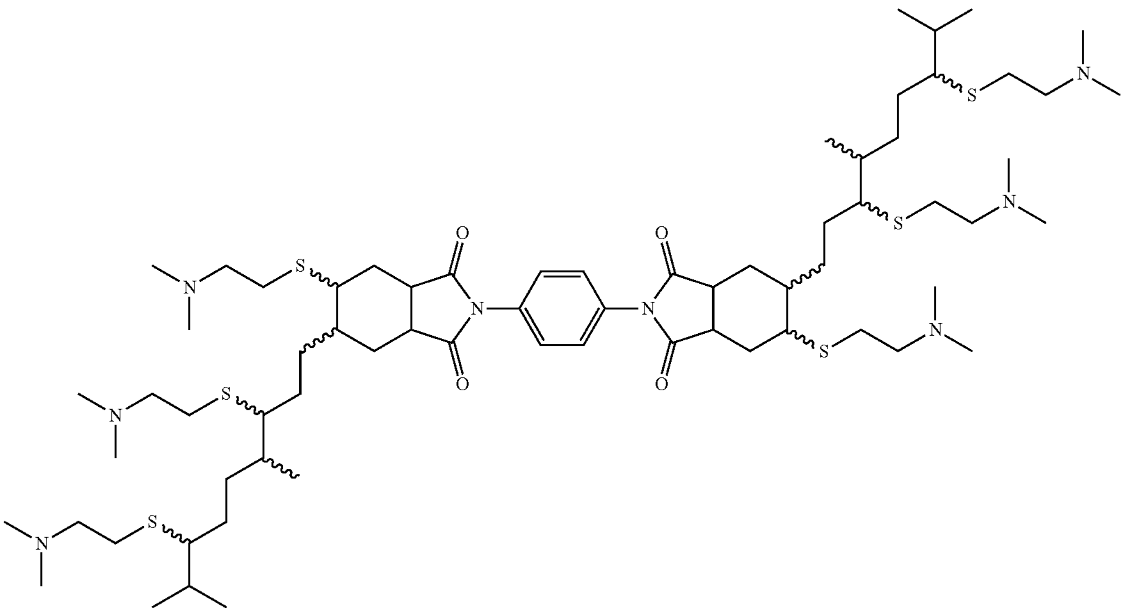
,

-continued
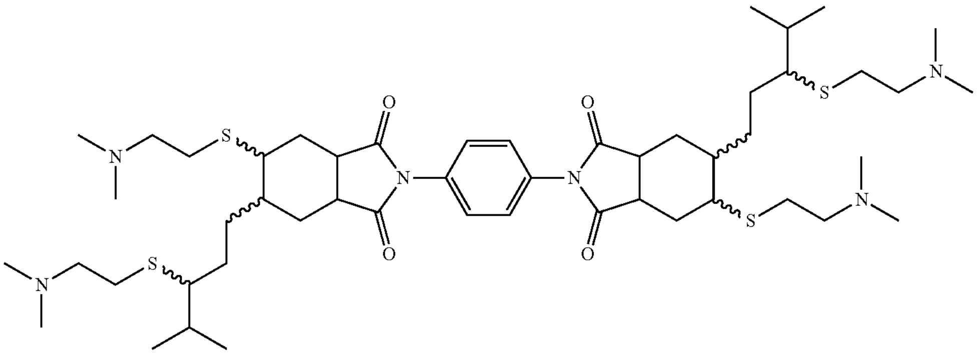
,
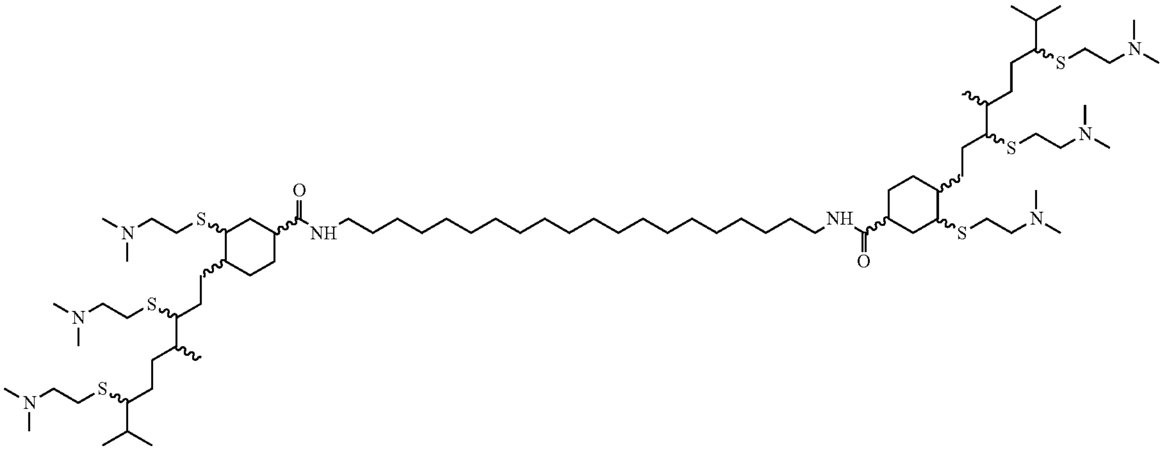
,
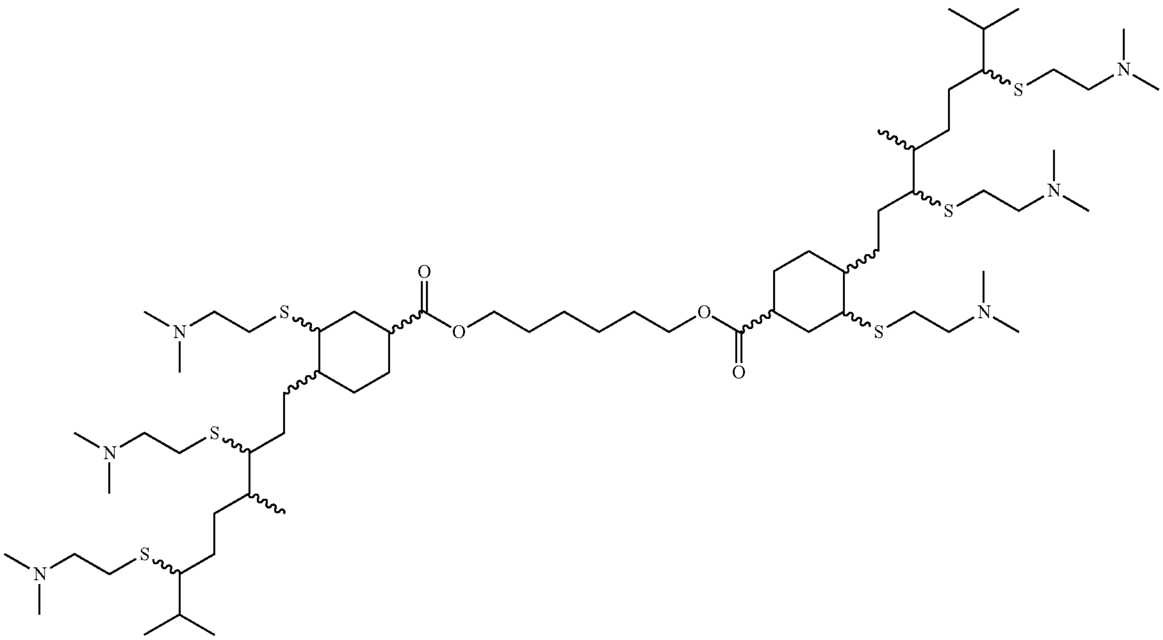
,

-continued
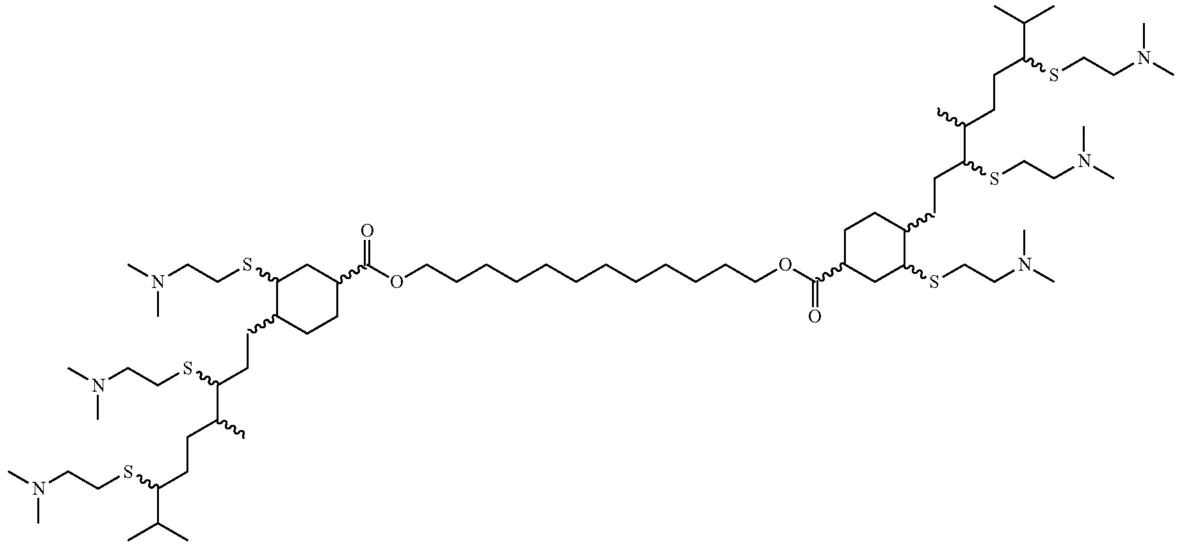
,
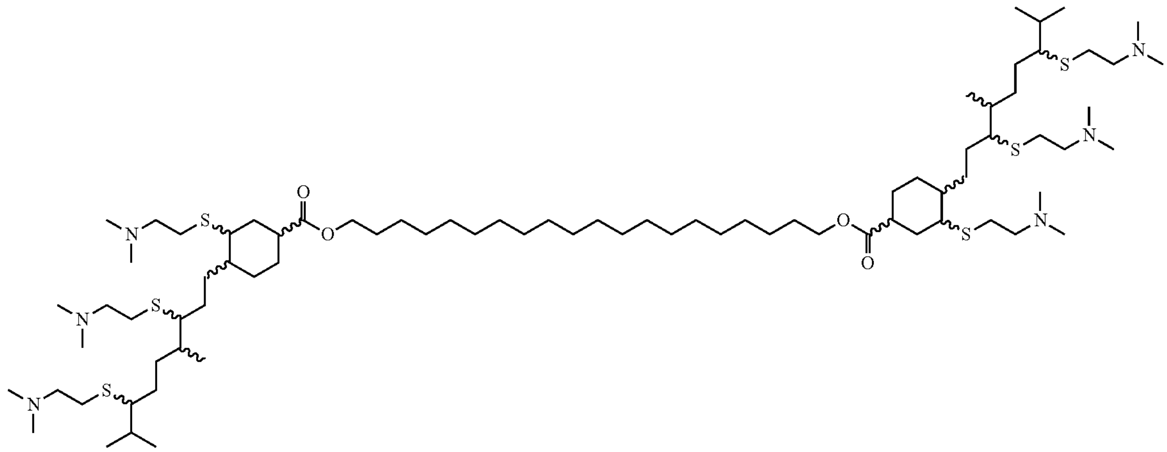
,
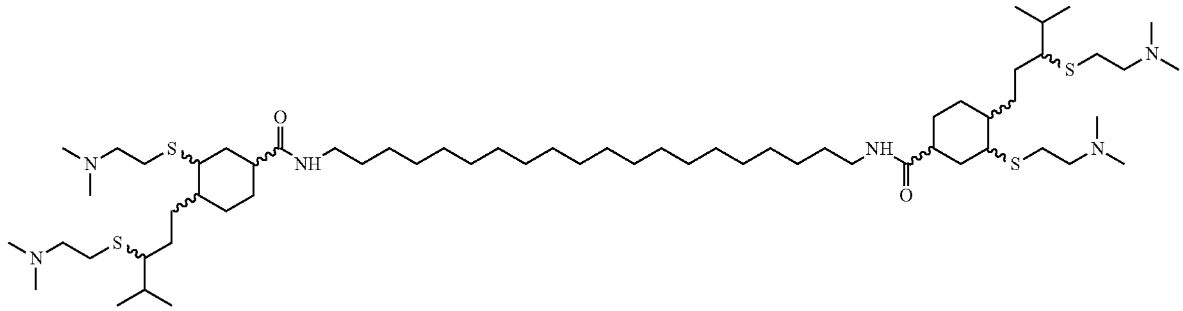
,
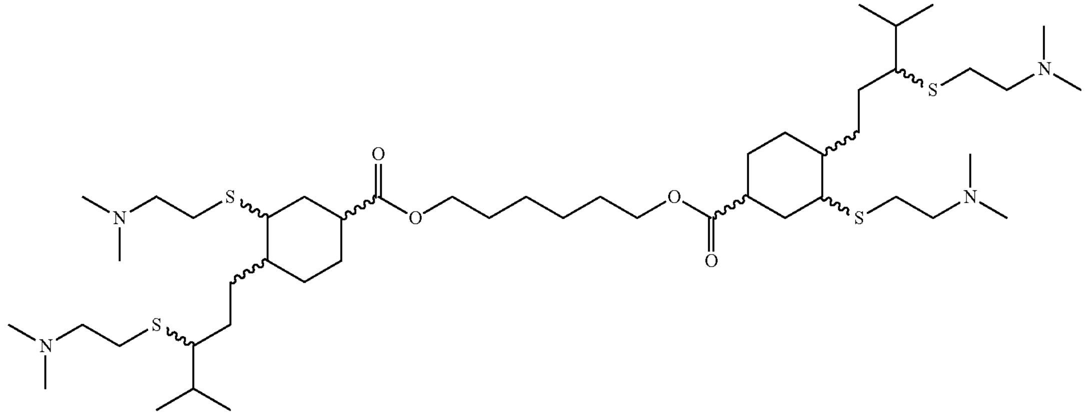
,

-continued
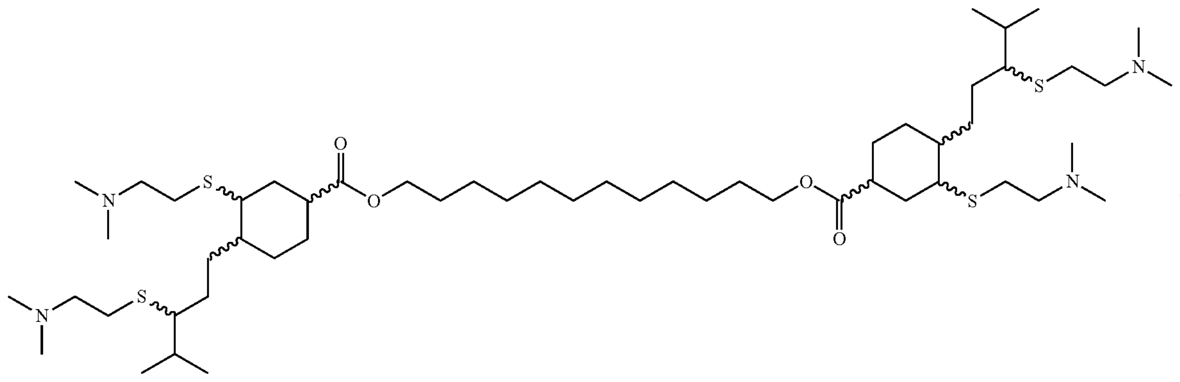
,
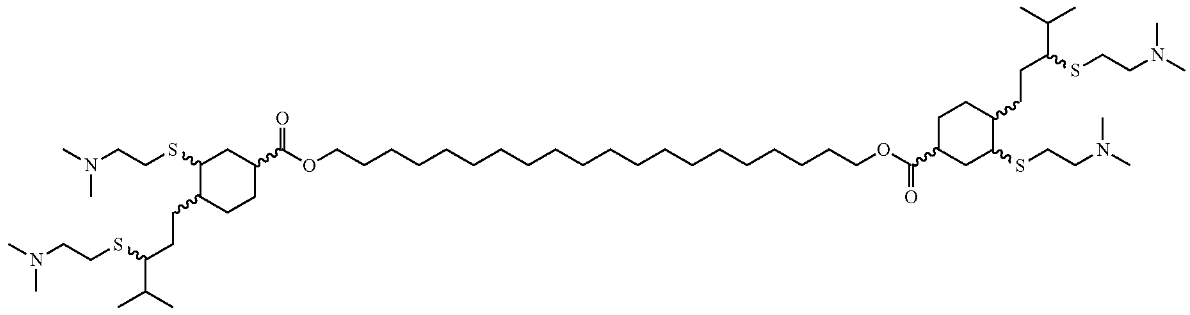
,
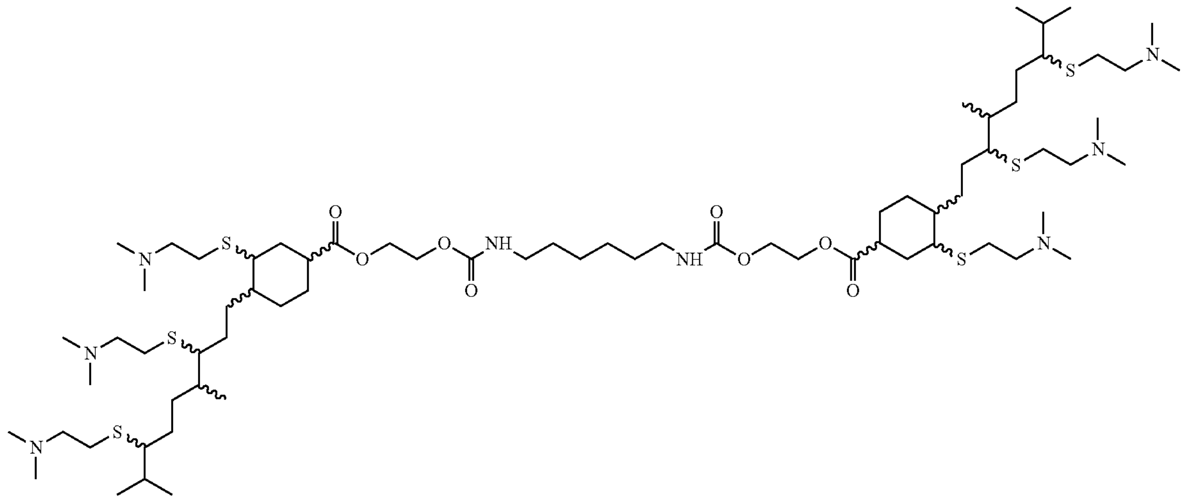
,
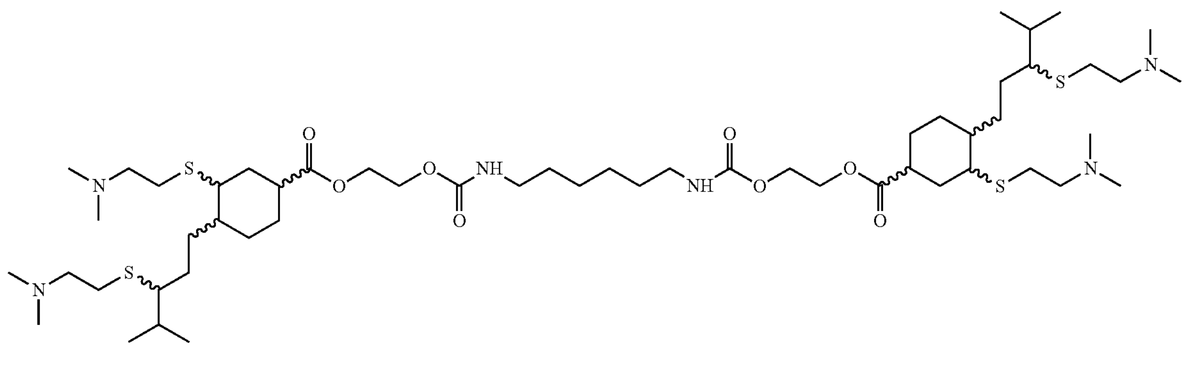
,

-continued
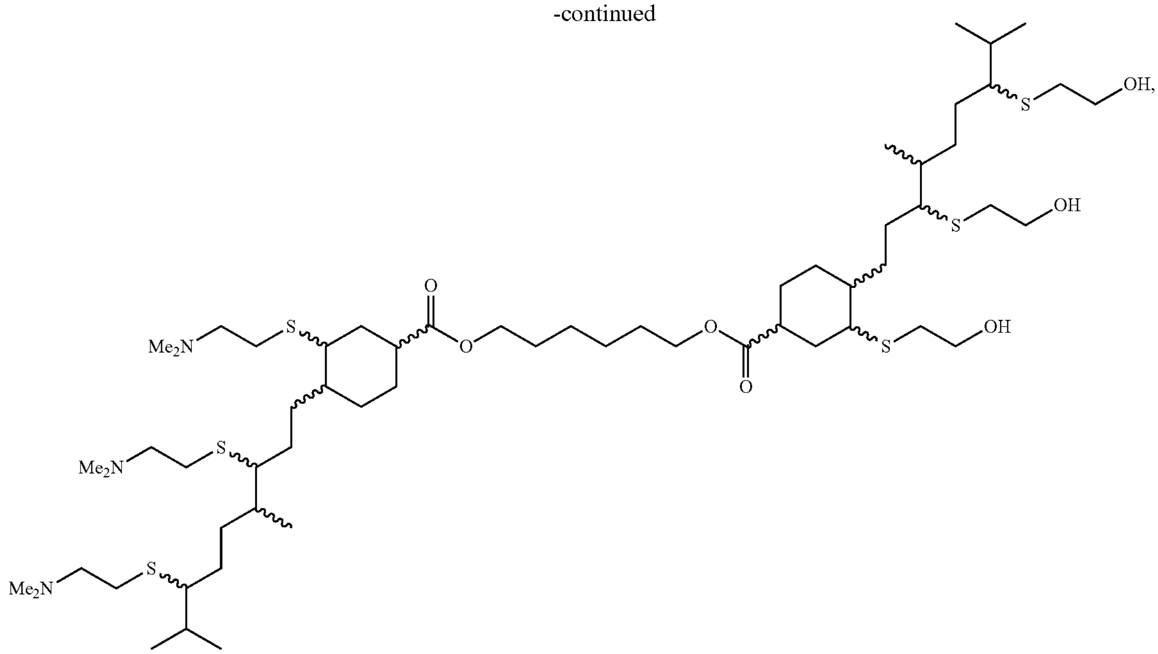
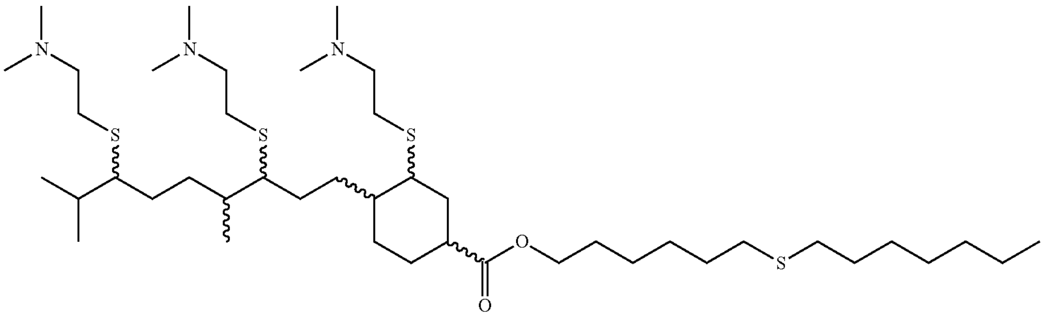
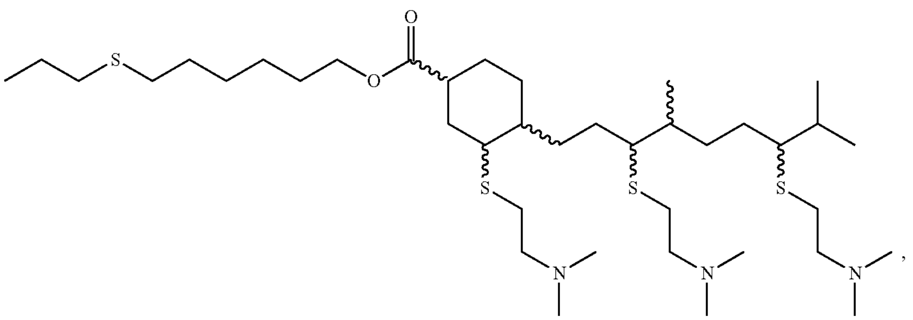
, or

-continued

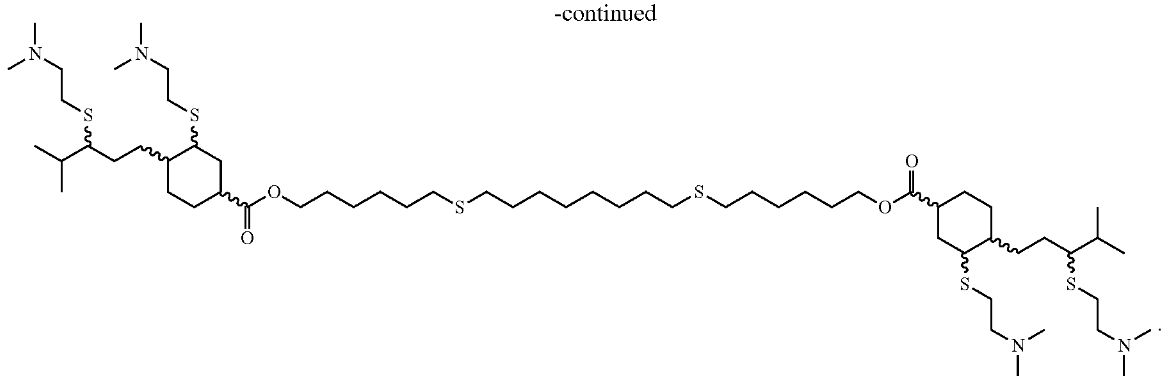

9. The composition of claim 2, wherein the at least one RNA molecule is an mRNA molecule, wherein the mRNA molecule further comprises a 5'-CAP.

10. The composition of claim 2, wherein the at least one RNA molecule comprises a nucleic acid sequence encoding at least one transposase, wherein the transposase is a *Trichoplusia ni* or *Bombyx mori* transposase or a hyperactive variant thereof, a synthetic salmonid fish transposase or a hyperactive variant thereof, a helitron transposase, a Tol2 transposase, or a *Triboliu castaneum* transposase or a variant thereof.

11. The composition of claim 2, wherein the at least one DNA molecule is a circular DNA molecule, covalently closed linear DNA molecule, a DNA plasmid, a DNA nanoplasmid, or a linearized DNA molecule, wherein the DNA molecule is a covalently closed linear DNA molecule or a DNA nanoplasmid.

12. The composition of claim 1, wherein the at least one nucleic acid molecule comprises a nucleic acid sequence encoding:
(i) at least one therapeutic protein; or
ii) at least one transposon, wherein the transposon comprises a nucleic acid sequence encoding at least one therapeutic protein.

13. The composition of claim 12, wherein the at least one therapeutic protein is:
(a) A chimeric antigen receptor (CAR);
(b) An ornithine transcarbamylase (OTC) polypeptide;
(c) A methylmalonyl-CoA mutase polypeptide;
(d) A Factor VIII (FVIII) polypeptide; or
(e) Any combination thereof.

14. A pharmaceutical composition comprising the composition of claim 1 and at least one pharmaceutically-acceptable excipient or diluent.

15. A method of delivering at least one nucleic acid to at least one cell comprising contacting the at least one cell with the composition of claim 1.

16. A method of genetically modifying at least one cell comprising contacting the at least one cell with the composition of claim 1.

17. The method of claim 16, wherein the at least one cell is:
(a) a liver cell, wherein the liver cell is a hepatocyte, a hepatic stellate cell, Kupffer cell or liver sinusoidal endothelial cell;
(b) a T-cell, wherein the T-cell is an activated T-cell, a resting T-cell or a stem memory T cell ($T_{SCM}$ cell); or
(c) a hematopoietic stem cell (HSC).

18. At least one cell modified by the method of claim 16.

19. A method of treating at least one disease or disorder in a subject in need thereof comprising administering to the subject a therapeutically effective amount of the composition of claim 14.

20. The method of claim 19, wherein the at least one disease or disorder is:
(i) a liver disease or disorder, wherein the liver disease or disorder is:
(a) a metabolic liver disorder;
(b) a urea cycle disorder (UCD), wherein the UCD is N-Acetylglutamate Synthetase (NAGS) Deficiency, Carbamoylphosphate Synthetase I Deficiency (CPSI Deficiency), Ornithine Transcarbamylase (OTC) Deficiency, Argininosuccinate Synthetase Deficiency (ASSD) (Citrullinemia I), Citrin Deficiency (Citrullinemia II), Argininosuccinate Lyase Deficiency (Argininosuccinic Aciduria), Arginase Deficiency (Hyperargininemia), Ornithine Translocase Deficiency (HHH Syndrome) or any combination thereof;
(ii) cancer; or
(iii) hemophilia A.

* * * * *